(12) United States Patent
Armistead et al.

(10) Patent No.: US 7,074,789 B2
(45) Date of Patent: Jul. 11, 2006

(54) KINASE INHIBITORS

(75) Inventors: David M. Armistead, Sudbury, MA (US); Jean E. Bemis, Arlington, MA (US); John L. Buchanan, Brookline, MA (US); Lucian V. DiPietro, Gloucester, MA (US); Daniel Elbaum, Newton, MA (US); Stephanie D. Geuns-Meyer, Medford, MA (US); Gregory J. Habgood, Merrimack, MA (US); Joseph L. Kim, Wayland, MA (US); Teresa L. Marshall, Stow, MA (US); Perry M. Novak, Milford, MA (US); Joseph J. Nunes, Andover, MA (US); Vinod F. Patel, Acton, MA (US); Leticia M. Toledo-Sherman, Venice, CA (US); Xiaotian Zhu, Watertown, MA (US)

(73) Assignee: Amgen Inc., Thousand Oaks, CA (US)

( * ) Notice: Subject to any disclaimer, the term of this patent is extended or adjusted under 35 U.S.C. 154(b) by 243 days.

(21) Appl. No.: 10/699,518

(22) Filed: Oct. 31, 2003

(65) Prior Publication Data
US 2004/0116388 A1 Jun. 17, 2004

Related U.S. Application Data

(63) Continuation of application No. 09/685,053, filed on Oct. 6, 2000, now abandoned.

(60) Provisional application No. 60/219,801, filed on Jul. 20, 2000, provisional application No. 60/215,576, filed on Jun. 30, 2000, provisional application No. 60/183,263, filed on Feb. 17, 2000, provisional application No. 60/170,378, filed on Dec. 13, 1999, provisional application No. 60/166,978, filed on Nov. 23, 1999, and provisional application No. 60/158,176, filed on Oct. 7, 1999.

(51) Int. Cl.
C07D 403/12 (2006.01)
C07D 403/14 (2006.01)
A61K 31/4155 (2006.01)
A61P 35/04 (2006.01)

(52) U.S. Cl. .................. 514/241; 544/206; 544/207; 544/208; 544/209; 544/210; 544/219

(58) Field of Classification Search .............. 544/206, 544/207, 208, 209, 210, 219; 514/241

See application file for complete search history.

(56) References Cited

U.S. PATENT DOCUMENTS

| 2,474,194 A | 6/1949 | Thurston et al. |
| 3,136,816 A | 6/1964 | Cutler et al. |
| 4,983,608 A | 1/1991 | Effland et al. |
| 5,043,317 A | 8/1991 | Chapman et al. |
| 5,215,569 A | 6/1993 | Drewes et al. |
| 5,869,030 A | 2/1999 | Dumler et al. |
| 5,935,966 A | 8/1999 | Suto et al. |
| 5,958,935 A | 9/1999 | Davis et al. |
| 6,080,858 A | 6/2000 | Schumacher |

FOREIGN PATENT DOCUMENTS

| CH | 261812 | 9/1949 |
| EP | 0 002 341 | 6/1979 |
| EP | 0 379 806 B1 | 8/1990 |
| EP | 0 945 443 | 9/1999 |
| EP | 1 040 831 A2 | 4/2000 |
| GB | 1390235 | 4/1975 |
| WO | WO 94/26733 | 11/1994 |
| WO | WO 95/33750 | 12/1995 |
| WO | WO 96/05177 | 2/1996 |
| WO | WO 97/19065 | 5/1997 |
| WO | WO 98/18782 | 5/1998 |
| WO | WO 99/01136 | 1/1999 |
| WO | WO 99/31073 | 6/1999 |
| WO | WO 99/31121 | 6/1999 |
| WO | WO 99/41253 | 8/1999 |
| WO | WO 99/50250 | 10/1999 |
| WO | WO 99/65909 | 12/1999 |
| WO | WO 00/12485 | 3/2000 |
| WO | WO 00/27825 | 5/2000 |
| WO | WO 00/39101 | 7/2000 |
| WO | WO 00/43373 | 7/2000 |
| WO | WO 00/53595 | 9/2000 |
| WO | WO 00/59892 | 10/2000 |
| WO | WO 00/63204 | 10/2000 |
| WO | WO 00/78731 | 12/2000 |
| WO | WO 01/00213 | 1/2001 |
| WO | WO 01/22938 | 4/2001 |
| WO | WO 01/29009 | 4/2001 |
| WO | WO 01/40218 | 6/2001 |

OTHER PUBLICATIONS

Shapiro, et al., *Guanamine Diuretics*, Journal of the American Chemical Society, American Chemical Society, Washington DC, US, XP-002110860, vol. 79, 5064-5071 (1957).

Arteaga et al. "*HER (erbB) Tyrosine Kinase Inhibitors in the Treatment of Breast Cancer*" Seminars in Oncology 29(No. 2 Suppl. 11) 4–10 (2002).

Bolen et al., "*Leukocyte Protein Tyrosine Kinases: Potential Targets for Drug Discovery*" Annu. Rev. Immunology 15:371–404 (1997).

Cao et al., "*Neutralizing monoclonal antibodies to hepatocyte growth factor/scatter factor (HGF/SF) display antitumor activity in animal models*" PNAS (Proceedings of the National Academy of Sciences of the United States of America) 98:13 7443–7448.

(Continued)

*Primary Examiner*—Venkataraman Balasubramanian
(74) *Attorney, Agent, or Firm*—Joseph W. Bulock

(57) ABSTRACT

The invention relates to inhibitors of enzymes that bind to ATP or GTP and/or catalyze phosphoryl transfer, compositions comprising the inhibitors, and methods of using the inhibitors and inhibitor compositions. The inhibitors and compositions comprising them are useful for treating disease or disease symptoms. The invention also provides for methods of making phosphoryl transferase inhibitor compounds, methods of inhibiting phosphoryl transferase activity, and methods for treating disease or disease symptoms.

7 Claims, No Drawings

OTHER PUBLICATIONS

Khandwala et al. "*The effects of Insulin–like growth factors on Tumorigenesis and Neoplastic Growth*" Endocrine Reviews 21(3):215–244 (2000).

Muller et al., "*Expression of angiopoietin–1 and its receptor TEK in hematopoietic cells from patients with myeloid leukemia*" Leukemia Research 26:163–168 (2002).

Raymond et al., "Epidermal Growth Factor Receptor Tyrosine Kinase as a Target for Anticancer Therapy" Drugs 60 Suppl.1: 15–23 (2000).

Scheijen et al. "Tyrosine kinase oncogenes in normal hematopoiesis and hemtological disease" Oncogene 21: 3314–3333 (2002).

Sweeney et al., "Treatment of polycystic kidney disease with a novel tyrosine kinase inhibitor" Kidney International, 57:33–40 (2000).

KINASE INHIBITORS

This application is a continuation of application Ser. No. 09/685,053, filed Oct. 6, 2000 now abandoned, which is hereby incorporated by reference.

This application claims priority benefit under Title 35 USC § 119(e) of U.S. Provisional Application Nos. 60/158,176 filed Oct. 7, 1999, 60/166,978 filed Nov. 23, 1999, 60/170,378 filed Dec. 13, 1999, 60/183,263 filed Feb. 17, 2000, 60/215,576 filed Jun. 30, 2000, and Ser. No. 60/219,801 filed Jul. 20, 2000, and entitled *Kinase Inhibitors*, the entire contents of each which are incorporated herein by reference.

BACKGROUND OF THE INVENTION

The invention relates to inhibitors of enzymes that catalyze phosphoryl transfer and/or that bind ATP/GTP nucleotides, compositions comprising the inhibitors, and methods of using the inhibitors and inhibitor compositions. The inhibitors and compositions comprising them are useful for treating or modulating disease in which phosphoryl transferases, including kinases, may be involved, symptoms of such disease, or the effect of other physiological events mediated by phosphoryl transferases, including kinases. The invention also provides for methods of making the inhibitor compounds and methods for treating diseases in which one or more phosphoryl transferase, including kinase, activities is involved.

Phosphoryl transferases are a large family of-enzymes that transfer phosphorous-containing groups from one substrate to another. By the conventions set forth by the Nomenclature Committee of the International Union of Biochemistry and Molecular Biology (IUBMB) enzymes of this type have Enzyme Commission (EC) numbers starting with 2.7.-.—(See, Bairoch A., The ENZYME database in *Nucleic Acids Res*. 28:304–305(2000)). Kinases are a class of enzymes that function in the catalysis of phosphoryl transfer. The protein kinases constitute the largest subfamily of structurally related phosphoryl transerfases and are responsible for the control of a wide variety of signal transduction processes within the cell. (See, Hardie, G. and Hanks, S. (1995) *The Protein Kinase Facts Book, I and II*, Academic Press, San Diego, Calif.). Protein kinases are thought to have evolved from a common ancestral gene due to the conservation of their structure and catalytic function. Almost all kinases contain a similar 250–300 amino acid catalytic domain. The protein kinases may be categorized into families by the substrates they phosphorylate (e.g., protein-tyrosine, protein-serine/threonine, histidine, etc.). Protein kinase sequence motifs have been identified that generally correspond to each of these kinase families (See, for example, Hanks, S. K., Hunter, T., *FASEB J*., 9:576–596 (1995); Knighton et al., *Science*, 253:407–414 (1991); Hiles et al., *Cell*, 70:419–429 (1992); Kunz et al., *Cell*, 73:585–596 (1993); Garcia-Bustos et al., *EMBO J*., 13:2352–2361 (1994)). Lipid kinases (e.g. P13K) constitute a separate group of kinases with structural similarity to protein kinases.

Since the X-ray structure of the catalytic subunit of cAMP-dependent protein kinase (cAPK) was elucidated, approximately two dozen additional protein kinase structures and one lipid kinase structure have been solved as either apo enzymes or binary and ternary complexes (with ATP, ATP analogs, metal ions, ADP, ATP competitive inhibitors in the absence or presence of peptide substrate or peptide inhibitors). These proteins share structurally conserved catalytic domains (kinase domains) comprising two lobes that can be further subdivided into twelve subdomains. The N-terminal portion forms the small lobe (including subdomains I–IV) whose architecture is composed of an antiparallel five-strand β-sheet and one α-helix, while the lower C-terminal domain forms another lobe (including subdomains VIA–XI) containing mostly α-helical architecture. Subdomain V spans the two lobes. The N-terminal domain is thought to participate in orienting the nucleotide (or other binding entity), while the C-terminal domain is thought to be responsible for binding peptide substrate and initiating phosphotransfer to the hydroxyl group of a serine, threonine, or tyrosine residue.

The N- and C-terminal domains are connected through a single peptide strand, to which the adenine moiety of ATP and/or GTP binds via an eleven membered hydrogen bond cycle, involving the N1 and the N6 amino group, and the backbone carbonyl and NH functions of two nonconsecutive residues. This linker acts as a hinge about which the domains can rotate with respect to each other without disruption of the secondary architecture of the kinase. Several torsion angle changes in the linker backbone allow this movement to occur. The ribose group of ATP is anchored to the enzyme via hydrogen bonds with residues within the ribose-binding pocket. The triphosphate group is held in position via various polar interactions with several variable residues from the glycine rich loop, the conserved DFG motif and the catalytic loop.

The "kinase domain" appears in a number of polypeptides which serve a variety of functions. Such polypeptides include, for example, transmembrane receptors, intracellular receptor associated polypeptides, cytoplasmic located polypeptides, nuclear located polypeptides and subcellular located polypeptides. The activity of protein kinases can be regulated by a variety of mechanisms. It must be noted, however, that an individual protein kinase may be regulated by more than one mechanism. These mechanisms include, for example, autophosphorylation, transphosphorylation by other kinases, protein-protein interactions, protein-lipid interactions, protein-polynucleotide interactions, ligand binding, and post-translational modification.

Protein and lipid kinases regulate many different cell processes including, but not limited to, proliferation, growth, differentiation, metabolism, cell cycle events, apoptosis, motility, transcription, translation and other signaling processes, by adding phosphate groups to targets such as proteins or lipids. Phosphorylation events catalyzed by kinases act as molecular on/off switches that can modulate or regulate the biological function of the target protein. Phosphorylation of target proteins occurs in response to a variety of extracellular signals (hormones, neurotransmitters, growth and differentiation factors, etc.), cell cycle events, environmental or nutritional stresses, etc. Protein and lipid kinases can function in signaling pathways to activate or inactivate, or modulate the activity of (either directly or indirectly) the targets. These targets may include, for example, metabolic enzymes, regulatory proteins, receptors, cytoskeletal proteins, ion channels or pumps, or transcription factors. Uncontrolled signaling due to defective control of protein phosphorylation has been implicated in a number of diseases and disease conditions, including, for example, inflammation, cancer, allergy/asthma, disease and conditions of the immune system, disease and conditions of the central nervous system (CNS), cardiovascular disease, dermatology, and angiogenesis.

Initial interest in protein kinases as pharmacological targets was stimulated by the findings that many viral oncogenes encode structurally modified cellular protein kinases with constitutive enzyme activity. These findings pointed to the potential involvement of oncogene related protein kinases in human proliferative disorders. Subsequently, deregulated protein kinase activity, resulting from a variety of more subtle mechanisms, has been implicated in the pathophysiology of a number of important human disorders including, for example, cancer, CNS conditions, and inmmunologically related diseases. The development of selective protein kinase inhibitors that can block the disease pathologies and/or symptoms resulting from aberrant protein kinase activity has therefore generated much interest.

SUMMARY OF THE INVENTION

The invention relates to compounds of the formula:

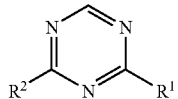

wherein,

Each $R^1$ and $R^2$ is independently $R^3$; $R^8$; $NHR^3$; $NHR^5$; $NHR^6$; $NR^5R^5$; $NR^5R^6$; $SR^5$; $SR^6$; $SR^3$; $OR^5$; $OR^6$; $OR^3$; $C(O)R^3$; heterocyclyl optionally substituted with 1–4 independent $R^4$ on each ring; or C1–C10 alkyl substituted with 1–4 independent $R^4$;

Each $R^3$ is independently aryl; phenyl optionally substituted with 1–5 independent $R^4$ on each ring; or heteroaryl optionally substituted with 1–4 independent $R^4$ on each ring; and the remaining groups are as defined herein. The invention also relates to compositions comprising these compounds, methods of making these compounds, methods of inhibiting enzyme activity, particularly kinase activity, through use of these compounds, and methods of treating disease or disease symptoms in a mammal, particularly where modulation of enzyme activity, and more particularly kinase activity, can affect disease outcome.

DETAILED DESCRIPTION OF THE INVENTION

The invention provides compounds useful in inhibiting kinase activity and inhibiting kinases or other polypeptides having sequences or subsequences homologous to kinase sequences or subsequences. In one embodiment, the inhibitory compound has the formula:

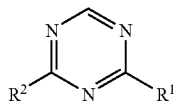

wherein,

Each $R^1$ and $R^2$ is independently $R^3$; $R^8$; $NHR^3$; $NHR^5$; $NHR^6$; $NR^5R^5$; $NR^5R^6$; $SR^5$; $SR^6$; $SR^3$; $OR^5$; $OR^6$; $OR^3$; $C(O)R^3$; heterocyclyl optionally substituted with 1–4 independent $R^4$ on each ring; or C1–C10 alkyl substituted with 1–4 independent $R^4$;

Each $R^3$ is independently aryl; phenyl optionally substituted with 1–5 independent $R^4$ on each ring; or heteroaryl optionally substituted with 1–4 independent $R^4$ on each ring;

Each n is independently 1 or 2;

Each m is independently 0, 1, 2, 3, or 4;

Each $R^4$ is independently selected from H, C1–C10 alkyl; C2–C10 alkenyl; C2–C10 alkynyl; C3–C10 cycloalkyl; C4–C10 cycloalkenyl; aryl; $R^8$; halo; haloalkyl; $CF_3$; $SR^5$; $OR^5$; $OC(O)R^5$; $NR^5R^5$; $NR^5R^6$; $NR^5R^{16}$; $COOR^5$; $NO_2$; CN; $C(O)R^5$; $C(O)C(O)R^5$; $C(O)NR^5R^5$; $S(O)_nR^5$; $S(O)_nNR^5R^5$; $NR^5C(O)NR^5R^5$; $NR^5C(O)C(O)R^5$; $NR^5C(O)R^5$; $NR^5(COOR^5)$; $NR^5C(O)R^8$; $NR^5S(O)_nNR^5R^5$; $NR^5S(O)_nR^5$; $NR^5S(O)_nR^8$; $NR^5C(O)C(O)NR^5R^5$; $NR^5C(O)C(O)NR^5R^6$; $OC(O)NR^5R^5$; $OS(O)_nNR^5R^5$; $NR^5S(O)_nOR^5$; $P(O)(OR^5)_2$; C1–C10 alkyl substituted with 1–3 independent aryl, $R^7$ or $R^8$; or C2–C10 alkenyl substituted with 1–3 independent aryl, $R^7$ or $R^8$;

Each $R^5$ is independently H; C1–C10 alkyl; C2–C10 alkenyl; C2–C10 alkynyl; C3–C10 cycloalkyl; C4–C10 cycloalkenyl; aryl; $R^9$; haloalkyl; C1–C10 alkyl substituted with 1–3 independent aryl, $R^7$ or $R^9$ groups; C3–C10 cycloalkyl substituted with 1–3 independent aryl, $R^7$ or $R^9$ groups; or C2–C10 alkenyl substituted with 1–3 independent aryl, $R^7$ or $R^9$;

Each $R^6$ is independently $C(O)R^5$, $COOR^5$, $C(O)NR^5R^5$, $C(NR^5)NR^5R^5$, or $S(O)_nR^5$;

Each $R^7$ is independently halo, $CF_3$, $SR^{10}$, $OR^{10}$, $OC(O)R^{10}$, $NR^{10}R^{10}$, $NR^{10}R^{11}$, $NR^{11}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$, $S(O)_nNR^{10}R^{10}$; $NR^{10}S(O)_n NR^{10}R^{10}$; $NR^{10}S(O)_nR^{10}$; or $P(O)(OR^5)_2$;

Each $R^8$ is independently a 3–8 membered monocyclic, 7–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms independently selected from O, N, or S, which may be saturated or unsaturated, and wherein 0, 1, 2, 3 or 4 atoms of each ring may be substituted by a substituent independently selected from C1–C10 alkyl; C2–C10 alkenyl; C2–C10 alkynyl; C3–C10 cycloalkyl; C4–C10 cycloalkenyl; aryl; $R^9$; halo; sulfur; oxygen; $CF_3$; $SR^5$; $OR^5$; $OC(O)R^5$; $NR^5R^5$; $NR^5R^6$; $NR^6R^6$; $COOR^5$; $NO_2$; $C(O)R^5$; $C(O)NR^5R^5$; $S(O)_nNR^5R^5$; $NR^5C(O)NR^5R^5$; $NR^5C(O)R^9$; $NR^5S(O)_nNR^5R^5$; $NR^5S(O)_nR^9$; C1–C10 alkyl substituted with 1–3 independent $R^7$, $R^9$ or aryl; or C2–C10 alkenyl substituted with 1–3 independent $R^7$, $R^9$ or aryl;

Each $R^9$ is independently a 3–8 membered monocyclic, 7–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms independently selected from O, N, or S, which may be saturated or unsaturated, and wherein 0, 1, 2 or 3 atoms of each ring may be substituted by a substituent independently selected from C1–C10 alkyl; C2–C10 alkenyl; C2–C10 alkynyl; C3–C10 cycloalkyl; C4–C10 cycloalkenyl; halo; sulfur; oxygen; $CF_3$; haloalkyl; $SR^{10}$; $OR^{10}$; $NR^{10}R^{10}$; $NR^{10}R^{11}$; $NR^{11}R^{11}$; $COOR^{10}$; $NO_2$; CN; $C(O)R^{10}$; $S(O)_nR^{10}$; $S(O)_nNR^{10}R^{10}$; or $C(O)NR^{10}R^{10}$;

Each $R^{10}$ is independently H; C1–C10 alkyl; C2–C10 alkenyl; C2–C10 alkynyl; C3–C10 cycloalkyl; C4–C10 cycloalkenyl; haloalkyl; C1–C10 alkyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^5$, $SR^5$, $NR^5R^5$, $COOR^5$, $NO_2$, CN, $C(O)R^{12}$, $C(O)NR^{12}R^{12}$, $NR^{12}C(O)R^{12}$, $N(R^{12})(COOR^{12})$, $S(O)_nNR^{12}R^{12}$, or $OC(O)R^{12}$; or phenyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NR^{12}C(O)R^{12}$, $N(R^{12})(COOR^{12})$, $S(O)_nNR^{12}R^{12}$, or $OC(O)R^{12}$;

Each $R^{11}$ is independently $C(O)R^{10}$, $COOR^{10}$, $C(O)NR^{10}R^{10}$ or $S(O)_nR^{10}$;

Each $R^{12}$ is independently H; C1–C10 alkyl; C2–C10 alkenyl; C2–C10 alkynyl; C3–C10 cycloalkyl; C4–C10 cycloalkenyl; C1–C10 alkyl substituted with 1–3 independent C2–C10 alkenyl, C2–C10 alkynyl, C3–C10 cycloalkyl, C4–C10 cycloalkenyl, halo, $CF_3$, $OR^{13}$, $SR^{13}$, $NR^{13}R$, $COOR^{13}$, $NO_2$, $CN^{13}$, $C(O)R^{13}$, $C(O)NR^{13}R^{13}$, $NR^{13}C(O)R^{13}$, or $OC(O)R^{13}$; or phenyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NR^{13}C(O)R^{13}$, or $OC(O)R^{13}$;

Each $R^{13}$ is independently H; C1–C10 alkyl; C2–C10 alkenyl; C2–C10 alkynyl; C3–C10 cycloalkyl; C4–C10 cycloalkenyl; C1–C10 alkyl optionally substituted with halo, $CF_3$, $OR^{14}$, $SR^{14}$, $NR^{14}R^{14}$, $COOR^{14}$, $NO_2$, CN; or phenyl optionally substituted with halo, $CF_3$, $OR^{14}$, $SR^{14}$, $NR^{14}R^{14}$, $COOR^{14}$, $NO_2$, CN;

Each $R^{14}$ is independently H; C1–C10 alkyl; C3–C10 cycloalkyl or phenyl;

Each $R^{15}$ is independently H; $CF_3$; CN; $COOR^5$; or C1–C10 alkyl substituted with 1–3 independent $OR^5$, $SR^5$, or $NR^5R^5$;

Each $R^{16}$ is independently H, C1–C10 alkyl; C2–C10 alkenyl; C2–C10 alkynyl; C3–C10 cycloalkyl; C4–C10 cycloalkenyl; aryl; $R^8$; halo; haloalkyl; $CF_3$; $COOR^5$; $C(O)R^5$; $C(O)C(O)R^5$; $C(O)NR^5R^5$; $S(O)_nR^5$; $S(O)_nNR^5R^5$; C1–C10 alkyl substituted with 1–3 independent aryl, $R^7$, $R^8$, or phenyl optionally substituted with substituted with 1–4 independent $R^{23}$; or C2–C10 alkenyl substituted with 1–3 independent aryl, $R^7$ or $R^8$;

Each $R^{19}$ is independently $NR^5R^{16}$; $OR^5$; $SR^5$; or halo;

Each $R^{18}$ is independently C1–C10 alkyl; C2–C10 alkenyl; C2–C10 alkynyl; C3–C10 cycloalkyl; C4–C10 cycloalkenyl; aryl; $R^8$; halo; haloalkyl; $CF_3$; $COOR^5$; $C(O)R^5$; $C(O)C(O)R^5$; $C(O)NR^5R^5$; $S(O)_nR^5$; $S(O)_nNR^5R^5$; C1–C10 alkyl substituted with 1–3 independent aryl, $R^7$ or $R^8$; or C2–C10 alkenyl substituted with 1–3 independent aryl, $R^7$ or $R^8$;

Each $R^{19}$ is independently H or C1–C6 alkyl;

Each $R^{20}$ is independently $NR^5R^{18}$; $OR^5$; $SR^5$; or halo;

Each $R^{21}$ is independently t-butyl, 4-carboxyphenyl, 4-carbomethoxyphenyl, or furyl substituted with 1–4 independent $R^4$;

Each $R^{22}$ is independently C2–C9 alkyl substituted with 1–2 independent aryl, $R^7$, or $R^8$;

Each $R^{23}$ is independently selected from H, C1–C10 alkyl; C2–C10 alkenyl; C2–C10 alkynyl; C3–C10 cycloalkyl; C4–C10 cycloalkenyl; aryl; $R^8$; halo; haloalkyl; $CF_3$; $SR^5$; $OR^5$; $OC(O)R^5$; $NR^5R^5$; $NR^5R^6$; $COOR^5$; $NO_2$; CN; $C(O)R^5$; $C(O)C(O)R^5$; $C(O)NR^5R^5$; $S(O)_nR^5$; $S(O)_nNR^5R^5$; $NR^5C(O)NR^5R^5$; $NR^5C(O)C(O)R^5$; $NR^5C(O)R^5$; $NR^5(COOR^5)$; $NR^5C(O)R^8$; $NR^5S(O)_nNR^5R^5$; $NR^5S(O)_nR^5$; $NR^5S(O)_nR^8$; $NR^5C(O)C(O)NR^5R^5$; $NR^5C(O)C(O)NR^5R^5$; $OC(O)NR^5R^5$; $OS(O)_nNR^5R^5$; $NR^5S(O)NR^5$; $P(O)(OR^5)_2$; C1–C10 alkyl substituted with 1–3 independent aryl, $R^7$ or $R^8$; or C2–C10 alkenyl substituted with 1–3 independent aryl, $R^7$ or $R^8$;

Each $R^{24}$ is independently selected from C1–C10 alkyl; C2–C10 alkenyl; C2–C10 alkynyl; C3–C10 cycloalkyl; C4–C10 cycloalkenyl; aryl; $R^9$; halo; sulfur; oxygen; $CF_3$; $SR^5$; $OR^5$; $OC(O)R^5$; $NR^5R^5$; $NR^5R^6$; $NR^6R^6$; $COOR^5$; $NO_2$; CN; $C(O)R^5$; $C(O)NR^5R^5$; $S(O)_nNR^5R^5$; $NR^5C(O)NR^5R^5$; $NR^5C(O)R^5$; $NR^5S(O)_nNR^5R^5$; $NR^5S(O)_nR^9$; C1–C10 alkyl substituted with 1–3 independent $R^7$, $R^9$ or aryl; or C2–C10 alkenyl substituted with 1–3 independent $R^7$, $R^9$ or aryl;

Each X is independently O or S;

Each V, W, Y, and Z is independently N or $CR^4$;

Each haloalkyl is independently a C1–C10 alkyl substituted with one or more halogen atoms, selected from F, Cl, Br, or I, wherein the number of halogen atoms may not exceed that number that results in a perhaloalkyl group;

Each aryl is independently a 6-carbon monocyclic, 10-carbon bicyclic or 14-carbon tricyclic aromatic ring system optionally substituted with 1–3 independent C1–C10 alkyl; C2–C10 alkenyl; C2–C10 alkynyl; C3–C10 cycloalkyl; C4–C10 cycloalkenyl; $R^9$; halo; haloalkyl; $CF_3$; $OR^{10}$; $SR^{10}$; $NR^{10}R^{10}$; $NR^{10}OR^{11}$; $COOR^{10}$; $NO_2$; CN; $C(O)R^{10}$; $C(O)C(O)R^{10}$; $C(O)NR^{10}R^{10}$; $N(R^{10})C(O)NR^{10}R^{10}$; $N(R^{10})C(O)R^{10}$; $N(R)S(O)_nR^{10}$; $N(R^{10})(COOR^{10})$; $NR^{10}C(O)C(O)R^{10}$; $NR^{10}C(O)R^9$; $NR^{10}S(O)_nNR^{10}R^{10}$; $NR^{10}S(O)_nR^9$; $NR^2C(O)C(O)NR^{12}R^{12}$; $S(O)_nR^{10}$; $S(O)_nNR^{10}R^{10}$; $OC(O)R^{10}$; C1–C10 alkyl substituted with 1–3 independent $R^9$, halo, $CF_3$, $OR^{10}$, $SR^{10}$, $OC(O)R^{10}$, $NR^{11}R^{11}$, $NR^{10}R^{10}$, $N^{10}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$, $S(O)_nNR^{10}R^{10}$; $R^{10}$; or C2–C10 alkenyl substituted with 1–3 independent $R^9$, halo, $CF_3$, $OR^{10}$, $SR^{10}$, $OC(O)R^{10}$, $NR^{11}R^{11}$, $NR^{10}OR^{10}$, $NR^{10}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$, $S(O)_nNR^{10}R^{10}$;

Each heterocyclyl is independently a 3–8 membered nonaromatic monocyclic, 8–12 membered nonaromatic bicyclic, or 11–14 membered nonaromatic tricyclic, ring system comprising 1–4 heteroatoms if monocyclic, 1–8 heteroatoms if bicyclic, or, 1–10 heteroatoms if tricyclic, said heteroatoms independently selected from O, N, or S; and Each heteroaryl is independently a 5–8 membered aromatic monocyclic, 8–12 membered aromatic bicyclic, or 11–14 membered aromatic tricyclic ring system comprising 1–4 heteroatoms if monocyclic, 1–8 heteroatoms if bicyclic, or 1–10 heteroatoms if tricyclic, said heteroatoms independently selected from O, N, or S. Unless stated otherwise, the groups referenced in the formulae described herein have the definitions as delineated above.

In one embodiment, the compound is that of any of the formulae herein wherein,

Each $R^1$ and $R^2$ is independently $R^3$; $NHR^3$; $NHR^5$; or $NHR^6$;

In one embodiment, the compound is that of any of the formulae herein wherein, $R^1$ is independently $R^3$; and $R^2$ is independently $NHR^3$.

In one embodiment, the compound is that of any of the formulae herein wherein, $R^1$ is independently heteroaryl optionally substituted with 1–4 independent $R^4$ on each ring (and alternatively, wherein at least one $R^4$ is not H); and $R^2$ is independently $NHR^3$.

In one embodiment, the compound is that of any of the formulae herein wherein,

R¹ is independently phenyl optionally substituted with 1–5 independent R⁴ ring (and alternatively, wherein at least one R⁴ is not H); and R² is independently NHR³.

In one embodiment, the compound is that of any of the formulae herein wherein,

R¹ is independently aryl; and

R² is independently NHR³.

In one embodiment, the compound is that of any of the formulae herein wherein,

R¹ is not phenyl, 4-bromophenyl or 2-hydroxyphenyl.

In one embodiment, the compound is that of any of the formulae herein wherein,

Each R¹ and R² is independently NHR³. Alternatively, another embodiment of this embodiment is that wherein in R¹ and R², both R³ groups may not simultaneously be phenyl, 4-chlorophenyl, 3-aminophenyl, 4-aminophenyl, 4-nitrophenyl, 2-methylphenyl, thiazolyl, pyridyl, or 3-methylphenyl; or may not simultaneously be 4-nitrophenyl and 3-nitrophenyl, or 4-aminophenyl and 3-aminophenyl, or phenyl and 3-nitrophenyl; or may not simultaneously be 4-cyanophenyl and any one of the following: 2,4,6-trimethylphenyl, 2,6-dibromo-4-methylphenyl, 2,6-dimethyl-4-bromophenyl, 2,6-dibromo-4-isopropylphenyl, 2,-6-dimethyl-4-t-butylphenyl, or 2,6-dimethyl-4-cyanophenyl.

In one embodiment, the compound is that of any of the formulae herein wherein,

Each R¹ and R² is independently NHR³, wherein each R³ may not be 4-cyanophenyl.

In one embodiment, the compound is that of any of the formulae herein wherein,

Each R¹ and R² is independently NHR³, wherein each R³ may not be phenyl, pyridinyl, pyrimidinyl, pyrazinyl, thiazolyl, or pyridazinyl, either substituted or unsubstituted by additional substituents.

In one embodiment, the compound is that of any of the formulae herein wherein,

R¹ is independently NHR⁵; and

R² is independently NHR³.

Alternatively, another embodiment of this embodiment is that wherein in R¹ and R², both R³ and R⁵ groups may not simultaneously be phenyl, 4-chlorophenyl, 3-aminophenyl, 4-aminophenyl, 4-nitrophenyl, 2-methylphenyl, thiazol-2-yl, pyrid-2-yl, or 3-methylphenyl; or may not simultaneously be 4-nitrophenyl and 3-nitrophenyl, or 4-aminophenyl and 3-aminophenyl, or phenyl and 3-nitrophenyl; or may not simultaneously be 4-cyanophenyl and any one of the following: 2,4,6-trimethylphenyl, 2,6-dibromo-4-methylpbenyl, 2,6-dimethyl-4-bromophenyl, 2,6-dibromo-4-isopropylphenyl, 2,-6-dimethyl-4-t-butylphenyl, or 2,6-dimethyl-4-cyanophenyl; or may hot simultaneously be.

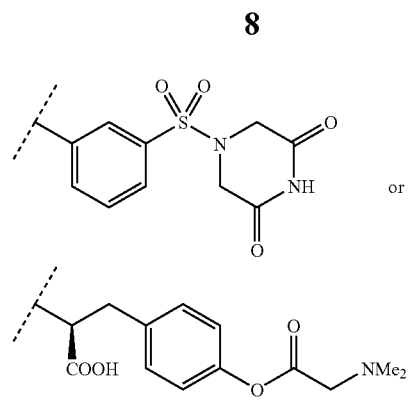

In one embodiment, the compound is that of any of the formulae herein wherein,

R² is independently NHR⁶; and

R² is independently NHR³.

In another embodiment, the compound is that of any of the formulae herein having the formula:

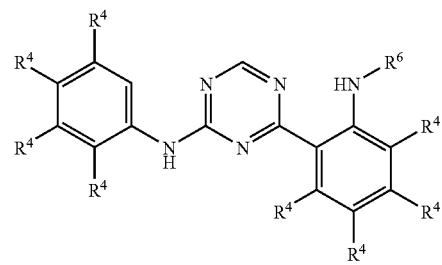

wherein, R⁴ and R⁶ are as defined above.

In another embodiment, the compound is that of any of the formulae herein having the formula:

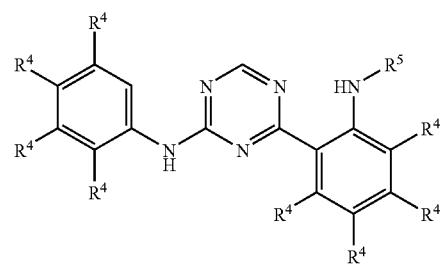

wherein, R⁴ and R⁵ are as defined above.

In another embodiment, the compound is that of any of the formulae herein having the formula:

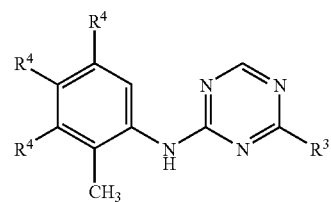

In another embodiment, the compound is that of any of the formulae herein having the formula:

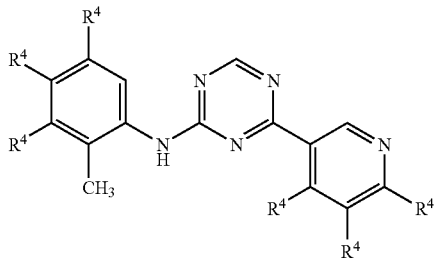

In another embodiment, the compound is that of any of the formulae above wherein, R² is independently NHR³; and
R¹ is one of the following groups:

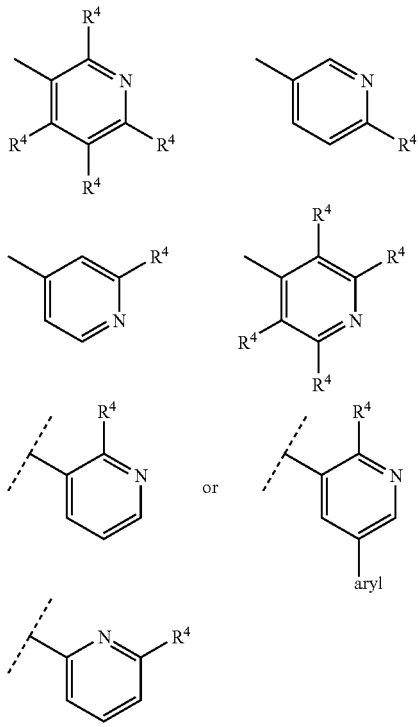

In another embodiment, the compound is that of any of the formulae above wherein, R² is independently NHR³; and R¹ is

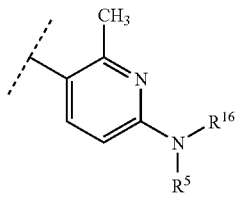

In another embodiment, the compound is that of any of the formulae above wherein, R² is independently NHR³; and R² is one of the following groups:

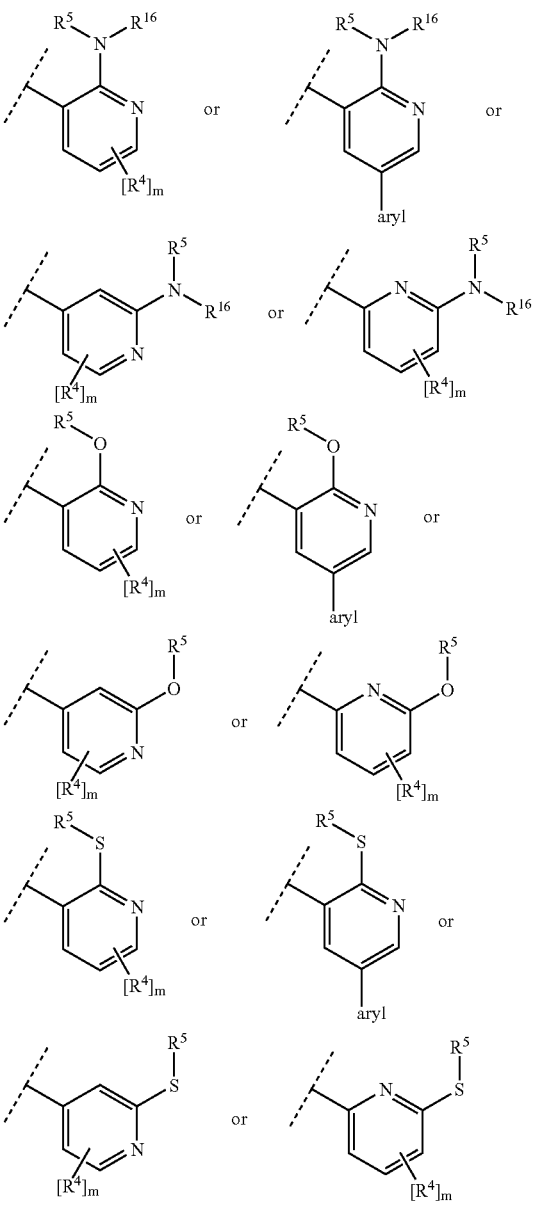

In another embodiment, the compound is that of any of the formulae above wherein, R² is independently NHR³; and
R¹ is independently heteroaryl substituted with 1–4 independent R⁴ on each ring wherein at least one R⁴ is not H, and wherein that at least one R⁴ that is not H is any one of NHR³; NHR⁵; NR⁵R⁶; SR⁵; SR⁶; SR³; OR⁵; OR⁶; or OR³; and is attached at the ring atom alpha to the ring atom attached to the triazinyl group. Alternatively, the heteroaryl group is monocyclic.

In another embodiment, the compound is that of any of the formulae above wherein, R² is independently NHR³; and
R¹ is independently heterocyclyl substituted with substituted with 1–4 independent R⁴ on each ring wherein at least one R⁴ is not H, and wherein that at least one R⁴ that is not H is any one of NHR³; NHR⁵; NR⁵R⁶; SR⁵; SR⁶; SR³; OR⁵; OR⁶; or OR³; and is attached at the ring atom alpha to the ring atom attached to the triazinyl group.

In another embodiment, the compound is that of any of the formulae above wherein, R² is independently NHR³; and R¹ is one of the following groups: pyrrazolyl, triazolyl, benzimidazolyl, imidazolyl, or pyrrolyl, each optionally substituted with 1–4 independent R⁴ on each ring (and alternatively, wherein at least one R⁴ is not H).

In another embodiment, the compound is that of any of the formulae above wherein, R² is independently NHR³; and R¹ is one of the following groups: indolyl or tetrahydroquinolinyl, each optionally substituted with 1–4 independent R⁴ on each ring (and alternatively, wherein at least one R⁴ is not H).

In other embodiments, the compound is that of the formula first delineated above wherein, R¹ is independently heterocyclyl optionally substituted with 1–4 independent R⁴ on each ring (and alternatively, wherein at least one R⁴ is not H), wherein said heterocyclyl is not unsubstituted piperidine; and R² is independently NHR³; alternatively wherein, Each R¹ is independently heteroaryl substituted with 1–4 independent R⁴ on each ring (and alternatively, wherein at least one R⁴ is not H), wherein said heteroaryl comprises at least one nitrogen heteroatom and said heteroaryl is attached at said nitrogen heteroatom;

alternatively wherein,

Each R¹ is independently heteroaryl substituted with 1–4 independent R⁴ on each ring (and alternatively, wherein at least one R⁴ is not H), wherein said heteroaryl comprises at least one nitrogen heteroatom and said heteroaryl is attached at said nitrogen heteroatom; and Each R² is independently NHR³, alternatively wherein, Each R¹ is independently heterocyclyl substituted with 1–4 independent R⁴ on each ring (and alternatively, wherein at least one R⁴ is not H), wherein said heterocyclyl is not unsubstituted piperidine, and said heterocyclyl comprises at least one nitrogen heteroatom and said heterocyclyl is attached at said nitrogen heteroatom; alternatively wherein, Each R¹ is independently heterocyclyl substituted with 1–4 independent R⁴ on each ring (and alternatively, wherein at least one R⁴ is not H), wherein said heterocyclyl is not unsubstituted piperidine, unsubstututed piperazine, 4-ethoxycarbonylpiperazine, or 4-(4-chlorophenyl)piperazine, and said heterocyclyl comprises at least one nitrogen heteroatom and said heterocyclyl is attached at said nitrogen heteroatom; alternatively wherein, Each R¹ is independently heterocyclyl substituted with 1–4 independent R⁴ on each ring (and alternatively, wherein at least one R⁴ is not H), wherein said heterocyclyl is not unsubstituted piperidine, and said heterocyclyl comprises at least one nitrogen heteroatom and said heterocyclyl is attached at said nitrogen heteroatom; and Each R² is independently NHR³; alternatively wherein, Each R² is independently NHR³; and Each R¹ is independently of the formula:

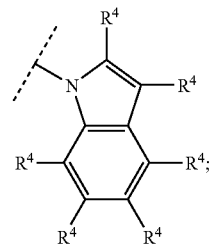

alternatively wherein,

Each R² is independently NHR³; and

Each R¹ is independently of the formula:

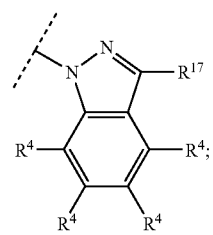

alternatively wherein,

Each R² is independently NHR³; and

Each R¹ is independently of the formula:

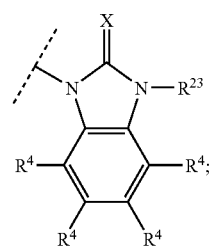

alternatively wherein,

Each R² is independently NHR³; and

Each R¹ is independently of the formula:

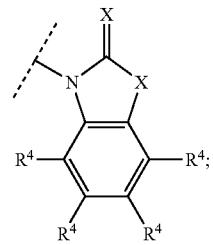

alternatively wherein,

Each R² is independently NR³; and

Each $R^1$ is independently of the formula:

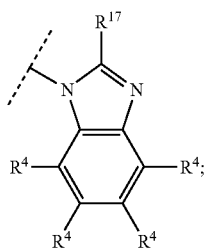

alternatively wherein $R^2$ is independently $NHR^5$;
alternatively wherein $R^2$ is independently $NHR^5$, wherein $R^5$ may not be C2–C4 alkyl;
allyl; ethyl optionally substituted with amino, diethylamino, morpholinyl, or pipridinyl; $C(CH_3)CH_2COOH$; $CH_2CH_2COOH$; $CH_2CH(CH_3)COOH$; $C(OH)C(Cl)_3$; or $CH(4\text{-chlorophenyl}) CH_2CH_3$;
alternatively wherein each $R^1$ is independently any one of following formulae:

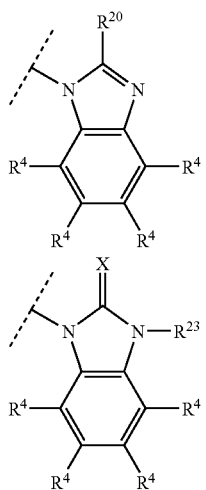

and alternatively wherein $R^1$ is independently any of of formulae above and $R^2$ is independently $NHR^5$.

Alternate embodiments of the invention are those of any of the formulae delineated herein, wherein each $R^1$ is independently

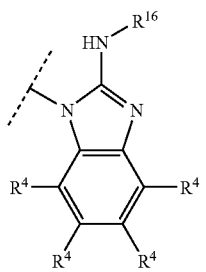

wherein each $R^{16}$ is independently C1–C10 alkyl substituted with 1–3 independent aryl, $R^7$ or $R^8$; or alternatively, independently C1–C10 alkyl substituted with 1–3 independent aryl or $R^8$.

Alternate embodiments of the invention are those of any of the formulae delineated herein, wherein each $R^1$ is independently

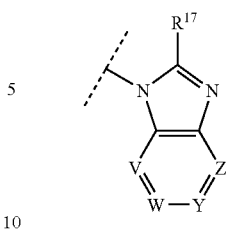

wherein each V, W, Y, and Z is each independently N or $CR^4$, alternatively wherein at least one, and alternatively at least two of V, W, Y, and Z is independently N, and alternatively wherein not more than any two of V, W, Y, and Z is independently N.

Alternate embodiments of the invention are those of any of the formulae delineated herein, wherein each $R^1$ is independently any one of the following groups:

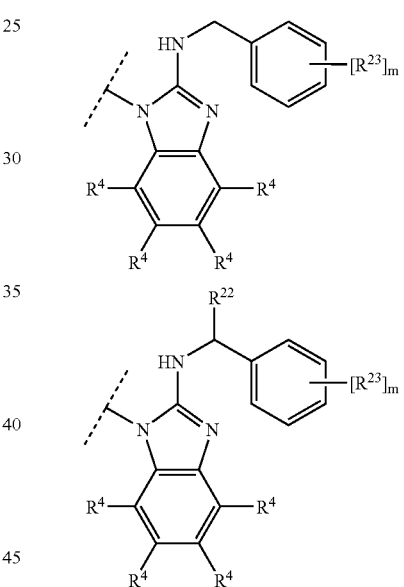

wherein m is 0, 1, 2, 3 or 4; or alternatively m is 1, 2, 3 or 4, or alternatively wherein, Each $R^1$ is independently any one of the following groups:

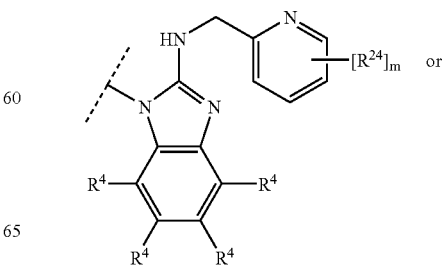

-continued

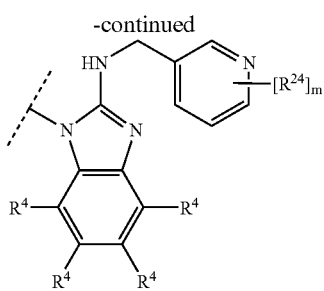

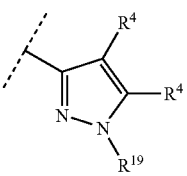

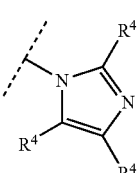

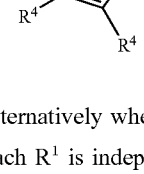

wherein m is 0, 1, 2, 3 or 4; or alternatively m is 1, 2, 3 or 4; or alternatively wherein, Each R$^1$ is independently

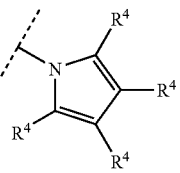

wherein at least one R$^4$ is not H;
or alternatively wherein,

Each R$^1$ is independently

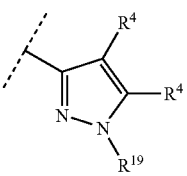

wherein R$^{19}$ is independently H or C1–C6 alkyl, or alternatively wherein R$^{19}$ is H;
or alternatively wherein, Each R$^1$ is independently

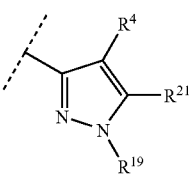

or alternatively wherein,

Each R$^1$ is independently

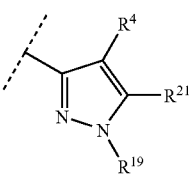

wherein each R$^{19}$ is independently H or C1–C6 alkyl; or alternatively wherein R$^{19}$ is H; and Each R$^{21}$ is independently t-butyl, 4-carboxyphenyl, 4-carbomethoxyphenyl, or furyl substituted with 1–4 independent R$^4$;

or alternatively wherein,

Each R$^1$ is independently

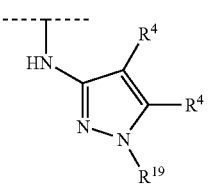

wherein $R^{19}$ is independently H or C1–C6 alkyl; or alternatively wherein $R^{19}$ is H;

or alternatively wherein,

Each $R^1$ is independently

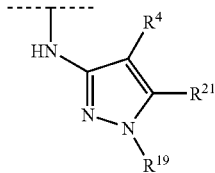

wherein each $R^{19}$ is independently H or C1–C6 alkyl; or alternatively wherein $R^{19}$ is H; and Each $R^{21}$ is independently t-butyl, 4-carboxyphenyl, 4-carbomethoxyphenyl, or furyl substituted with 1–4 independent $R^4$; or alternatively wherein, Each $R^1$ is independently

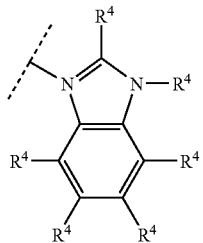

or alternatively wherein,

Each $R^1$ is independently any one of the following groups:

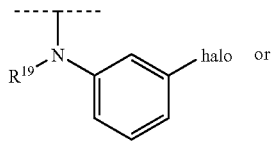

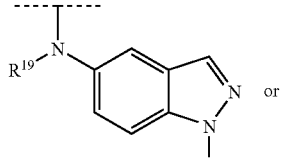

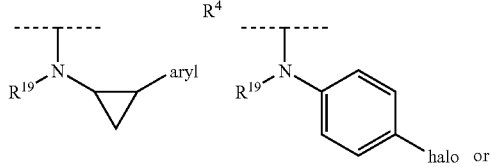

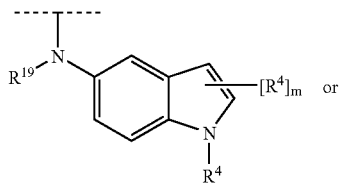

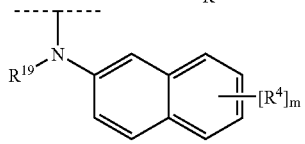

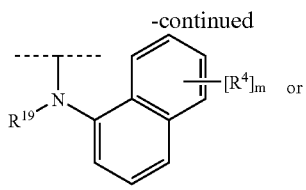

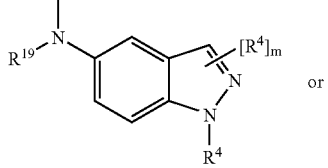

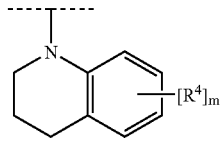

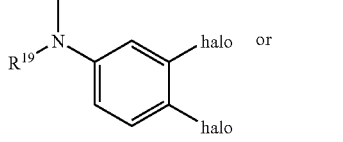

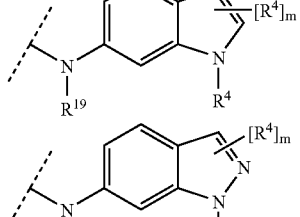

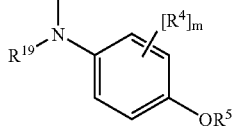

wherein $R^{19}$ is independently H or C1–C6 alkyl; or alternatively wherein $R^{19}$ is H; halo, aryl, m, $R^4$ and $R^5$ are as defined herein.

In one embodiment, the compound is that of any of the formulae herein wherein, $R^1$ is independently $SR^5$; (alternatively where $R^5$ is not H); and $R^2$ is independently $NHR^3$;

In one embodiment, the compound is that of any of the formulae herein wherein, $R^1$ is independently $OR^5$; (alternatively where $R^5$ is not H); and $R^2$ is independently $NHR^3$;

In one embodiment, the compound is that of any of the formulae herein wherein, $R^1$ is independently $SR^3$; and $R^2$ is independently $NHR^3$.

In one embodiment, the compound is that of any of the formulae herein wherein, $R^1$ is independently $OR^3$; and $R^2$ is independently $NHR^3$.

In one embodiment, the compound is that of any of the formulae herein wherein, $R^1$ is independently $SR^9$; and $R^2$ is independently $NHR^3$.

In one embodiment, the compound is that of any of the formulae herein wherein, $R^1$ is independently $OR^9$; and
$R^2$ is independently $NHR^3$.

In one embodiment, the compound is that of any of the formulae herein wherein, $R^1$ is independently S-aryl; and
$R^2$ is independently $NHR^3$.

In one embodiment, the compound is that of any of the formulae herein wherein, $R^1$ is independently O-aryl; and
$R^2$ is independently NHR Alternate embodiments of the invention are those of any of the formulae delineated herein, wherein each $R^1$ is independently $NHR^3$; those wherein $R^2$ is independently $NHR^3$ and said $R^3$ is phenyl substituted with 1–4 independent $R^4$ (and alternatively where at least one, alternatively at least two, and alternatively at least three, of said $R^4$ is not H); those wherein $R^2$ is independently $NHR^3$ and said $R^3$ is heteroaryl substituted with 1–4 independent (and alternatively where at least one, alternatively at least two, and alternatively at least three, of said $R^4$ is not H); those wherein each $R^2$ is independently $NHR^3$, wherein said $R^3$ is 3,4,5-trimethoxyphenyl; and those wherein each $R^2$ is independently $NHR^3$, wherein said $R^3$ is carboxymethylphenyl or $C(O)NH_2$-substituted phenyl; those wherein $R^1$ is independently $SR^3$ and said $R^3$ is phenyl substituted with 1–4 independent $R^4$ (and alternatively where at least one, alternatively at least two, and alternatively at least three, of said $R^4$ is not H); those wherein $R^1$ is independently $SR^3$ and said $R^3$ is heteroaryl substituted with 1–4 independent (and alternatively where at least one, alternatively at least two, and alternatively at least three, of said $R^4$ is not H);. those wherein $R^1$ is independently $OR^3$ and said $R^3$ is phenyl substituted with 1–4 independent $R^4$ (and alternatively where at least one, alternatively at least two, and alternatively at least three, of said $R^4$ is not H); those wherein $R^1$ is independently $OR^3$ and said $R^3$ is heteroaryl substituted with 1–4 independent (and alternatively where at least one, alternatively at least two, and alternatively at least three, of said $R^4$ is not H).

Alternate embodiments of the invention are those of any of the formulae delineated herein, wherein each $R^1$ and $R^2$ is independently $R^3$; $R^8$; $NHR^3$; $NHR^5$; $NHR^6$; $NR^5R^5$; $NR^5R^6$; $SR^5$; $SR^6$; $OR^5$; $OR^6$; $C(O)R^3$; heterocyclyl optionally substituted with 1–4 independent $R^4$ on each ring; or C1–C10 alkyl substituted with 1–4 independent $R^4$;

Alternate embodiments of the invention are those of any of the formulae delineated herein, wherein each $R^4$ is independently selected from H, C1–C10 alkyl; C2–C10 alkenyl; C2–C10 alkynyl; C3–C10 cycloalkyl; C4–C10 cycloalkenyl; aryl; $R^8$; halo; haloalkyl; $CF_3$; $SR^5$; $OR^5$; $OC(O)R^5$; $NR^5R^5$; $NR^5R^6$; $NR^5R^{16}$; $COOR^5$; $NO_2$; CN; $C(O)R^5$; $C(O)C(O)R^5$; $C(O)NR^5R^5$; $S(O)_nR^5$; $S(O)_nNR^5R^5$; $NR^5C(O)NR^5R^5$; $NR^5C(O)C(O)R^5$; $NR^5C(O)R^5$; $NR^5(COOR^5)$; $NR^5C(O)R^8$; $NR^5S(O)_nNR^5R^5$; $NR^5S(O)_nR^5$; $NR^5S(O)_nR^8$; $NR^5C(O)C(O)NR^5R^5$; $NR^5C(O)C(O)NR^5R^6$; C1–C10 alkyl substituted with 1–3 independent aryl, $R^7$ or $R^8$; or C2–C10 alkenyl substituted with 1–3 independent aryl, $R^7$ or $R^8$.

Alternate embodiments of the invention are those of any of the formulae delineated herein, wherein each $R^4$ is independently selected from halo.

Alternate embodiments of the invention are those of any of the formulae delineated herein, wherein each $R^4$ is independently selected from C1–C10 alkyl substituted with 1–3 independent aryl, $R^7$ or $R^8$.

Alternate embodiments of the invention are those of any of the formulae delineated herein, wherein each $R^4$ is independently selected from C1–C10 alkyl; C2–C10 alkenyl; or C2–C10 alkynyl.

Alternate embodiments of the invention are those of any of the formulae delineated herein, wherein each $R^4$ is independently selected from haloalkyl.

Alternate embodiments of the invention are those of any of the formulae delineated herein, wherein each $R^4$ is independently selected from $SR^5$.

Alternate embodiments of the invention are those of any of the formulae delineated herein, wherein each $R^4$ is independently selected from $OR^5$.

Alternate embodiments of the invention are those of any of the formulae delineated herein, wherein each $R^4$ is independently selected from $NR^5R^5$.

Alternate embodiments of the invention are those of any of the formulae delineated herein, wherein each $R^4$ is independently selected from $NR^5R^6$.

Alternate embodiments of the invention are those of any of the formulae delineated herein, wherein each $R^4$ is independently any one of $COOR^5$; CN; $C(O)R^5$; or $C(O)NR^5R^5$.

Alternate embodiments of the invention are those of any of the formulae delineated herein, wherein each $R^4$ is independently any one of $NR^5C(O)NR^5R^5$; $NR^5C(O)R^5$; $NR^5(COOR^5)$; $NR^5C(O)R^8$; $NR^5S(O)_nNR^5R^5$; $NR^5S(O)_nR^5$; or $NR^5S(O)_nR^8$.

Alternate embodiments of the invention are those of any of the formulae delineated herein, wherein each $R^4$ is independently selected from C1–C10 alkyl substituted with 1–3 independent aryl.

Alternate embodiments of the invention are those of any of the formulae delineated herein, wherein each $R^4$ is independently selected from C1–C10 alkyl substituted with 1–3 independent $R^7$.

Alternate embodiments of the invention are those of any of the formulae delineated herein, wherein each $R^4$ is independently selected from C1–C10 alkyl substituted with 1–3 independent $R^8$.

Alternate embodiments of the invention are those of any of the formulae delineated herein, wherein each $R^7$ is independently halo, $CF_3$, $SR^{10}$, $OR^{10}$, $OC(O)R^{10}$, $NR^{10}R^{10}$, $NR^{10}R^{11}$, $NR^{11}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$, $S(O)_nNR^{10}R^{10}$.

Alternate embodiments of the invention are those of any of the formulae delineated herein, wherein each $R^6$ is independently $C(O)R^5$, $COOR^5$, $C(O)NR^5R^5$, or $S(O)_nR^5$;

Alternate embodiments of the invention are those of any of the formulae delineated herein, wherein when any group (e.g., phenyl, benzimidazolyl, heteroaryl, heterocyclyl, and the like) may be substituted, or optionally substituted, with 1–4 (or alternatively 1–5) independent $R^4$, wherein at least one, or alternatively at least two, or alternatively at least three of the independent $R^4$, is not H.

Alternate embodiments of the invention are those of any of the formulae delineated herein, wherein each heterocyclyl is independently a 3–8, or alternatively a 5–8, or alternatively a 5–6, or alternatively a 5, or alternatively a 6, membered nonaromatic monocyclic, a 7–12, or alternatively an 8–12, or alternatively an 8–10, membered nonaromatic bicyclic, or 11–14 membered nonaromatic tricyclic, ring system comprising 1–4 heteroatoms if monocyclic, 1–8 heteroatoms if bicyclic, or 1–10 heteroatoms if tricyclic, said heteroatoms independently selected from O, N, or S, and substituted as delineated herein.

Alternate embodiments of the invention are those of any of the formulae delineated herein, wherein each $R^8$ or $R^9$ is independently a 3–8, or alternatively a 5–8, or alternatively a 5–6, or alternatively a 5, or alternatively a 6, membered monocyclic, a 7–12, or alternatively an 8–12, or alternatively an 8–10, membered bicyclic, or a 10–14, or alternatively 11–14 membered tricyclic, ring system comprising 1–4 heteroatoms if monocyclic, 1–8 heteroatoms if bicyclic, or 1–10 heteroatoms if tricyclic, said heteroatoms independently selected from O, N, or S, and substituted as delineated herein.

Alternate embodiments of the invention are those of any of the formulae delineated herein, wherein additionally, each $R^1$ group may not simultaneously be the same as each $R^2$ group.

Alternate embodiments of the invention are those of any of the formulae delineated herein, wherein additionally, each $R^1$ and $R^2$ group is not $NHC(O)R^5$, and alternatively, not NHAc.

Alternate embodiments of the invention are those of any of the formulae delineated herein, wherein additionally, each $R^1$ and $R^2$ group is not $NH_2$.

Alternate embodiments of the invention are those of any of the formulae delineated herein, wherein additionally, each $R^1$ and $R^2$ group is not OH, SH, or $NH_2$.

Alternate embodiments of the invention are those of any of the formulae delineated herein, wherein when both $R^1$ and $R^2$ groups are $NHR^3$, and $R^3$ is pyridyl, or aryl, or phenyl optionally substituted with 1–5 $R^4$, each $R^1$ group may not simultaneously be the same as each $R^2$ group.

The invention also relates to methods of inhibiting enzyme or polypeptide activity, particularly of an enzyme or polypeptide described herein, such as a phosphoryl tranferase, or alternatively a kinase, in a mammal comprising the step of administering to said mammal a compound of any of the formulae described herein or a composition comprising a compound of any of the formulae described herein. In one embodiment, the invention relates to a method of inhibiting phosphoryl transferase, alternatively kinase, activity in a mammal comprising the step of administering to said mamnmal a compound, or a composition comprising a compound, of any one of the formulae described herein. Preferably, the mammal is a human.

In another embodiment, the invention relates to a method of inhibiting enzyme activity in a mammal comprising the step of administering to said mammal a compound, or a composition comprising a compound, of any of the formulae described herein. Preferably, the mammal is a human.

The invention also relates to methods of treating disease and/or disease symptoms, particularly those mediated by an enzyme or polypeptide described herein, such as phosphoryl transferase mediated, or kinase mediated, disease or disease symptoms, in a mammal comprising the step of administering to said mammal a compound of any of the formulae described herein or a composition comprising a compound of any of the formulae described herein. Such diseases or disease symptoms are described herein. "Kinase mediated" disease or disease symptoms refers to disease or disease symptoms in which kinase activity is involved. In one embodiment, this invention relates to a method of treating disease or disease symptoms, particularly kinase mediated disease or disease symptoms, in a mammal comprising the step of administering to said mammal a compound, or a composition comprising a compound, of any of the formulae described herein. Preferably, the mammal is a human.

In an alternate embodiment, this invention relates to a method of treating disease or disease symptoms in a mammal comprising the step of administering to said mammal a compound, or a composition comprising a compound, of any of the formulae described herein. Preferably, the mammal is a human.

In the compounds described herein, the term "halo" refers to any radical of fluorine, chlorine, bromine or iodine. The terms "alkyl", "alkenyl" and "alkynyl" refer to hydrocarbon chains that may be straight-chain or branched-chain, containing the indicated number of carbon atoms. For example, C1–C10 indicates the group may have from 1 to 10 (inclusive) carbon atoms in it. The terms "ring" and "ring system" refer to a ring comprising the delineated number of atoms, said atoms being carbon or, where indicated, a heteroatom such as nitrogen, oxygen or sulfur. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

Leaving groups are species that may be detached from a molecule during a reaction and are known in the art. Examples of such groups include, but are not limited to, halogen groups (e.g., I, Br, F, Cl), sulfonate groups (e.g., mesylate, tosylate), sulfide groups (e.g., $SCH_3$), and the like. Nucleophiles are species that may be attached to a molecule during reaction and are known in the art. Examples of such groups include, but are not limited to, amines, Grignard reagents, anionic species (e.g., alkoxides, amides, carbanions) and the like.

In the methods described herein, said mammal is preferably a human. The inhibitors described herein, however, are useful in inhibiting kinase activity in human cells and useful in rodent (e.g., murine) and other species used as surrogates for investigating activity in vitro and in vivo in humans and against human kinases. The inhibitors described herein are also useful for investigating inhibition and activity of kinases originating from species other than humans.

The compounds and compositions described herein are useful for inhibition of kinase activity of one or more enzymes. Kinases include, for example, protein kinases (e.g., tyrosine, serone/threonine, histidine), lipid kinases (e.g., phosphatidylinositol kinases PI-3, PI-4) and carbohydrate kinases. Further information relating to kinase structure, function and and their role in disease or disease symptoms is available at the Protein Kinase Resource web site (http://www.sdsc.edu/Kinases/pk home.html). Kinases may be of prokaryotic, eukaryotic, bacterial, viral, fungal or archaea origin. Specifically, the compounds described herein are useful as inhibitors of tyrosine, serine/threonine or histidine protein kinases, (including combinations or those of mixed specificity, that is for example, those that phosphorylate both tyrosine and serine/threonine residues) or lipid kinases. Examples of kinases that are inhibited by the compounds and compositions described herein and against which the methods described s herein are useful include, but are not limited to, LCK, IRK (=INSR=Insulin receptor), IGF-1 receptor, SYK, ZAP-70, IRAK1, BLK, BMX, BTK, FRK, FGR, FYN, HCK, ITK, LYN, TEC, TXK, YES, ABL, SRC, EGF-R (=ErbB-1), ErbB-2 (=NEU=$HER^2$), ErbB-4, FAK, FGFIR (=FGR-1), FGF2R (=FGR-2), IKK-1 (=IKK-ALPHA=CHUK), IKK-2 (=IKK-BETA), MET (=c-MET), NIK, PDGF receptor ALPHA, PDGF receptor BETA, TIE1, TIE2 (=TEK), VEGFR1 (=FLT-1), VEGFR2 (=KDR), FLT-3, FLT-4, KIT, CSK, JAK1, JAK2, JAK3, TYK2, RIP, RIP-2, LOK, TAK1, RET, ALK, MLK3, COT, TRKA, PYK2, Activin-like Kinases (Alk1–7), EPHA(1–8), EPHB (1–6), RON, GSK3(A and B), Ilk, PDK1, SGK, Fes, Fer, MatK, Ark(1–3), Plk(1–3), LimK(1 and 2), RhoK, Pak (1–3), Raf(A,B, and C), PknB, CDK(1–10), Chk(1 and 2), CamK(I–IV), CamKK, CK1, CK2, PKR, Jnk(1–3), EPHB4, UL13, ORF47, ATM, PKA ($\alpha,\beta$, and $\gamma$), P38($\alpha,\beta$, and $\gamma$), Erk(1–3), PKB (including all PKB subtypes) (=AKT-1, AKT-2, AKT-3), and PKC (including all PKC subtypes). The compounds and compositions of the invention are therefore also particularly suited for treatment of diseases and disease symptoms that involve one or more of the aforementioned protein kinases. In one embodiment, the compounds, compositions or methods of this invention are particularly suited for inhibition of or treatment of disease or disease symptoms mediated by any of LCK, ZAP, LYN, EGFR, ERBB-2, KDR, c-MET, SYK, or IGF-1R. In another embodiment, the compounds, compositions or methods of this invention are particularly suited for inhibition of or treatment of disease or disease symptoms mediated by kinases defined by Hardie & Hanks, ed. supra as in the the Src family (PTK-I), Syk/Zap family (PTK-VI), EGFR family (PTK-X), HGF Family (PTK-XXI), Insulin receptor family (PTK-XVI), Tie/Tek family (PTK-XIII), Platelet-derived growth factor receptor family (PTK-XIV), or Fibroblast growth factor receptor family (PTK-XV), and more particularly, KDR, FLT-1, FLT-3 or RET; or EGFR, c-MET, ErbB2, or IGF-1R. The compounds and compositions are also suited for regulating or modulating signal transduction in signal transduction pathways that involve one or more kinases, thus affecting events in a cell, and are therefor useful in methods for regulating or modulating signal transduction.

The inhibitors described herein are also useful for inhibiting the biological activity of any enzyme comprising greater than 90%, alternatively greater than 85%, or alternatively greater than 70% sequence homology with a phosphoryl transferase sequence, or alternatively a kinase sequence, including the kinases mentioned herein. The inhibitors described herein are also useful for inhibiting the biological activity of any enzyme comprising a subsequence, or variant thereof, of any enzyme that comprises greater than 90%, alternatively greater than 85%, or alternatively greater than 70% sequence homology with a phosphoryl transferase subsequence, or alternatively kinase subsequence, including subsequences of the kinases mentioned herein. Such subsequence preferably comprises greater than 90%, alternatively greater than 85%, or alternatively greater than 70% sequence homology with the sequence of an active site or subdomain of a phosphoryl transferase, or alternatively kinase, enzyme. The subsequences, or variants thereof, comprise at least about 300, or alternatively at least about 200, amino acids.

The inhibitors described herein are useful for inhibiting the biological activity of any enzyme that binds ATP and/or GTP and thus for treating disease or disease symptoms mediated by any enzyme that binds ATP and/or GTP. The inhibitors described herein are also useful for inhibiting the biological activity of any enzyme that binds adenine or guanine nucleotides. The inhibitors described herein are also useful for inhibiting the biological activity of any enzyme that is involved in phosphotransfer and thus for treating disease or disease symptoms mediated by any enzyme that is involved in phosphotransfer.

The inhibitors described herein are also useful for inhibiting the biological activity of a polypeptide or enzyme having: sequence homology with a phosphoryl transferase, or alternatively kinase, sequence and thus for treating disease or disease symptoms mediated by such polypeptide or enzyme. Such polypeptides or enzymes may be identified by comparison of their sequence with phosphoryl transferase, alternatively kinase, sequences and phosphoryl transferase, alternatively kinase, catalytic domain sequences. Such sequences may be found, for example, in databases such as GENEBANK, EMBO, or other similar databases known in the art. For example, one method of comparison involves the database PROSITE (http://expasy.hcuge.ch) (See, Hofinann K., Bucher P., Falquet L., Bairoch A., The PROSITE database, its status in 1999, Nucleic Acids Res. 27:215–219 (1999)), containing "signatures" or sequence patterns (or motifs) or profiles of protein families or domains. Thus, the inhibitors described herein are useful for inhibiting the biological activity of a polypeptide or enzyme comprising a sequence that comprises a "signature" or sequence pattern or profile derived for, and identified in PROSITE as relating to kinases, and for treating disease or disease symptoms mediated by such polypeptide or enzyme. Examples of such PROSITE motifs or consensus patterns identified as relating to kinases include PS00107, PS00108, PS00109, PS00112, PS00583, PS00584, PS50011, PS50290, PS00915, and PS00916.

The inhibitors described herein are also useful for inhibiting the biological activity of ATP/GTP binding proteins. Many ATP/GTP binding proteins have consensus motifs that can be used to identify them. For example, PROSITE entry PDOC00017 titled "ATP/GTP-binding site motif A (P-loop)" describes a consensus pattern (called the A consensus sequence or the P-loop) for a large group of nucleotide binding proteins including ATP synthases, DNA and RNA helicases, ABC transporters, Kinesin and kinesin-like proteins, among many others. Other nucleotide binding proteins have motifs similar to this P-loop, but take slightly different forms. Examples of these include tubulins, lipid kinases and protein kinases. The ATP binding motif of protein kinases have also been defined within PROSITE entry PS00107. Yet other AGBPs have nothing similar to the P-loop motif. Examples of these include E1–E2 ATPases and the glycolytic kinases.

The compounds, compositions and methods described herein are useful in inhibiting kinase activity. As such, the compounds, compositions and methods of this invention are useful in treating kinase-mediated disease or disease symptoms in a mammal, particularly a human. Kinase mediated diseases are those wherein a protein kinase is involved in signaling, mediation, modulation, or regulation of the disease process or symptoms. Kinase mediated diseases are exemplified by the following disease classes: cancer, autoimmunological, metabolic, inflammatory, infection (bacterial, viral, yeast, fungal, etc.), diseases of the central nervous system, degenerative neural disease, allergy/asthma, dermatology, angiogenesis, neovascularization, vasculogenesis, cardiovascular, and the like.

The compounds, compositions and methods described herein are useful in treating or preventing diseases, including, transplant rejection (e.g., kidney, liver, heart, lung, pancreas (islet cells), bone marrow, comea, small bowel, skin allografts or xenografts), graft versus host disease, osteoarthritis, rheumatoid arthritis, multiple sclerosis, diabetes, diabetic retinopathy, asthma, allergy, inflammatory bowel disease (Crohn's disease, ulcerative colitis), renal disease, cachexia, septic shock, lupus, diabetes mellitus, myasthenia gravis, psoriasis, dermatitis, eczema, seborrhea, Alzheimer's disease, Parkinson's disease, depression, stem cell protection during chemotherapy, ex vivo selection or ex vivo purging for autologous or allogeneic bone marrow transplantation, leukemia (acute myeloid, chronic myeloid, acute lymphoblastic, etc.), cancer (breast, lung, colorectal, ovary, prostate, renal, squamous cell, prostate, glioblastoma, melanoma, pancreatic, Kaposi's sarcoma, etc.), occular disease, retinopathies, (e.g., macular degeneration, diabetic retinopathy), corneal disease, glaucoma, bacterial infections, viral infections, fungal infections and heart disease, including but not limited to, restenosis. In one embodiment, the compositions and methods described herein are useful in treating or preventing rheumatoid arthritis, macular degeneration, diabetic retinopathy, psoriasis, restenosis, Kaposi's sarcoma, or cancer. In another embodiment, the compositions and methods described herein are useful in treating or preventing macular degeneration, retinopathies, ocular disease, or cancer.

Another embodiment envisioned by this invention relates to the use of the kinase inhibitory compounds described herein for use as reagents that effectively bind to kinases. As reagents, the compounds of this invention, and their derivatives, may be derivatized to bind to a stable resin as a tethered substrate for affinity chromatography applications. Such derivatives may be used in purification of enzymes, including phosphoryl transferases and kinases. The compounds of this invention, and their derivatives, may also be modified (e.g., radiolabelled or affinity labelled, etc.) in order to utilize them in the investigation of enzyme or polypeptide characterization, structure, and/or function. Additionally, the compounds described herein are useful as reagents for chemical validation of drug targets. These and other uses that characterize kinase inhibitors will be evident to those of ordinary skill in the art.

In another embodiment, the inhibitors described herein are useful for crystallizing or co-crystallizing with a protein kinase. Such crystals or crystal complexes may additionally comprise additional peptides and or metal ions. The crystals or crystal complexes may be used for investigation and determination of enzyme characteristics including, for example, structure of the kinase enzyme, enzyme active site domains, and inhibitor-enzyme interactions. This information is useful in developing inhibitor compounds with modified characteristics and for understanding structure-function relationships of the enzymes and their enzyme-inhibitor interactions.

In an alternate embodiment, the inhibitory compounds described herein may be used as platforms or scaffolds which may be utilized in combinatorial chemistry techniques for preparation of derivatives and/or chemical libraries of compounds. Such derivatives and libraries of compounds have kinase inhibitory activity and are useful for identifying and designing compounds possessing kinase inhibitory activity. Combinatorial techniques suitable for utilizing the compounds described herein are known in the art as exemplified by Obrecht, D. and Villalgrodo, J. M., *Solid-Supported Combinatorial and Parallel Synthesis of Small-Molecular Weight Compound Libraries*, Pergamon-Elsevier Science Limited (1998), and include those such as the "split and pool" or "parallel" synthesis techniques, solid-phase and solution-phase techniques, and encoding techniques (see, for example, Czamik, A. W., *Curr. Opin. Chem. Bio.*, (1997) 1, 60. Thus, one embodiment relates to a method of using the compounds described in the formulae herein for generating derivatives or chemical libraries comprising: 1) providing a body comprising a plurality of wells; 2) providing one or more compounds of the formulae described herein in each well; 3) providing an additional one or more chemicals in each well; 4) isolating the resulting one or more products from each well. An alternate embodiment relates to a method of using the compounds described in the formulae herein for generating derivatives or chemical libraries comprising: 1) providing one or more compounds of the formulae described herein attached to a solid support; 2) treating the one or more compounds of the formulae described herein attached to a solid support with one or more additional chemicals; 3) isolating the resulting one or more products from the solid support. In the methods described above, "tags" or identifier or labeling moieties may be attached to and/or detached from the compounds of the formulae herein or their derivatives, to facilitate tracking, identification or isolation of the desired products or their intermediates. Such moieties are known in the art. The chemicals used in the aforementioned methods may include, for example, solvents, reagents, catalysts, protecting group and deprotecting group reagents and the like. Examples of such chemicals are those that appear in the various synthetic and protecting group chemistry texts and treatises referenced herein.

The compounds of the formulae herein may be used to study the mechanism and role of enzymes in biological pathways and processes involving kinases. The compounds of the formulae herein may also be used as probes to identify new kinase enzymes or polypeptides with sequence homology to kinases. The inhibitor compounds may be tethered to a support or modified (e.g., tagged, radiolabeled or other identifiable detection method) such that the compound may be detected and isolated in the presence of the kinase enzyme or polypeptide. Thus, another embodiment relates to a method of identifying and/or isolating a kinase enzyme or polypeptide with sequence homology to a kinase enzyme sequence or subsequence, comprising, contacting a tethered or modified compound of any of the formulae herein with one or more polypeptides, isolating a polypeptide/inhibitor complex, and identifying or isolating the sequence of the polypeptide in the polypeptide/inhibitor complex. The identification of the polypeptide sequence may be performed while in the polypeptide/inhibitor complex or after the polypeptide is decomplexed from the tethered or modified compound of any of the formulae herein.

The compounds are also useful in inhibiting enzymes, including kinases, that play a role in plant metabolism regulation, plant growth or growth inhibition. As such the compounds and compositions of the invention are useful as plant growth regulators, and as herbicides. Such compositions comprise the compounds of the invention as well as any agricultural or other acceptable carrier for dispersal of the active compound.

Table 1 lists representative individual compounds of the invention and compounds employed in the compositions and methods of this invention.

TABLE 1
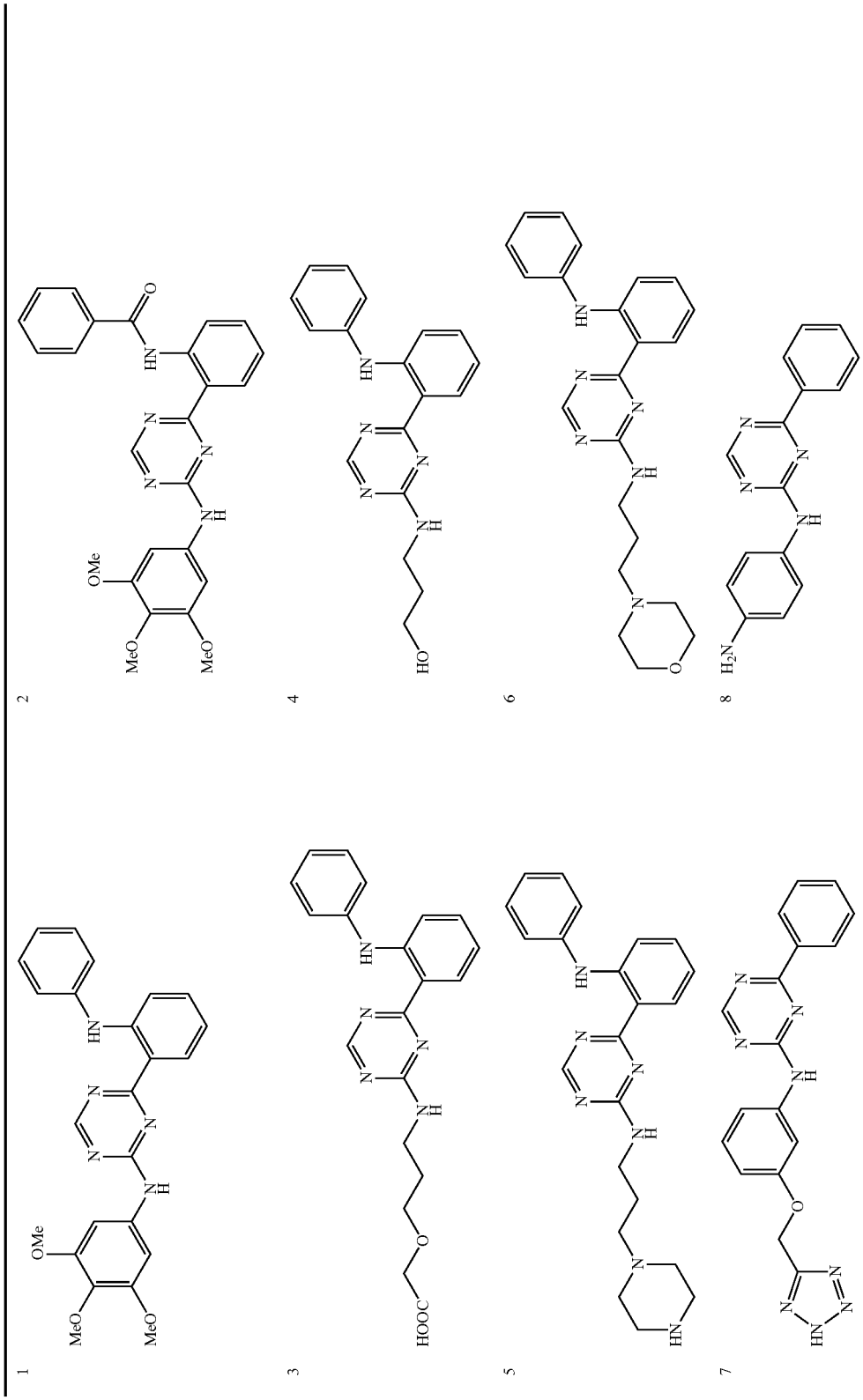

TABLE 1-continued

TABLE 1-continued
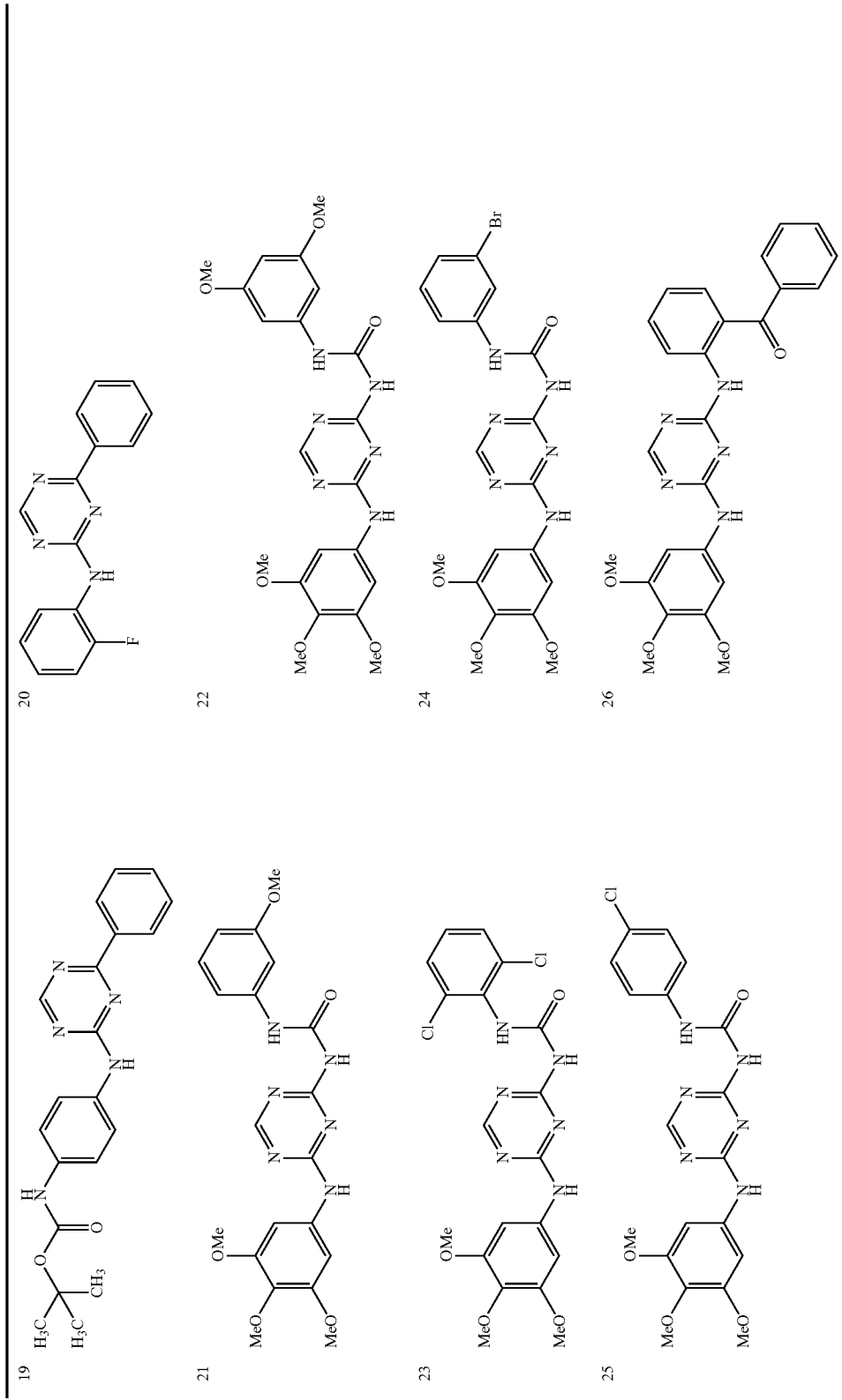

TABLE 1-continued

| 27 | 28 |
| 29 | 30 |
| 31 | 32 |
| 33 | 34 |
| 35 | 36 |

TABLE 1-continued

TABLE 1-continued

TABLE 1-continued
| 55 | 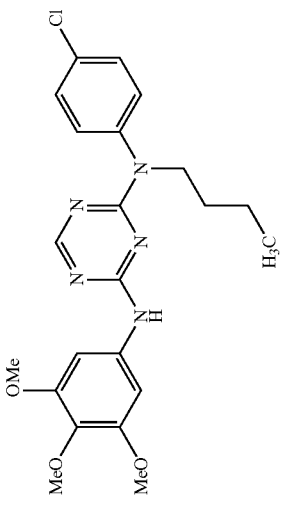 | 56 | 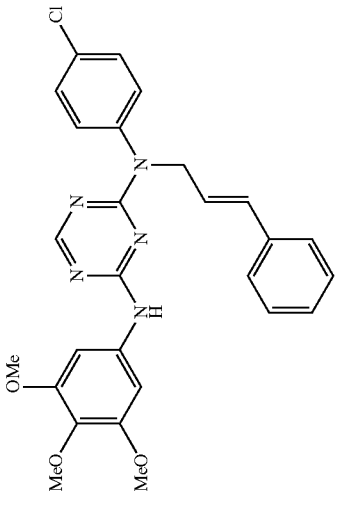 |
| 57 | 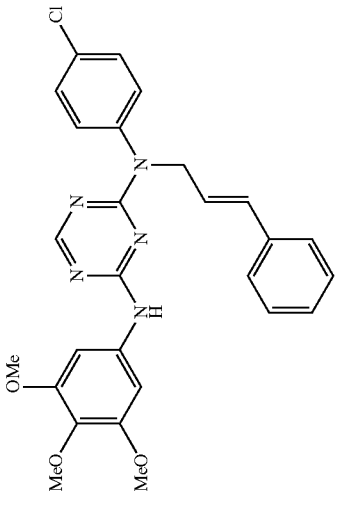 | 58 | 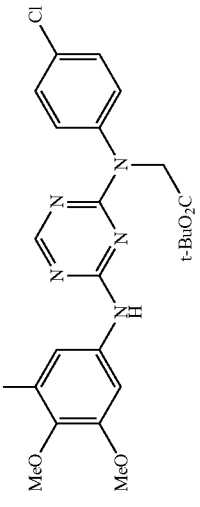 |
| 59 | 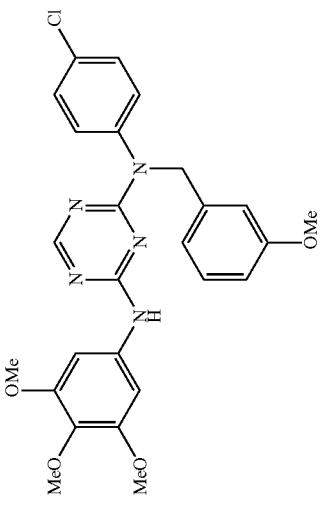 | 60 | 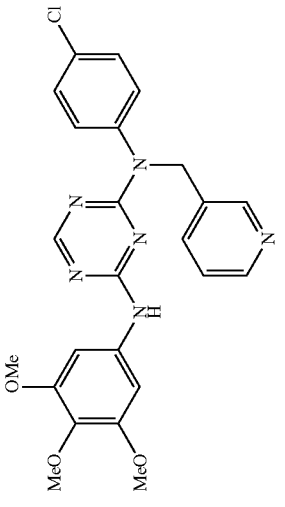 |

TABLE 1-continued

TABLE 1-continued
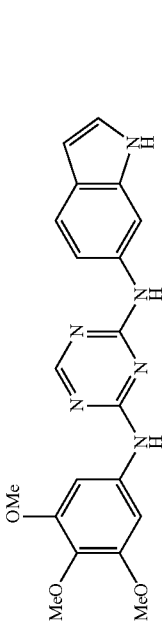

TABLE 1-continued

TABLE 1-continued

TABLE 1-continued
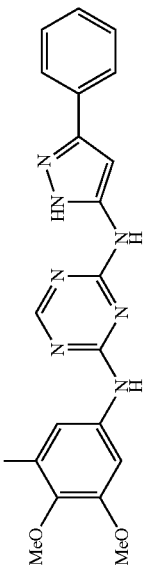

TABLE 1-continued

TABLE 1-continued

TABLE 1-continued

TABLE 1-continued

TABLE 1-continued
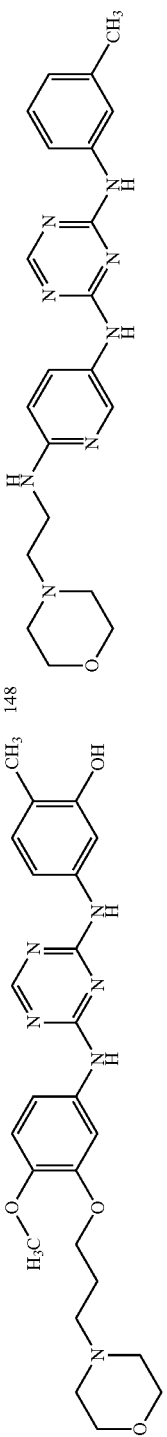

TABLE 1-continued
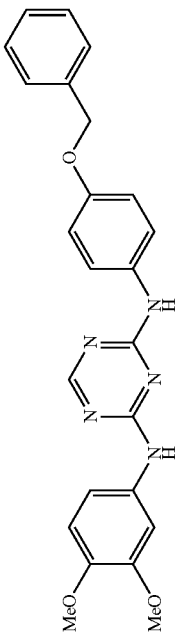

TABLE 1-continued

TABLE 1-continued
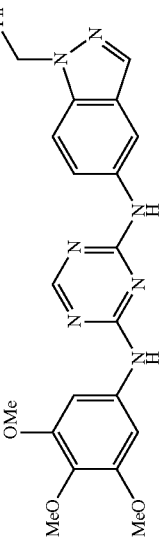

TABLE 1-continued

TABLE 1-continued

TABLE 1-continued
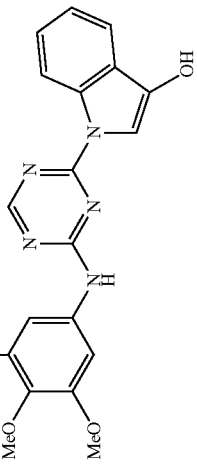

TABLE 1-continued

TABLE 1-continued

| # | Structure |
|---|---|
| 221 | 4-methylphenyl-pyrimidin-2-yl-NH-(3,4,5-trimethoxyphenyl) |
| 222 | 4-fluorophenyl-pyrimidin-2-yl-NH-(3,4,5-trimethoxyphenyl) |
| 223 | 3-methylphenyl-pyrimidin-2-yl-NH-(3,4,5-trimethoxyphenyl) |
| 224 | 3-fluorophenyl-pyrimidin-2-yl-NH-(3,4,5-trimethoxyphenyl) |
| 225 | 2-furyl-pyrimidin-2-yl-NH-(3,4,5-trimethoxyphenyl) |
| 226 | 3-thienyl-pyrimidin-2-yl-NH-(3,4,5-trimethoxyphenyl) |
| 227 | 2-chlorophenyl-pyrimidin-2-yl-NH-(3,4,5-trimethoxyphenyl) |
| 228 | 4-chlorophenyl-pyrimidin-2-yl-NH-(3,4,5-trimethoxyphenyl) |

TABLE 1-continued

| 229 | 230 |
| 231 | 232 |
| 233 | 234 |
| 235 | 236 |

TABLE 1-continued

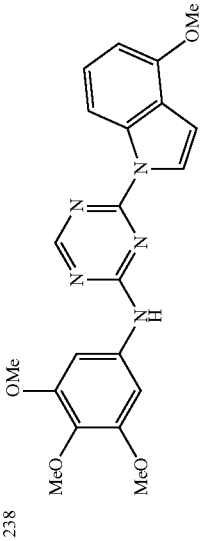
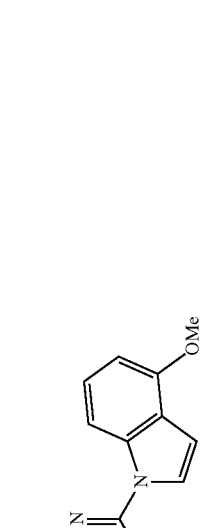

TABLE 1-continued

TABLE 1-continued

TABLE 1-continued

TABLE 1-continued

TABLE 1-continued

TABLE 1-continued

TABLE 1-continued

TABLE 1-continued

TABLE 1-continued

TABLE 1-continued

TABLE 1-continued

TABLE 1-continued
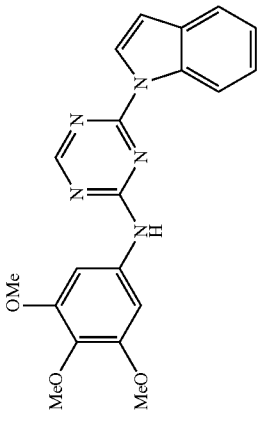
327
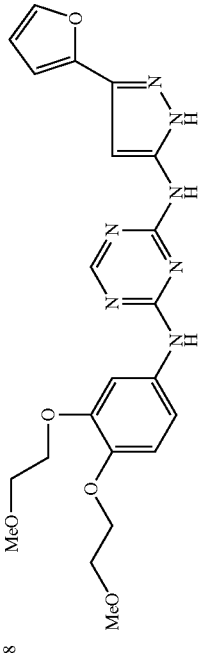
328
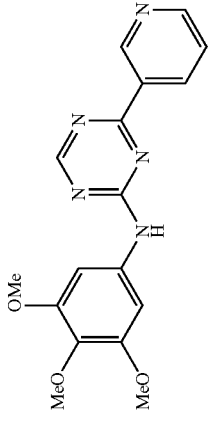
329
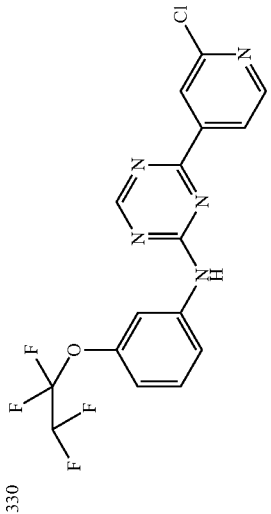
330
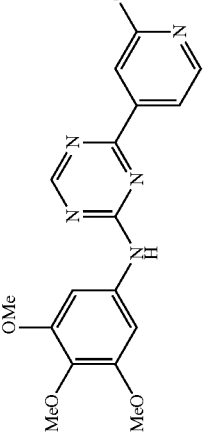
331
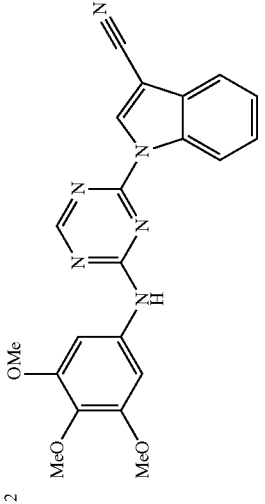
332

TABLE 1-continued

TABLE 1-continued
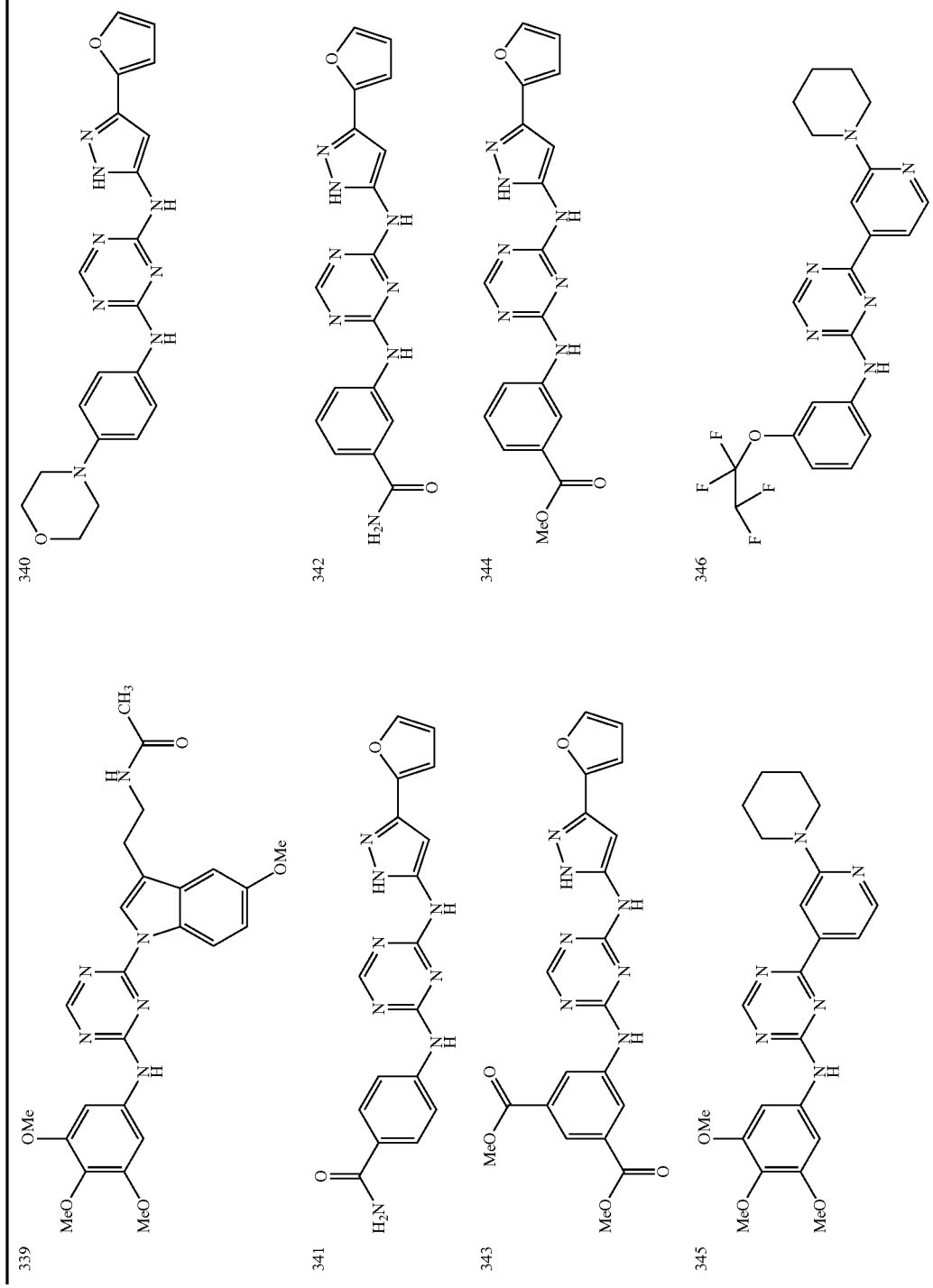

TABLE 1-continued
347
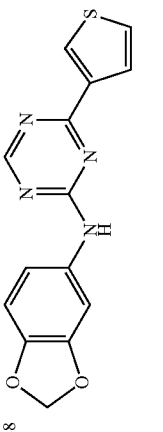
348
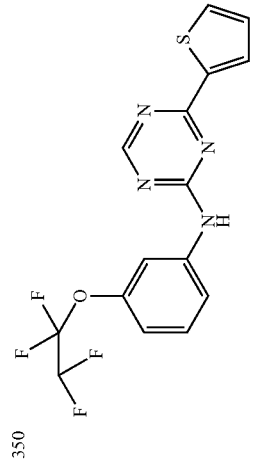
349
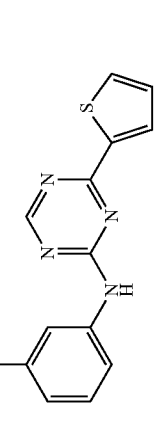
350
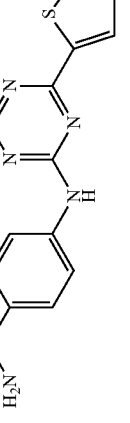
351
352
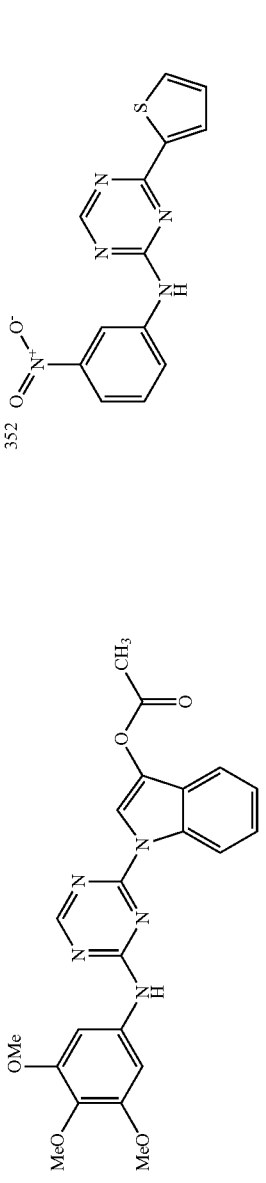
353
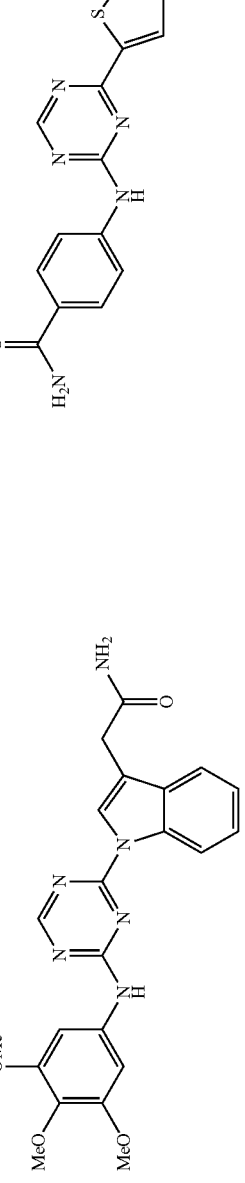
354

TABLE 1-continued

TABLE 1-continued

TABLE 1-continued

TABLE 1-continued

TABLE 1-continued

| 385 | 386 |
| 387 | 388 |
| 389 | 390 |

TABLE 1-continued

TABLE 1-continued

TABLE 1-continued

TABLE 1-continued

TABLE 1-continued

TABLE 1-continued

TABLE 1-continued
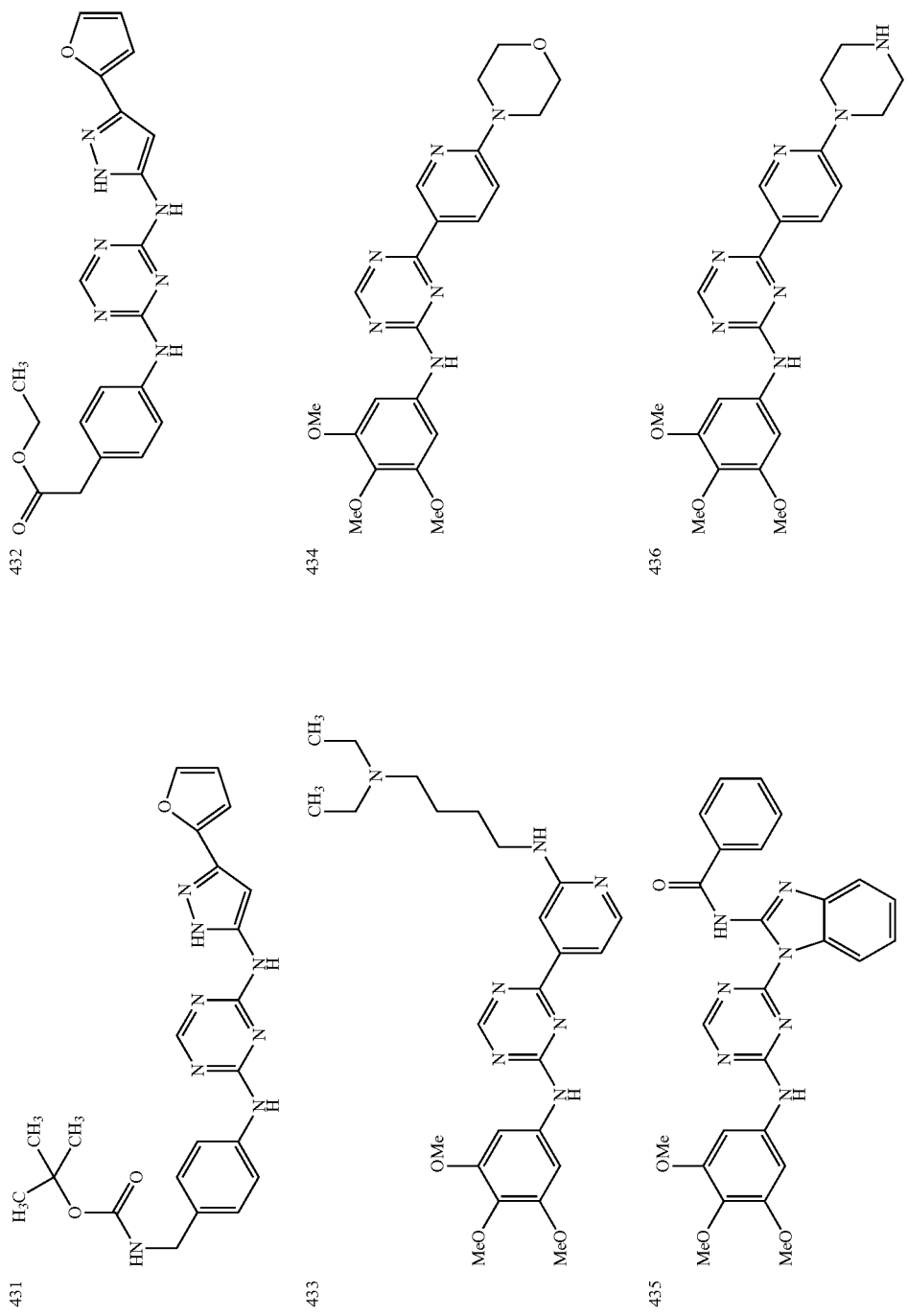

TABLE 1-continued
437 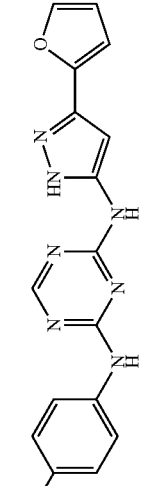
438 
439 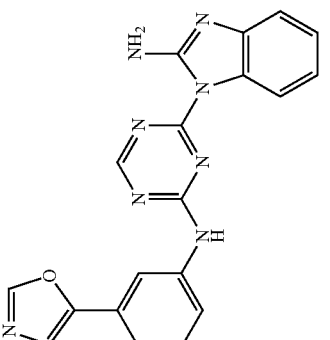
440 
441 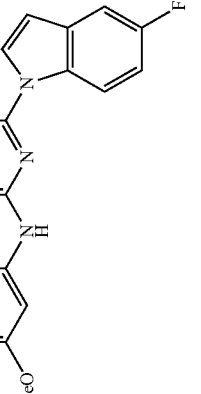
442 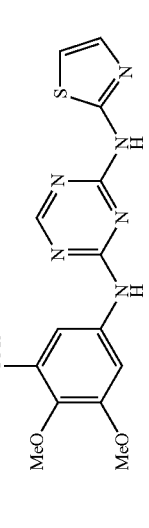

TABLE 1-continued
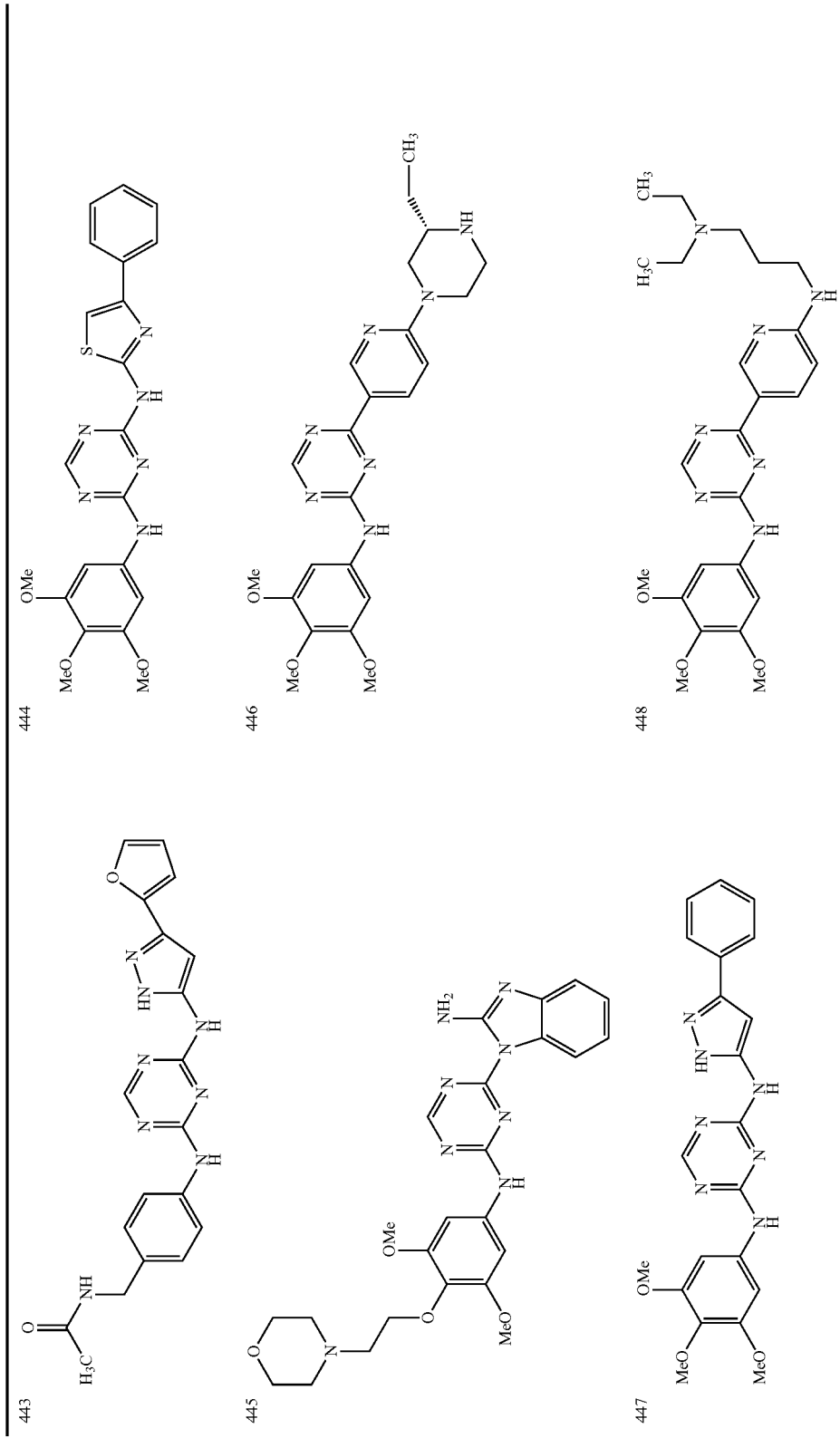

TABLE 1-continued

| 449 | 450 |
| 451 | 452 |
| 453 | 454 |

TABLE 1-continued
| 455 | 456 | 457 | 458 | 459 | 460 |

TABLE 1-continued

TABLE 1-continued
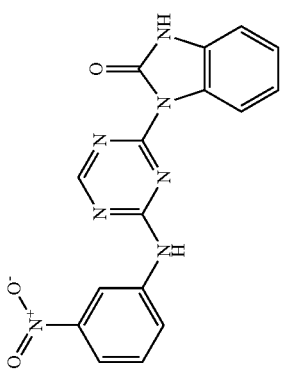
467
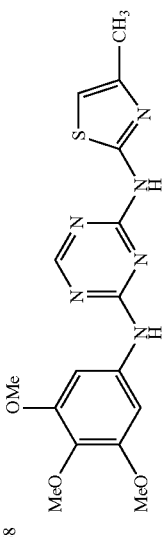
468
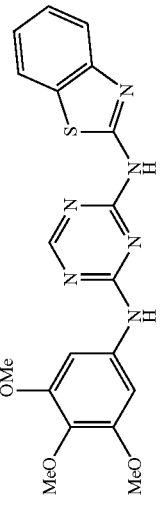
469
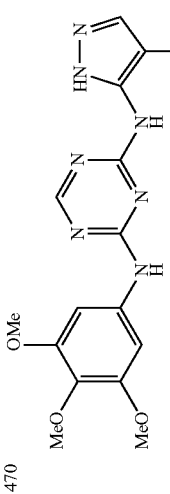
470
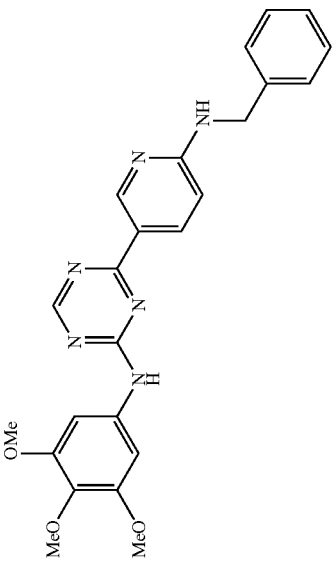
471
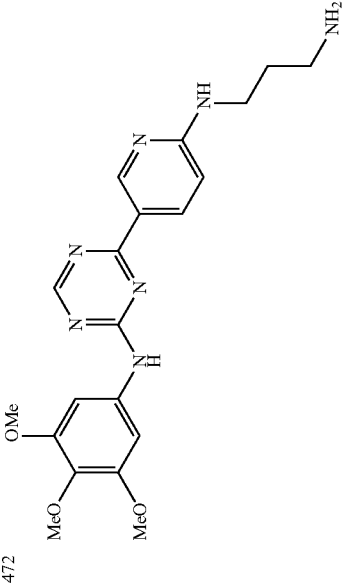
472

TABLE 1-continued
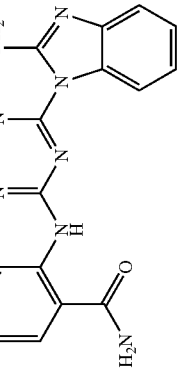
473
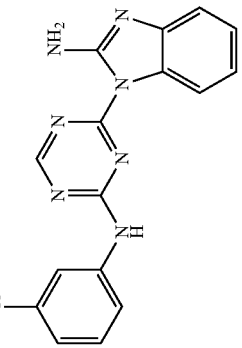
474
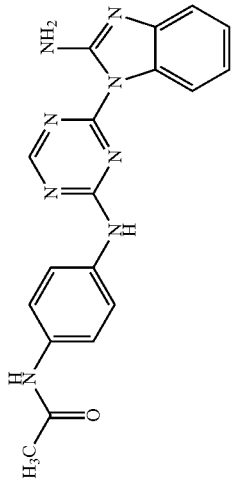
475
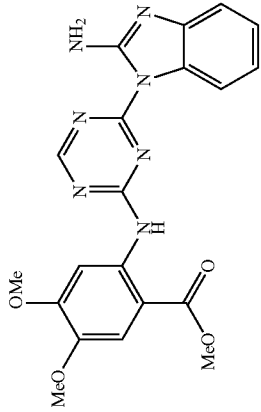
476
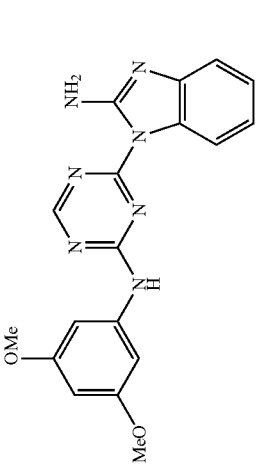
477
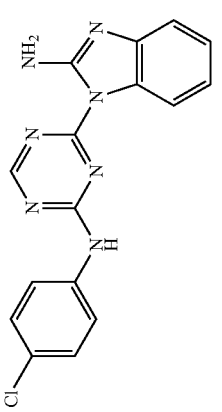
478
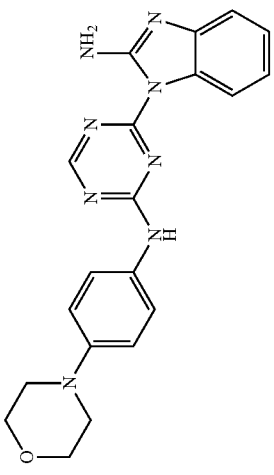
479
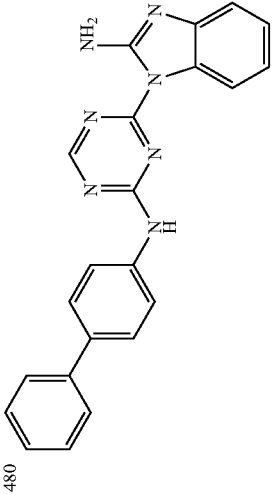
480

TABLE 1-continued
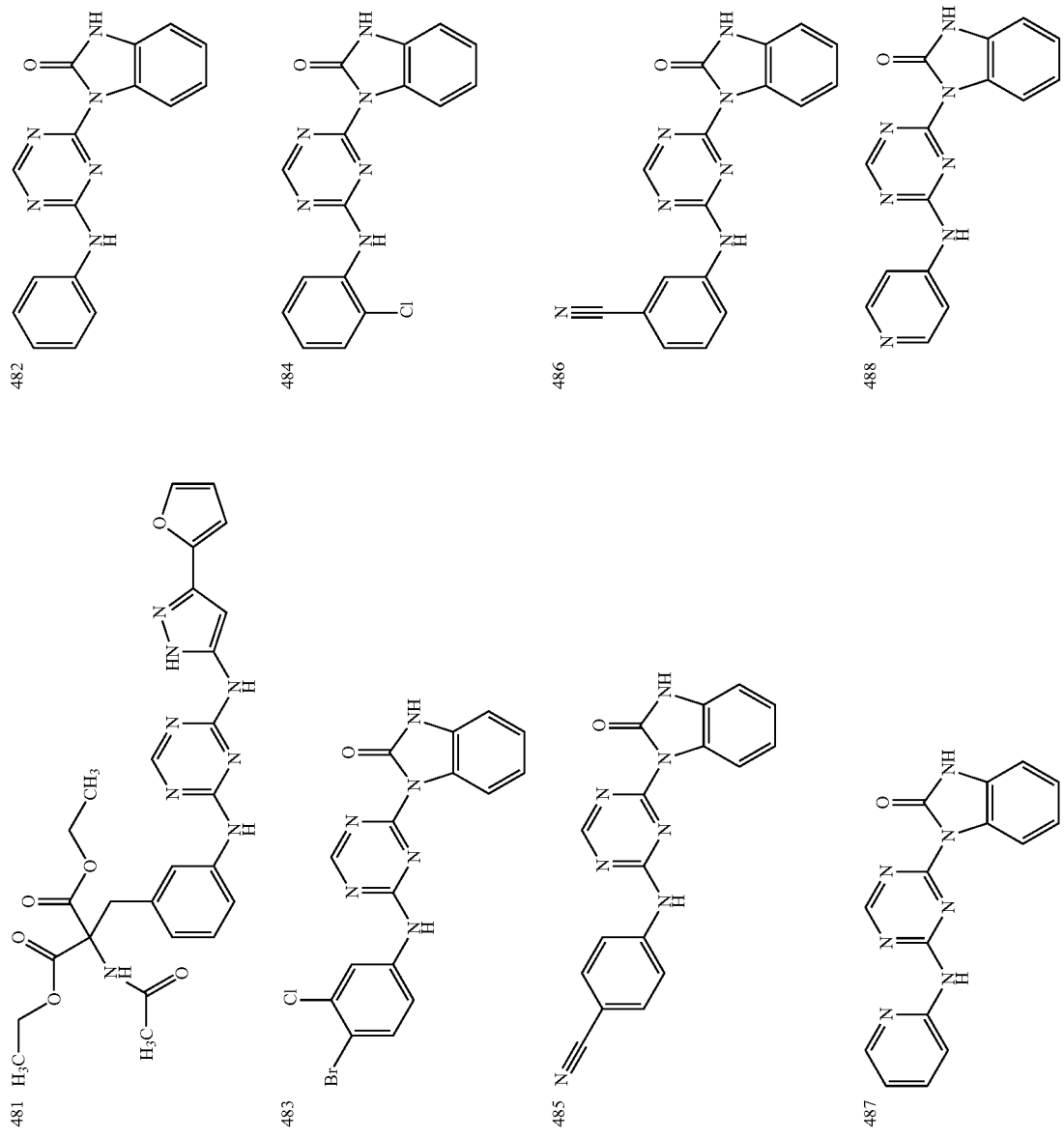

TABLE 1-continued

TABLE 1-continued

TABLE 1-continued
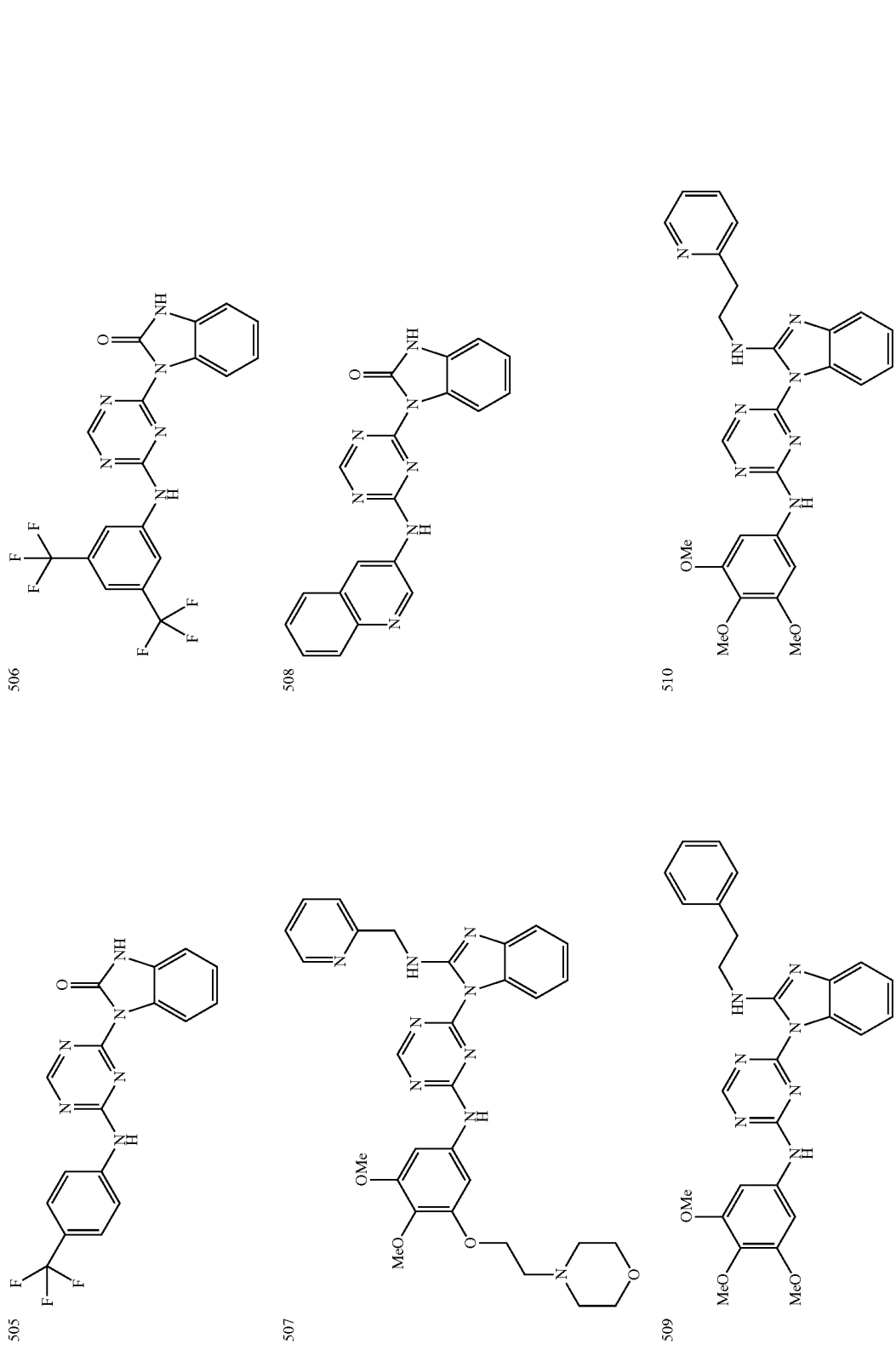

TABLE 1-continued

TABLE 1-continued

TABLE 1-continued

TABLE 1-continued
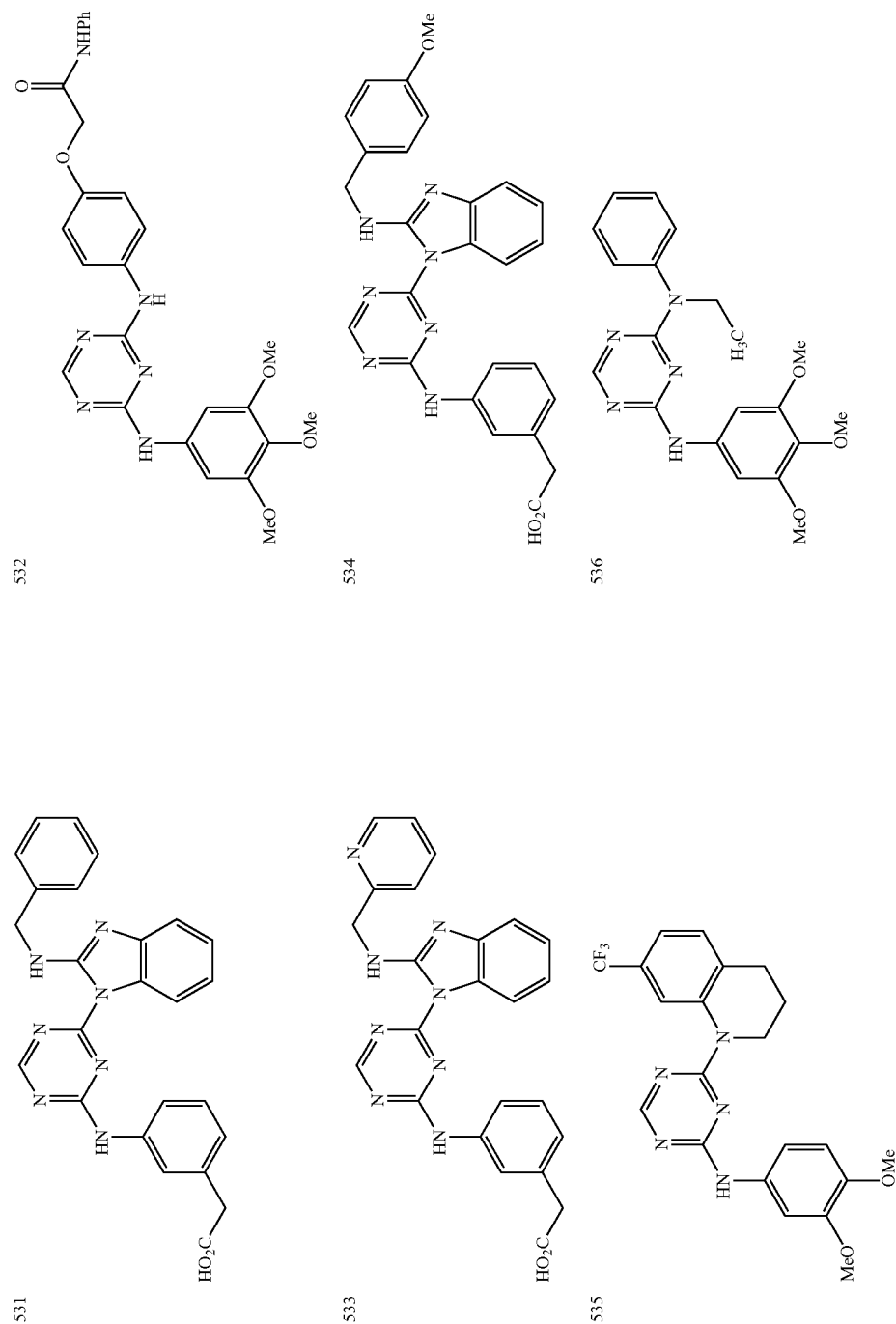

TABLE 1-continued

TABLE 1-continued
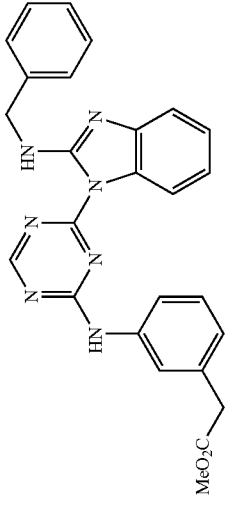
545
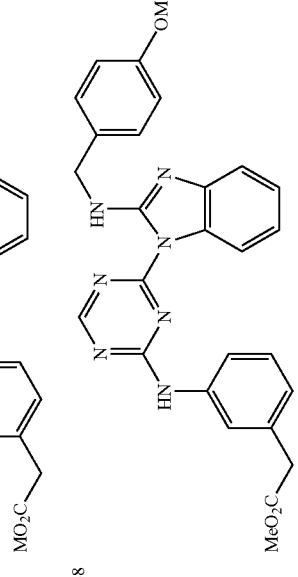
546
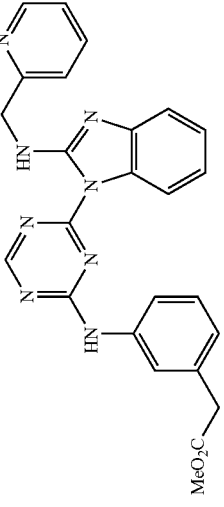
547
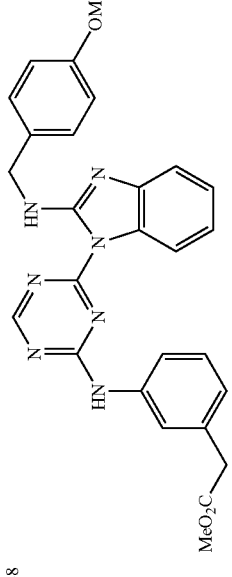
548
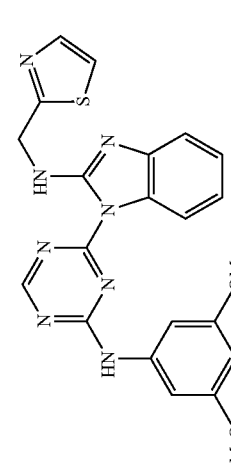
549
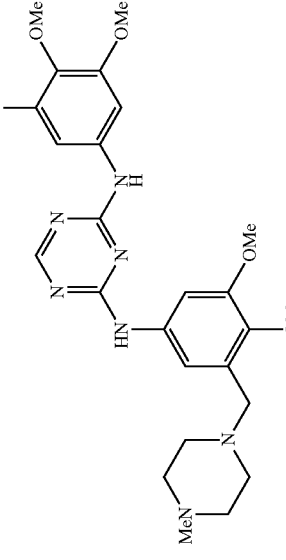
550
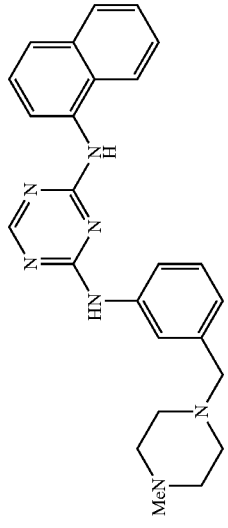
551
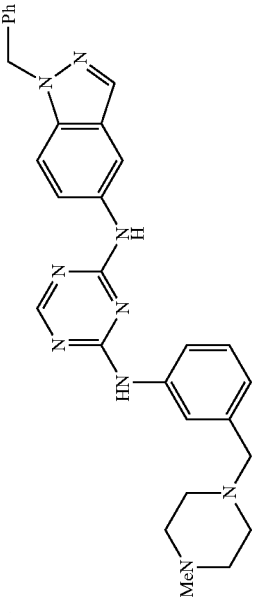
552

TABLE 1-continued
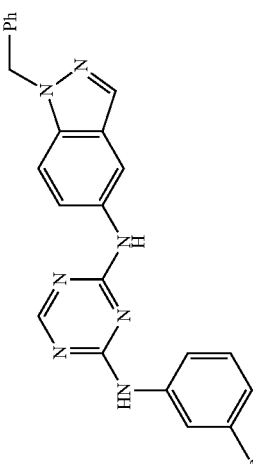
553
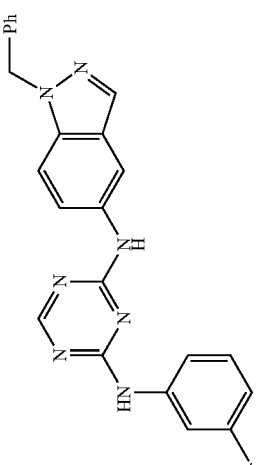
554
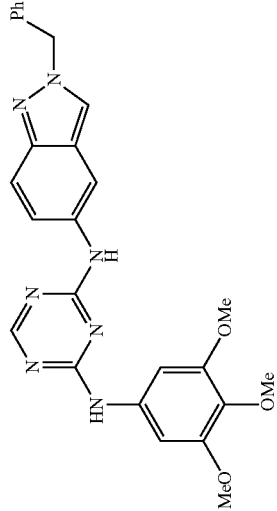
555
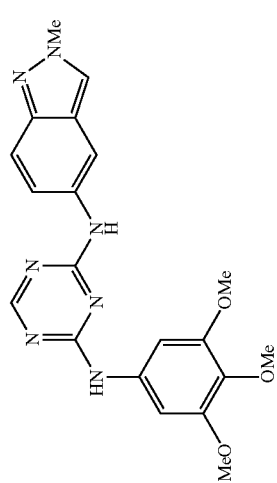
556
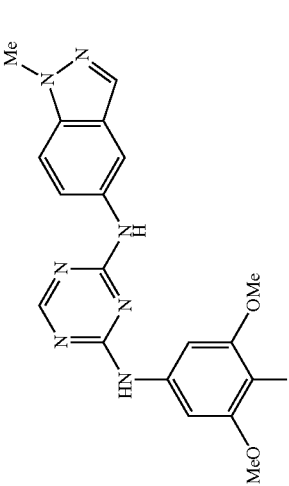
557
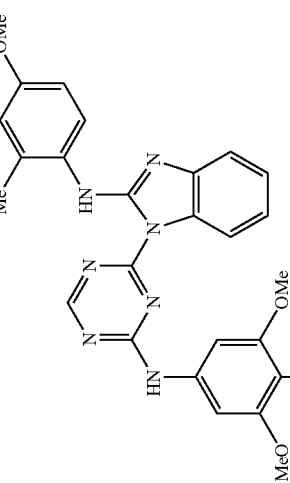
558

TABLE 1-continued
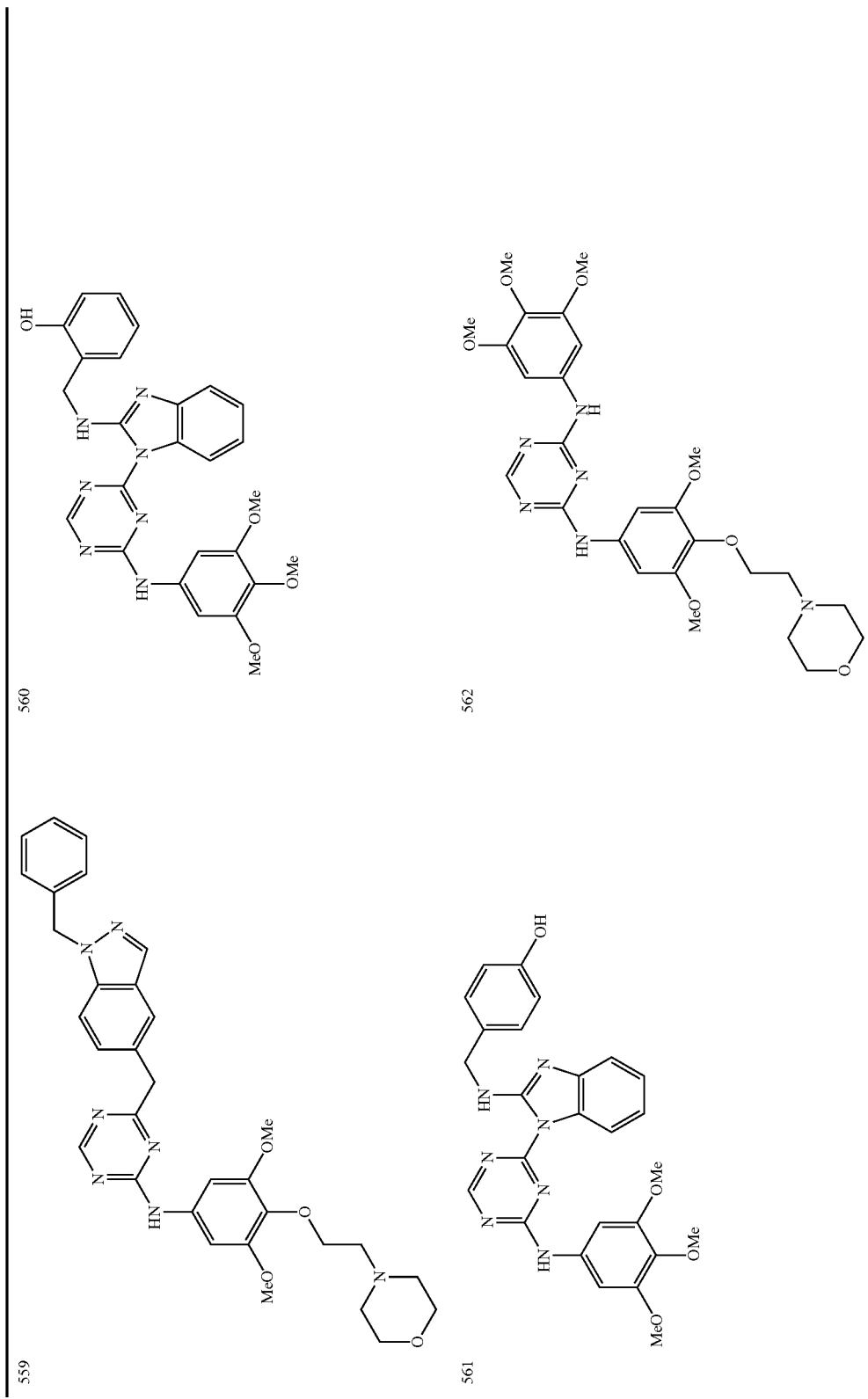

TABLE 1-continued
563
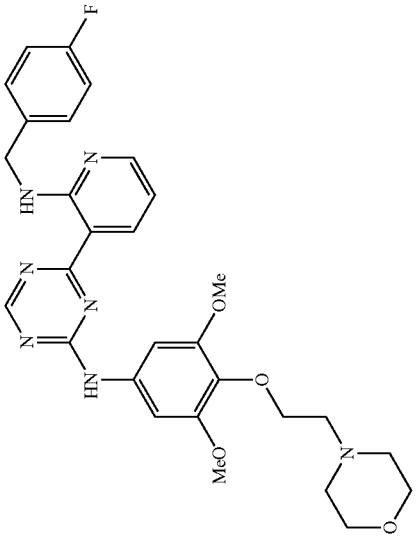
564
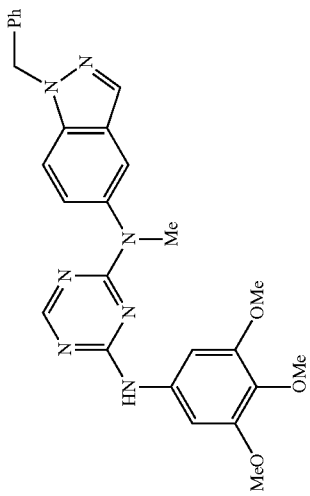
565
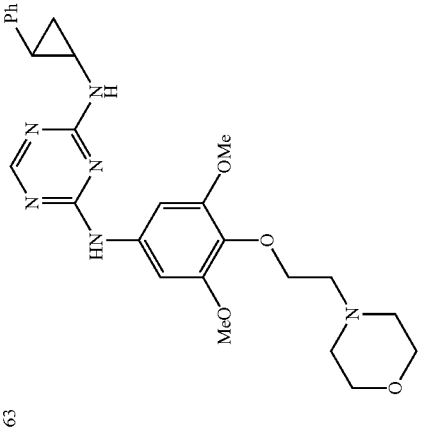
566
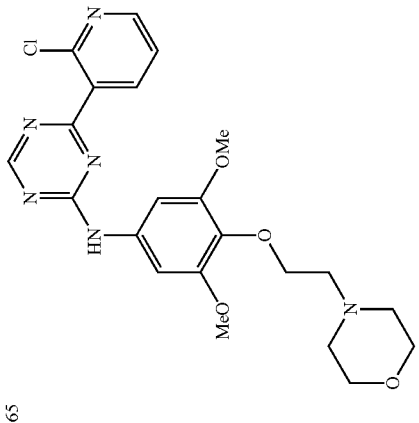

TABLE 1-continued

TABLE 1-continued
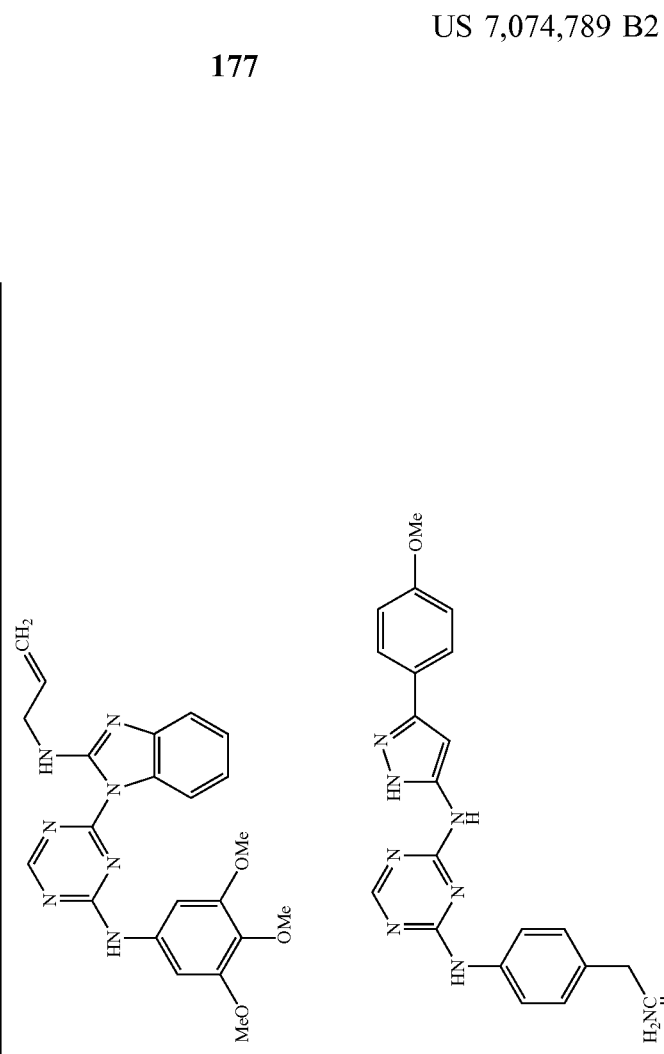
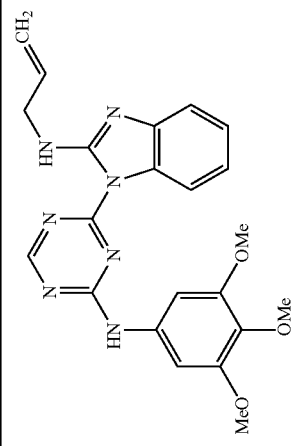
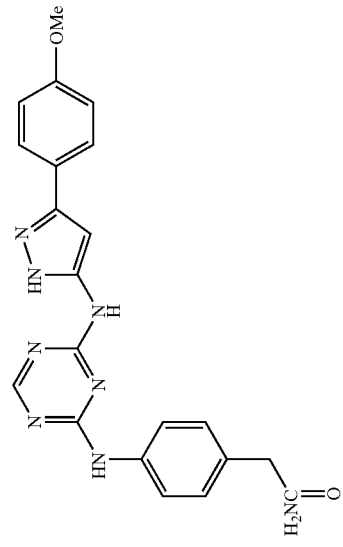
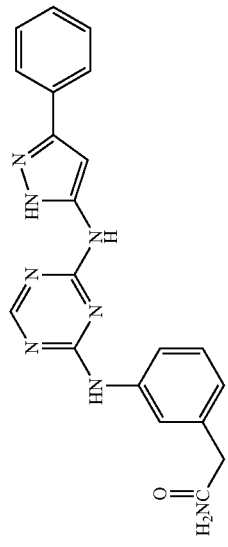
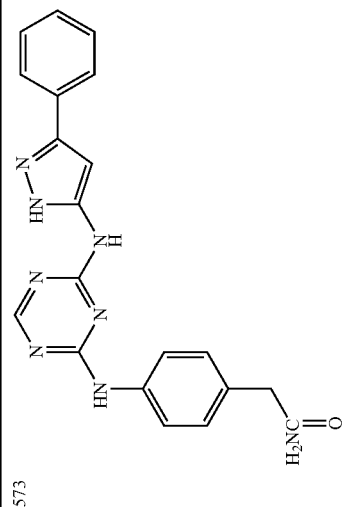
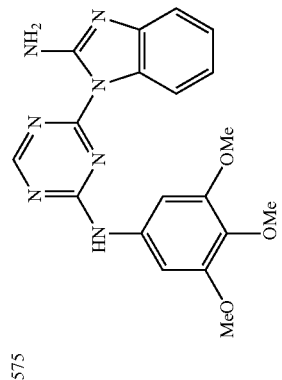
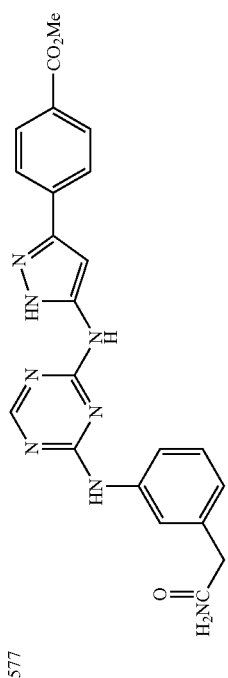

TABLE 1-continued

TABLE 1-continued 585, 586, 587, 588, 589, 590

TABLE 1-continued

TABLE 1-continued 597, 598, 599, 600, 601, 602

TABLE 1-continued
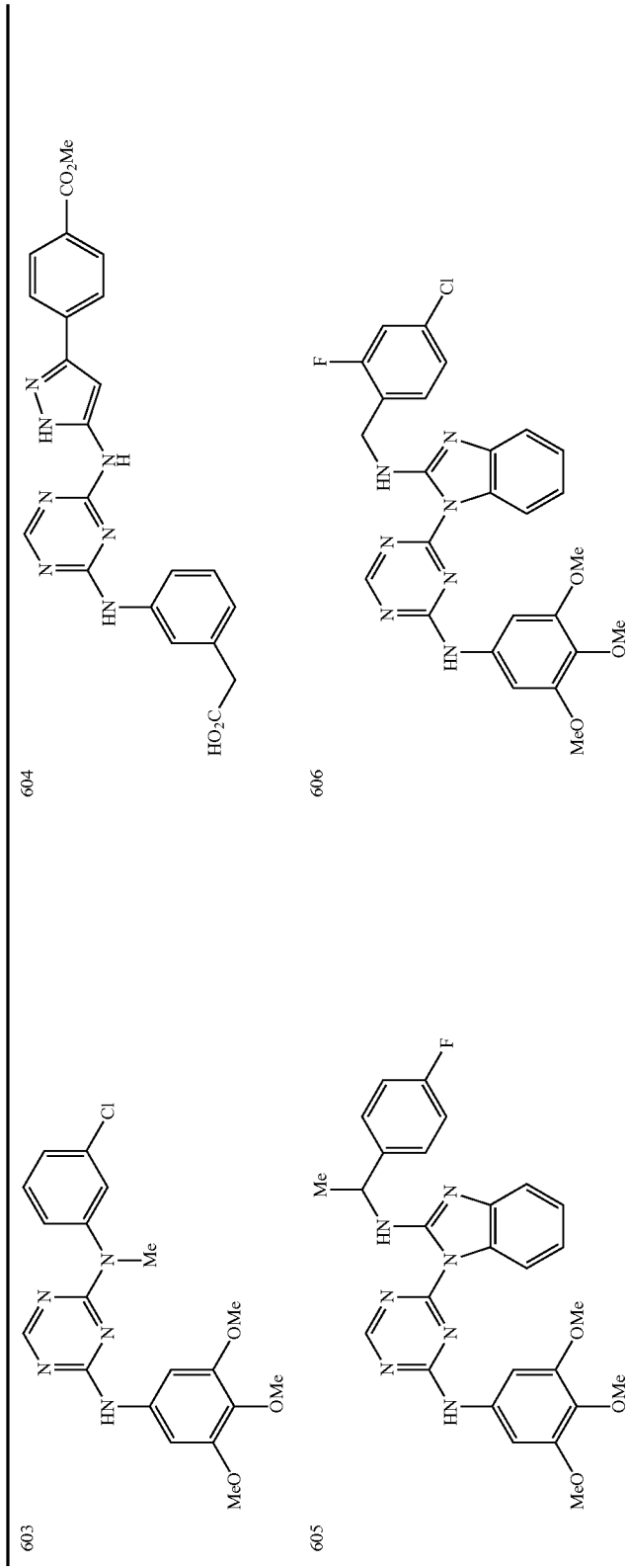

TABLE 1-continued

TABLE 1-continued

TABLE 1-continued

TABLE 1-continued

TABLE 1-continued

TABLE 1-continued

| 647 | 648 |
| 649 | 650 |

TABLE 1-continued

TABLE 1-continued

657

658

659

660

TABLE 1-continued

TABLE 1-continued
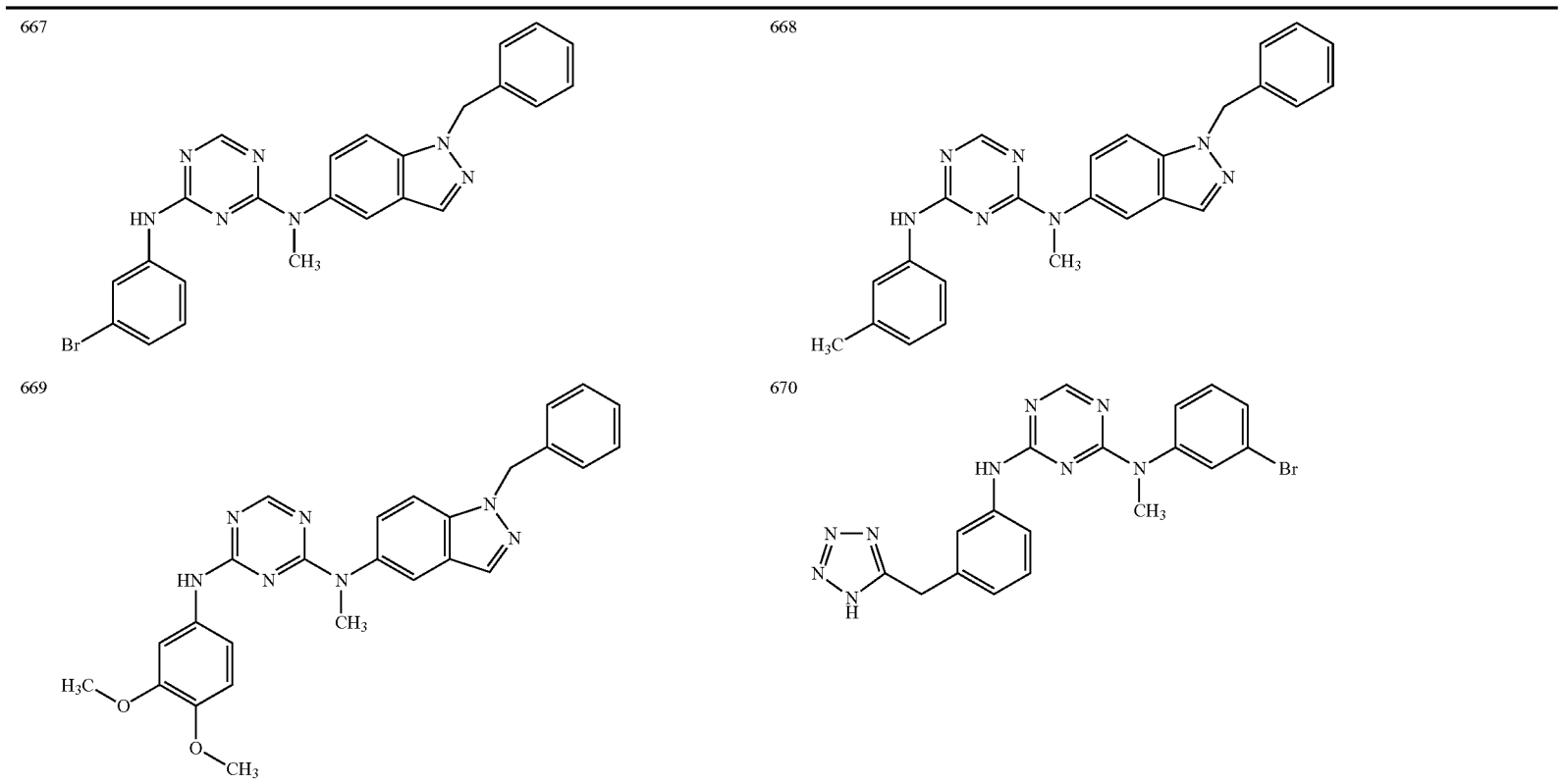

TABLE 1-continued
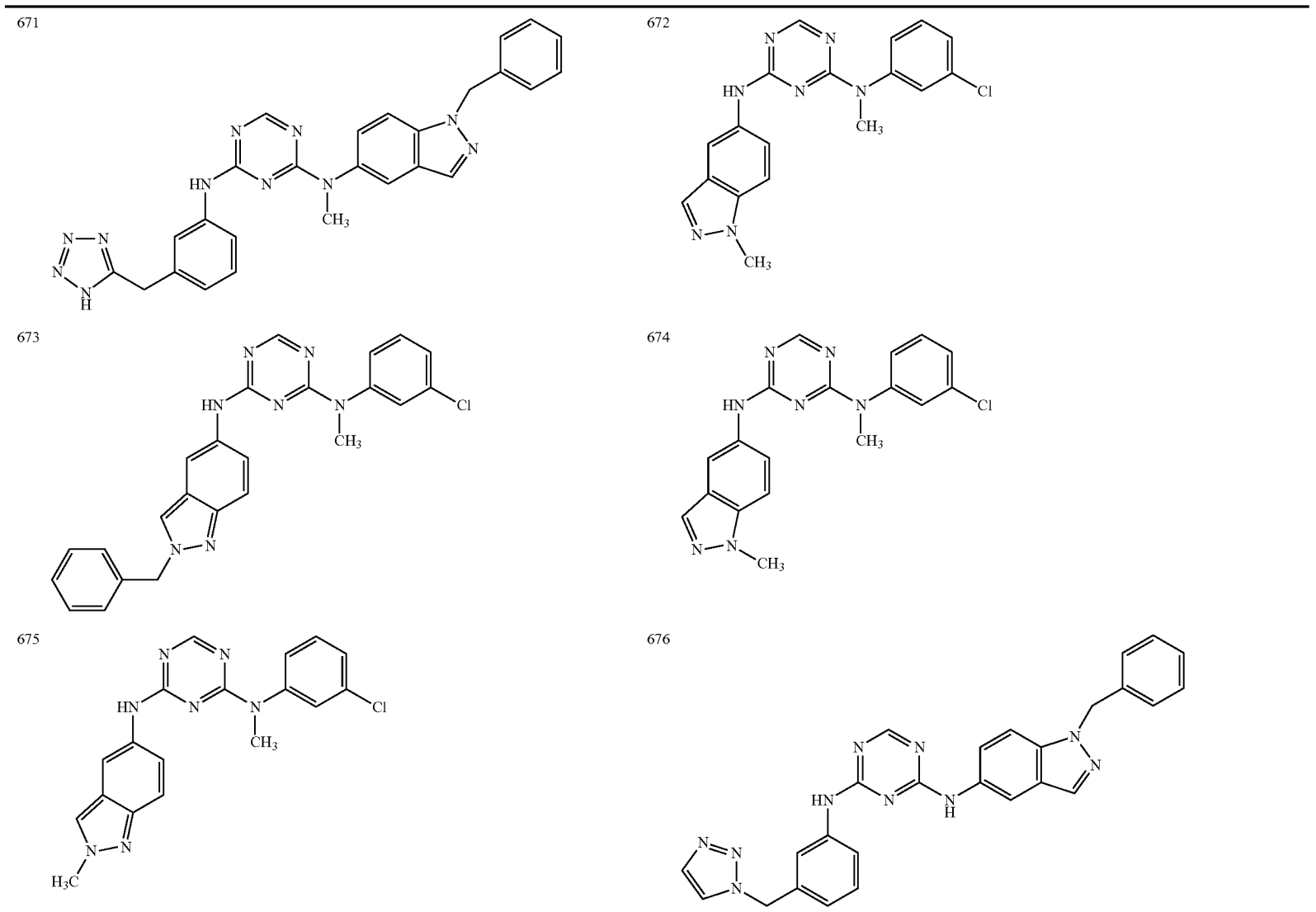

TABLE 1-continued
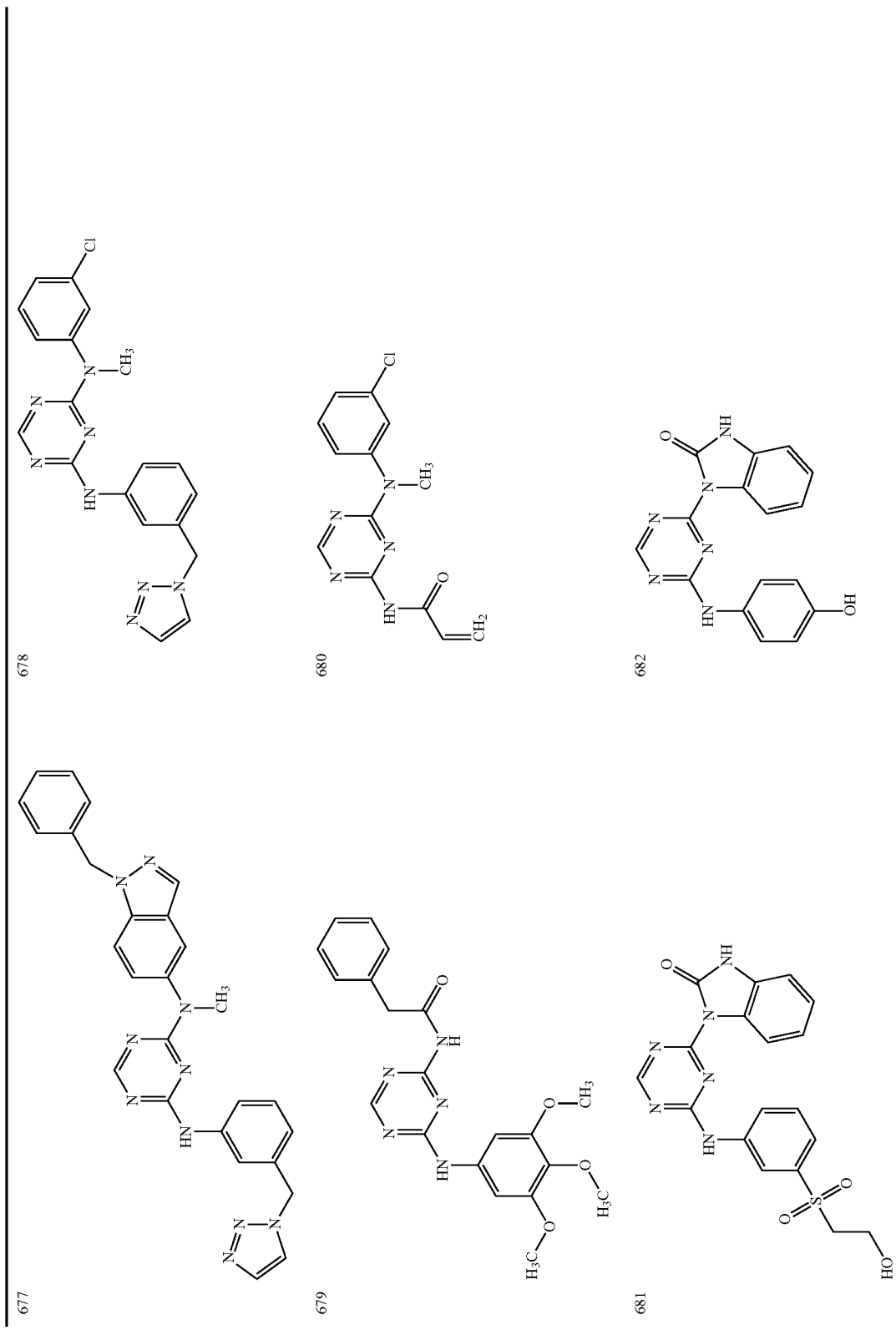

TABLE 1-continued
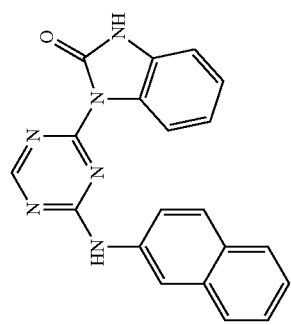
684
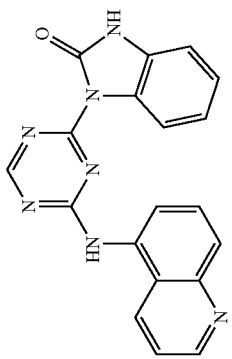
686
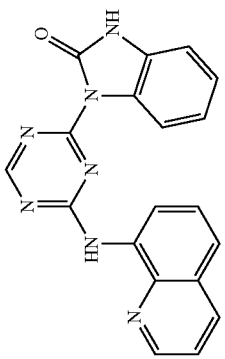
688
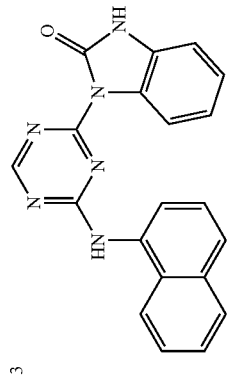
683
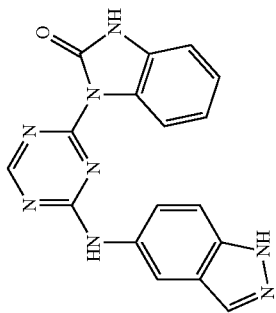
685
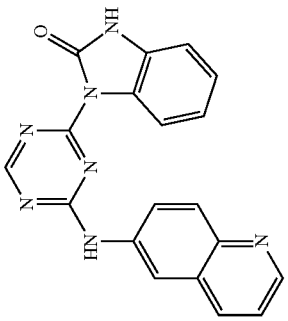
687

TABLE 1-continued
689
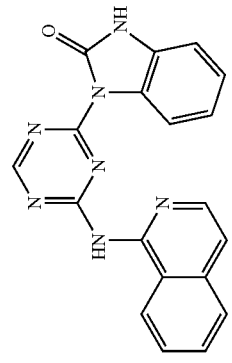
690
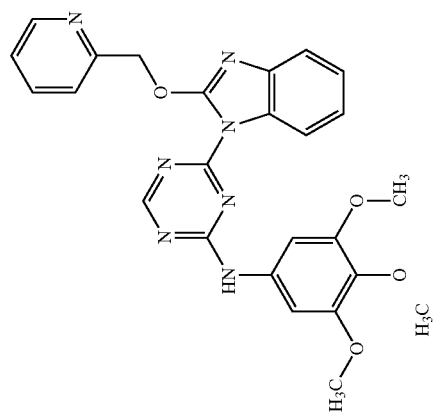
691
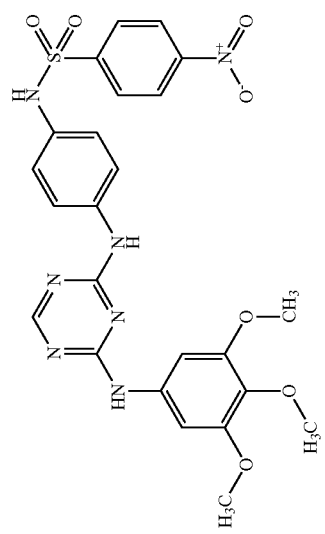
692
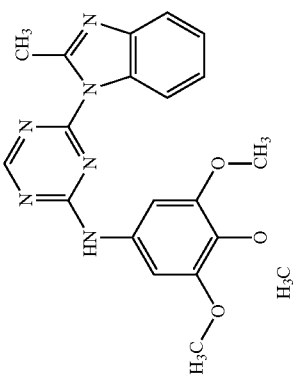
693
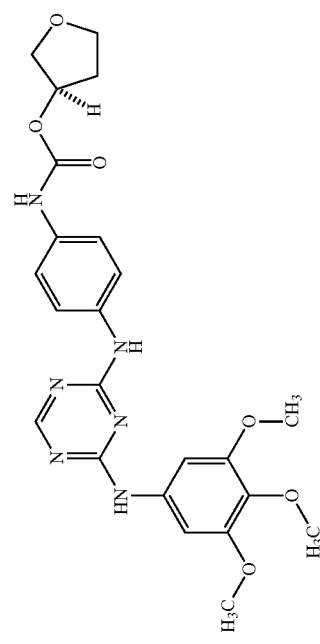
694
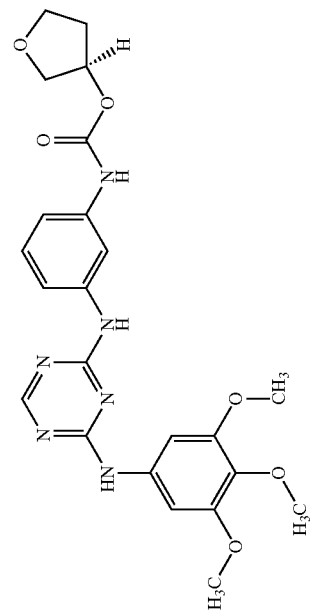

TABLE 1-continued

695

696

697

698

TABLE 1-continued
| 699 | 700 | 701 | 702 | 703 | 704 |
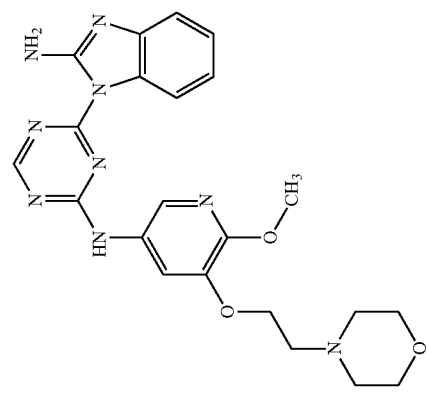
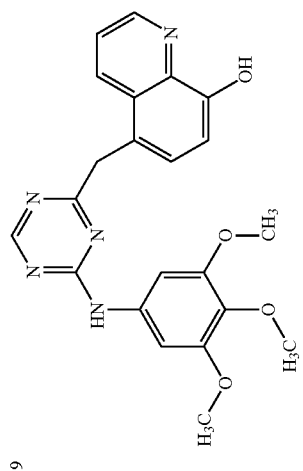
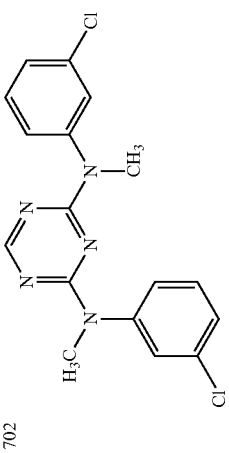
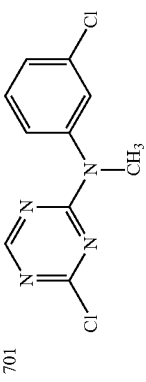
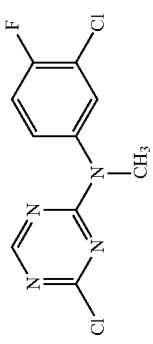
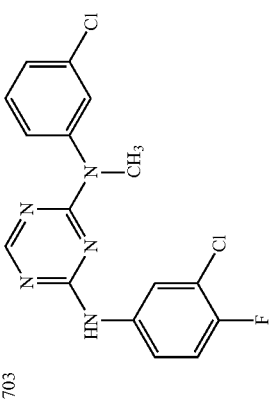

TABLE 1-continued

TABLE 1-continued 711, 712, 713, 714, 715, 716

TABLE 1-continued
717 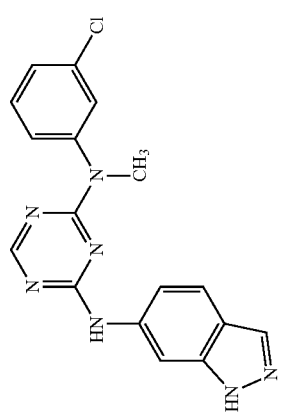
718 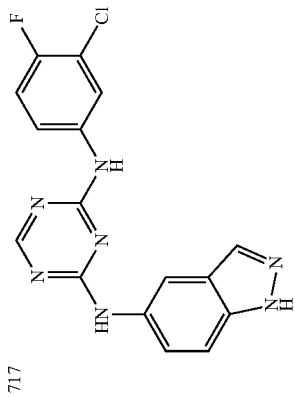
719 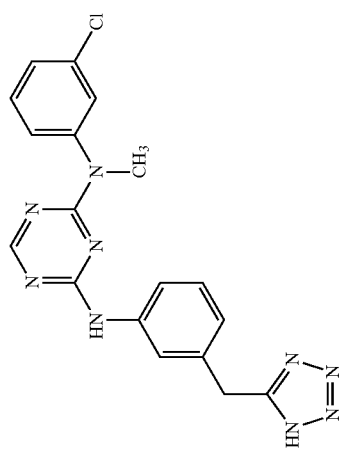
720 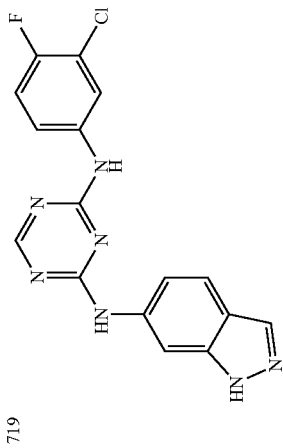
721 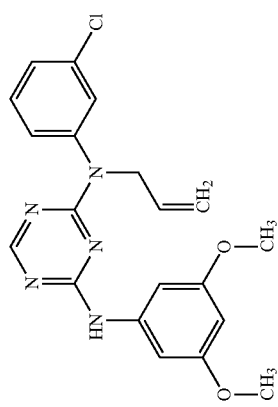
722 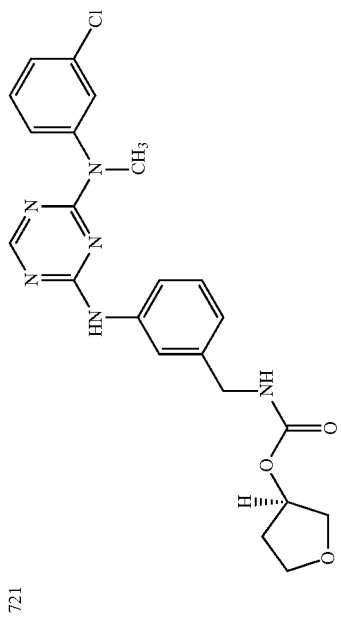

TABLE 1-continued
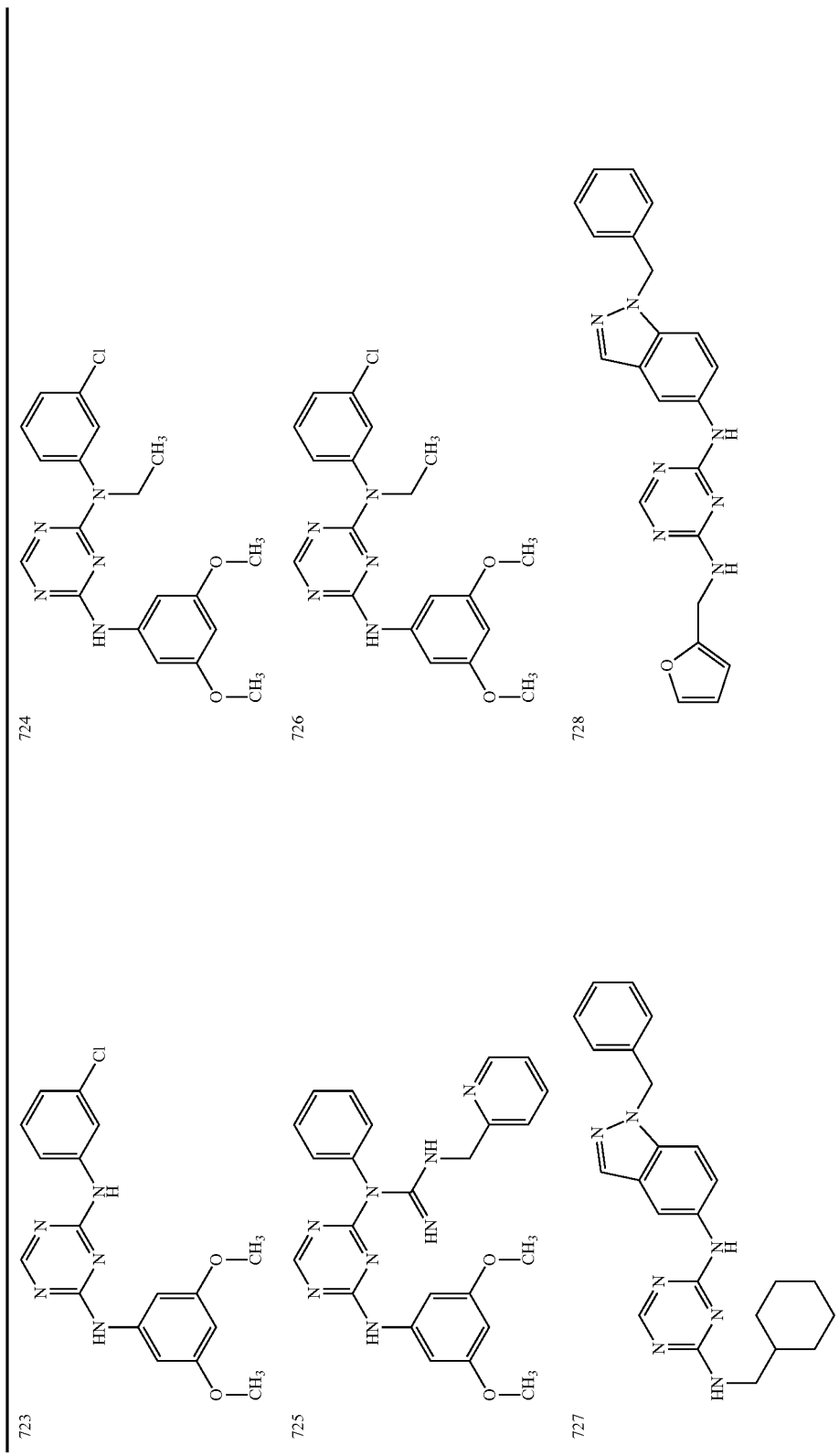

TABLE 1-continued
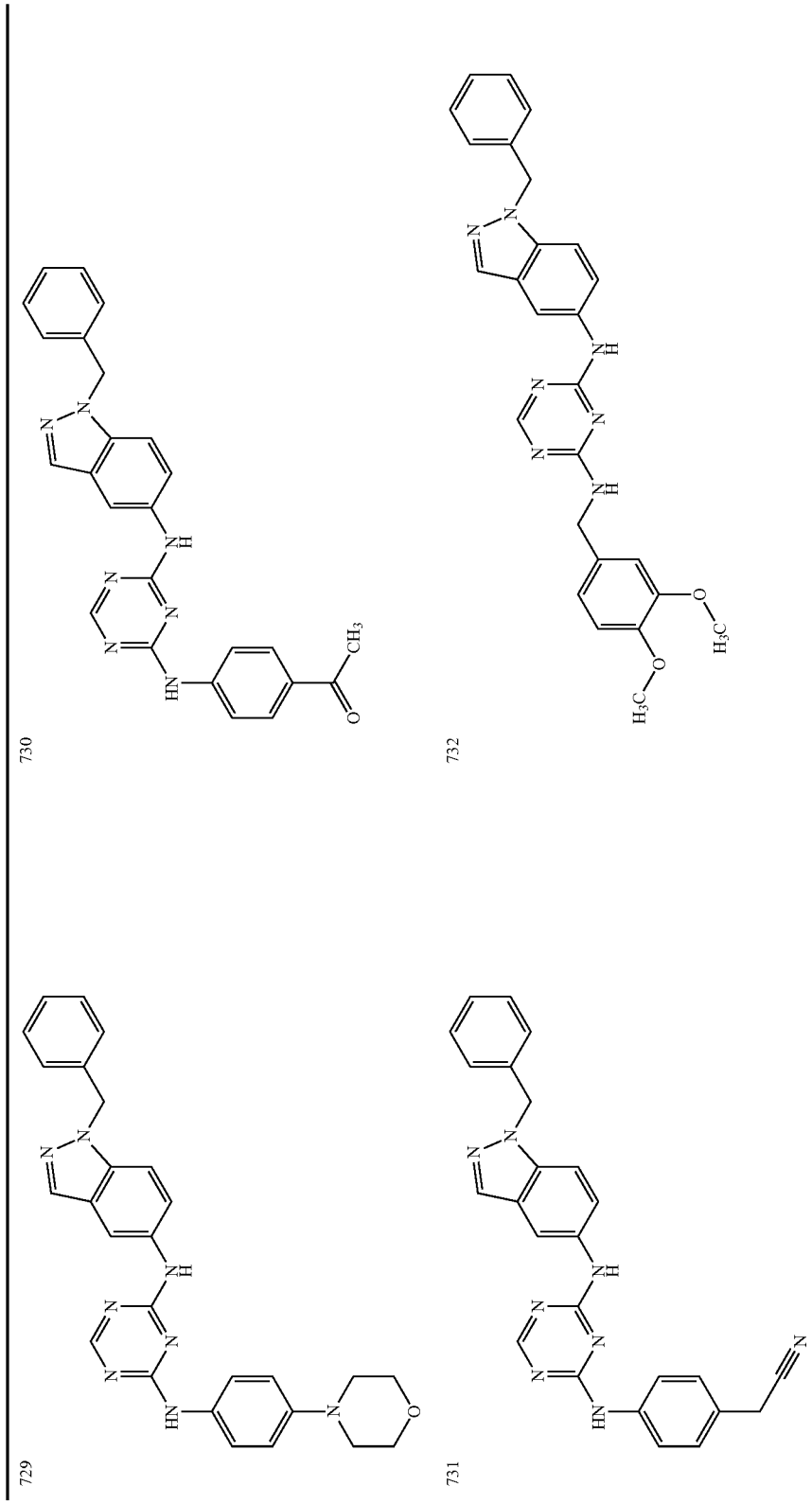

TABLE 1-continued
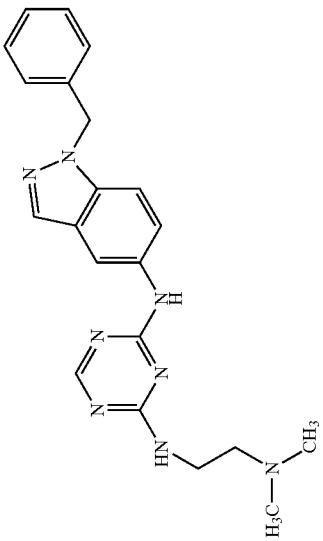
734
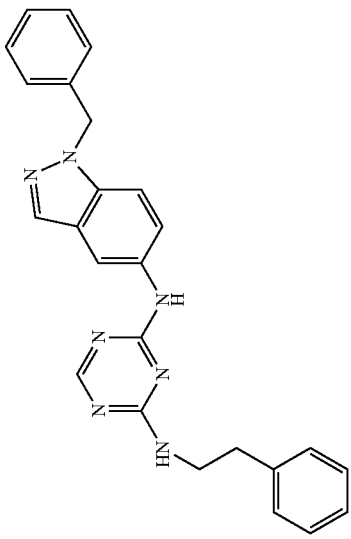
736
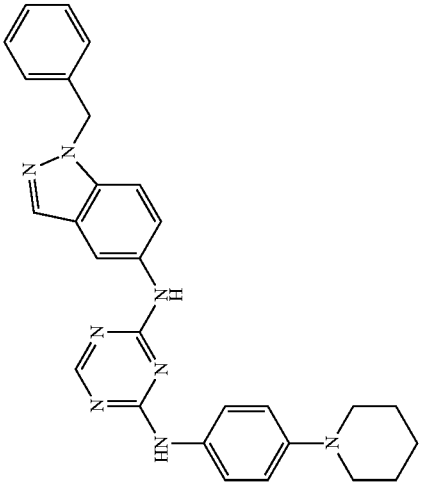
733
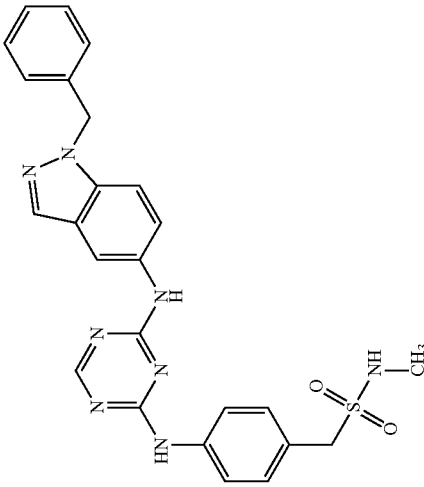
735

TABLE 1-continued
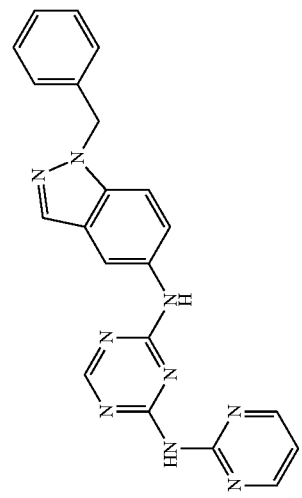
737
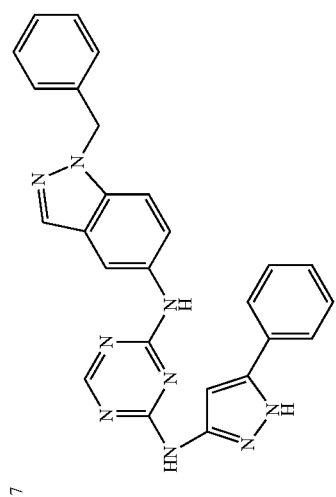
738
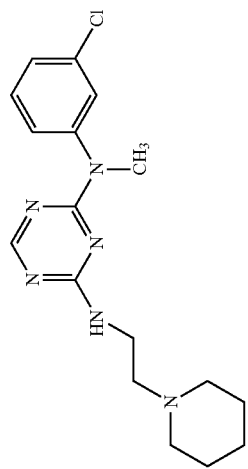
739
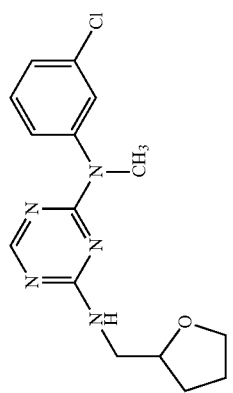
740
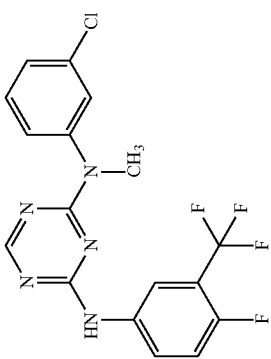
741
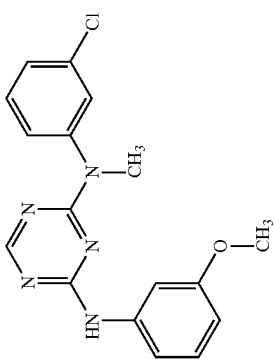
742

TABLE 1-continued 743, 744, 745, 746, 747, 748

TABLE 1-continued

TABLE 1-continued

TABLE 1-continued
| 761 | 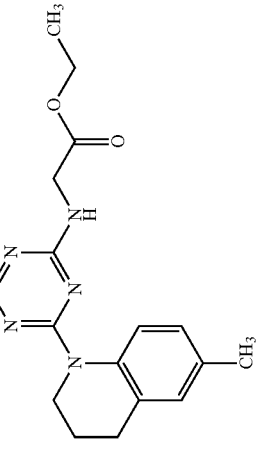 | 762 | 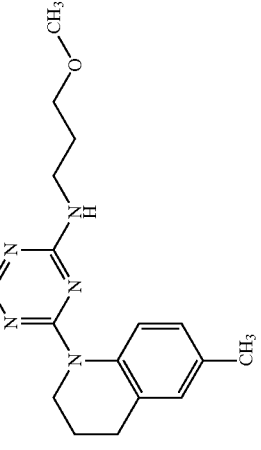 |
| 763 | 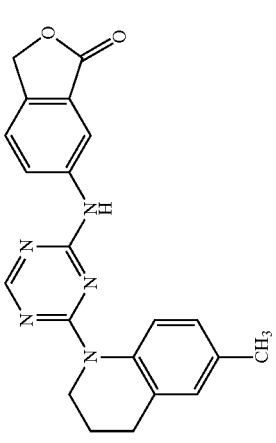 | 764 | 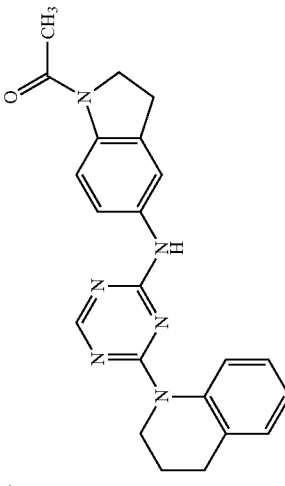 |
| 765 | 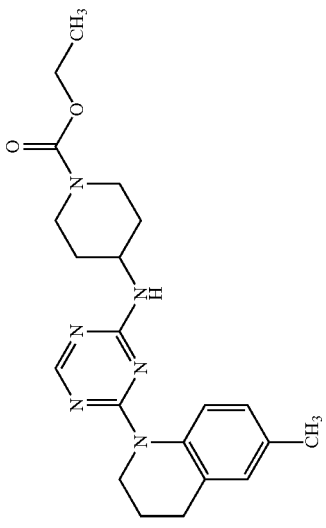 | 766 | 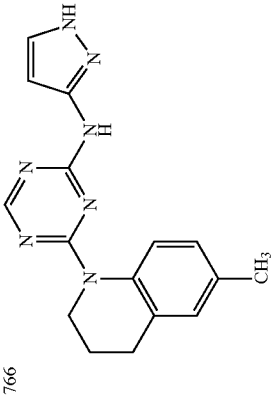 |

TABLE 1-continued

TABLE 1-continued
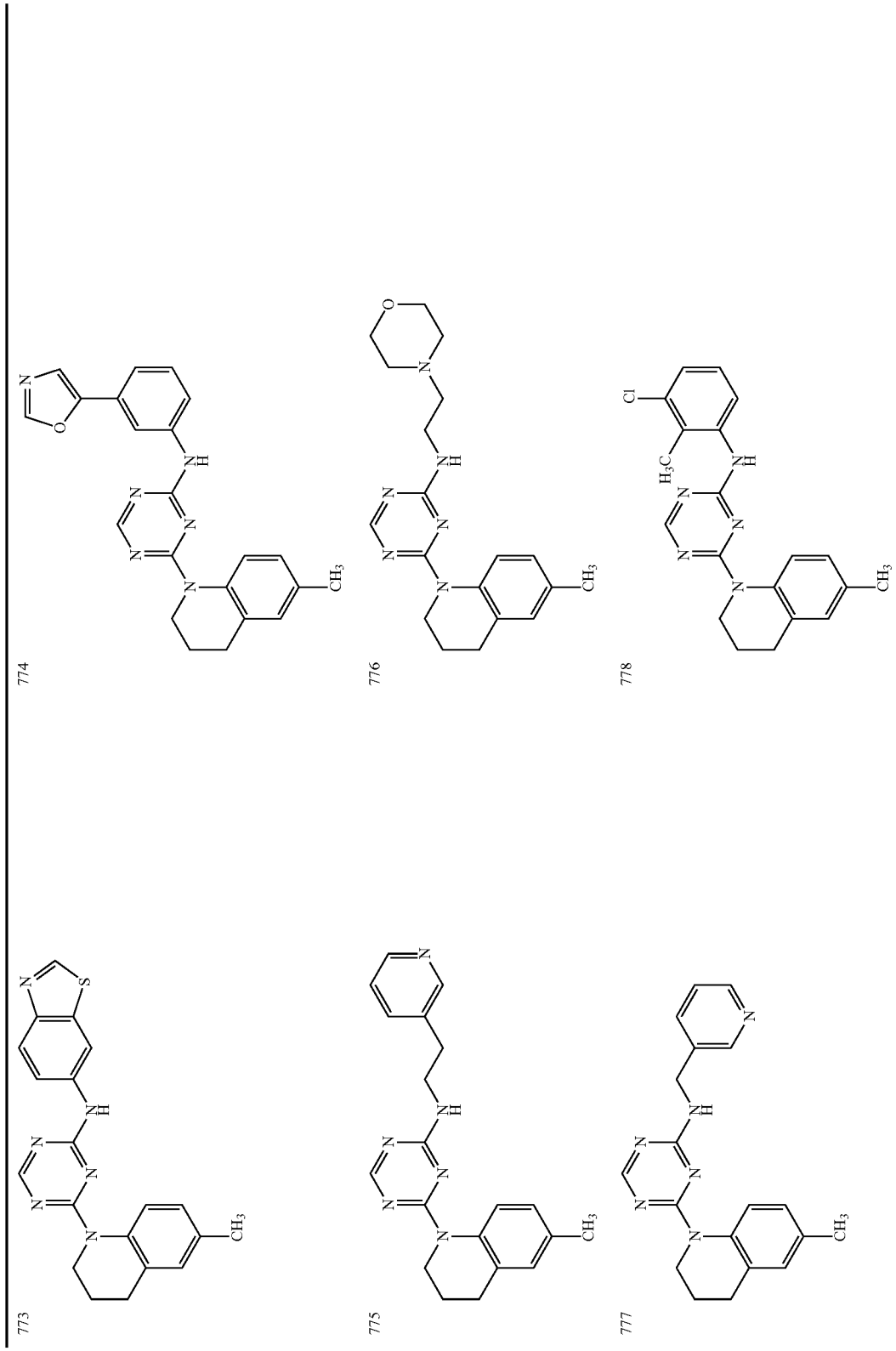

TABLE 1-continued

TABLE 1-continued 785, 786, 787, 788, 789, 790

TABLE 1-continued

TABLE 1-continued
| 797 | 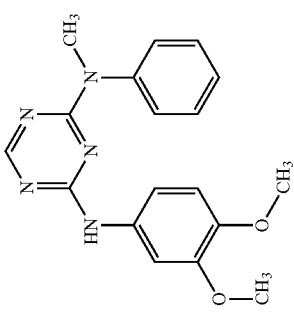 | 799 | 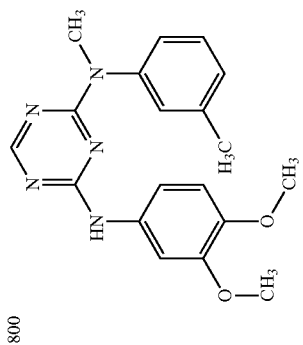 | 801 | 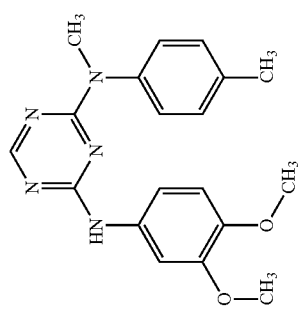 |
| 798 | 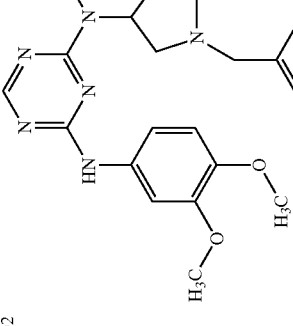 | 800 | 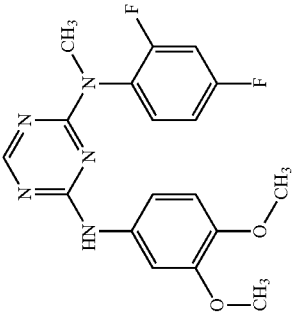 | 802 | 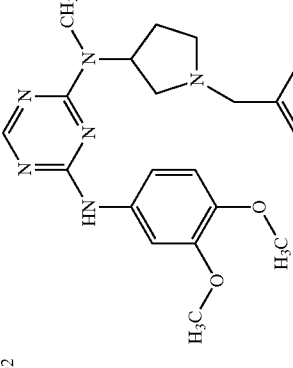 |

TABLE 1-continued
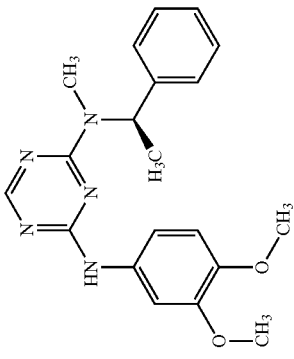
803
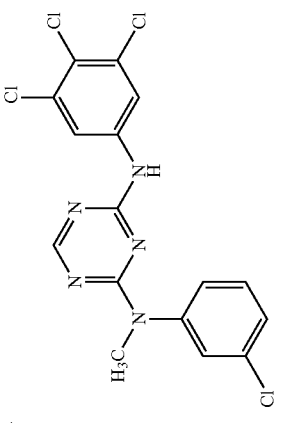
804
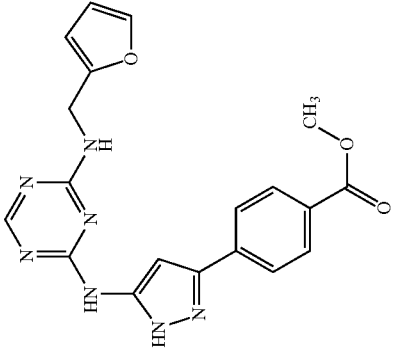
805
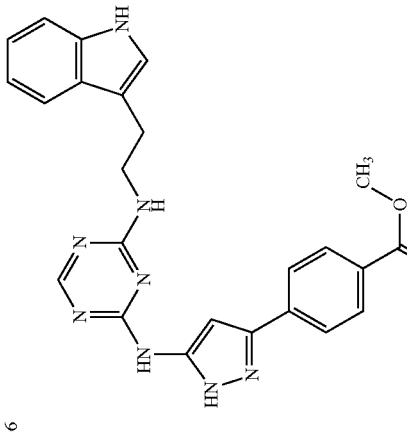
806

TABLE 1-continued
807
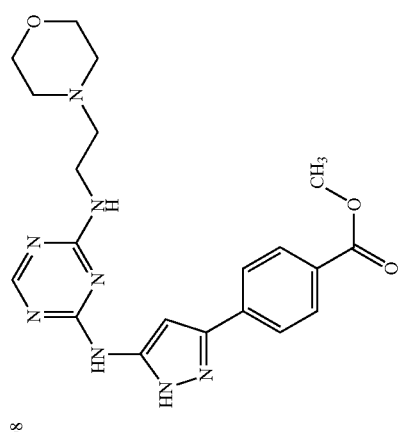
808
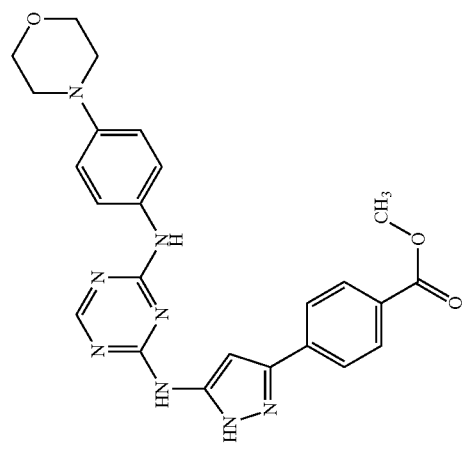
809
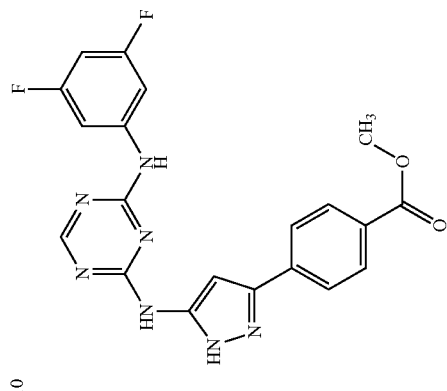
810
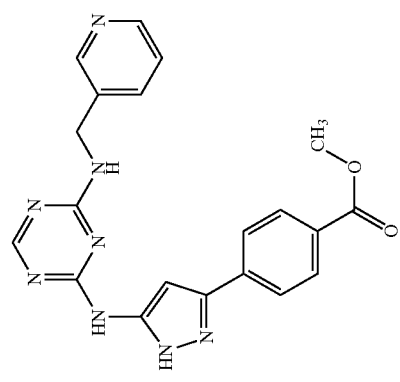

TABLE 1-continued
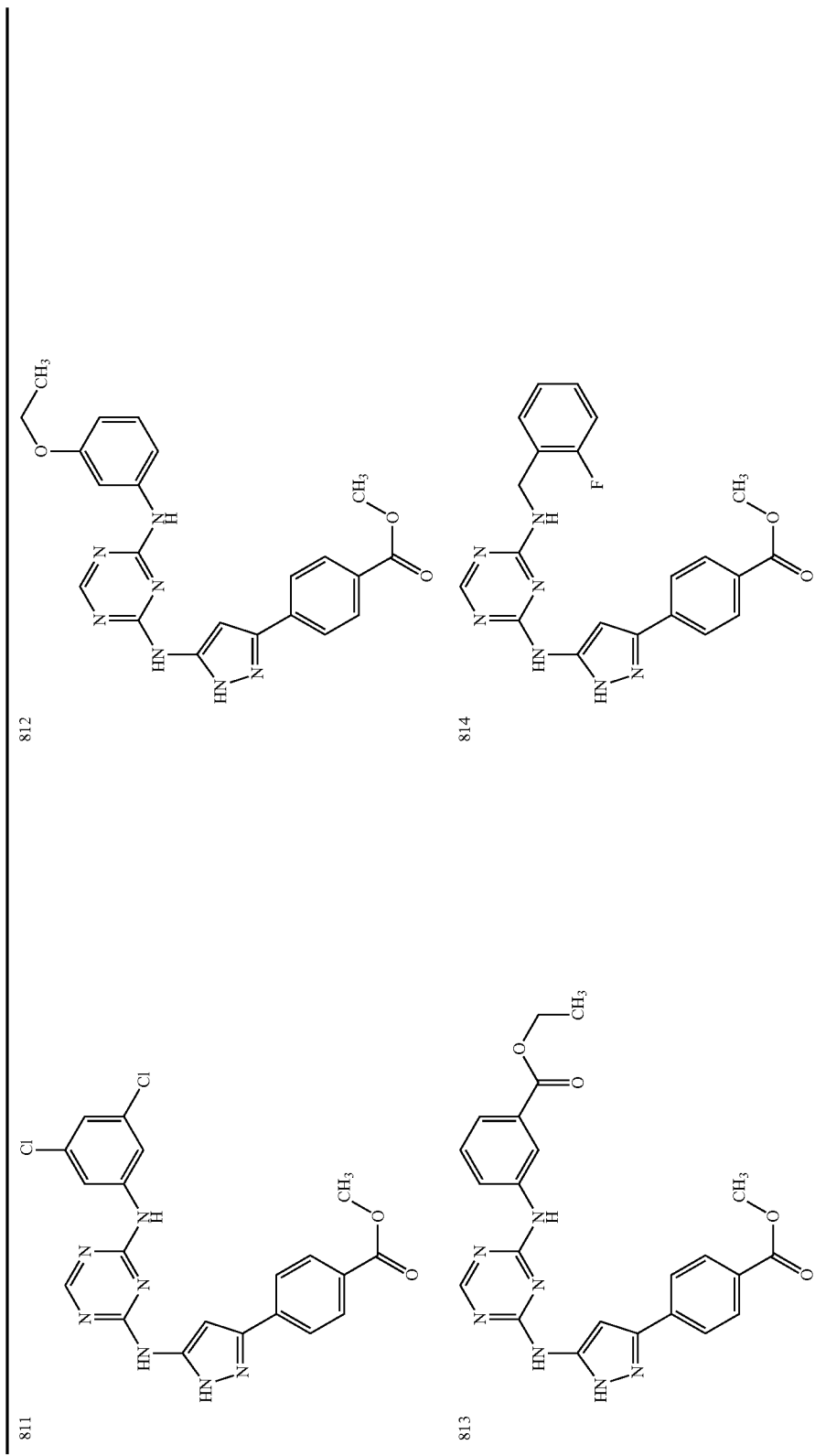

TABLE 1-continued
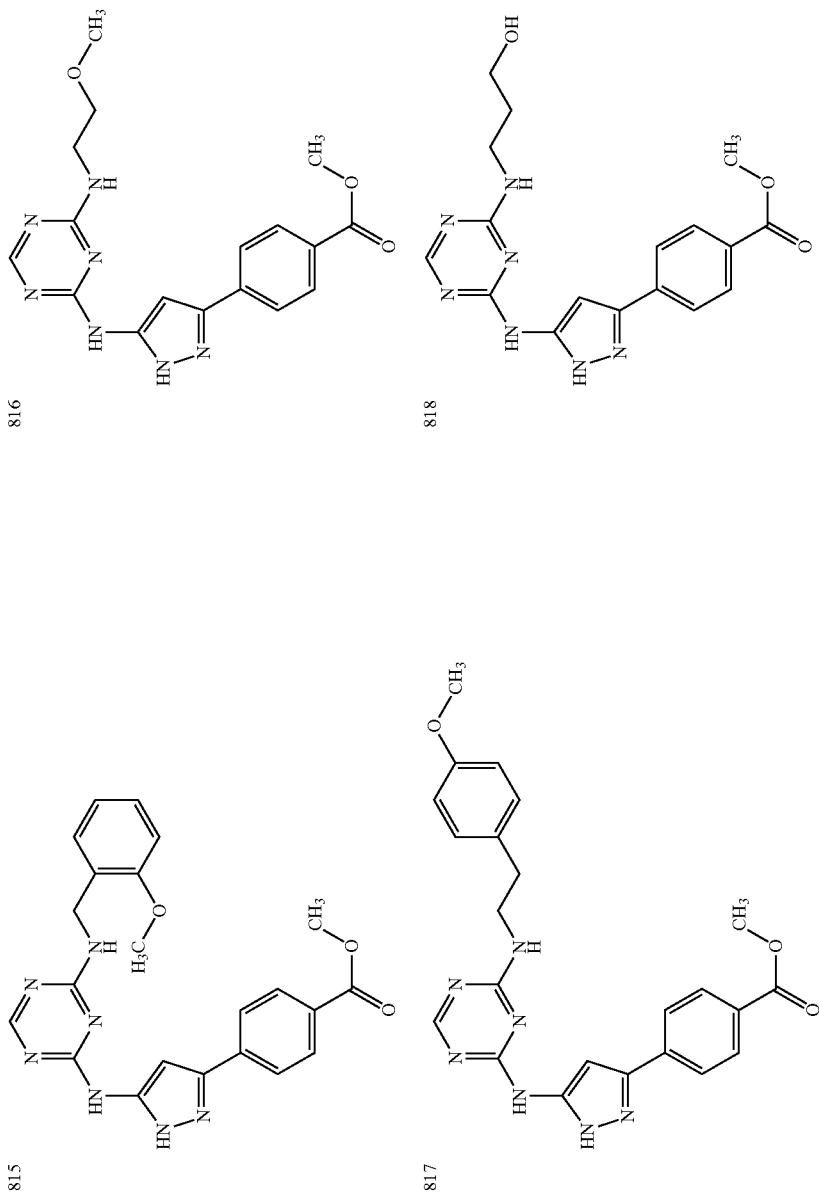

TABLE 1-continued
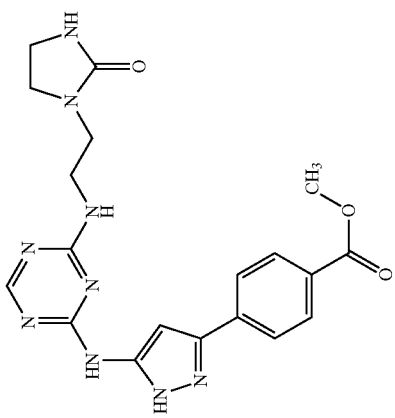
820
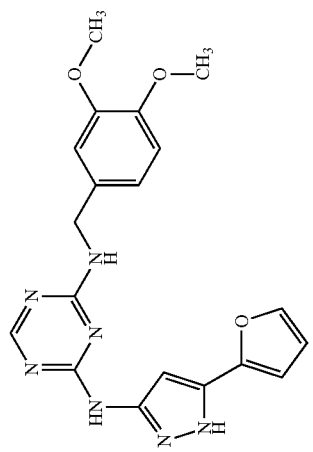
822
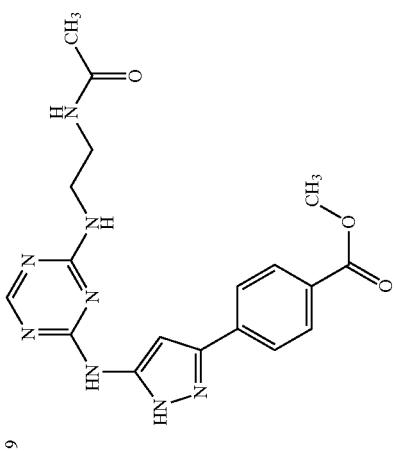
819
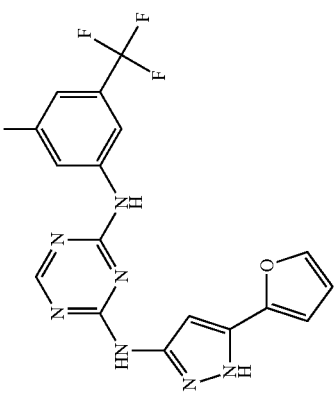
821

TABLE 1-continued 823 824 825 826

TABLE 1-continued
828
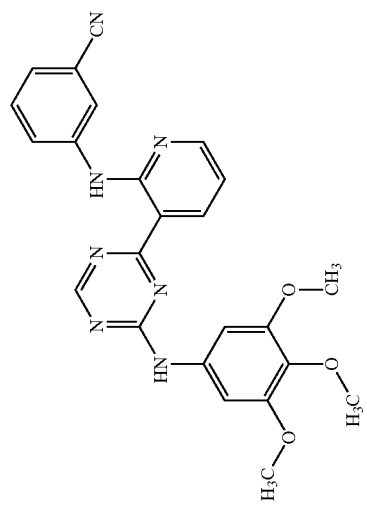
830
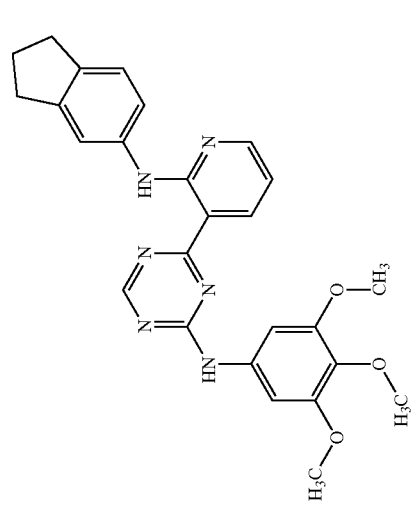
827
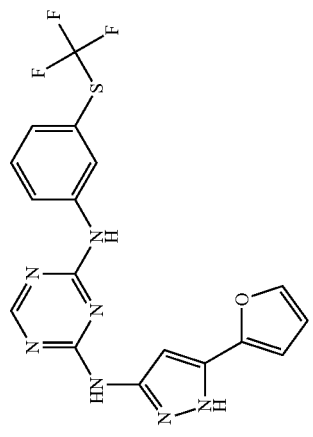
829
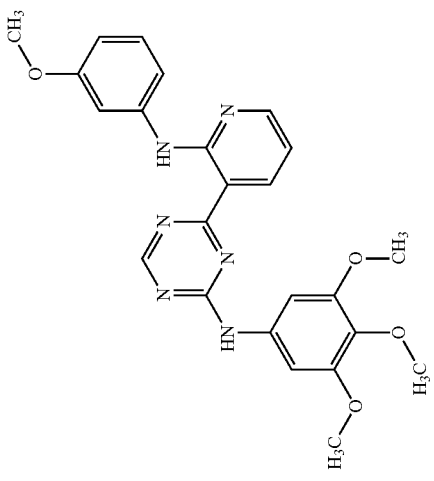

TABLE 1-continued 831, 832, 833, 834

TABLE 1-continued
836 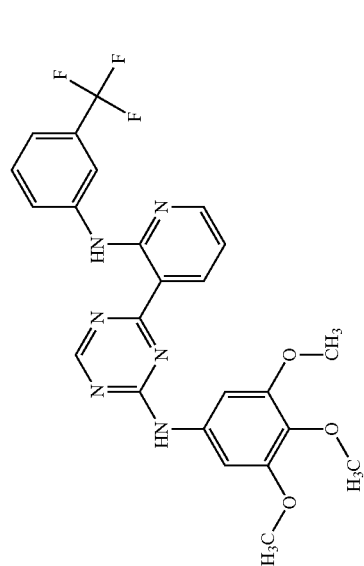
838 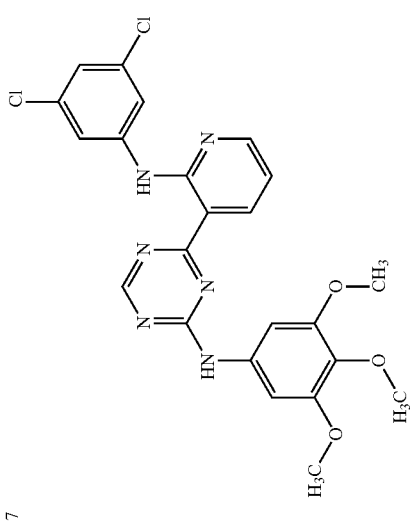
835 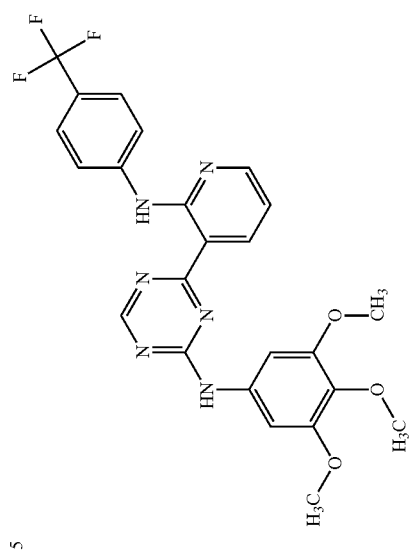
837 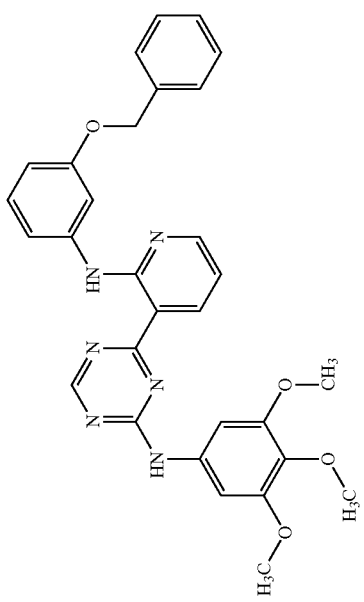

TABLE 1-continued

839

840

841

842

TABLE 1-continued

843

844

845

846

TABLE 1-continued

| 847 | 848 |
| 849 | 850 |

TABLE 1-continued
851
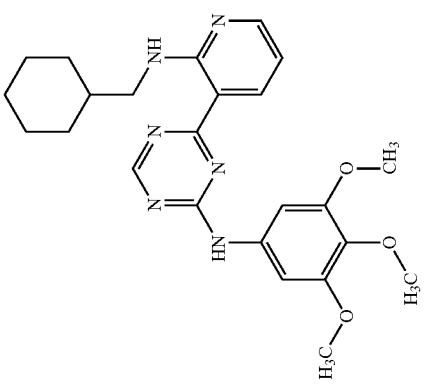
852
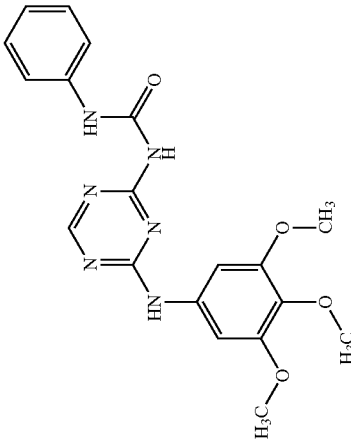
853
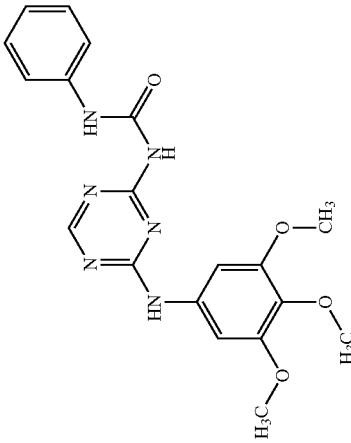
854
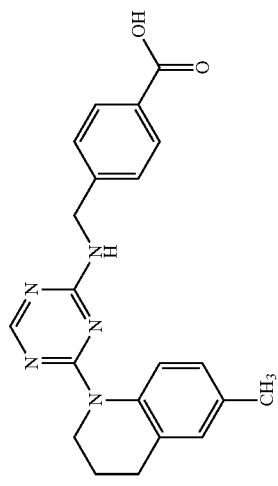

TABLE 1-continued
855 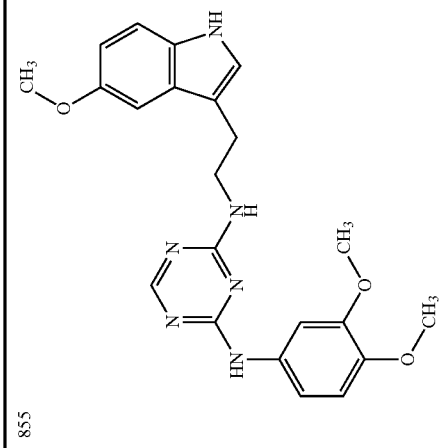
857 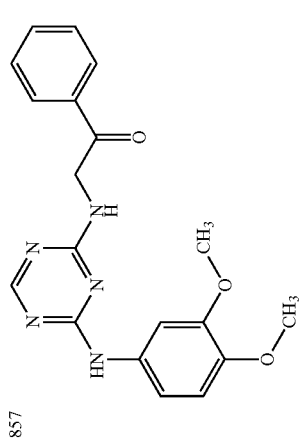
859 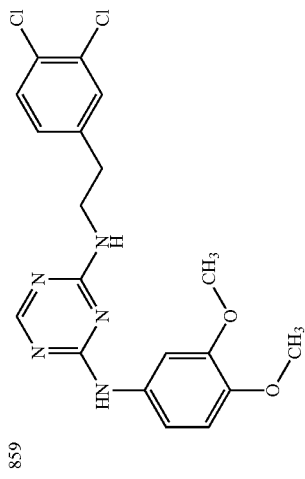
856 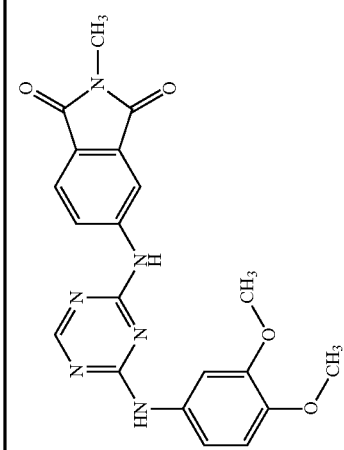
858 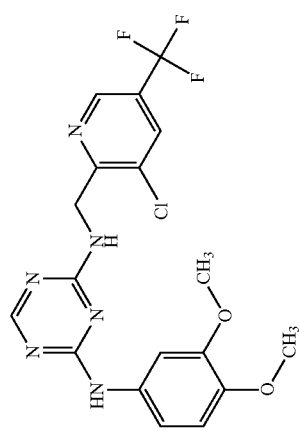
860 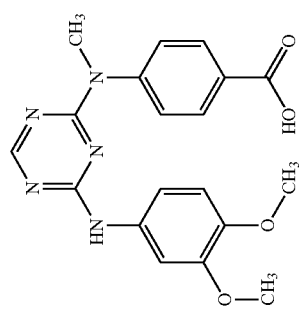

TABLE 1-continued

TABLE 1-continued
867 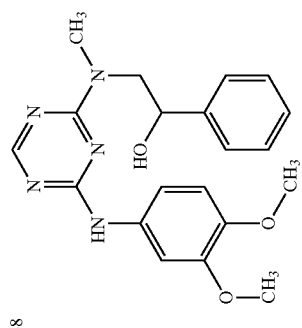
869 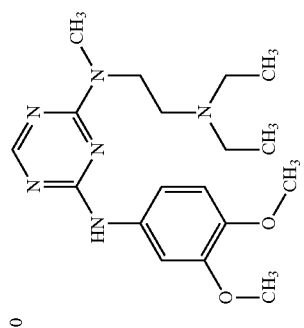
871 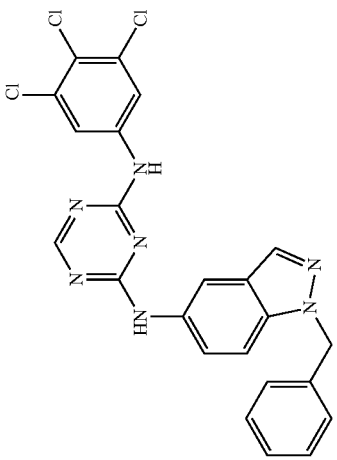
868 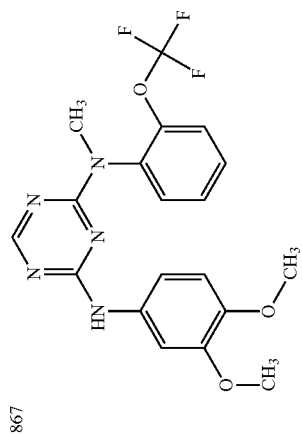
870 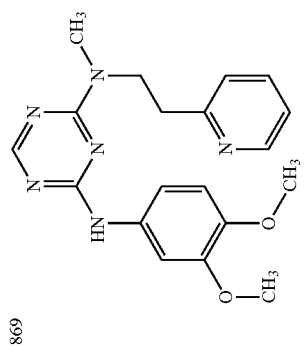
872 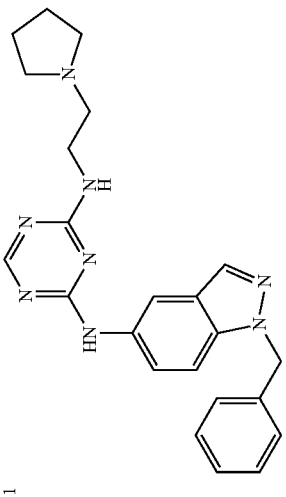

TABLE 1-continued
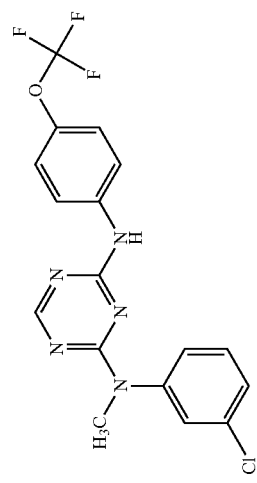
873
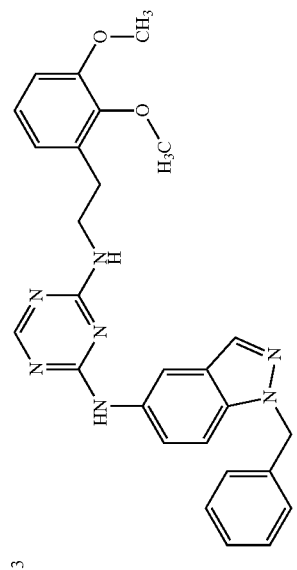
874
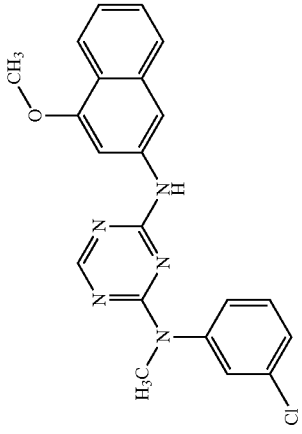
875
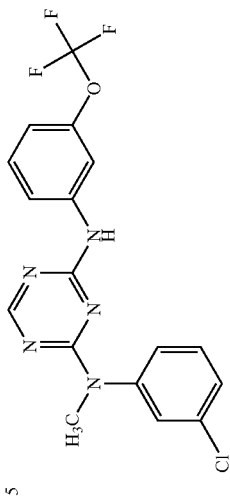
876
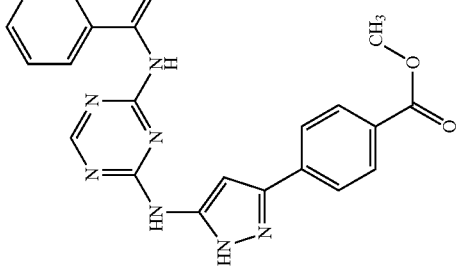
877
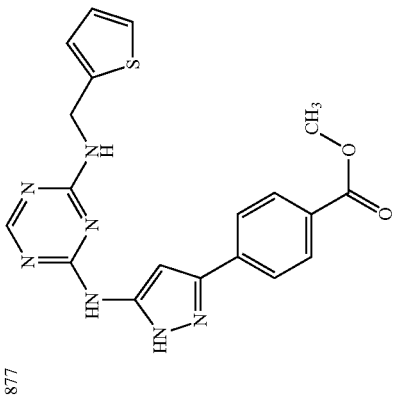
878

TABLE 1-continued
880
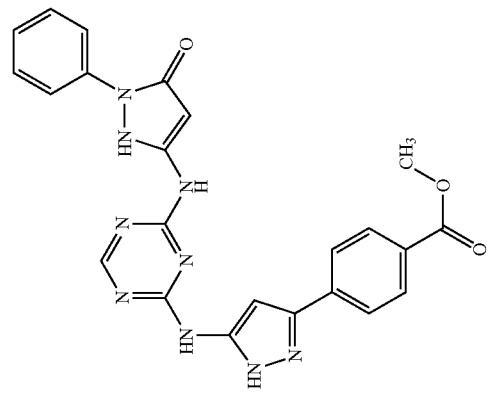
882
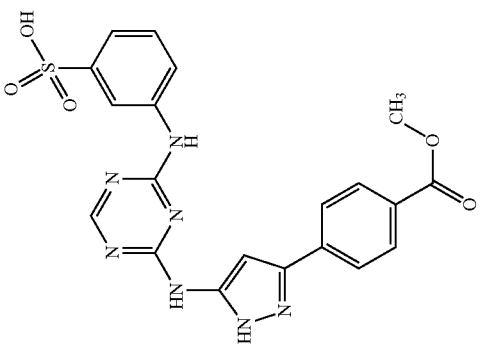
879
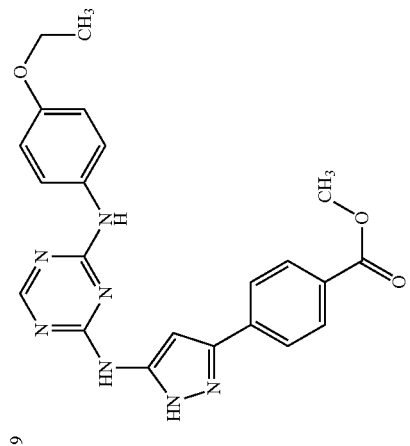
881
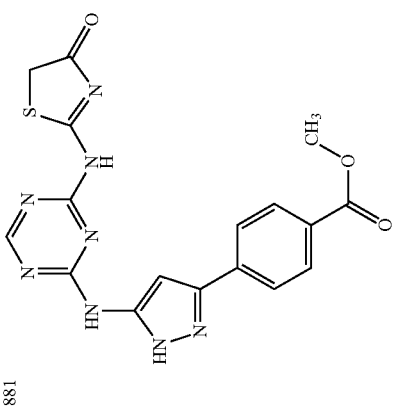

TABLE 1-continued
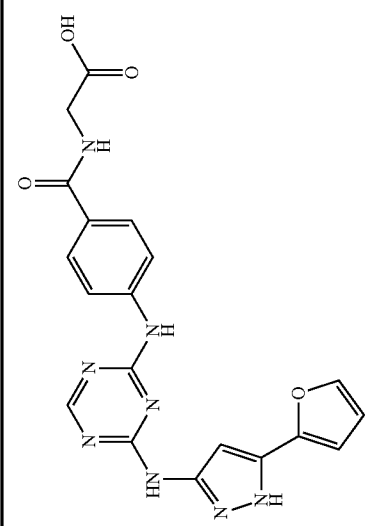
884
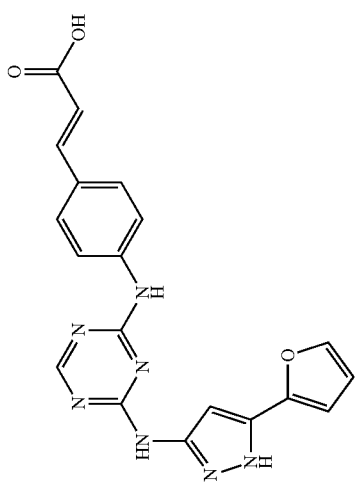
886
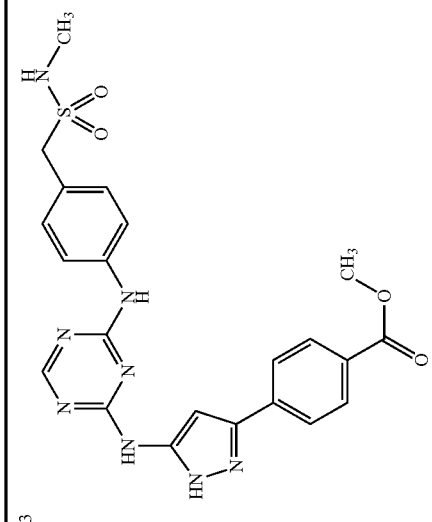
883
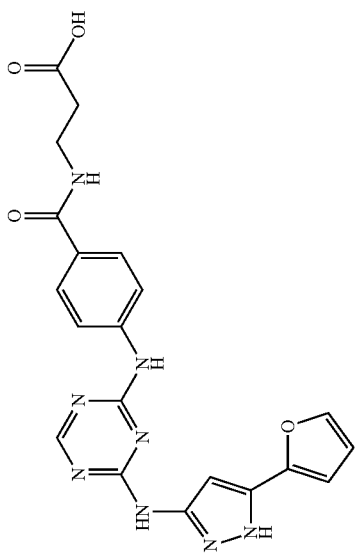
885

TABLE 1-continued

887

888

889

890

TABLE 1-continued

TABLE 1-continued
897
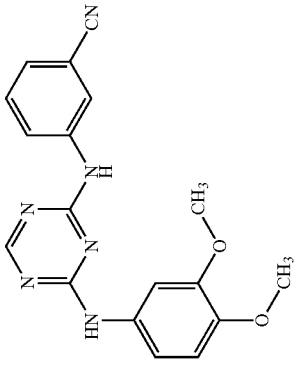
898
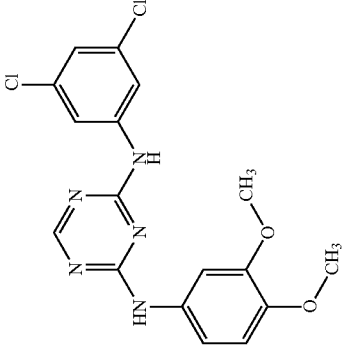
899
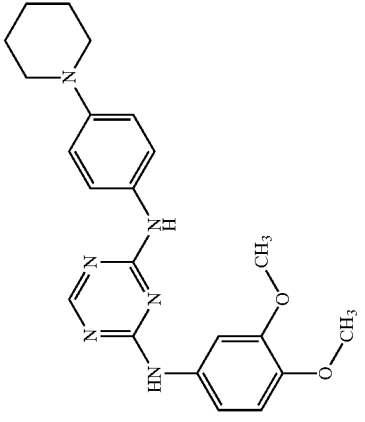
900
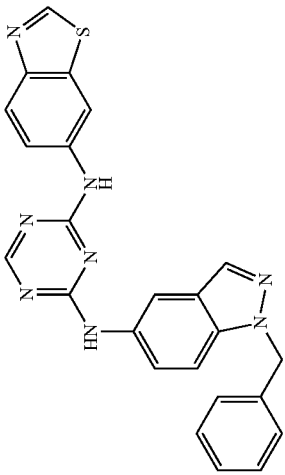
901
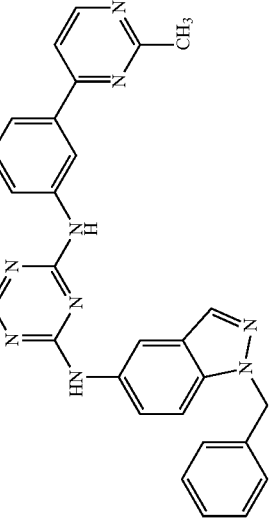
902
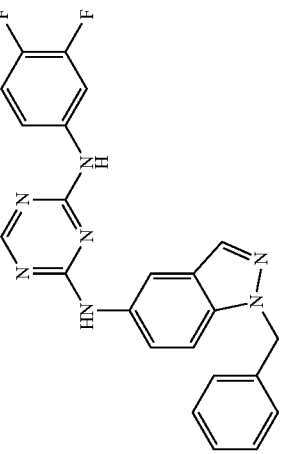

TABLE 1-continued
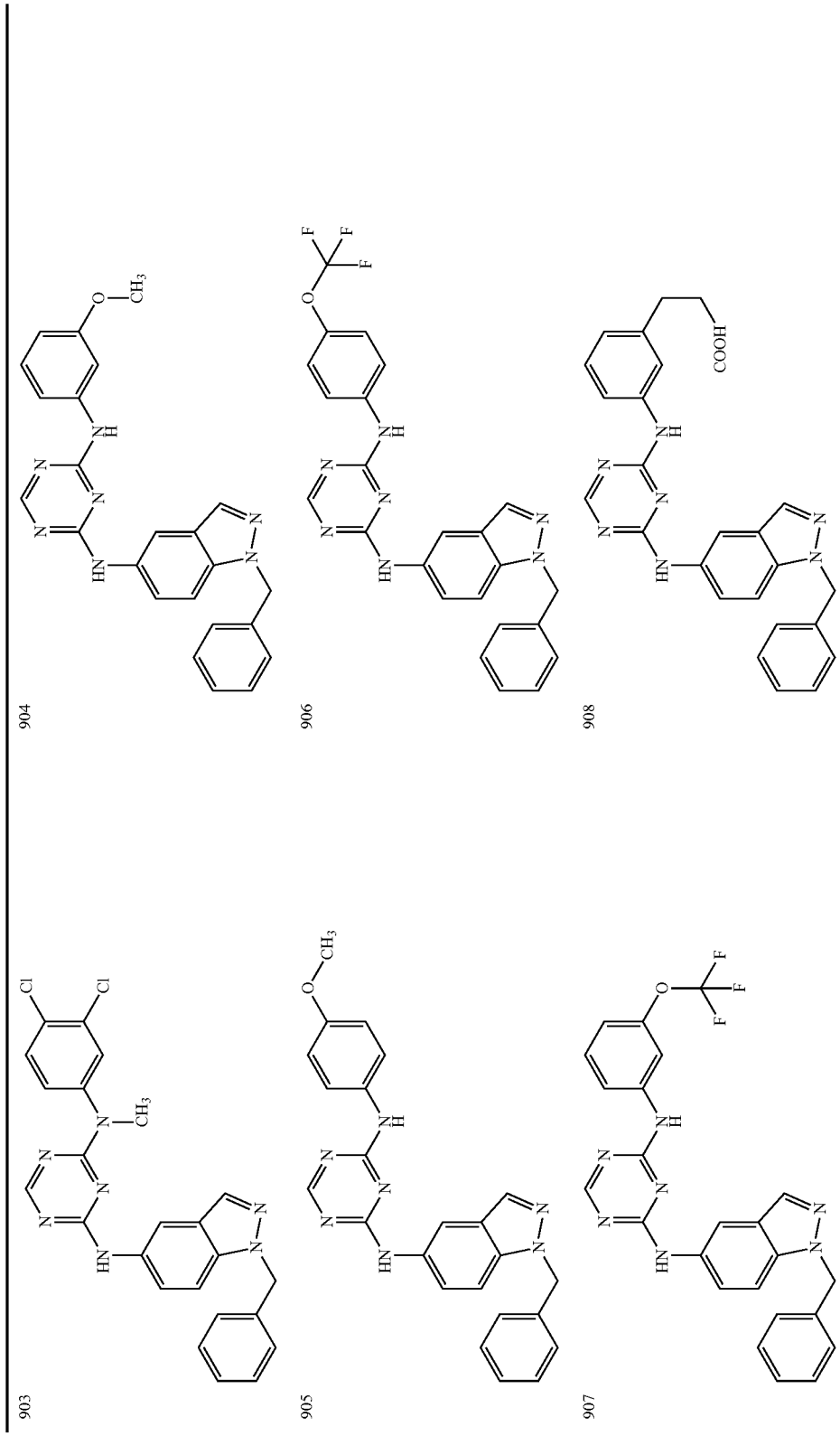

TABLE 1-continued
909 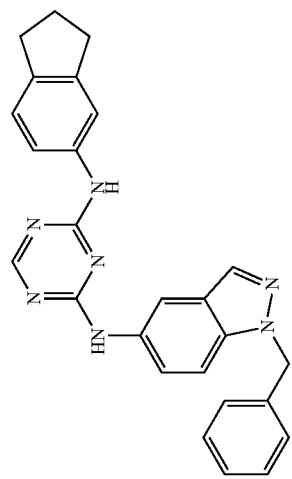
910 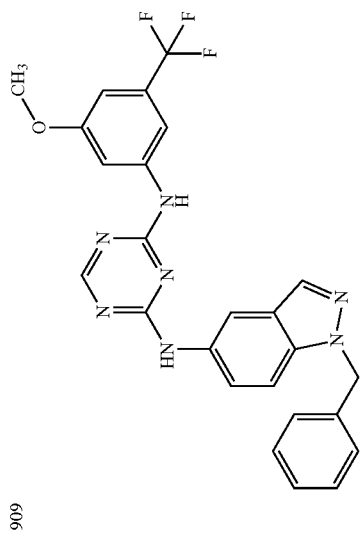
911 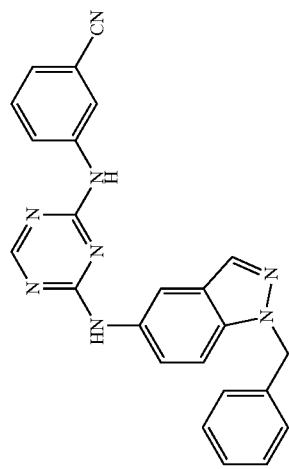
912 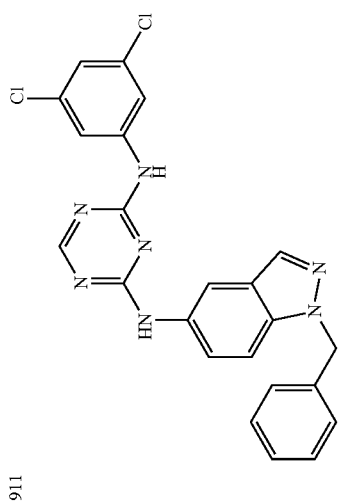
913 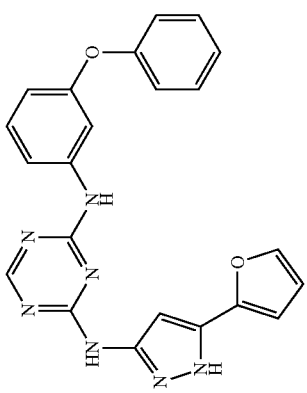
914 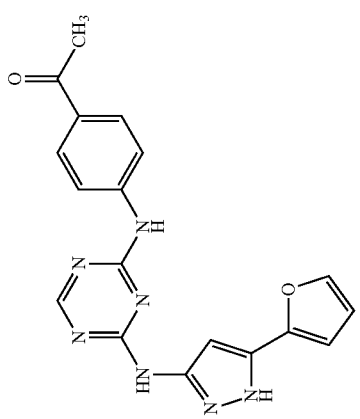

TABLE 1-continued
915 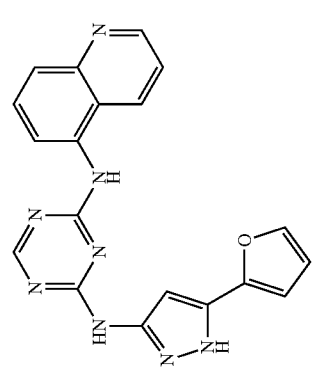
916 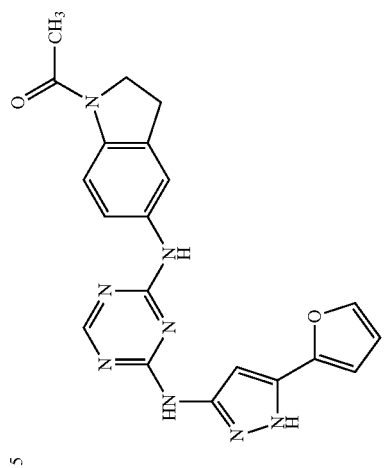
917 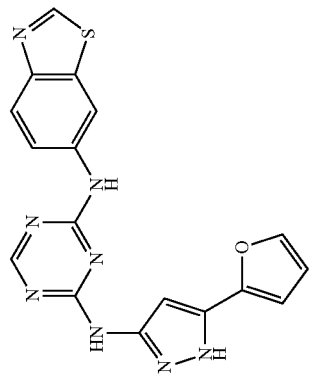
918 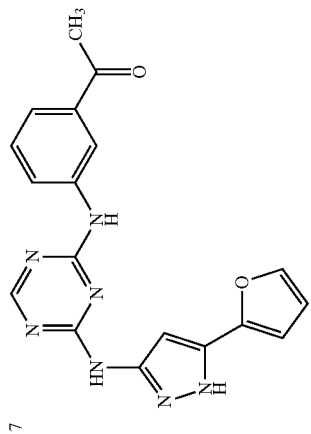
919 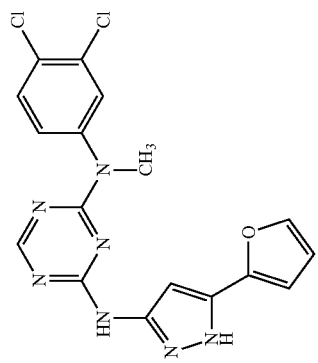
920 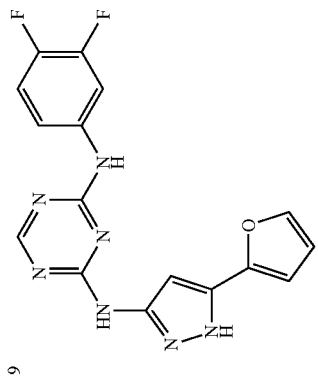

TABLE 1-continued
| 921 | 922 |
|---|---|
| 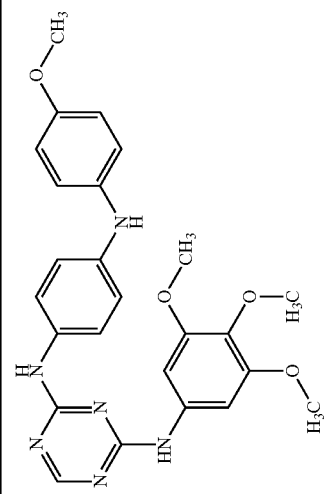 | 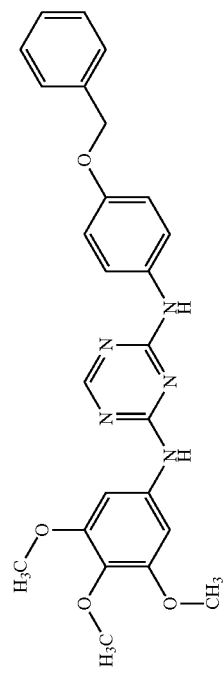 |
| 923 | 924 |
|---|---|
| 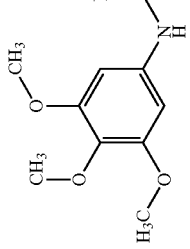 | 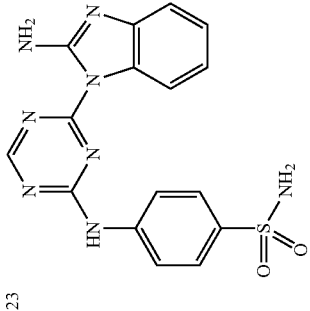 |
| 925 | 926 |
|---|---|
| 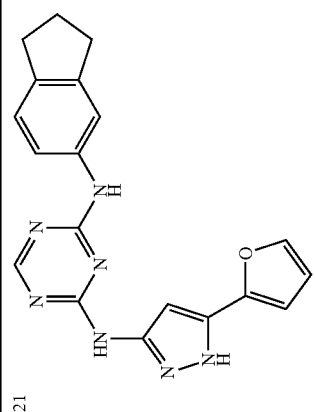 | 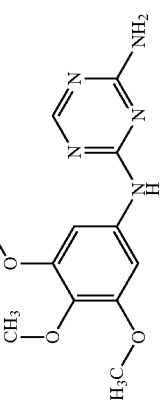 |

TABLE 1-continued

TABLE 1-continued

TABLE 1-continued
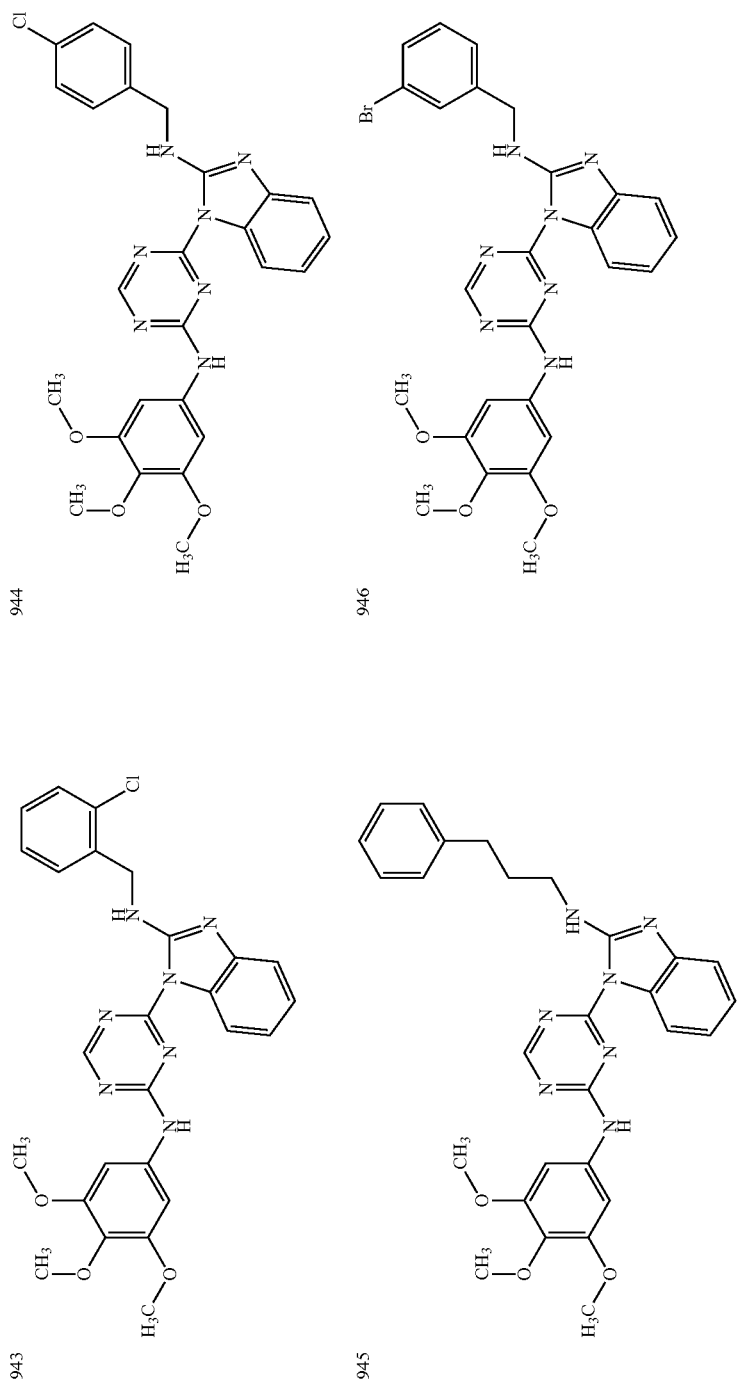

TABLE 1-continued 947, 948, 949, 950, 951, 952

TABLE 1-continued

TABLE 1-continued
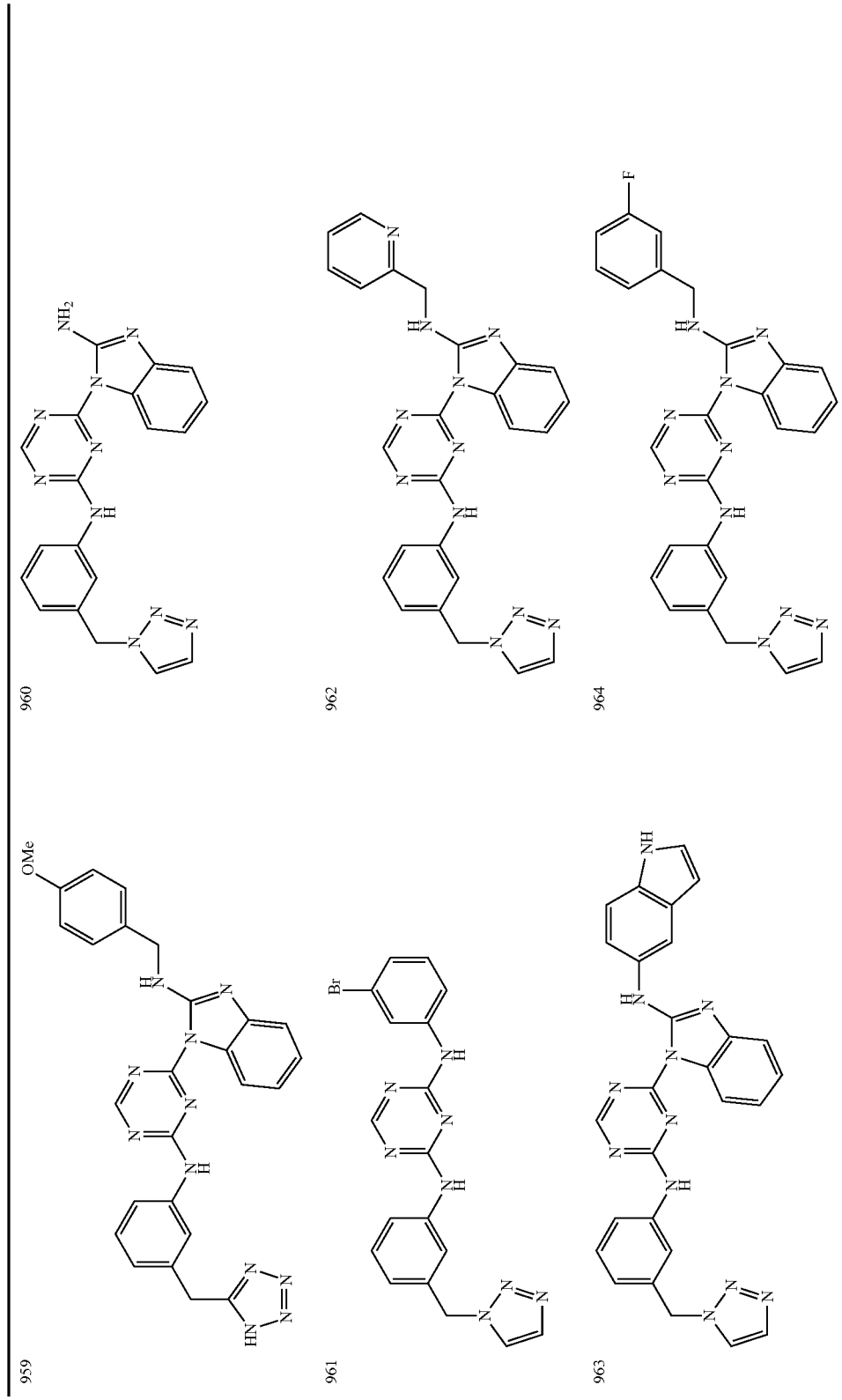

TABLE 1-continued
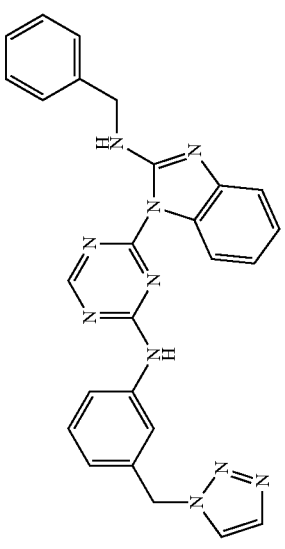
965
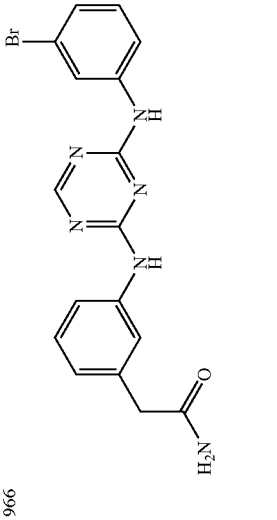
966
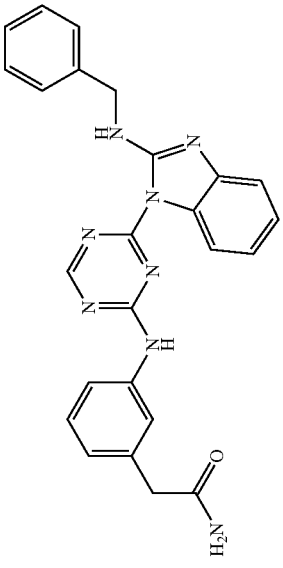
967
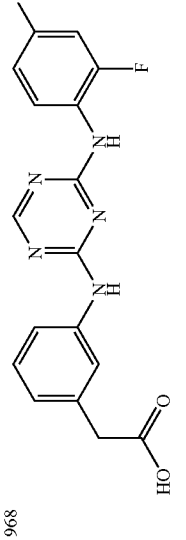
968
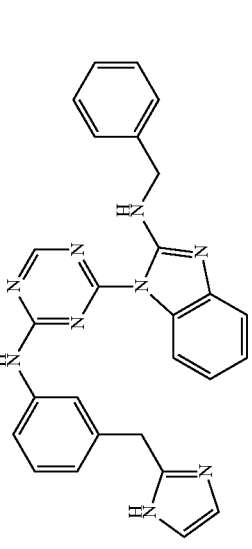
969
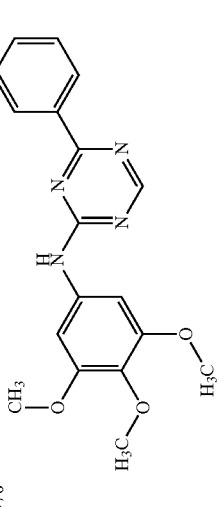
970

TABLE 1-continued

TABLE 1-continued
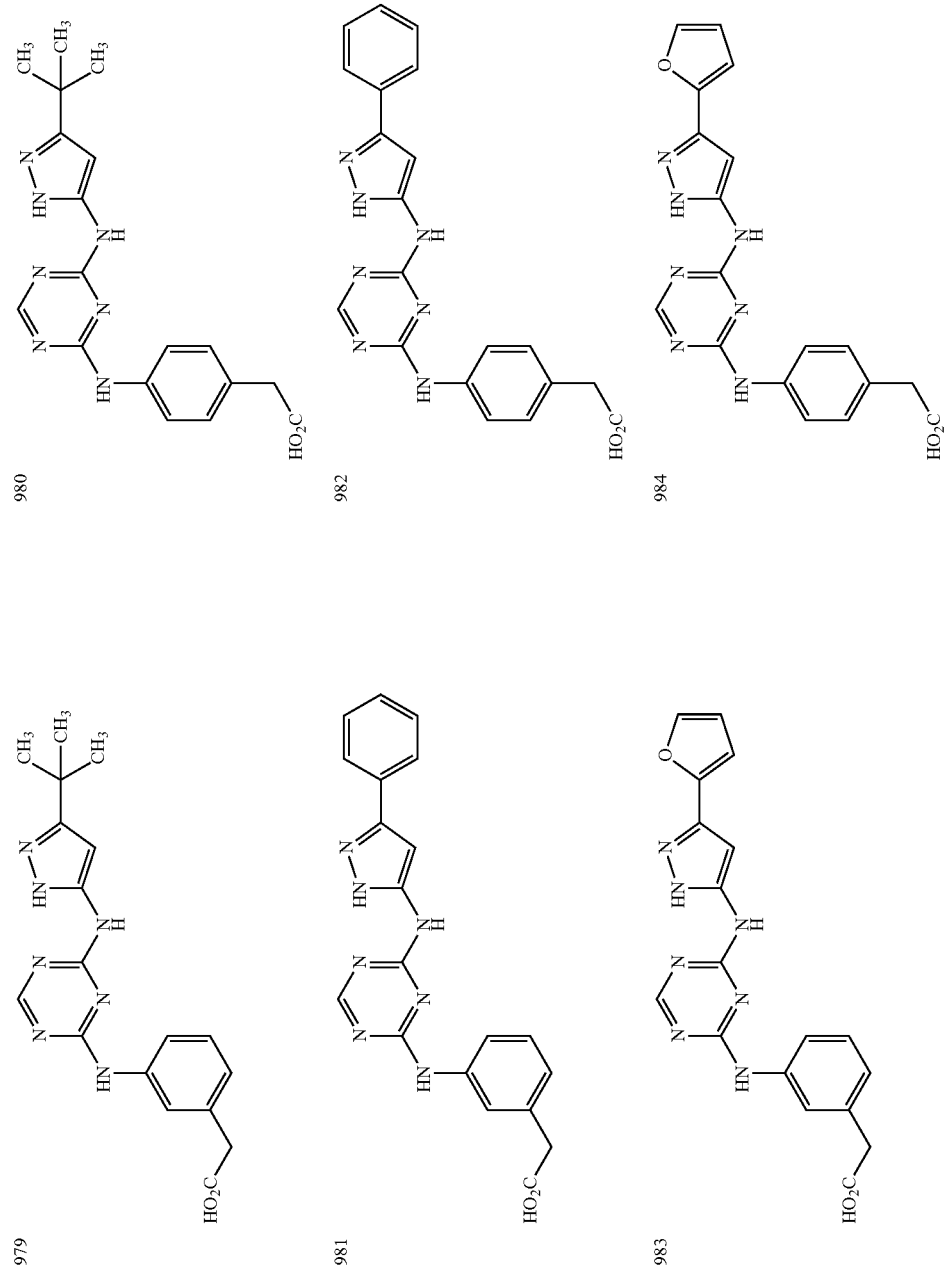

TABLE 1-continued
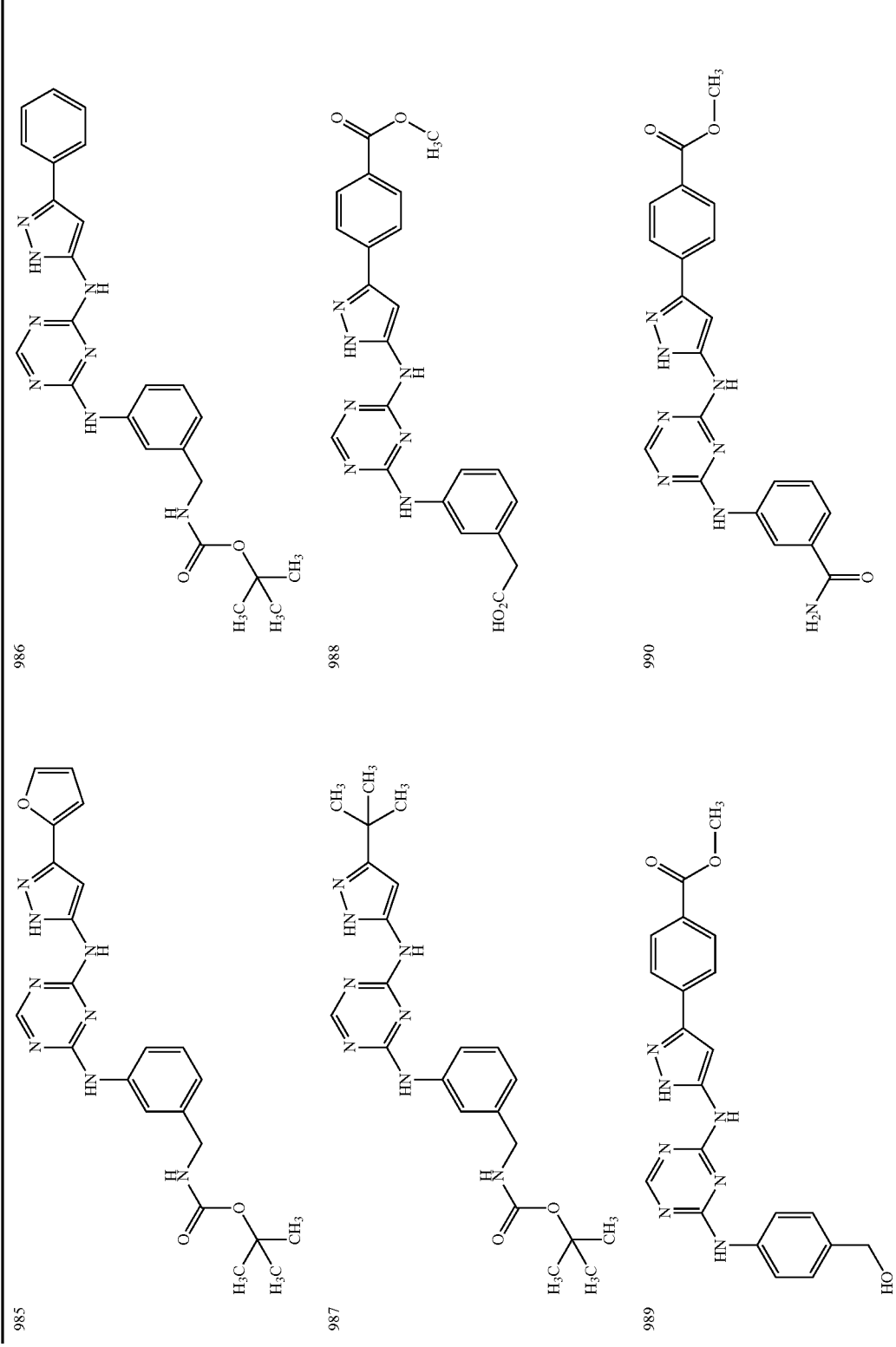

TABLE 1-continued
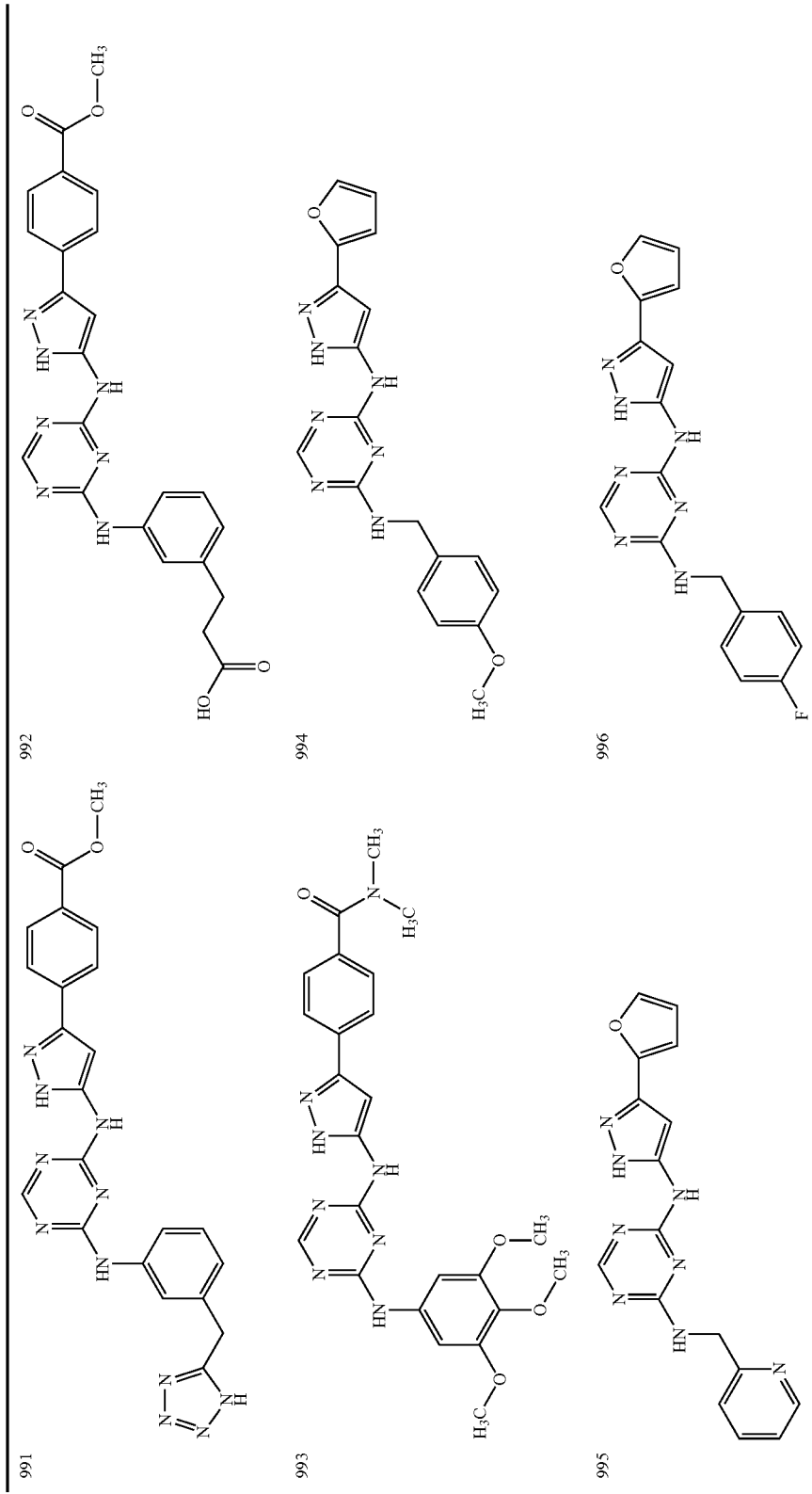

TABLE 1-continued 997, 998, 999, 1000, 1001, 1002

TABLE 1-continued
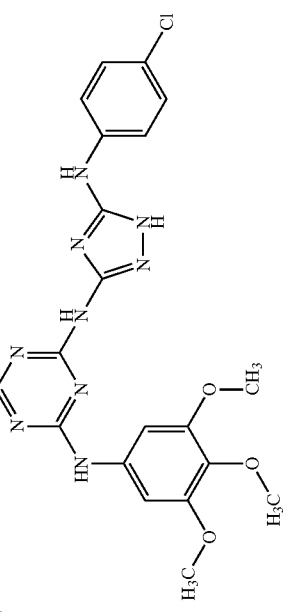
1003
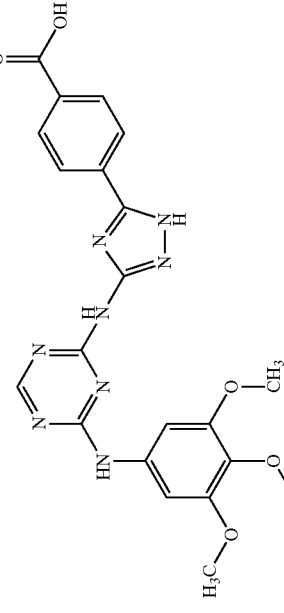
1004
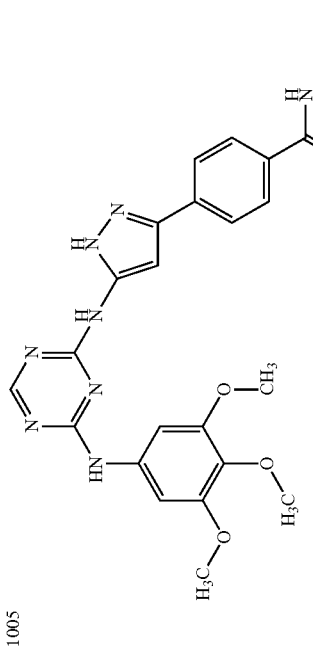
1005
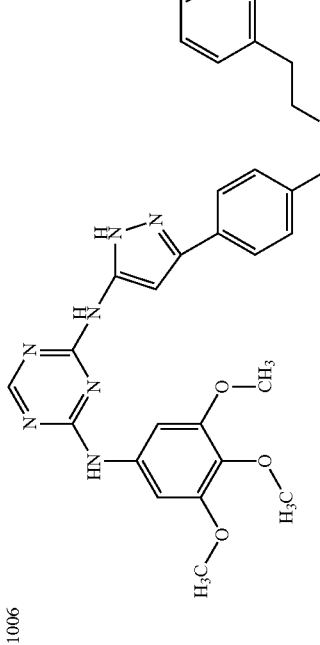
1006
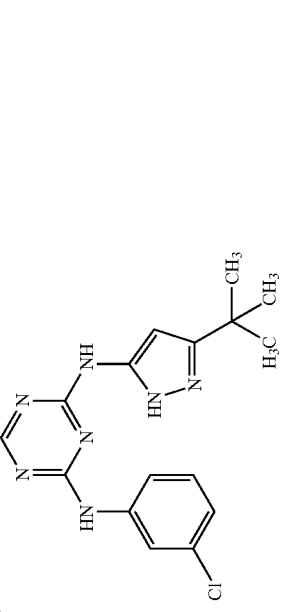
1007
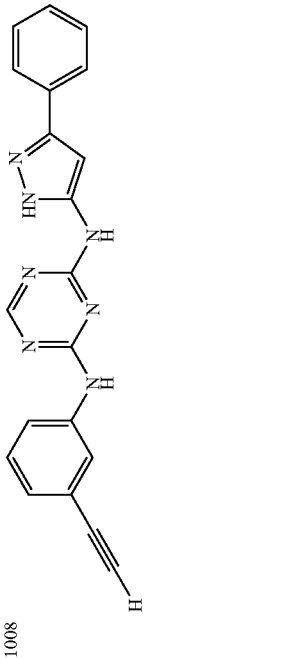
1008

TABLE 1-continued

| 1009 | 1010 |
| 1011 | 1012 |
| 1013 | 1014 |
| 1015 | 1016 |

TABLE 1-continued

TABLE 1-continued 1027, 1028, 1029, 1030, 1031, 1032

TABLE 1-continued
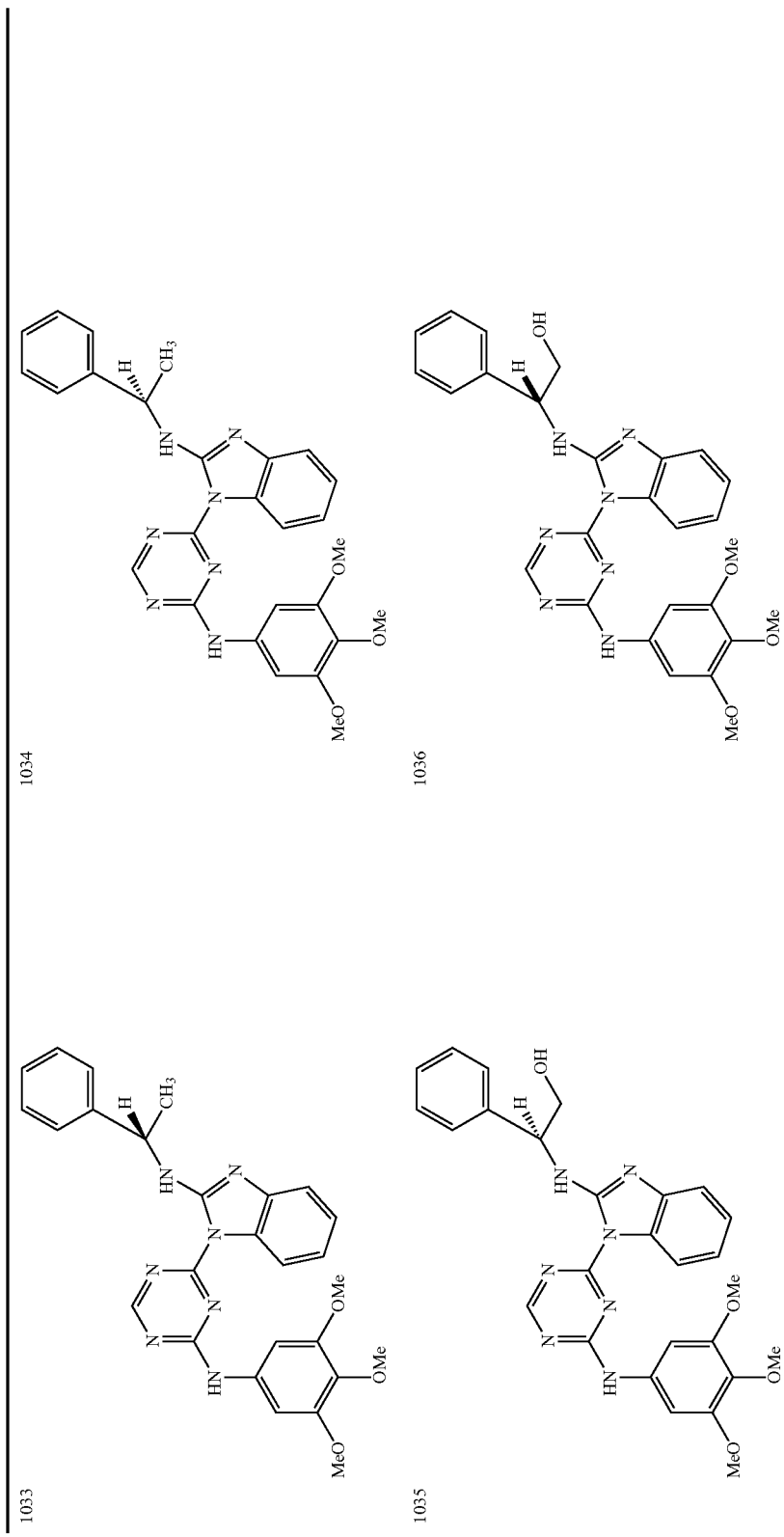

TABLE 1-continued
1038 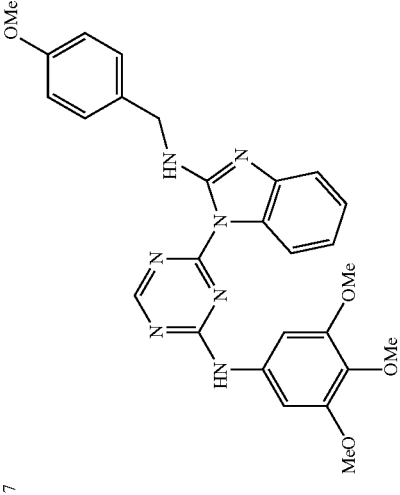
1040 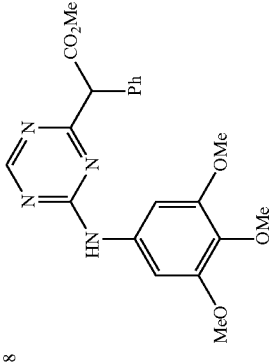
1037 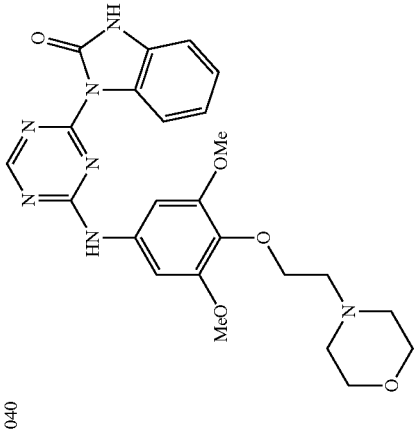
1039 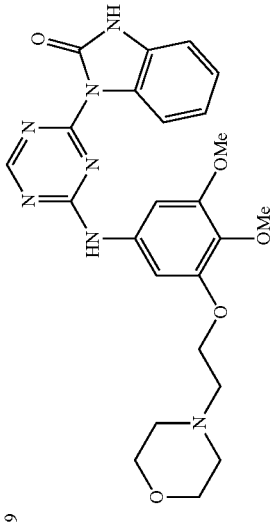

TABLE 1-continued

1041

1042

1043

1044

TABLE 1-continued

1045

1046

1047

1048

TABLE 1-continued

| 1049 | 1050 |
| 1051 | 1052 |
| 1053 | 1054 |

TABLE 1-continued

1055

1056

1057

1058

TABLE 1-continued

1059

1060

1061

1062

TABLE 1-continued

1063

1064

1065

1066

TABLE 1-continued 1067 1068

1069 1070

1071 1072

TABLE 1-continued
| 1073 | 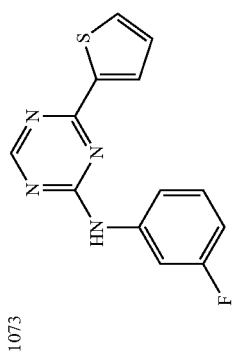 |
| 1074 | 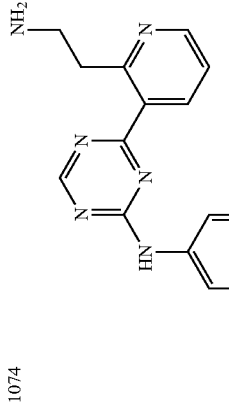 |
| 1075 | 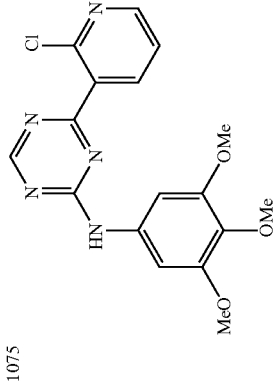 |
| 1076 | 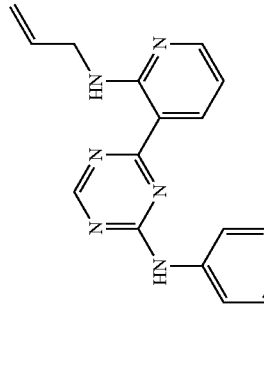 |
| 1077 | 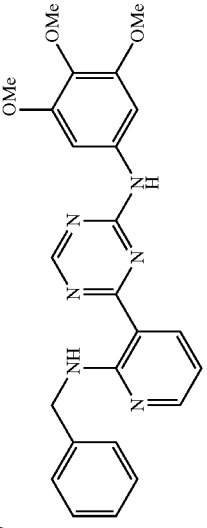 |
| 1078 | 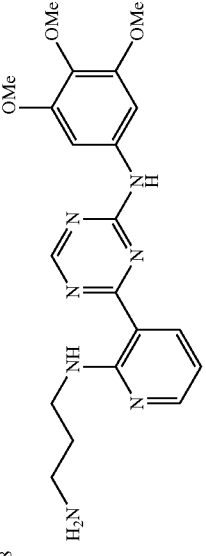 |

TABLE 1-continued

TABLE 1-continued

TABLE 1-continued

TABLE 1-continued
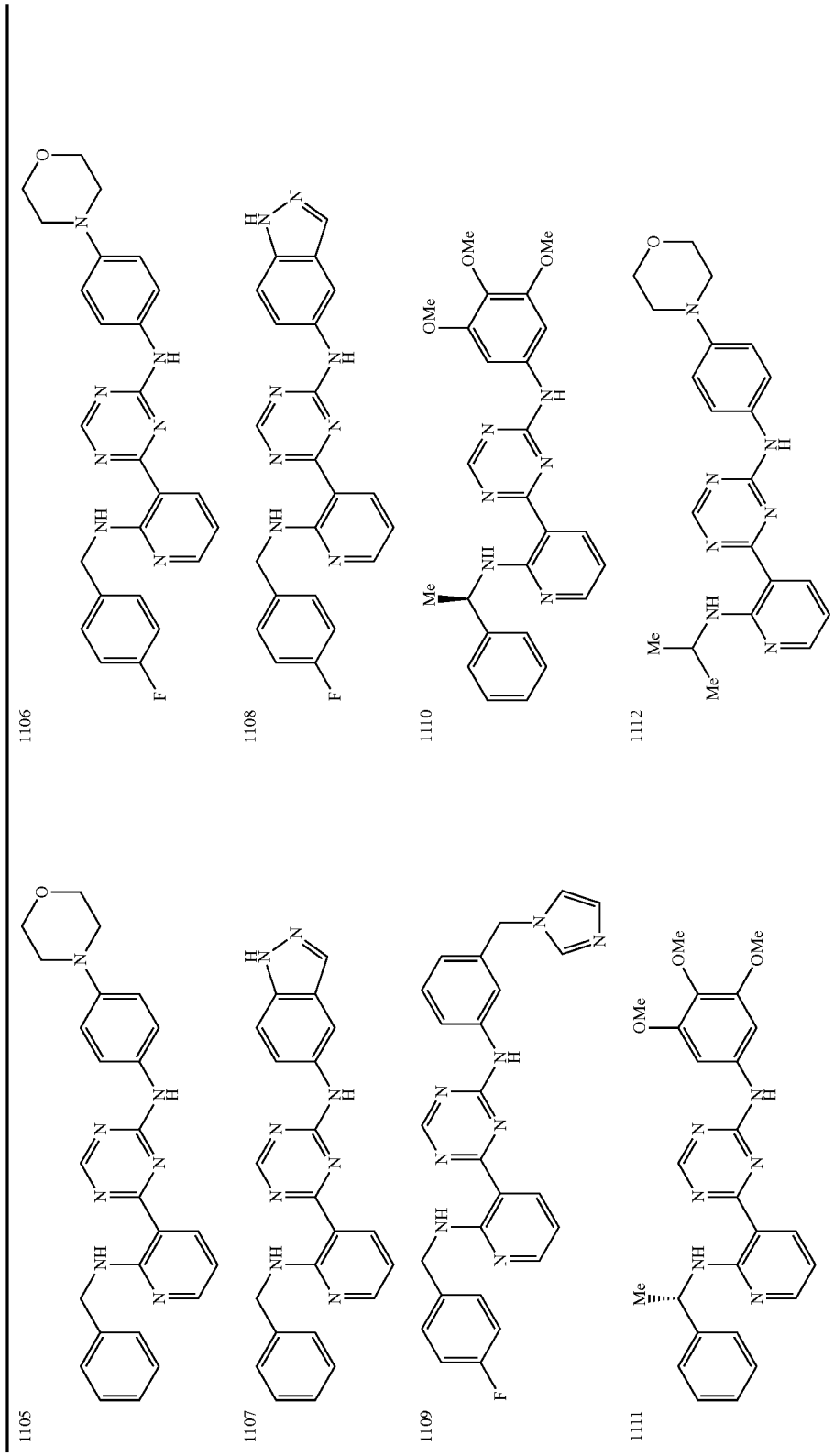

TABLE 1-continued

| 1113 | 1114 |
| 1115 | 1116 |
| 1117 | 1118 |

TABLE 1-continued

TABLE 1-continued

| | |
|---|---|
| 1127 | 1128 |
| 1129 | 1130 |
| 1131 | 1132 |
| 1133 | 1134 |
| 1135 | 1136 |

TABLE 1-continued

| 1137 | 1138 |
| 1139 | 1140 |
| 1141 | 1142 |
| 1143 | 1144 |

TABLE 1-continued
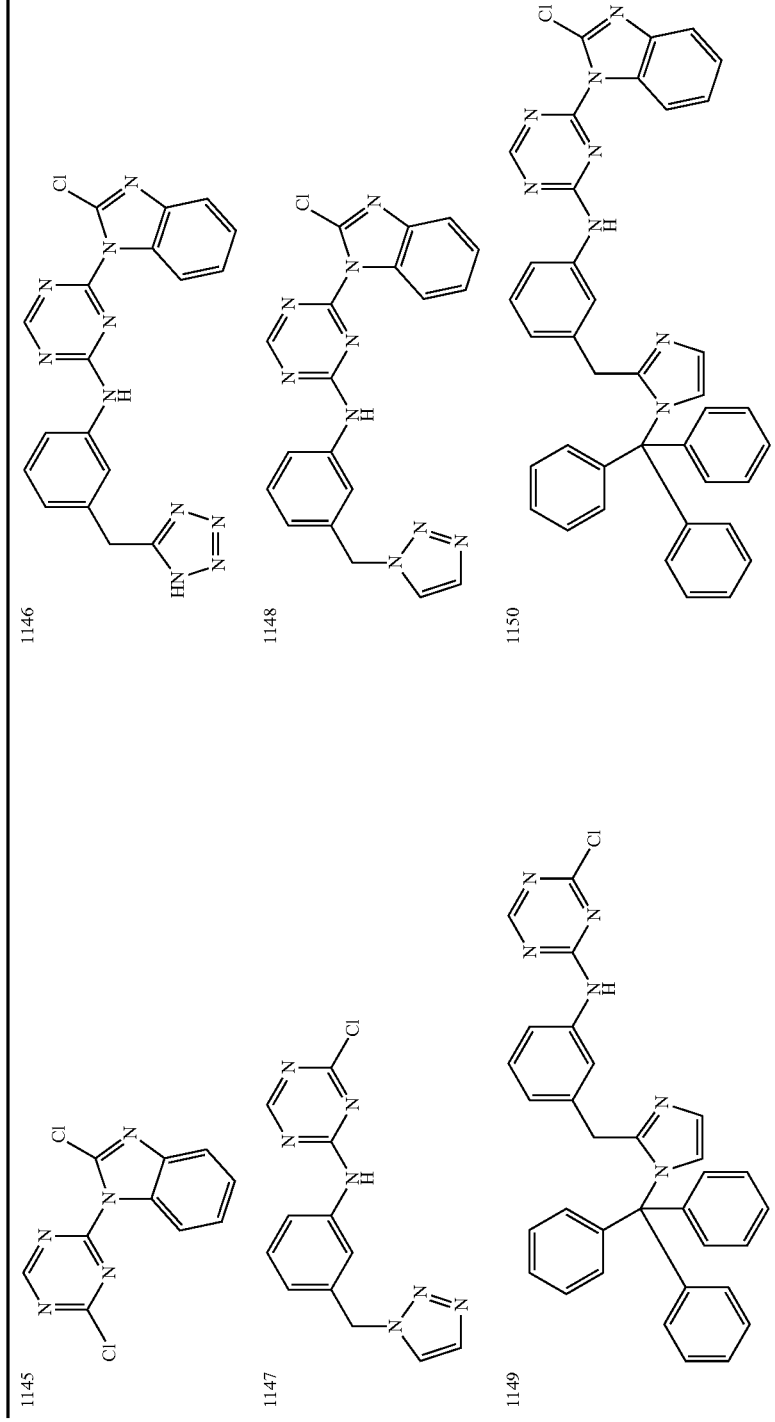

TABLE 1-continued

| 1151 | 1152 |
| --- | --- |
| | 1154 |
| | 1156 |
| | 1158 |
| 1153 | |
| 1155 | |
| 1157 | |

TABLE 1-continued
| 1159 | 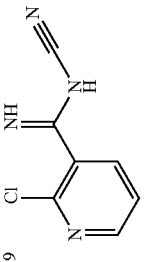 | 1160 | 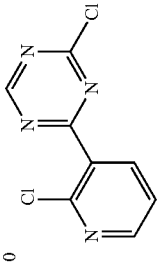 |
| 1161 | 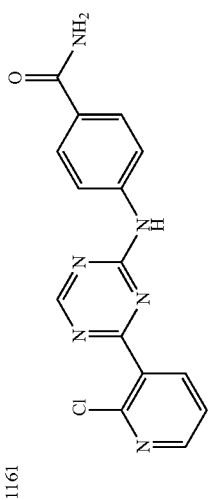 | 1162 | 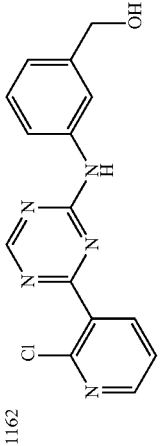 |
| 1163 | 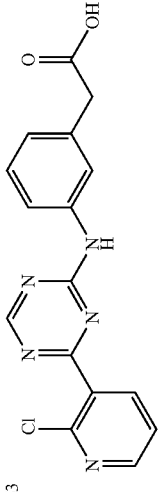 | 1164 | 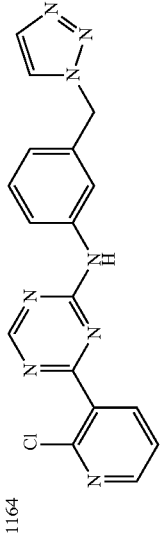 |
| 1165 | 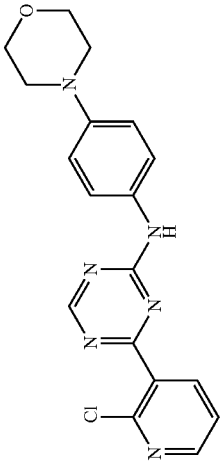 | 1166 | 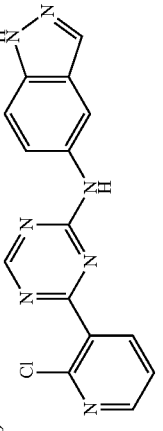 |

TABLE 1-continued

TABLE 1-continued

TABLE 1-continued

| 1181 | 1182 | 1183 | 1184 | 1185 | 1186 |

TABLE 1-continued

| 1187 | 1188 |
| 1189 | 1190 |
| 1191 | 1192 |

TABLE 1-continued

TABLE 1-continued
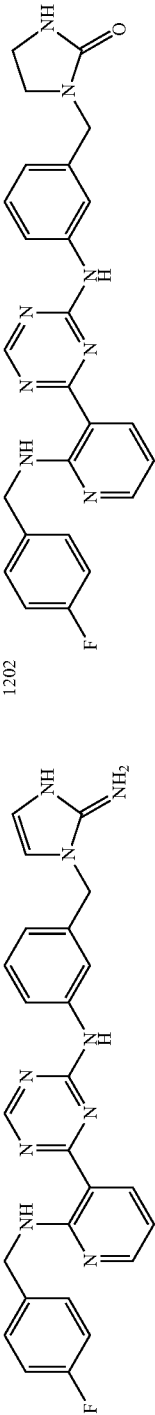

TABLE 1-continued
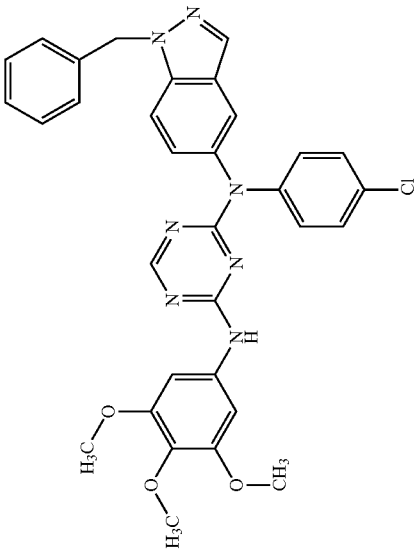
1208
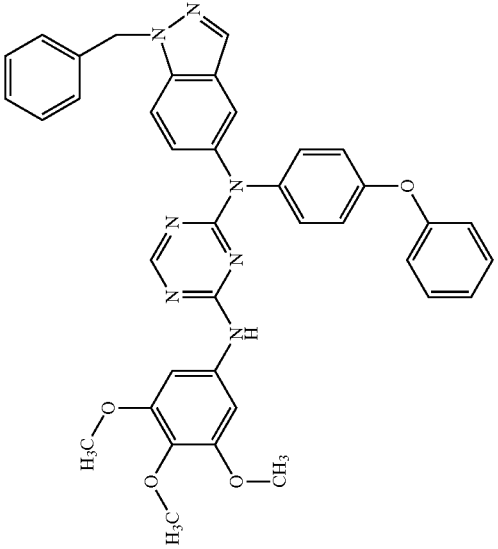
1210
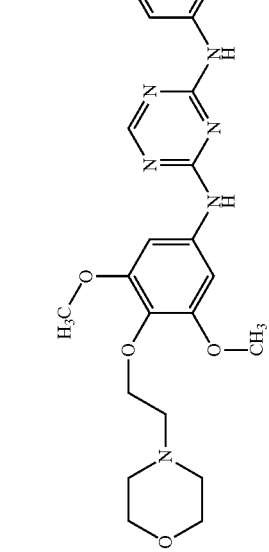
1207
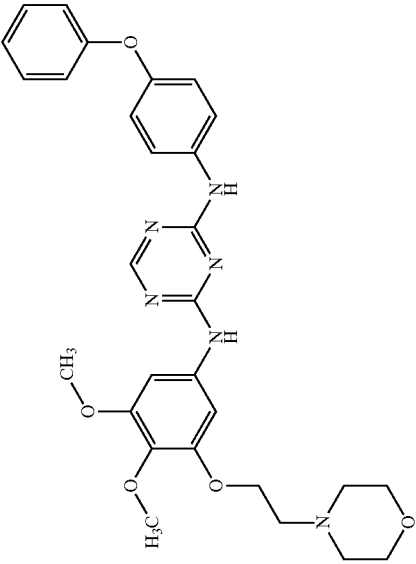
1209

TABLE 1-continued

1211

1212

1213

1214

TABLE 1-continued

| 1215 | 1216 | 1217 | 1218 | 1219 | 1220 |

TABLE 1-continued
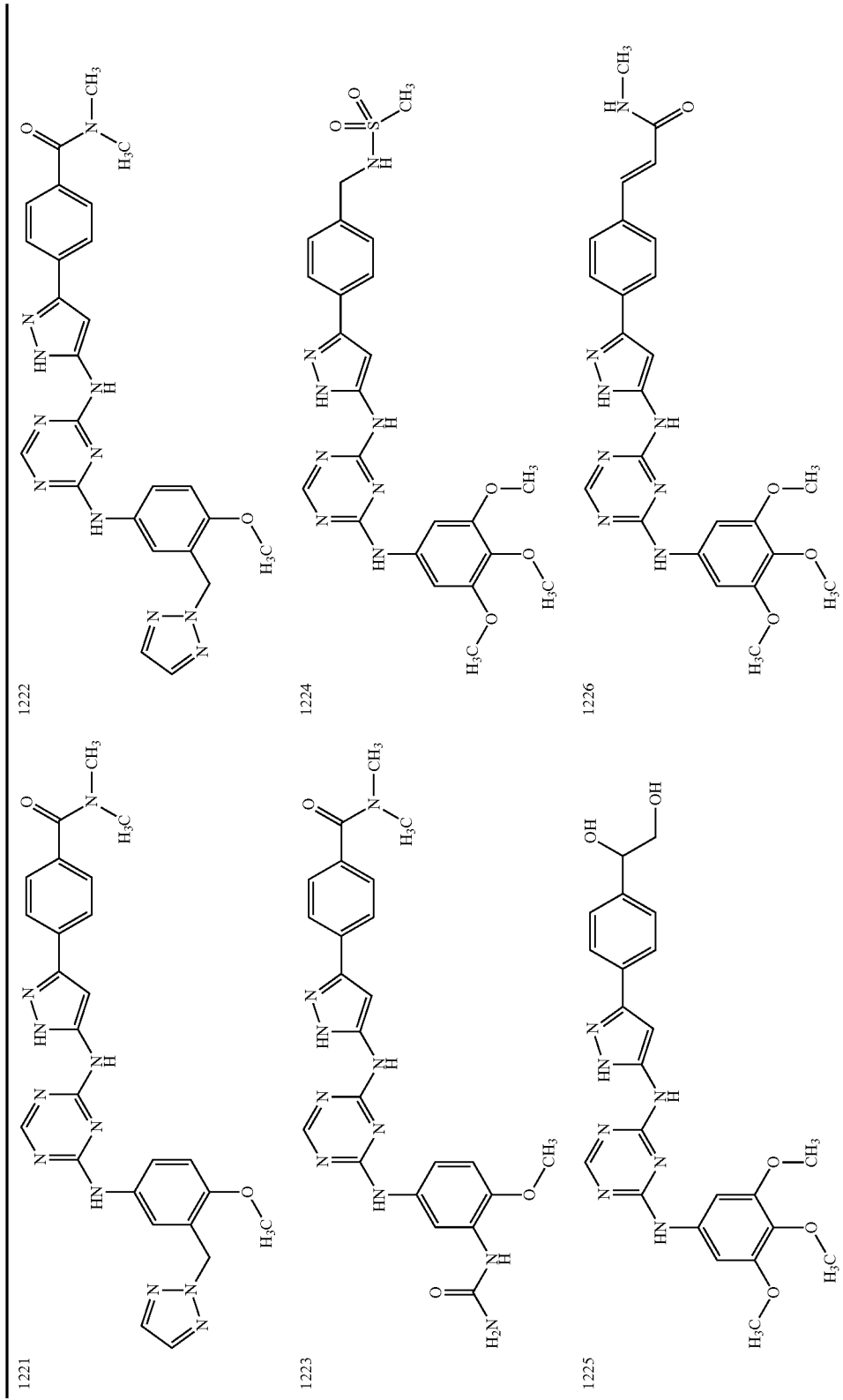

TABLE 1-continued
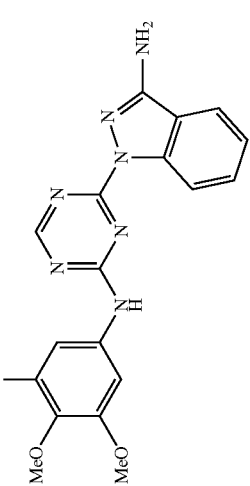
1227
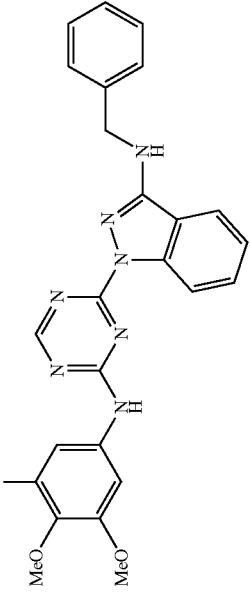
1228
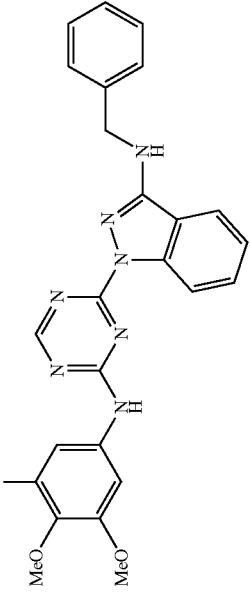
1229
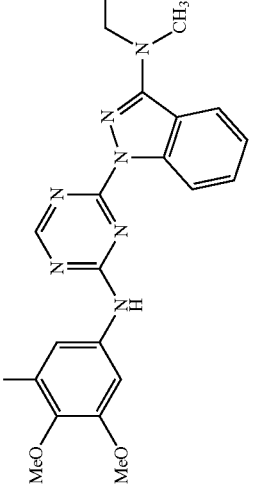
1230
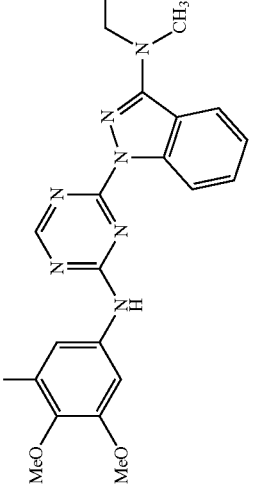
1231
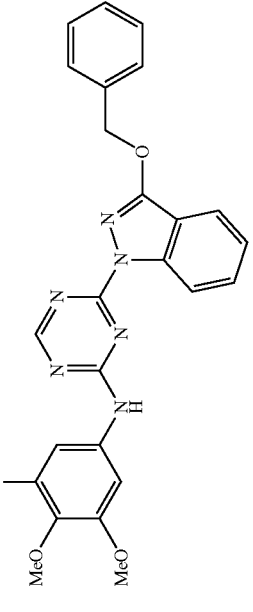
1232

TABLE 1-continued

TABLE 1-continued
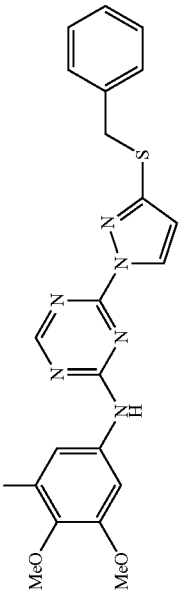
1241
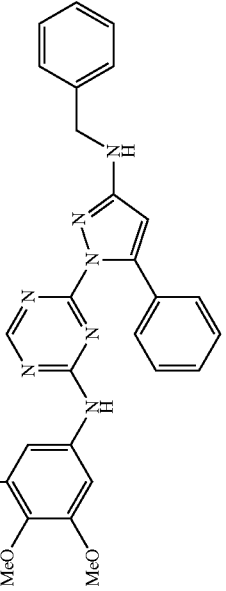
1242
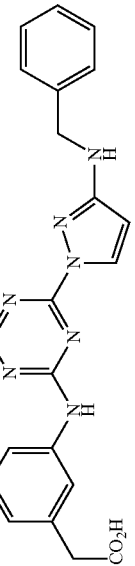
1243
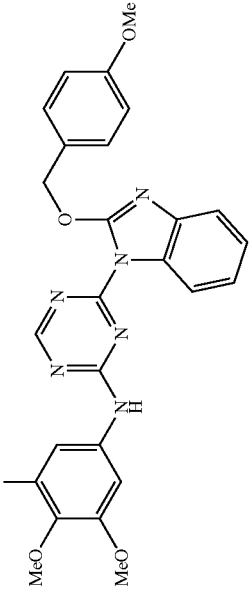
1244
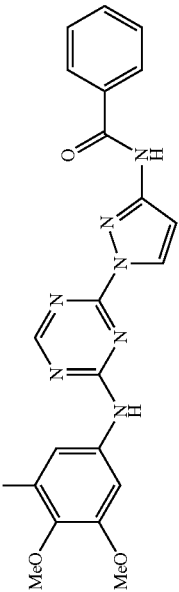
1245
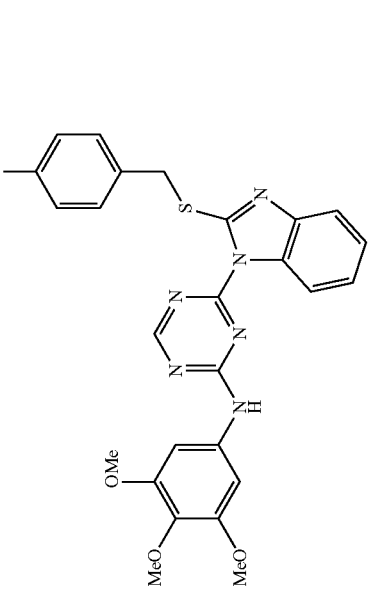
1246

TABLE 1-continued
| 1247 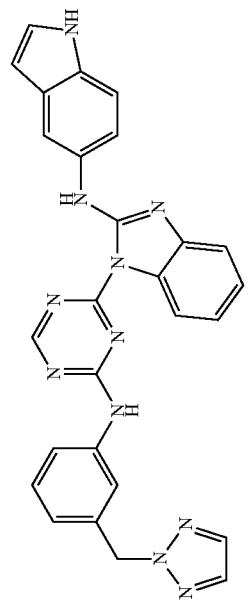 | 1248 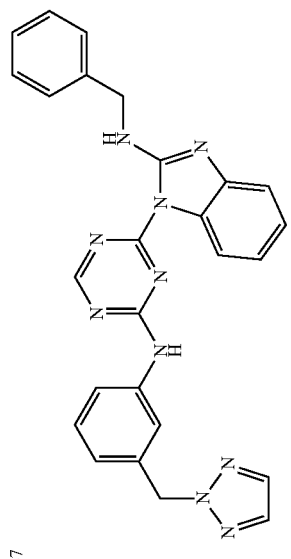 |
| --- | --- |
| 1249 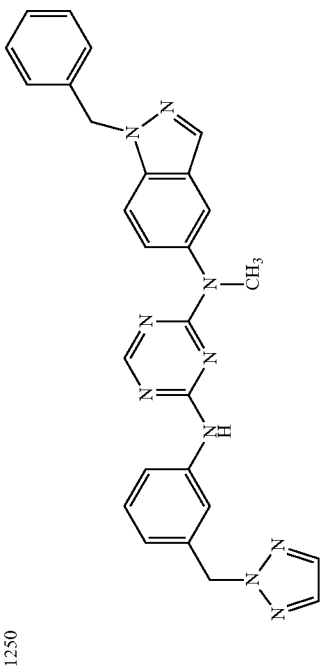 | 1250 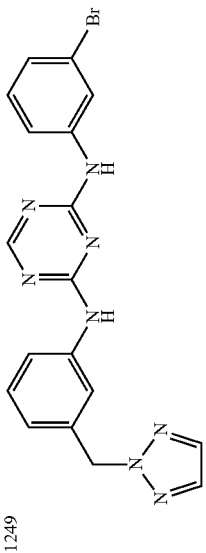 |
| 1251 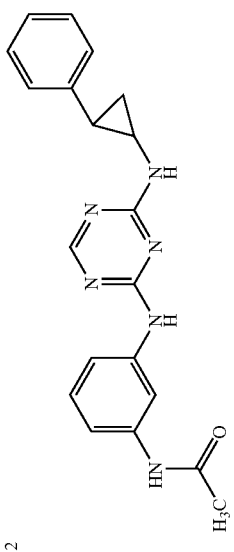 | 1252 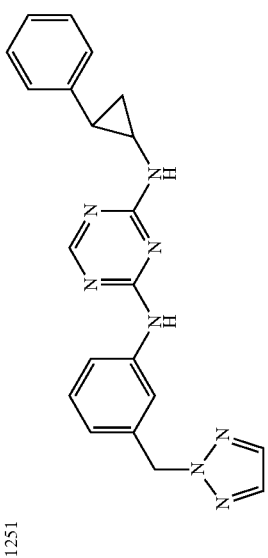 |

TABLE 1-continued
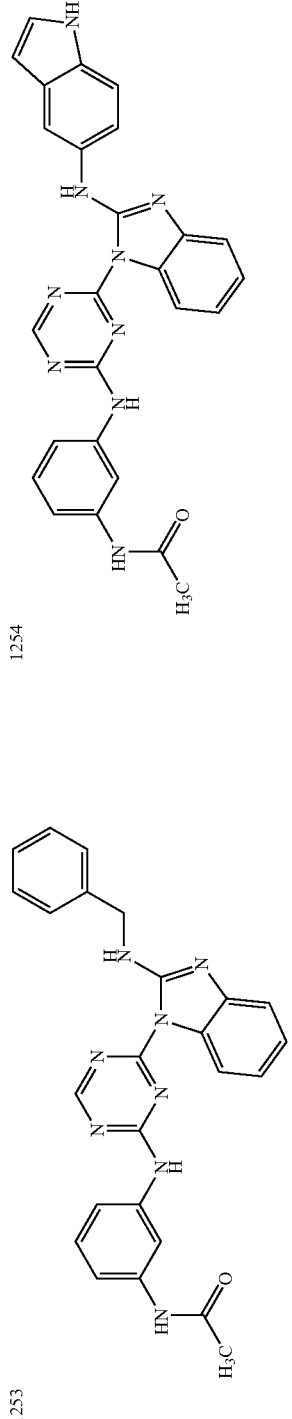
1253
1255
1257
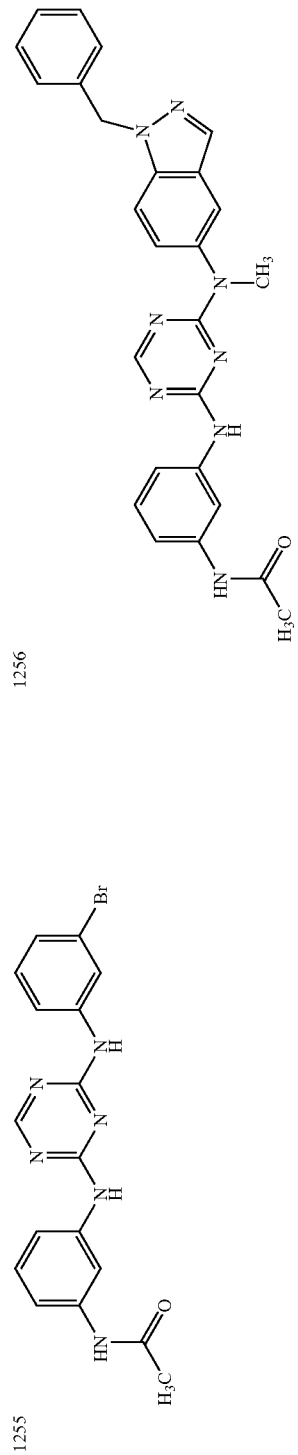
1254
1256
1258
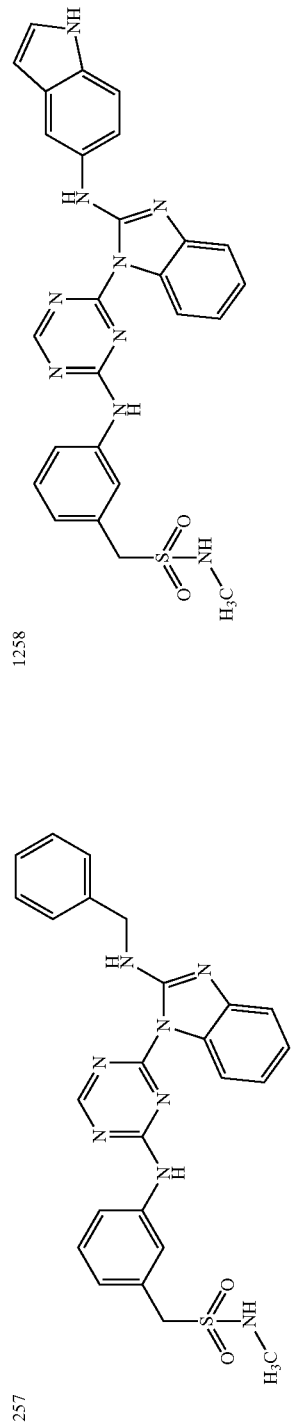

TABLE 1-continued 1259
1260
1261
1262
1263
1264

TABLE 1-continued

| 1265 | 1266 |
| 1267 | 1268 |
| 1269 | 1270 |

TABLE 1-continued
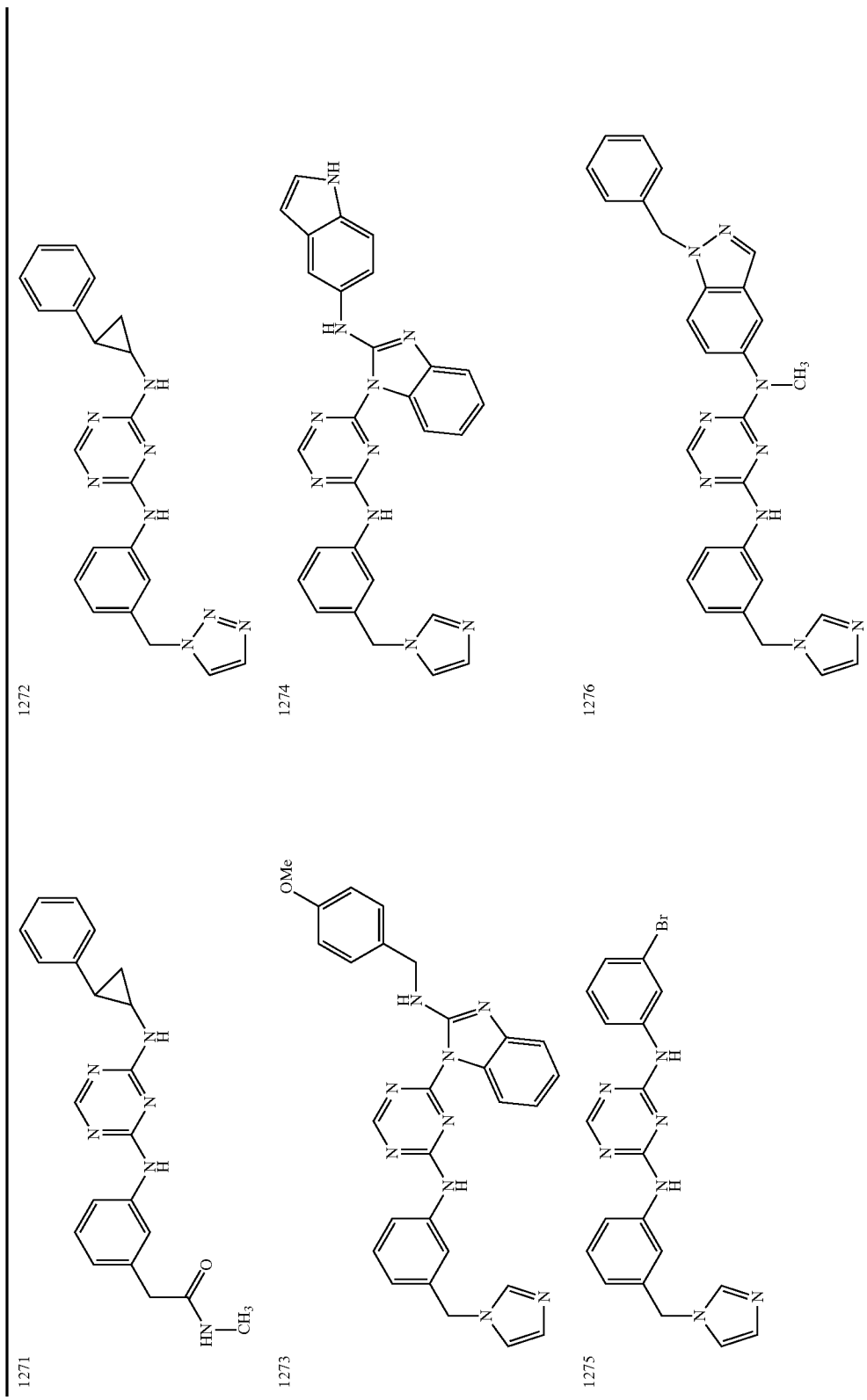

TABLE 1-continued
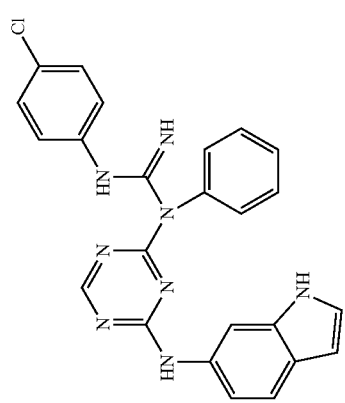
1277
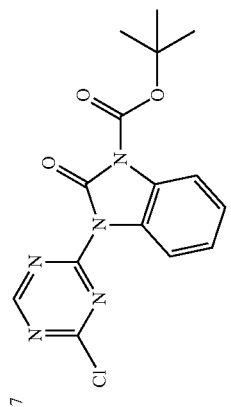
1278
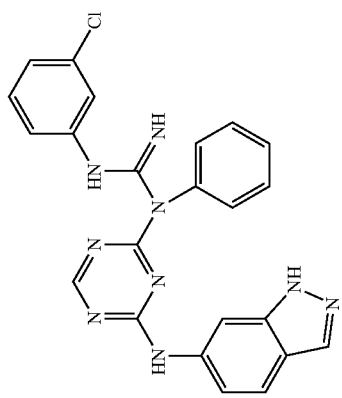
1279
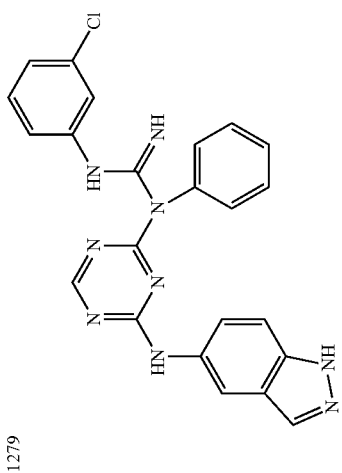
1280
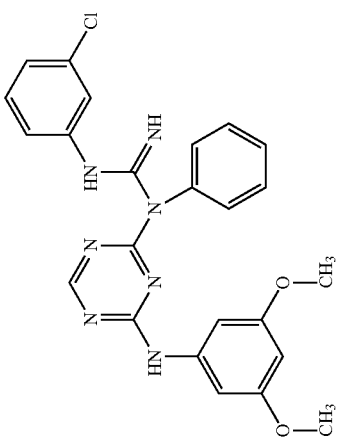
1281
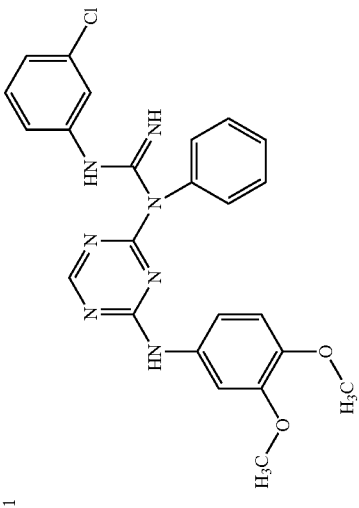
1282

TABLE 1-continued 1283, 1284, 1285, 1286, 1287, 1288

TABLE 1-continued

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of excessive moisture for at least one week.

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

The compounds of this invention may be synthesized using conventional techniques. Advantageously, these compounds are conveniently synthesized from readily available starting materials. In general, the compounds of the formulae described herein are conveniently obtained via methods illustrated in General Synthetic Schemes 1–2 and the Examples herein. These general schemes are also exemplified by the specific methods described in the Examples section below. General Synthetic Schemes 1–2 and the examples utilize general chemical group descriptors (e.g., X, $R^3$, $R^5$) that are meant to be representative of any group suitable for synthesis of the compounds delineated herein. Such groups are exemplified by and include, but are not limited to, those defined in the definitions of the groups designated $R^3$, $R^4$, $R^5$, $R^{16}$, $R^{17}$, and $R^{20}$, for example, in the formulae herein.

Thus, one embodiment relates to a method of making a compound of the formulae described herein, comprising synthesizing any one or more intermediates illustrated in the synthetic schemes herein and then converting that internediate(s) to a compound of the formulae described herein. Another embodiment relates to a method of making a compound of the formulae described herein, comprising synthesizing any one or more intermediates illustrated in the examples herein and then converting that internediate(s) to a compound of the formulae described herein. Nucleophilic agents are known in the art and are described in the chemical texts and treatises referred to herein. The chemicals used in the aforementioned methods may include, for example, solvents, reagents, catalysts, protecting group and deprotecting group reagents and the like. The methods described above may also additionally comprise steps, either before or after the steps described specifically herein, to add or remove suitable protecting groups in order to ultimately allow synthesis of the compound of the formulae described herein.

General Synthetic Scheme 1

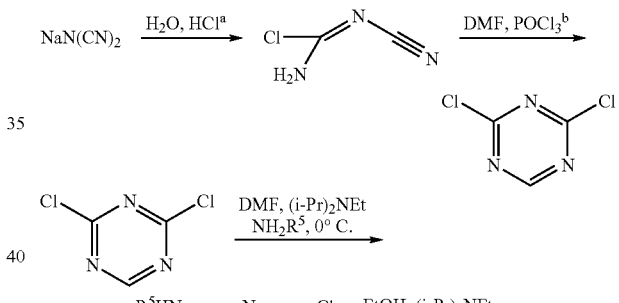

Further Variations[e]:

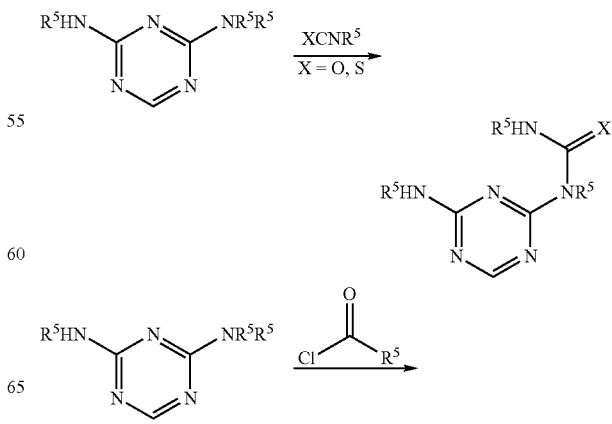

-continued

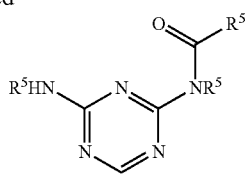

a. E. Allenstein, Z. Anorg. Allgem. Chem., 322, 265 (1963).
b. R. L. N. Harris, Synthesis, 11, 907 (1981).
c. See also, Chemistry of Heterocyclic Compounds, 23, 3, 298–304 (1987).
d. For example, reaction of an appropriate nucleophile (e.g. ROH, RSH, etc.) with a suitable base results in the desired product (e.g. ether, thioether, etc.).

General Synthetic Scheme 2

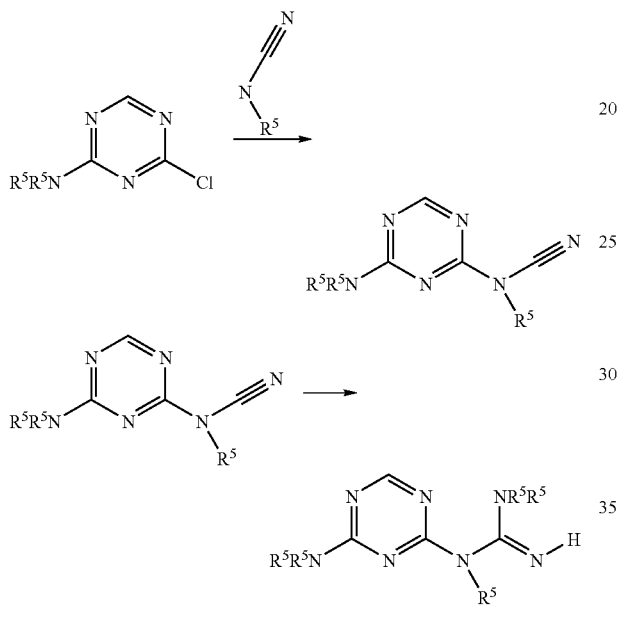

In one embodiment, the invention relates to a process for making a compound of any of the formulae described herein, comprising reacting a triazine of one or more of the formulae:

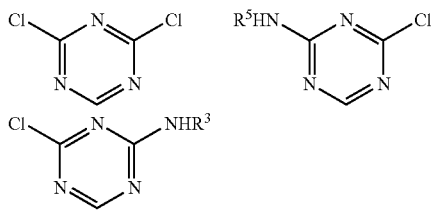

with an appropriate nucleophilic agent or agents, wherein the groups in said formulae are as defined herein.

In one embodiment, the invention relates to a process for making a compound of any of the formulae described herein, comprising reacting a triazine of one or more of the formulae:

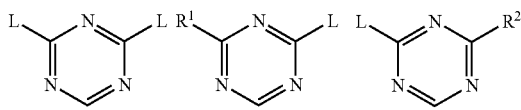

with an appropriate nucleophilic agent or agents, wherein L is defined as a leaving group and the groups in said formulae are as defined herein.

In one embodiment, the invention relates to a process for making a compound of the formula

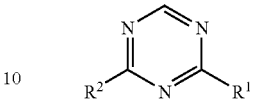

wherein

Each $R^1$ and $R^2$ is independently $R^3$; $R^8$; $NHR^3$; $NHR^5$; $NHR^6$; $NR^5R^5$; $NR^5R^6$; $SR^5$; $SR^6$; $SR^3$; $OR^5$; $OR^6$; $OR^3$; $C(O)R^3$; heterocyclyl optionally substituted with 1–4 independent $R^4$ on each ring; or C1–C10 alkyl substituted with 1–4 independent $R^4$; or alternatively each $R^1$ and $R^2$ is independently $R^3$; $R^8$; $NHR^3$; $NHR^5$; $NHR^6$; $NR^5R^5$; $NR^5R^6$; $SR^5$; $SR^6$; $OR^5$; $OR^6$; $C(O)R^3$; heterocyclyl optionally substituted with 1–4 independent $R^4$ on each ring; or C1–C10 alkyl substituted with 1–4 independent $R^4$;

Each $R^3$ is independently aryl; phenyl optionally substituted with 1–5 independent $R^4$ on each ring; or heteroaryl optionally substituted with 1–4 independent $R^4$ on each ring; and all other substituents are as defined herein; comprising the steps of:

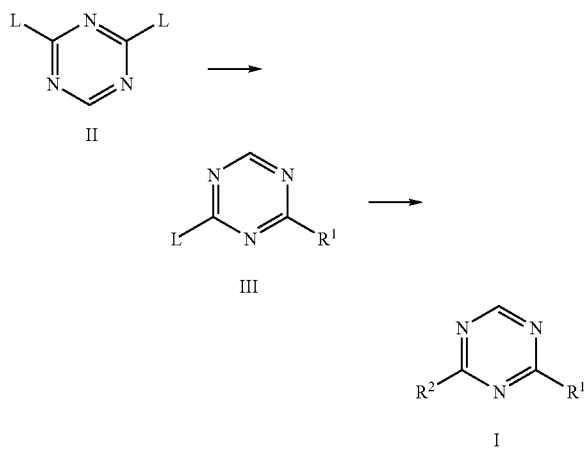

a) reacting a compound of formula (II) wherein each L is independently a leaving group as defined herein, with a nucleophile of formula H—$R^1$ (or salt thereof) to give a compound of formula (III); and b) reacting the compound of formula (III) with a nucleophile of formula H—$R^2$ (or salt thereof) to give a compound of formula (I).

In another embodiment, the process above is carried out by utilizing a nucleophile H—$R^2$ in step (a), then utilizing a nucleophile H—$R^1$ in step (b), as shown:

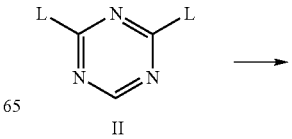

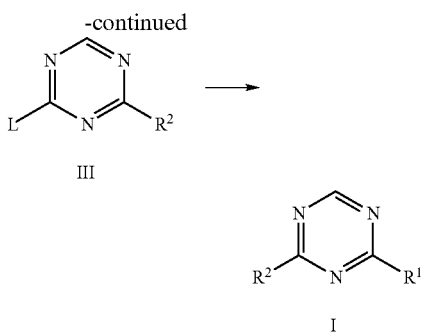

L is defined as a leaving group, and $R^1$ and $R^2$ are as defined herein.

Alternatively, a compound of any of the formulae delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction inert solvents, additional reagents, such as bases (e.g., LDA, diisopropylethylamine, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, simulated moving bed ("SMB")), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The novel compounds of the present invention are excellent ligands for protein kinases, subsequences thereof, and homologous polypeptides. Accordingly, these compounds are capable of targeting and inhibiting kinase enzyme and subsequences thereof Inhibition can be measured by various methods, including, for example, those methods illustrated in the examples below. The compounds described herein may be used in assays, including radiolabelled, antibody detection, colorimetric, and fluorometric, for the isolation, identification, or structural or functional characterization of enzymes, peptides or polypeptides. Other suitable assays include direct ATP competition displacement assays where no phosphoryl transfer is necessary. Such assays include any assay wherein a nucleoside or nucleotide are cofactors or substrates of the polypeptide of interest, and particularly any assay involving phosphotransfer in which the substrates and or cofactors are ATP, GTP, Mg, Mn, peptides, polypeptides, lipids, or polymeric amino acids.

Pharmaceutical compositions of this invention comprise a compound of the formulae described herein or a pharmaceutically acceptable salt thereof; an additional agent selected from a kinase inhibitory agent (small molecule, polypeptide, antibody, etc.), an immunosuppressant, an anti-cancer agent, an anti-viral agent, antuinflammatory agent, antifungal agent, antibiotic, or an anti-vascular hyperproliferation compound; and any pharmaceutically acceptable carrier, adjuvant or vehicle. Alternate compositions of this invention comprise a compound of the formulae described herein or a pharmaceutically acceptable salt thereof; and a pharmaceutically acceptable carrier, adjuvant or vehicle. Such compositions may optionally comprise one or more additional therapeutic agents, including, for example, kinase inhibitory agents (small molecule, polypeptide, antibody, etc.), immunosuppressants, anti-cancer agents, anti-viral agents, antiinflammatory agents, antifungal agents, antibiotics, or anti-vascular hyperproliferation compounds.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may comprise formulations utilizing liposome or microencapsulation techniques. Such techniques are known in the art.

The pharmaceutical-compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdernal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 75 mg/kg body weight per day of the kinase inhibitory compounds described herein are useful in a monotherapy and/or in combination therapy for the prevention and treatment of kinase mediated disease. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a kinase inhibitor of the formulae described herein and one or more additional therapeutic or prophylactic agents, both the kinase inhibitor and the additional agent should be present at dosage levels of between about 10 to 100%, and more preferably between about 10 to 80% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

According to one embodiment, the pharmaceutical compositions of this invention may comprise an additional kinase inhibitory agent. Such additional kinase inhibitory agents are those which may modulate, regulate or otherwise affect kinase enzyme activity. Such effects may lead to modulation of disease pathology and/or symptoms. Kinase inhibitory agents include, for example, small molecules, polypeptides, antibodies (including for example, monoclonals, chimeric, humanized, single chain, immunokines, etc.), and the like. Examples of additional kinase inhibitory small molecule agents include, but are not limited to, SU-6668, SU-5416, ZD-4190, ZD-1839, STI-571, CP-358774, LY-333531 and the like.

According to one embodiment, the pharmaceutical compositions of this invention comprise an additional immunosuppression agent. Examples of additional immunosuppression agents include, but are not limited to, cyclosporin A, FK506, rapamycin, leflunomide, deoxyspergualin, prednisone, azathioprine, mycophenolate mofetil, OKT3, ATAG, interferon and mizoribine.

According to an alternate embodiment, the pharmaceutical compositions of this invention may additionally comprise antibodies (including for example, monoclonals, chimeric, humanized, single chain, immunokines, etc.), cytotoxic or hormonal anti-cancer agents or combinations thereof. Examples of anti-cancer agents include, but are not limited to, cis-platin, actinomycin D, doxorubicin, vincristine, vinblastine, etoposide, amsacrine, mitoxantrone, tenipaside, taxol, taxotere, colchicine, phenothiazines, interferons, thioxantheres, anti-estrogens (e.g., tamoxifen), aromatase inhibitors, anti-androgens, LNRH antagonists, progetins, and GnRH antagonists.

According to another alternate embodiment, the pharmaceutical compositions of this invention may additionally comprise an anti-viral agent. Examples of anti-viral agents include, but are not limited to, Cytovene, Ganciclovir, trisodium phosphonoformate, Ribavirin, d4T, ddI, AZT, amprenavir and acyclovir.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

In an alternate embodiment, this invention provides methods of treating, preventing, or relieving symptoms of disease in a mammal comprising the step of administrating to said mammal any of the pharmaceutical compositions and combinations described above. Preferably, the mammal is a human. If the pharmaceutical composition only comprises the inhibitor of this invention as the active component, such methods may additionally comprise the step of administering to said mammal an additional therapeutic agent, such as an antiinflammatory agent, immunosuppressant, an anti-cancer agent, an anti-viral agent, or an anti-vascular hyperproliferation compound. Such additional agent may be administered to the mammal prior to, concurrently with, or following the administration of the inhibitor composition.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention. The compounds of this invention may also be represented in multiple tautomeric forms, for example, as illustrated below:

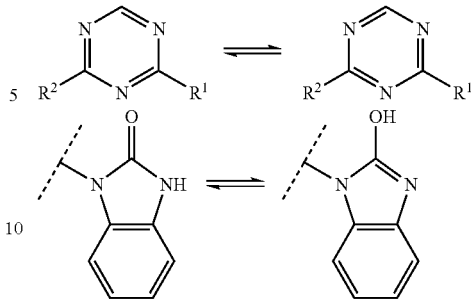

the invention expressly includes all tautomeric forms of the compounds described herein. The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom (see below), whereby they are intended to be attached at any available atom that is not already substituted by an atom other than H (hydrogen). For example, a structure drawn as:

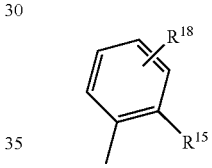

is intended to encompass all of the following structures:

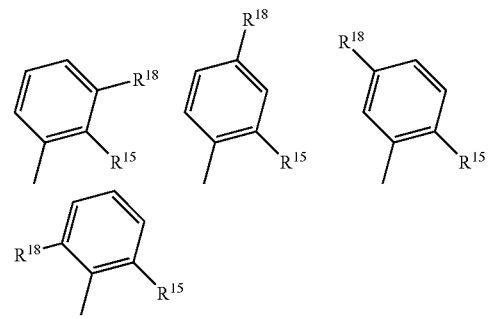

The compounds of this invention may contain heterocyclic ring systems attached to another ring system (e.g., a triazinylyl core ring, an $R^8$ substituent as defined herein, or a heteroaryl group). Such heterocyclic ring systems may be attached through a carbon atom or a heteroatom in the ring system. In instances wherein a heterocyclic or heteroaryl ring system is stated to be attached at a heteroatom (e.g., nitrogen atom), this refers to the heterocyclic or heteroaryl ring system being attached to the designated functional group at said nitrogen heteroatom. To illustrate, for example, when an $R^1$ or $R^2$ substituent on a triazinyl core is a heteroaryl defined as being attached at a nitrogen atom, this definition includes, but is not limited to, structures such as those exemplified below:

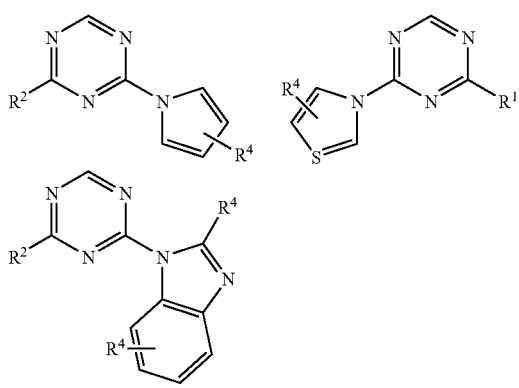

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

In order that the invention described herein may be more readily understood, the following examples are set forth. It should be understood that these examples are for illustrative purposes only and are not to be construed as limiting this invention in any manner. NMR and MS spectra obtained for compounds described in the examples below and those described herein are consistent with that of the compounds of the formulae herein.

Analytical Methods:

Unless otherwise indicated all HPLC analyses are run on a HP-1050 system with an HP Zorbax SB-C18 (5μ) reverse phase column (4.6×150 mm) run at 30 degrees C. with a flow rate of 1.00 ml/minute.

The mobile phase used solvent A (water/0.1% trifluoroacetic acid) and solvent B (acetonitrile/0.1% trifluoroacetic acid) with a 20-minute gradient from 10% to 90% acetonitrile. The gradient is followed by a 2-minute return to 10% acetonitrile and a 3 minute flush.

The peaks of interest eluted on the LC profiles at the times indicated.

LC-MS method for:

Method A:
1. Samples are run on a HP-1100 MSD system with a HP Zorbax SB-C8 (5μ) reverse phase column (4.6×50 mm) run at 30 degrees C. with a flow rate of 0.75 ml/minute.
2. The mobile phase used solvent A (water/0.1% acetic acid) and solvent B (acetonitrile/0.1% acetic acid) with a 10-minute gradient from 10% to 90% acetonitrile. The gradient is followed by a 1-minute return to 10% acetonitrile and a 2 minute flush.
3. The peaks of interest eluted on the LC profiles at the times indicated.

Method B:
4. Samples are run on an HP-1100 system with an HP Zorbax SB-C8 (5μ) reverse phase column (4.6×50 mm) run at 30 degrees C. with a flow rate of 1.5 ml/minute.
5. The mobile phase used solvent A (water/0.1% acetic acid) and solvent B (acetonitrile/0.1% acetic acid) with a 5-minute gradient from 10% to 90% acetonitrile. The gradient is followed by a 0.5-minute return to 10% acetonitrile and a 1.5 minute flush.
6. The peaks of interest eluted on the LC profiles at the times indicated.

Preparative HPLC: Where indicated, compounds of interest are purified via preparative HPLC using a Gilson workstation with a 20×50 mm column at 20 mL/min. The mobile phase used solvent A (water/0.1% trifluoroacetic acid) and solvent B (acetonitrile/0.1% trifluoroacetic acid) with a 10-minute gradient from 5% to 100% acetonitrile. The gradient is followed by a 2-minute return to 5% acetonitrile.

Proton NMR Spectra:

Unless otherwise indicated, all $^1$H NMR spectra are run on a Varian series Mercury 300 MHz instrument. All observed protons are reported as parts-per-million (ppm) downfield from Tetramethylsilane (TMS) or other internal reference in the appropriate solvent indicated.

Example A

Sodium dicyanamide (105.9 g, 1.19 mol) is nearly dissolved into water and added quickly to concentrated hydrochloric acid (530 ml) cooled to about −18° C. The slurry is stirred at −18° C. for about 15 minutes and then warmed to 35° C. before being cooled to 10° C. The white precipitate is then filtered, washed with small amounts of water, and dried under vacuum for twenty hours. About 50 g of N-cyanochloroformamidine is obtained: $^1$H NMR (DMSO-$d_6$) δ 7.59 (s, 1H). Dimethylformamide (27.3 ml) is dissolved into dichloromethane at room temperature. To this solution is added phosphoryl chloride (27.3 ml) and then, after about 5 minutes, 30 g of N-cyanochloroformamidine. The mixture is stirred overnight at room temperature and then washed 3 times with water and once with brine. The organic layer is then dried over sodium sulfate, filtered, and evaporated under reduced pressure. The white solid (20 g) thus obtained is identified as the 2,4-dichloro-1,3,5-triazine: $^1$H NMR (CDCl$_3$) δ 8.88 (s, 1H).

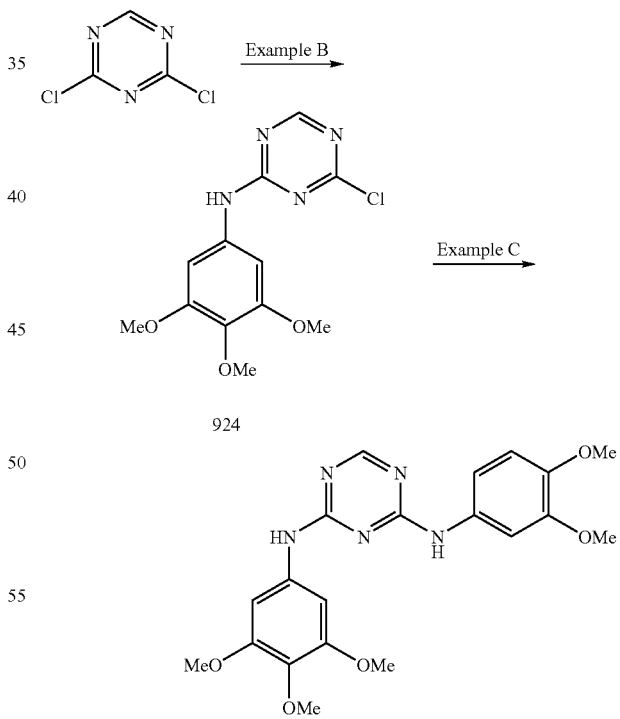

Example B 2,4-Dichloro-1,3,5-triazine (1.054 g, 7.028 mmol) is dissolved into DMF (5 ml) and cooled to 0° C. To this solution are added diisopropylethylamine (1.225 ml, 7.028 mmol) and 3,4,5-trimethoxyaniline (1.185 g, 6.47 mmol). The reaction mixture is kept at 0° C. for 15 to 30 minutes and then at room temperature for 15 minutes to 2 hours. The reaction mixture is then diluted with ethyl acetate and washed with brine. The organic layer is dried over sodium sulfate, filtered, and evaporated in vacuo. The residue is treated with methylene chloride. The product precipitates as a white solid that is filtered and dried under reduced pressure, to give material identified as 924 (711 mg, 37%): $^1$H NMR (300 MHz, DMSO-$d_6$) δ 10.58 (s, 1H), 8.59 (br s, 1H), 7.00 (s, 2H), 3.72 (s, 6H), 3.60 (s, 3H); HPLC Rt=11.19 min; MS i/z=279 [M-Cl+OH$_2$]$^+$.

Example C

To a slurry of intermediate 924 (75 mg, 0.253 mmol) in ethanol (5 ml) are added diisopropylethylamine (44 μl, 0.253 mmol) and 4-aminoveratrole (46 mg, 0.253 mmol). The mix is heated at 100° C. for 30 minutes. The solution is then cooled to room temperature and then to 0° C. A violet precipitate falls out of solution. The precipitate is filtered off and dried under reduced pressure to give 69 mg (66%) of 36: MS m/z=414 [M+H]$^+$; $^1$H NMR (300 MHz, DMSO-$d_6$) δ 9.48 (br s, 2H), 8.24 (s, 1H), 7.22 (s, 1H), 7.12 (m, 1H), 7.00 (br s, 2H), 6.82 (d, 1H), 3.68 (s, 6H), 3.57 (m, 9H); HPLC RT=9.47 min.

The following compounds are prepared according to the procedure described form compound 36, substituting the appropriate reagents.

| Compound | MS m/z | HPLC Rt |
|---|---|---|
| 27 | 397 | 7.58 |
| 28 | 385 | 9.48 |
| 29 | 446 | 13.221 |
| 33 | 397 | 7.86 |
| 36 | 414 | 9.47 |
| 39 | 355 | 8.30 |
| 40 | 355 | 8.27 |
| 41 | 451 | 12.80 |
| 61 | 406 | 12.28 |
| 62 | 440 | 11.36 |
| 63 | 384 | 9.04 |
| 64 | 368 | 11.19 |
| 65 | 372 | 10.77 |
| 66 | 396 | 12.89 |
| 67 | 368 | 10.49 |
| 68 | 438 | 10.33 |
| 69 | 469 | 12.06 |
| 70 | 394 | 8.90 |
| 72 | 388 | 12.10 |
| 73 | 460 | 13.41 |
| 74 | 378 | 11.34 |
| 75 | 433 | 12.15 |
| 76 | 466 | 9.80 |
| 77 | 404 | 9.13 |
| 78 | 370 | 8.81 |
| 79 | 394 | 8.11 |
| 81 | 425 | 8.87 |
| 82 | 434 | 12.44 |
| 83 | 384 | 9.81 |
| 85 | 370 | 8.31 |
| 86 | 414 | 11.02 |
| 87 | 384 | 10.69 |
| 89 | 384 | 10.19 |
| 90 | 384 | 10.71 |
| 91 | 354 | 10.46 |
| 92 | 369 | 6.81 |
| 93 | 459 | 9.93 |
| 94 | 398 | 9.27 |
| 95 | 442 | 13.33 |
| 96 | 404 | 12.32 |
| 97 | 405 | 10.83 |
| 98 | 404 | 11.33 |
| 99 | 405 | 9.19 |
| 100 | 430 | 13.42 |
| 101 | 439 | 8.81 |
| 104 | 398 | 9.09 |
| 105 | 446 | 13.58 |
| 106 | 398 | 10.91 |
| 135, 290 | 388 | 11.95 |
| 177 | 484 | 11.26 |
| 178 | 483 | 12.92 |
| 183 | 329 | 7.75 |
| 186 | 379 | 12.28 |
| 250 | 438 | 13.34 |
| 251 | 438 | 8.22 |
| 252 | 398 | 10.11 |
| 253 | 415 | 10.96 |
| 254 | Nd | 6.82 |
| 255 | 475 | 9.45 |
| 300 | 386 | 11.85 |
| 303 | 372 | 10.71 |
| 304 | 372 | 11.27 |
| 305 | 461 | 9.35 |
| 306 | 406 | 12.44 |
| 316 | 390 | 11.88 |
| 334 | nd | 9.62 |
| 562 | 543.2 | 7.91 |
| 613 | 483 | 12.55 |
| 614 | 422 | 12.23 |
| 617 | 479 | 9.32 |
| 618 | 4440 | 12.53 |
| 623 | 503 | 11.31 |
| 624 | 412 | 8.82 |
| 625 | 402 | 11.84 |
| 627 | 418 | 12.41 |
| 629 | 394 | 12.01 |
| 632 | 440 | 14.16 |
| 633 | 521 | 12.32 |
| 636 | 414 | 8.14 |
| 691 | 393 | (Method A) 7.47 |
| 692 | 554 | (Method A) 7.68 |
| 693 | 483 | (Method A) 6.26 |
| 694 | 483 | (Method A) 6.48 |
| 695 | 405 | (Method A) 5.38 |
| 696 | 396 | (Method A) 5.05 |
| 697 | 396 | (Method A) 6.76 |
| 698 | 396 | (Method A) 6.73 |
| 699 | 421 | (Method A) 5.2 |
| 926 | 460 | 13.14 |
| 927 | 384 | 8.61 |
| 928 | 393 | 9.57 |
| 930 | 368 | 11.15 |
| 931 | 400 | 8.68 |
| 932 | 382 | 11.38 |
| 933 | 398 | 9.03 |
| 934 | 412 | 12.20 |
| 935 | 382 | 7.81 |
| 936 | 468 | 13.68 |
| 937 | 386 | 11.31 |
| 1031 | 438 | 12.25 |
| 1047 | nd | 6.57 |
| 922 | 475 | (Method A) 8.13 |

To a slurry of intermediate 924 (79.6 mg, 0.2683 mmol) in isopropanol (2 ml) are added diisopropylethylamine (46.7 μl, 0.2683 mmol) and 4-methoxybenzylamine (37 mg, 0.2683 mmol). The mix is heated at 100° C. from 30 minutes to 40 hours. The solution is then cooled to room temperature and sonicated. The precipitate is filtered and dried under pressure, giving 51.6 mg (48%) of compound 80.

The following compounds are prepared according to the procedure described for compound 80, substituting the appropriate reagents.

| Compound | MS m/z | HPLC Rt |
| --- | --- | --- |
| 80 | 398 | 10.34 |
| 103 | 363 | 7.47 |
| 409 | 292 | 7.54 |
| 425 | 397.9 | 8.95 |
| 427 | 420.5(M + Na) | 8.92 |
| 428 | 393.9 | 10.71 |
| 570 | 382.3 | 10.40 |
| 570 | 382.1 | 10.36 |
| 581 | 394 | 10.93 |
| 619 | 408 | 11.40 |
| 620 | 408 | 11.40 |
| 628 | 382 | 10.87 |
| 630 | 368 | 10.25 |
| 1002 | 347 | 7.98 |

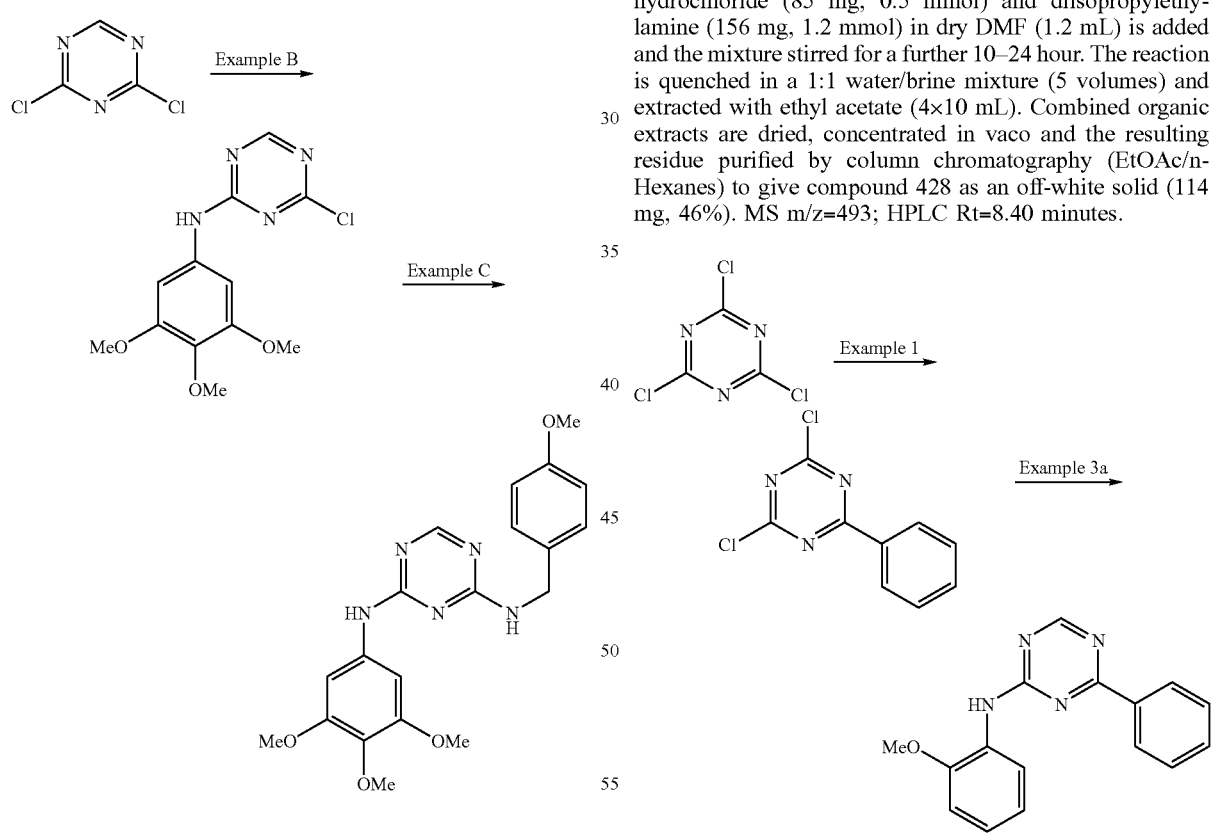

EXAMPLE 4

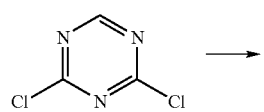

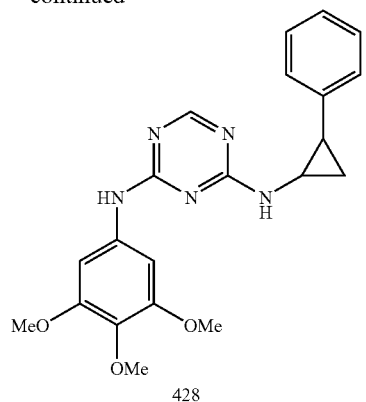

Compound 428

To a solution of dichlorotriazine (75 mg, 0.50 mmol) in dry DMF (3 mL) is added diisopropylethylamine (78 mg, 0.6 mmol) at 0° C. under a nitrogen atmosphere. The resulting yellow solution is stirred at 0° C. for 0.5–1 hour. Aniline (0.05 mmol) is added and the reaction stirred for 1–3 hours at room temperature. Finally, a solution of amine hydrochloride (85 mg, 0.5 mmol) and diisopropylethylamine (156 mg, 1.2 mmol) in dry DMF (1.2 mL) is added and the mixture stirred for a further 10–24 hour. The reaction is quenched in a 1:1 water/brine mixture (5 volumes) and extracted with ethyl acetate (4×10 mL). Combined organic extracts are dried, concentrated in vaco and the resulting residue purified by column chromatography (EtOAc/n-Hexanes) to give compound 428 as an off-white solid (114 mg, 46%). MS m/z=493; HPLC Rt=8.40 minutes.

EXAMPLE 1

To a solution of 5 g (27.1 mmol) of cyanuric chloride in 50 mL of dry diethyl ether at −20° C. is added, by slow dropwise addition, 26 mL of a 1M solution (26 mmol) of phenyl magnesium bromide. The reaction is stirred for 1 hour and warmed to 0° C. whereupon it is quenched with cold saturated ammonium chloride and partitioned between ethyl acetate and dilute sodium chloride solution. The organic layer is dried over magnesium sulfate, filtered and evaporated to yield crude product that could be used directly, without further purification, in subsequent reactions.

EXAMPLE 3a (One-pot procedure)

To a dry solution of dichlorotriazine (113 mg, 0.50 mmol) in DMF (1.5 mL) is added diisopropylethylamine (0.17 mL, 0.55 mmol) followed by neat o-anisidine (68 mg, 0.55 mmol). The resulting solution is stirred at room temperature under a nitrogen atmosphere for 1–5 h. The reaction is diluted with 2N aqueous HCl (10 mL), brine (5 mL) and extracted with EtOAc (3×6 mL). Combined organics is diluted with MeOH (3 mL) and 10% Pd—C (120 mg) and triethylamine (0.2 mL) added. Hydrogen gas is bubbled through the mixture for 1 h and the mixture allowed to stir at room temperature under a hydrogen atmosphere for 10–30 h. The mixture is filtered through celite and washed with MeOH. The fiftrate is concentrated in vacuo and the crude material purified by column chromatography (EtOAc/n-Hexanes) to provide compound 12 (90 mg, 65%) as a yellow solid.

EXAMPLE 3b

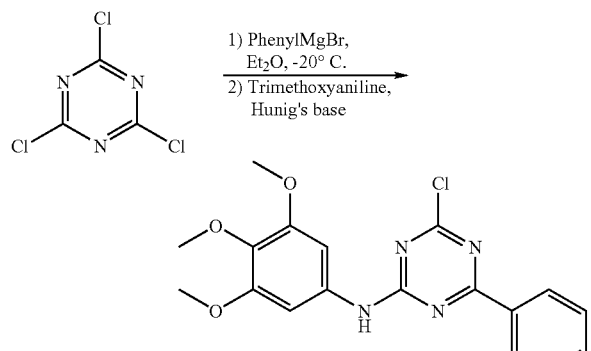

To a solution of 441 mg (2.4 mmol) of cyanuric chloride in 5 mL of dry diethyl ether at −20° C. is added, by slow dropwise addition, 2 mL of a 1M solution (2 mmol) of phenyl magnesium bromide. The reaction is stirred for 0.5 hour and warmed to 0° C. whereupon 439 mg (2.4 mmol) of 3,4,5-trimethoxy aniline and 416 µL (2.4 mmol) of diisopropyl ethylamine is added in rapid succession. The resulting solution is warmed to room temperature and stirred for one hour. The reaction is quenched with saturated ammonium chloride and partitioned between ethyl acetate and saturated sodium chloride solution. The organic layer is dried over magnesium sulfate, filtered and evaporated to yield crude product which is recrystallized from methanol to give material identified as the desired compound.

EXAMPLE 3c

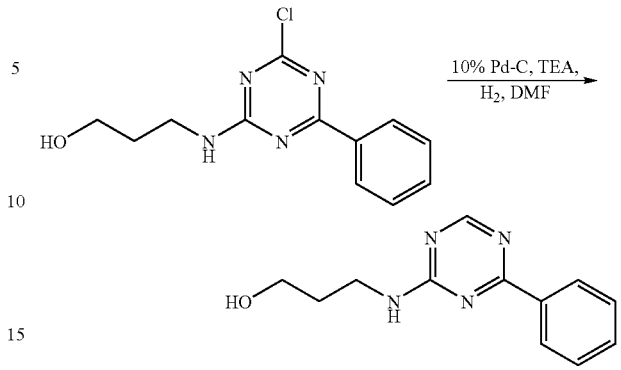

To 98 mg (0.37 mmol) of triazine in 2 mL of dimethylformamide is added 45 mg of 10% palladium on carbon. The flask is evacuated and flushed with hydrogen five times. To the sealed reaction flask is then added 517 µL (3.8 mmol) of triethylamine. The reaction is evacuated and flushed two more times and then stirred rapidly for four hours while maintaining an atmosphere of hydrogen. The completed reaction is diluted with ethyl acetate, filtered through celite, and partitioned between ethylacetate and water. The organic layer is washed with saturated brine, dried with magnesium sulfate, and filtered to yield crude product. The crude product is triturated with dichloromethane to give a white solid which can be filtered and dried to provide material identified as pure compound 971.

The following compounds are prepared according to the procedure outlined for compound 971, substituting the appropriate reagents.

| Cmpd # | HPLC Rt | MS |
|---|---|---|
| 8 | 8.22 | 265 |
| 11 | 10.64 | 264 |
| 12 | 16.05 | 279 |
| 13 | 14.95 | 279 |
| 14 | 13.85 | 280 |
| 15 | 15.17 | 309 |
| 16 | 6.32 | 231 |
| 17 | 11.88 | 274(M-tBu) |
| 18 | 11.71 | 265 |
| 19 | 15.47 | 308(M-tBu) |
| 20 | 15.11 | 267 |
| 151 | 10.27 | 291 |
| 154 | 9.63 | 392 |
| 155 | 13.40 | 323 |
| 163 | 15.41 | 307 |
| 164 | 15.21 | 335 |
| 165 | 11.36 | nd |
| 970 | 13.77 | 339 |
| 971 | 7.2 | 231 |

EXAMPLE 2

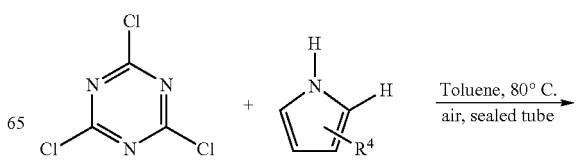

-continued

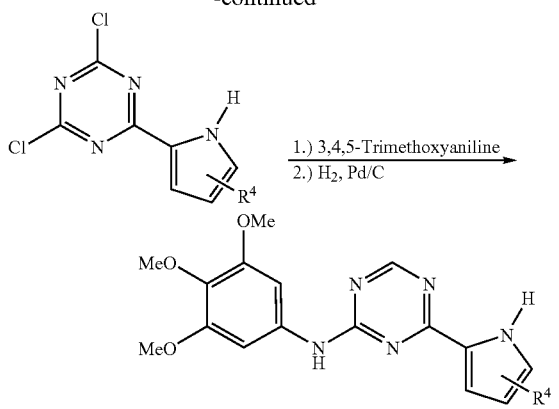

See: Chakrabarti, J. K.; Tupper, D. E. *J. of Heterocyclic Chem.*, 1974, 11, 417–421.

Cyanuric chloride (7 mmole) is dissolved into toluene (5 mL) air in a tube under air at room temperature. Pyrrole (7 mmole) is added, the tube is sealed, and the reaction heated to 80° C. for two hours, then cooled to room temperature. This gives a red-brown solid, which gives a series of spots by TLC (50% EtOAc:hexane, silica gel). This material is eluted through a column of silica gel with 100% methylene chloride giving the dichloride intermediate compound. Displacement of the chloride with an appropriate amine under standard conditions (described herein) followed by reduction of the remaining chloride by hydrogenation under standard conditions results in the desired product.

EXAMPLE 5

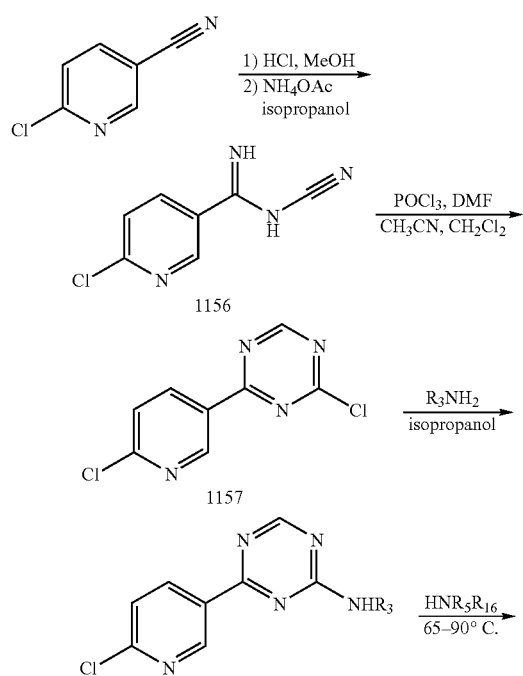

-continued

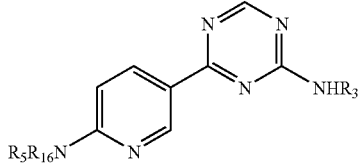

Compounds may be prepared according to the above scheme: 6-Chloronicotinonitrile (650 mg, 4.7 mmol) is dissolved in 30 ml dry EtOH at 0° C. HCl gas is bubbled through the solution until precipitate is present for 30 min. The vessel is sealed, refrigerated, thoroughly concentrated, and suspended in 30 mL isopropanol. Ammonium acetate (700 mg) is added and stirring continued for about 20 hours. The mixture is concentrated, and the residue is triturated with a small amount of isopropanol and filtered. The resulting amidine is suspended in 10 mL isopropanol with 500 mg solid cyanamide and the stirring solids are dissolved by addition of 30 mL of 5% aqueous $NaHCO_3$. After two days stirring, the white precipitate is collected and washed with a small amount of isopropanol.

By extension of the methodology of Roger Harris [*Synthesis* 1980, 841–842], the resulting cyanoamidine 1156 is converted to 2-chloro-4-(6-chloro-pyridin-3-yl)-[1,3,5] triazine 1157: to 555 mg compound 1156 suspended in 20 mL $CH_2CN$ at 0° C. is added reagent that is prepared by mixing $POCl_3$ (340 µl, 3.6 mmol) and DMF (280 µl, 3.6 mmol) in 7 mL $CH_2Cl_2$ at 0° C. Additional $CH_2CN$ (30 ml) allows the thick mixture to stir. After three hours, the now clear solution is concentrated and filtered through a plug of silica, using $CH_2Cl_2$/isopropanol as necessary to dissolve, and hexane/tBuOMe to elute. 2-Chloro-4-(6-chloro-pyridin-3-yl)-[1,3,5]triazine 1157: MS m/z=227 [M+H]$^+$; 1H NMR (300 MHz, DMSO-d6) 9.21 (s, 1H), 9.17 (d, J=2.6, 1H), 8.56 (dd, J=8.3, 2.5, 1H), 7.63 (d, J=8.2); HPLC Rt=13.1 min.

Compound 1157 reacts with an optionally substituted aryl or heterocyclic or heteroaryl amine (where $R^3$ is as defined in the formulae herein) at room temperature to produce the desired adduct. The remaining chloride may then be displaced by reaction with amine (neat or in a small amount of solvent) at elevated temperature. The product may be isolated by filtration, silica gel chromatography, or preparative HPLC.

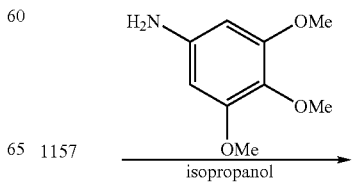

1157

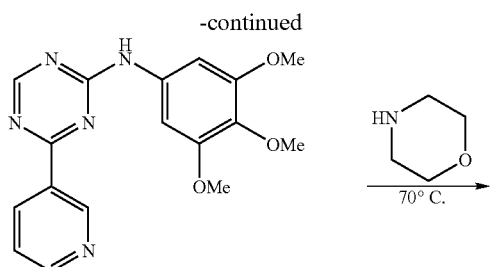

1158

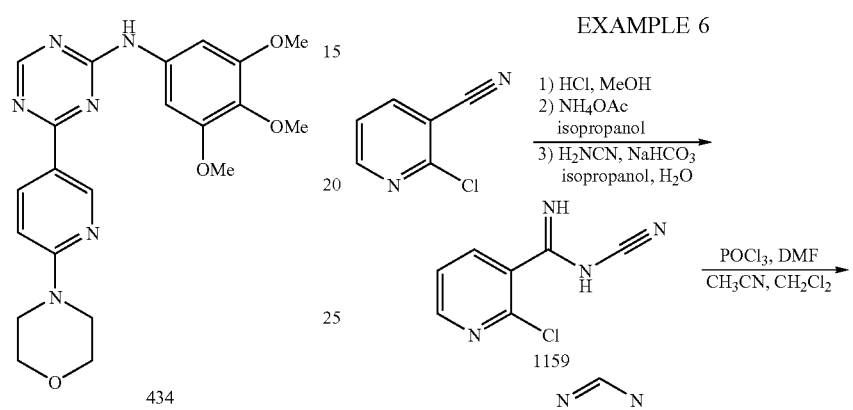

434

Compound 1157 (550 mg, 2.4 mmol) and trimethoxyaniline (530 mg, 2.9 mmol) are stirred in 25 mL isopropanol overnight. Et$_3$N (500 µl) is added to allow the now viscous reaction to proceed to completion. After two hours, the material is filtered and rinsed with isopropanol and t-BuOMe to obtain 870 mg yellow solid 1158. MS m/z=374 [M+H]$^+$; 1H NMR (300 MHz, DMSO-d6) 10.21 (s, 1H), 9.14 (s, 1H), 8.71 (s, 1H), 8.50 (m, J=8.2, finer coupling, 1H), 7.60 (d, J=8.2), 7.04 (s, 2H), 3.65 (s, 6H), 3.50 (s, 3H); HPLC Rt=13.2 min.

Compound 1158 (38 mg, 0.10 mmol) is heated with 500 µl morpholine overnight at 70° C. in a sealed tube. The mixture is triturated with isopropanol and filtered to obtain 434. MS m/z=425 [M+H]$^+$; 1H NMR (300 MHz, DMSO-d6) δ (s, 1H), 9.07 (d, J=2.3, 1H), 8.66 (s, 1H), 8.35 (dd, J=9.1, 2.3, 1H), 7.17 (s, 2H), 6.94 (d, J=9.1, 1H), 3.8–3.5 (m, 8H), 3.82 (s, 6H), 3.60 (s, 3H); HPLC Rt=8.96 min.

The following compounds are prepared according to the procedure outlined for compound 434, substituting the appropriate amine in the second reaction step:

Compound 448: MS m/z=468 [M+H]$^+$; 1H NMR (300 MHz, DMSO-d6) 9.94 (s, 1H), 8.99 (s, 1H), 8.62 (s, 1H), 8.19 (d, J=8.2, 1H)), 7.35 (m, 1H), 7.18 (s, 2H), 3.76 (s, 6H), 3.60 (s, 3H), 3.32–3.23 (m), 2.45–2.35 (m), 1.66–1.57 (m, 2H), 0.93–0.88 (m, 6H); HPLC Rt=7.47 min.

Compound 449: MS m/z=383 [M+H]$^+$; 1H NMR (300 MHz, DMSO-d6) 9.97 (s, 1H), 8.31 (dd, J=9.1, 2.2, 1H), 7.18 (s, 2H), 6.74 (d, J=8.8, 1H), 3.76 (s, 3H), 3.61 (s, 3H), 3.10 (s, 6H); HPLC Rt=8.32 min.

Compound 497: MS m/z=413 [M+H]$^+$; 1H NMR (300 MHz, DMSO-d6) 9.94 (s, 1H), 8.98 (s, 1H), 8.62 (s, 1H), 8.18 (d, J=8.5, 1H), 7.31–7.16 (m, 1H), 7.17 (s, 2H), 6.51 (d, J=8.8, 1H), 4.48–4.45 (m, 1H), 3.75 (s, 6H), 3.60 (s, 3H), 3.33–3.27 (m, 2H), 3.47–3.41 (m, 2H), 1.70–1.61 (m, 2H); HPLC Rt=7.86 min.

The following compounds are prepared according to the procedure outlined for compound 434, substituting the appropriate amine in the second reaction step:

| Compound | HPLC ret. | MS m/z |
|---|---|---|
| 436 | 7.69 min. | 424 |
| 446 | 8.36 min. | 452 |
| 471 | 10.37 min. | 445 |
| 472 | 7.20 min. | 412 |
| 1074 | 7.13 min. | 398 |

EXAMPLE 6

Compounds in example 6 may be prepared by a similar process as in Example 5: 5.0 g 2-chloronicotinamide (36 mmol) is dissolved in 100 mL dry EtOH at 0° C. HCl is bubbled through the mixture for three hours and the mixture is sealed and refrigerated overnight. After concentration, the residue is stirred with 5.5 g ammonium acetate in 100 mL isopropanol. After 12 hours, the pH is adjusted to 9 (from 4) using concentrated ammonium hydroxide solution, and stirring continued two more days. The mixture is concentrated and purified by flash chromatography (10:1:0.1 CH$_2$Cl$_2$/MeOH/NH$_4$OH). Triturating in hot tBuOMe/isopropanol removes some residual amide side-product to provide 3.6 g white solid amidine.

Amidine is converted to cyanoamidine as in example 5, with the modification that the bulk of the product is isolated by EtoAc extraction of the aqueous reaction mixture followed by flash chromatography using 95:5:0.5 CH$_2$Cl$_2$/MeOH/NH$_4$OH. Cyanoamidine 1159: MS m/z=181 [M+H]$^+$; HPLC Rt=4.93 min.

3.5 g cyanoamidine 1159 is added as a solid to a stirring, 0° C. solution of POCl₃ (2.3 ml, 25 mmol) and DMF (1.9 ml, 25 mmol) in 100 ml CH₃CN. The clear solution is stirred at room temperature for one hour, concentrated, and immediately filtered through a plug of silica as in Example 5. Concentration provides 3.7 g white solid 2-chloro-4-(2-chloro-pyridin-3-yl)-[1,3,5]triazine 1160. MS m/z=227 [M+H]⁺; 1H NMR (300 MHz, DMSO-d6) 9.29 (s, 1H), 8.50 (m, J=4.8, finer coupling, 1H), 8.20 (m, J=7.2, finer coupling, 1H)), 7.54–7.50 (m, 1H); HPLC Rt=10.69 min.

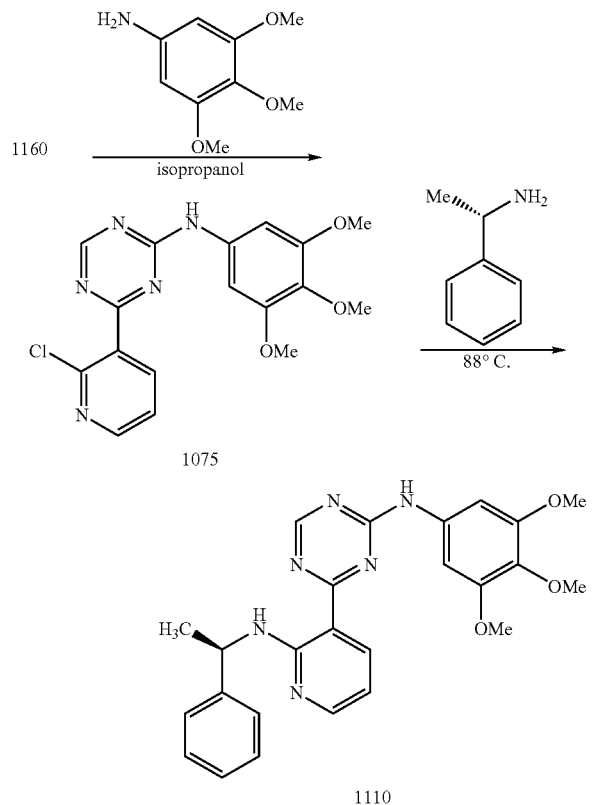

Compound 1160 reacts with an optionally substituted aryl or heterocyclic or heteroaryl amine (where R³ is as defined in the formulae herein) at room temperature to produce the desired adduct. The remaining chloride may then be displaced by reaction with neat amine (or in some cases with a small amount of isopropanol as solvent) at elevated temperature. The product may be isolated by filtration or silica gel chromatography.

Compound 1160 (1.7 g, 7.5 mmol) is stirred overnight at room temperature with 3,4,5-trimethoxyaniline (1.5 g, 8.3 mmol) in 200 mL isopropanol. After addition of 2 ml Et₃N, stirring is continued for an additional day. The mixture is concentrated, triturated with t-BuOMe and filtered, rinsing with a small amount of isopropanol. The 2.5 g of compound 1075 obtained contains one equivalent of Et₃N salt, but is otherwise pure; this material is used as is or is filtered through a plug of silica. MS m/z=374 [M+H]⁺; 1H NMR (300 MHz, DMSO-d6) 10.23 (s, 1H), 8.71 (s, 1H), 8.41–8.38 (m, 1H), 8.7–7.9 (br m, 1H), 7.45–7.41 (m, 1H), 7.00 (s, 2H), 3.57 (s, 6H), 3.45 (s, 3H); HPLC Rt=10.86 min.

Compound 1075 (31 mg, 0.083 mmol) is stirred in a sealed tube with 250 µl R-(+)-1-phenylethylamine at 88° C. for 8 hours. The mixture is diluted with t-BuOMe, and the resulting white precipitate (chloride salt of the reagent amine) is removed by filtration. The filtrate is concentrated, triturated with isopropanol, and the yellow solid 1110 is obtained by filtration. MS m/z=459 [M+H]⁺; 1H NMR (300 MHz, DMSO-d6) 10.02 (s, 1H), 9.47 (br d, J=7.6, 1H), 8.66 (s, 1H), 8.52 (m, J=7.5, finer coupling), 8.03–8.01 (m, 1H), 7.30–7.00 (m, 5H), 6.89 (s, 2H), 6.51 (dd, J=7.6, 4.7, 1H), 5.30–5.20 (br m, 1H), 3.62 (s, 6H), 3.43 (s, 3H), 1.50–1.10 (br m, 3H); HPLC Rt=11.42 min.

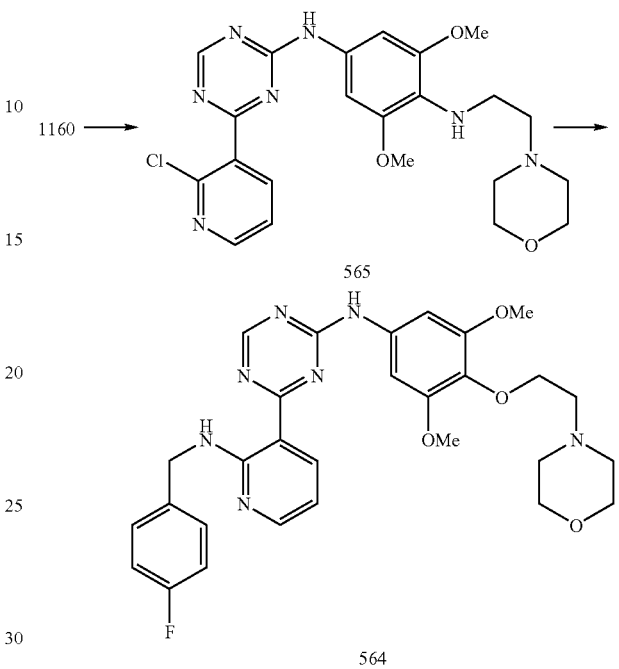

Compound 564 is prepared according to the procedure outlined for compound 1110, substituting the appropriate amines in each of the two reaction steps. Compound 565: MS m/z=473 [M+H]⁺; HPLC Rt=8.16 min. Compound 564: MS m/z=562 [M+H]⁺; HPLC Rt=8.82 min.

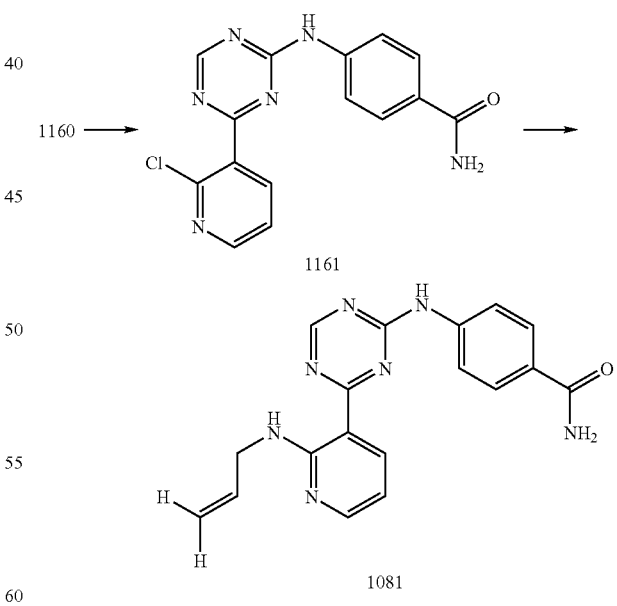

Compound 1081 is prepared according to the procedure outlined for compound 1110, substituting the appropriate amines in each of the two reaction steps. Intermediate compound 1161: MS m/z=327 [M+H]⁺; HPLC Rt=7.86 min; Compound 1081: MS m/z=348 [M+H]⁺; 1H NMR (300 MHz, DMSO-d6) 10.38 (s, 1H), 9.24 (br s, 1H), 8.71 (s, 1H), 8.53 (d, J=6.4), 8.12 (dd, J=4.5, 1.9, 1H), 7.82–7.55

(m, 5H), 7.14 (br s, 1H), 6.56 (dd, J=7.9, 4.7, 1H), 5.8 (br s, 1H), 4.99 (br d, J=17.3, 1H), 4.89 (br d, J=9.7, 1H), 4.02 (br s, 2H); HPLC Rt=7.23 min.

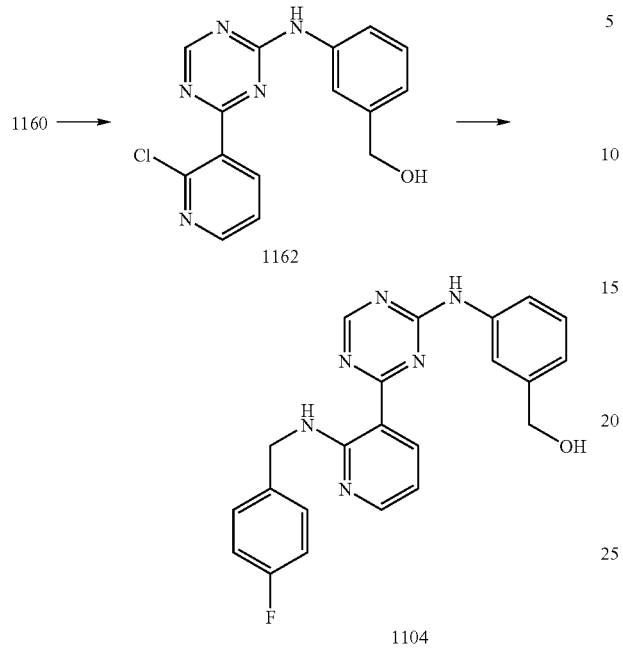

Compound 1104 above is prepared according to the procedure outlined for compound 1110, substituting the appropriate amines in each of the two reaction steps. Intermediate compound 1162: MS m/z=314 [M+H]$^+$; 1H NMR (300 MHz, DMSO-d6) 10.36 (s, 1H), 8.74 (s, 1H), 8.42 (dd, J=4.8, 1.9, 1H), 8.08 (br s, 1H), 7.56 (s, 1H), 7.50–7.42 (m, 2H), 7.14 (app t, J=7.8, 1H), 6.909 (d, J=7.6, 1H), 5.07–5.03 (m, 1H), 4.33 (d, J=5.6, 2H); HPLC Rt=8.84 min. Compound 1104: MS m/z=403 [M+H]$^+$; HPLC Rt=9.93 min.

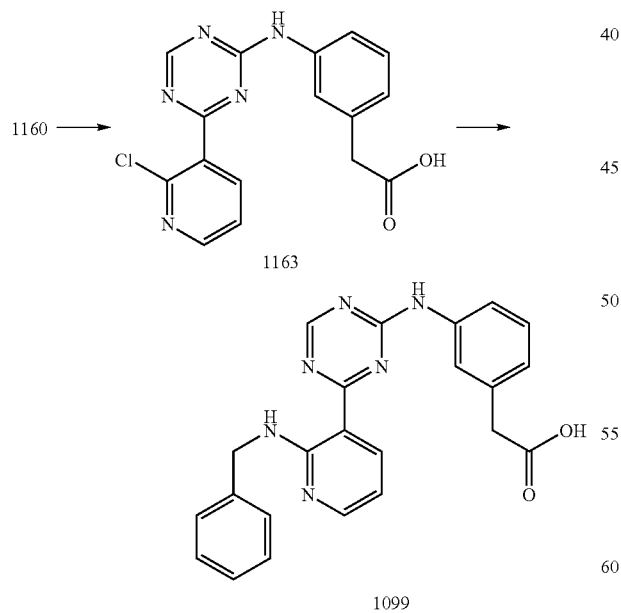

Compound 1099 is prepared according to the procedure outlined for compound 1110, substituting the appropriate amines in each of the two reaction steps. Intermediate compound 1163: MS m/z=342 [M+H]$^+$; HPLC Rt=9.48 min. Compound 1099: MS m/z=413 [M+H]$^+$; 1H NMR (300 MHz, DMSO-d6) 10.19 (br s, 1H), 9.77–9.53 (br m, 1H), 8.63 (s, 1H), 8.56 (d, J=7.0, 1H), 8.08–8.05 (m, 1H), 7.55–7.28 (br s, 1H), 7.41 (s, 1H), 7.20–7.03 (m, 7H), 6.84 (d, J=7.6, 1H), 6.54 (dd, J=7.6, 4.8, 1H), 4.74–4.48 (brm, 2H), 3.62 (s, 2H); HPLC Rt=10.18 min.

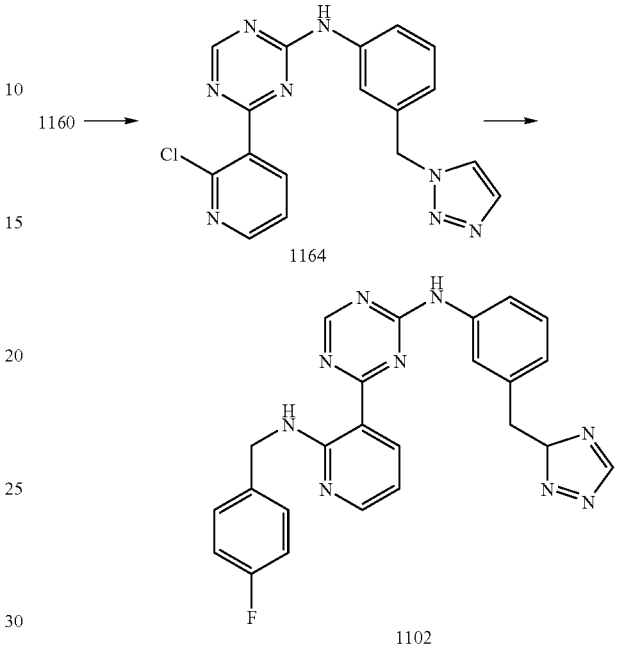

Compound 1102 is prepared according to the procedure outlined for compound 1110, substituting the appropriate amines in each of the two reaction steps. Intermediate compound 1164: MS m/z=365 [M+H]$^+$; HPLC Rt=9.65 min. Compound 1102: MS m/z=454 [M+H]$^+$; 1H NMR (300 MHz, DMSO-d6) 10.23, (s, 1H), 9.62 (br s, 1H), 8.64 (s, 1H), 8.51 (br s, 1H), 8.08 (br d, J=3.4, 1H), 8.04 (s, 1H), 7.60 (s, 1H), 7.60–7.40 (br m, 1H), 7.44 (s, 1H), 7.29–7.03 (m, 3H), 6.99–6.86 (m, 3H), 6.59 (br s, 1H), 5.48 (s, 2H), 4.59 (br s, 2H); HPLC Rt=10.50 min.

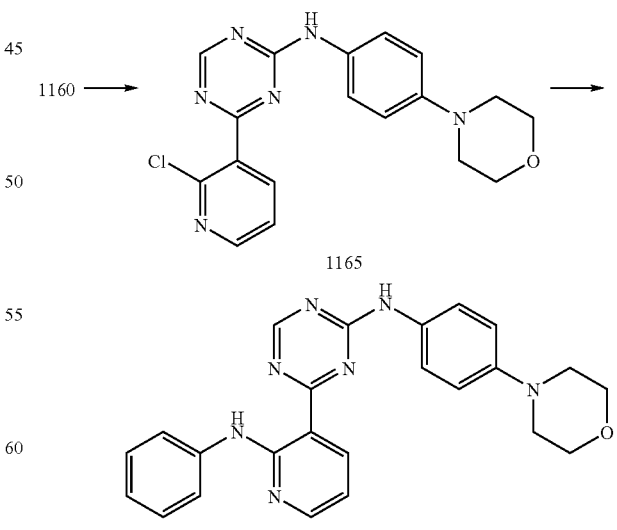

Compound 1113 is prepared according to the procedure outlined for compound 1110, substituting the appropriate amines in each of the two reaction steps. Intermediate compound 1165: MS m/z=369 [M+H]+; HPLC Rt=8.35 min. Compound 1113: MS m/z=426 [M+H]+; 1H NMR (300 MHz, DMSO-d6) 11.4–11.3 (m, 1H), 10.1–10.0 (m, 1H), 8.70–8.57 (m, 1H), 8.65 (s, 1H), 8.26–8.15 (m, 1H), 7.67 (br d, J=7.5, 1H), 7.42–7.00 (m, 5H), 6.91–6.72 (m, 4H), 3.64–3.54 (m, 4H), 2.96–2.86 (m, 4H); HPLC Rt=9.33 min.

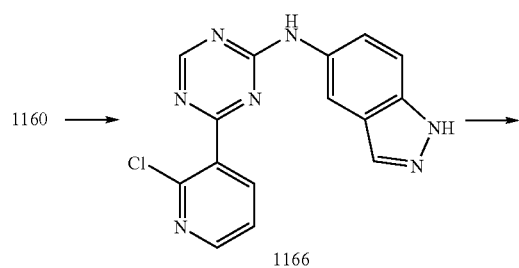

1160 →     1166 →

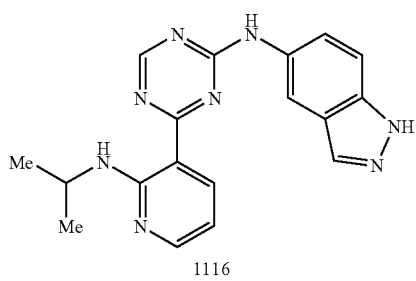

1116

Compound 1116 is prepared according to the procedure outlined for compound 1110, substituting the appropriate amines in each of the two reaction steps. Intermediate compound 1166: MS m/z=324 [M+H]+; HPLC Rt=8.75 min. Compound 1116: MS m/z=347 [M+H]+; 1H NMR (300 MHz, DMSO-d6) [rotamers] 10.1 (s, 1H), 9.0–8.9 & 8.7–8.4 (br m, 2H), 8.6 (s, 1H), 8.1–7.7 (br m, 2H), 7.9 (s, 1H), 7.5–7.3 (br m, 2H), 6.5–6.4 (br m, 1H), 4.3–3.9 (br m, 1H), 1.2–1.0 & 0.7–0.5 (br m, 6H); HPLC Rt=8.13 min.

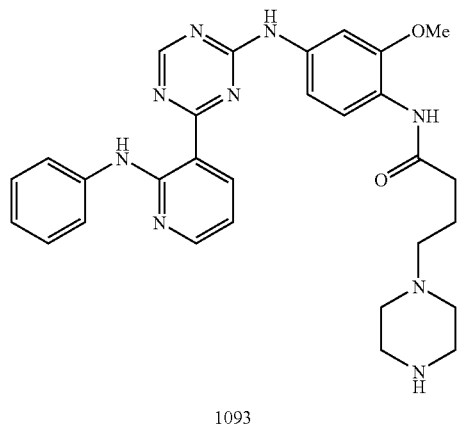

1093

Compound 1093 is prepared essentially according to the procedure outlined for compound 1110, substituting the appropriate amines in each of the two reaction steps, and adding a final deprotection step to remove the t-butyl carbamate (1:1 CF$_3$COOH/CH$_2$Cl$_2$, 0° C., 1 hour,): Compound 1093: MS m/z=540 [M+H]+; Rt=7.38 min.

The aniline used in the second reaction step to prepare compound 1093 is prepared as shown below:

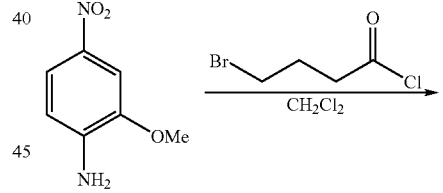

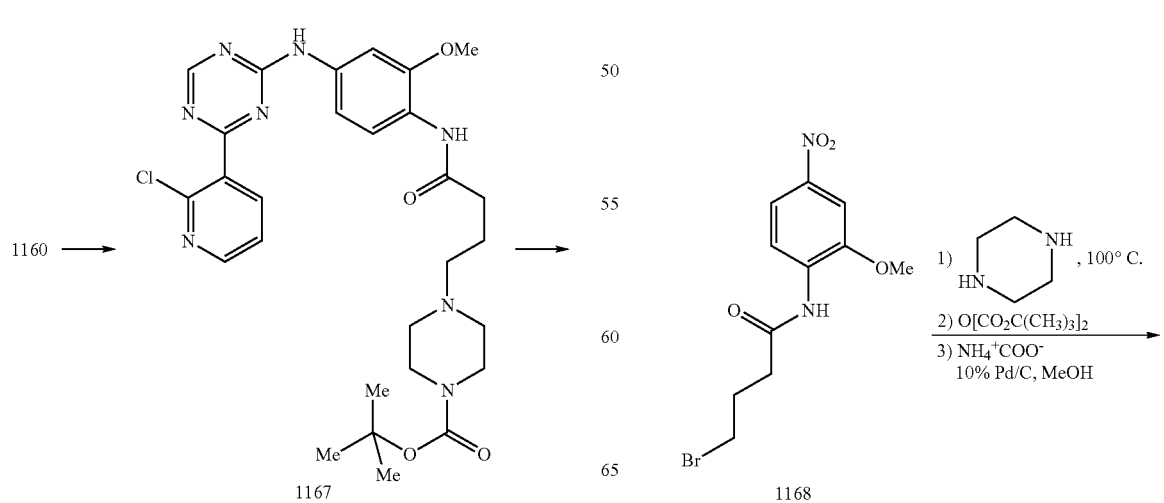

1160 →     1167

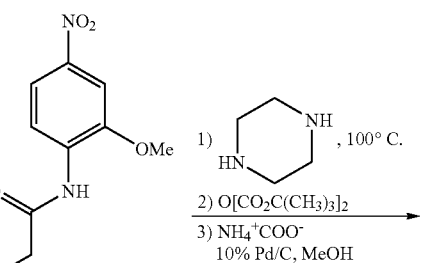

1168

-continued

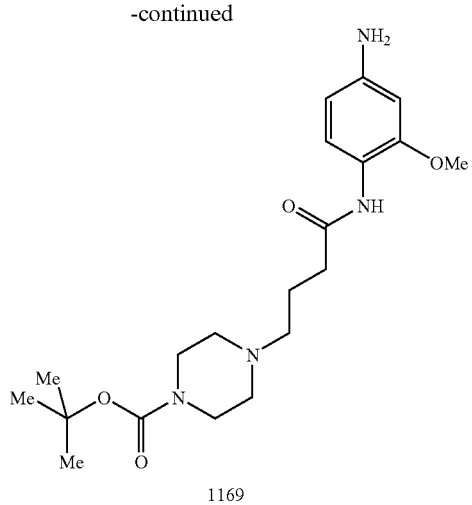

1169

2-Methoxy-4-nitroaniline (4.2 g, 25 mmol) and 4-bromobutyrylchloride (5.0 g, 27 mmol) are stirred overnight at room temperature in 100 mL CH$_2$Cl$_2$. After addition of 100 mL saturated aqueous NaHCO$_3$ and stirring 30 minutes, the mixture is diluted with 300 mL CH$_2$Cl$_2$, washed with 1 N HCl and brine, and dried with Mg$_2$SO$_4$. Concentration, trituration with t-BuOMe, and filtration provided 7.0 g acylated product 1168. A portion of this material (3.4 g, 11 mmol) and 3.3 g piperazine (38 mmol) are heated together as a melt at 100° C. for 10 minutes. The residue is triturated with MeOH and filtered; the filtrate is concentrated and purified by flash chromatography in 10:1:0.1 CH$_2$Cl$_2$/MeOH/NH$_4$OH to provide 2.1 g material, which is stirred with 1.4 g di-t-butyl dicarbonate in 40 mL CH$_2$Cl$_2$ at 0° C. to room temperature for 40 minutes. Chromatography in 1–4% MeOH in CH$_2$Cl$_2$ followed by trituration with t-BuOMe and filtration provides 2.2 g off-white solid. This nitroarene (440 mg, 1.0 mmol) is stirred in 20 mL MeOH at 46° C. under N$_2$ with 380 mg ammonium carbonate and 120 mg Pd/C. After 20 minutes, the mixture is diluted with EtOAC, filtered, and concentrated. Silica gel chromatography in EtOAc →95:5:0.5 CH$_2$Cl$_2$/MeOH/NH$_4$OH followed by concentration from t-BuOMe provided 400 mg of compound 1169 as a pinkish, glassy solid.

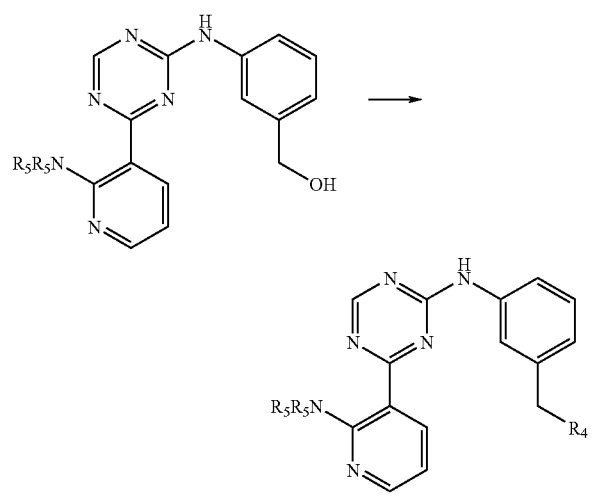

Compounds prepared according to the procedure of Example 6 in which 3-aminobenzyl alcohol is added in the second reaction step may be further modified: the benzylic alcohol may be converted to an intermediate which may be displaced with an appropriate nitrogen, oxygen, sulfur, or carbon nucleophile.

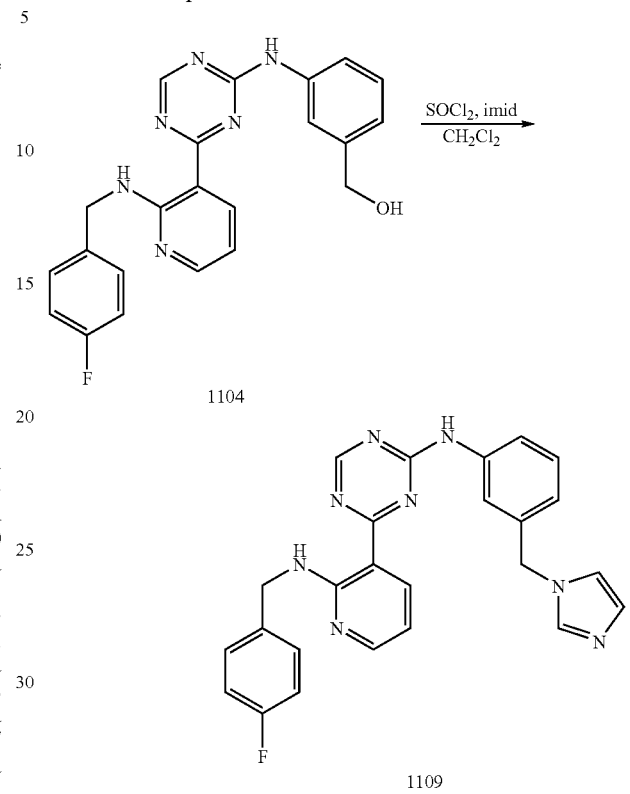

Compound 1104 (50 mg, 0.12 mmol) is stirred under N$_2$ with 22 µl thionyl chloride (0.31 mmol) and 42 mg imidazole (0.61 mmol) in 4 mL 1:1 CH$_2$Cl$_2$/CH$_3$CN. After 12 hours, 2 ml DMF is added, followed by 120 mg powdered K$_2$CO$_3$, 5 mg t-Bu4N$^+$I$^-$, and 30 mg additional imidazole. The mixture is stirred four hours at 53° C. After concentration, chromatography on silica gel in 2%→4% MeOH in CH$_2$Cl$_2$, trituration with t-BuOMe, and filtration provided 1109 as a white solid. MS m/z=453 [M+H]$^+$; Rt=8.71 min.

Compounds below are prepared according to the procedure for compound 1110, substituting the appropriate amines in each of the two reaction steps.

| Compound | HPLC ret. | MS m/z |
|---|---|---|
| 828 | (Method A) 7.86 min. | 456 |
| 829 | (Method A) 7.71 min. | 461 |
| 830 | (Method A) 8.42 min. | 471 |
| 831 | (Method A) 7.41 min. | 473 |
| 832 | (Method A) 7.44 min. | 473 |
| 833 | (Method A) 7.43 min. | 445 |
| 834 | (Method A) 8.50 min. | 479 |
| 835 | (Method A) 8.92 min. | 499 |
| 836 | (Method A) 8.86 min. | 499 |
| 837 | (Method A) 9.40 min. | 500 |
| 838 | (Method A) 8.77 min. | 537 |
| 839 | (Method A) 8.80 min. | 523 |
| 840 | (Method A) 8.94 min. | 523 |
| 841 | (Method A) 8.03 min | 485 |
| 842 | (Method A) 8.68 min. | 529 |
| 843 | (Method A) 7.60 min | 459 |

-continued

| Compound | HPLC ret. | MS m/z |
|---|---|---|
| 844 | (Method A) 8.14 min | 495 |
| 845 | (Method A) 8.50 min | 509 |
| 846 | (Method A) 7.92 min. | 471 |
| 847 | (Method A) 4.93 min. | 528 |
| 848 | (Method A) 6.38 min. | 437 |
| 849 | (Method A) 7.02 min. | 439 |
| 850 | (Method A) 8.24 min | 451 |
| 851 | (Method A) 8.24 min | 485 |
| 890 | (Method A) 7.28 min. | 473 |
| 1076 | 9.23 min. | 396 |
| 1077 | 10.65 min. | 446 |
| 1078 | 7.44 min. | 412 |
| 1079 | 8.92 min | 466 |
| 1080 | 9.06 min. | 446 |
| 1082 | 8.50 min. | 398 |
| 1083 | 8.55 min. | 404 |
| 1084 | 7.39 min. | 350 |
| 1085 | 10.69 min. | 475 |
| 1086 | 10.45 min. | 475 |
| 1087 | 11.05 min. | 463 |
| 1088 | 10.92 min. | 463 |
| 1089 | 9.22 min. | 397 |
| 1090 | 9.04 min. | 474 |
| 1091 | 8.64 min. | 355 |
| 1092 | 10.94 min. | 431 |
| 1094 | 9.75 min. | 399 |
| 1095 | 9.91 min. | 422 |
| 1096 | 6.78 min. | 506 |
| 1097 | 8.93 min. | 365 |
| 1098 | 8.88 min. | 388 |
| 1100 | 10.45 min. | 431 |
| 1101 | 10.22 min. | 436 |
| 1103 | 9.71 min. | 385 |
| 1105 | 9.73 min. | 440 |
| 1106 | 10.16 min. | 458 |
| 1107 | 9.26 min. | 395 |
| 1108 | 9.48 min. | 413 |
| 1111 | 11.40 min. | 459 |
| 1112 | 8.26 min. | 392 |
| 1114 | 8.31 min | 337 |
| 1115 | 9.19 min | 371 |
| 1117 | 8.64 min. | 381 |

EXAMPLE 7

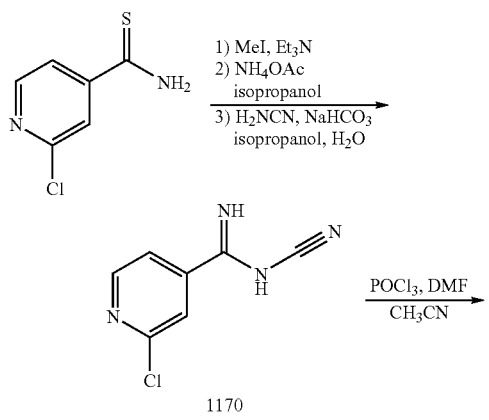

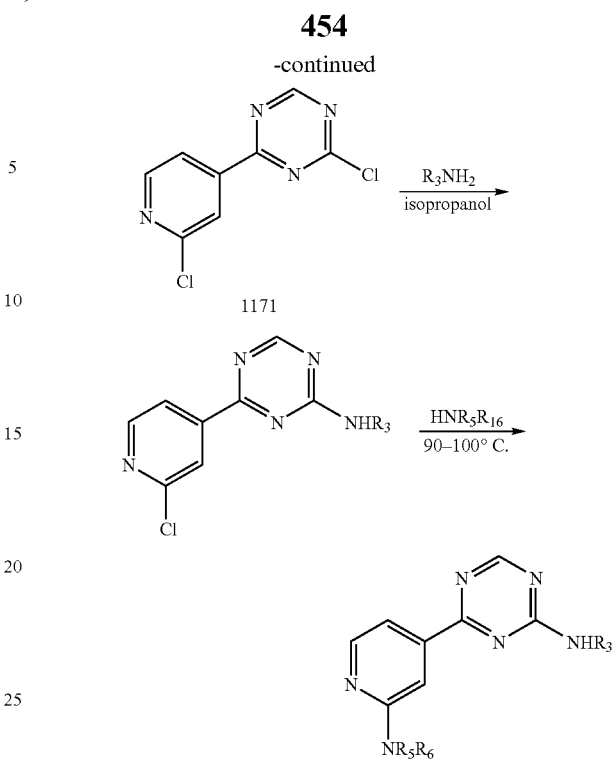

Compounds in example 7 may be prepared in a similar manner as those described in Example 5: the thioamide of 2-chloroisonicotinamide [prepared according to Libermann, D.; Rist, N.; Grumbach, F.; Cals, S.; Moyeux, M.; Rouaix, A. *Memoires Presentes a la Societe Chimique* 1958, 694–702] is alkylated with methyl iodide. The resulting thioimidate salt (4.3 g, 13.5 mmol) is stirred overnight in 100 ml isopropanol with 1.7 g ammonium acetate. After concentration and trituration with isopropanol/t-BuOMe, filtration provides the amidine as a solid (2.3 g). This material is stirred overnight with 3.5 g solid $NaHCO_3$, 2.4 ml of a 50% aqueous solution of $H_2NCN$, 40 ml isopropanol, and 100 ml $H_2O$. The resulting precipitate is triturated with a small amount of isopropanol to obtain 1.6 g cyanoamidine 1170. This material is suspended in $CH_2Cl_2/CH_3CN$ with 1.3 ml $POCl_3$ and 1 ml DMF at 0 °C. and the mixture is warm ed to room temperature. After several hours, the homogenous solution is poured into a 1:1 mixture of pH 7 buffer and saturated $NaHCO_3$. After extraction with EtOAc and filtration through a plug of silica, 1.6 g of 2-chloro-4-(2-chloro-pyridin-4-yl)-[1,3,5]triazine 1171 is obtained as a white solid. MS m/z=227 [M+H]$^+$; HPLC Rt=13.18 min.

Compound 1171 reacts with an optionally substituted aryl or heterocyclic or heteroaryl amine (where $R^3$ is as defined in the formulae herein) at room temperature to produce the desired adduct. The remaining chloride may then be displaced by reaction with amine (neat or in a small amount of solvent) at elevated temperature. The product may be isolated by filtration, silica gel chromatography, or preparative HPLC.

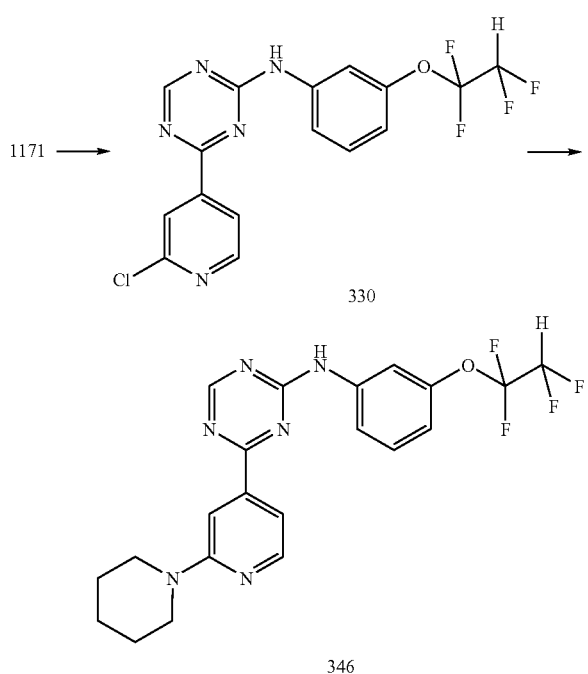

330

346

Compound 1171 (250 mg, 1.1 mmol) and 3-(1,1,2,2,-tetrafluoroethoxy)aniline (230 µl, 1.5 mmol) are stirred in 2 mL THF overnight. The mixture is diluted with t-BuOMe and filtered; the filtrate is concentrated, triturated with t-BuOMe, filtered, and washed with a small amount of isopropanol to obtain 320 mg compound 330 as an off-white solid. MS m/z=400 [M+H]$^+$; HPLC Rt=16.50 min.

Compound 330 (27 mg, 0.068 mmol) is stirred under N$_2$ 15 hours in 1 mL piperidine at 93–104° C. After concentration and silica gel chromatography in 95:5 CH$_2$Cl$_2$/MeOH and trituration with isopropanol, compound 346 is obtained as a yellow solid. MS m/z=449 [M+H]$^+$; HPLC Rt=12.53 min.

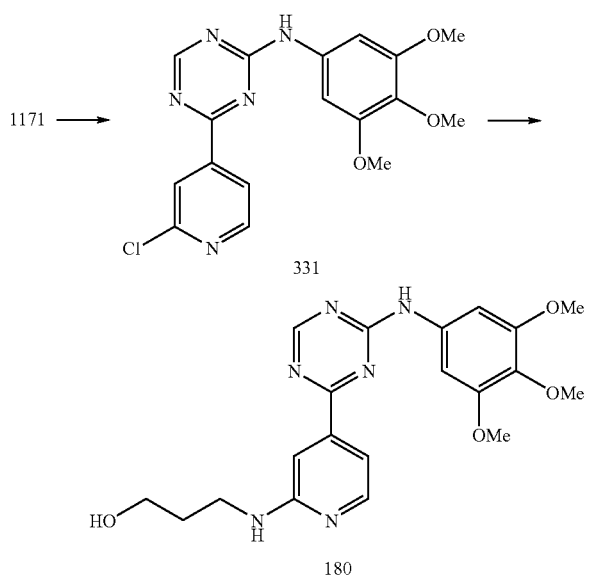

331

180

Compound 180 is prepared according to the procedure outlined for compound 346, substituting the appropriate amines in each of the two reaction steps. Intermediate compound 331: MS m/z=374 [M+H]$^+$; HPLC Rt=13.8 min. Compound 180; MS m/z=413 [M+H]$^+$; HPLC Rt=8.18 min.

Compound 433 is prepared from compound 331 according to the procedure outlined for compound 346, substituting the appropriate amine. Compound 443: MS m/z=468 [M+H]$^+$; 1H NMR (300 MHz, DMSO-d6) 10.22 (s, 1H), 8.80 (s, 1H), 8.09 (d, J=5.3, 1H), 7.35 (s, 1H), 7.23 (dd, J=5.3, 1.5, 1H), 7.16 (s, 2H), 6.87–6.81 (m, 1H), 3.75 (s, 6H), 3.61 (s, 3H), 3.3–3.2 (m), 2.5–2.3 (m), 1.64–1.58 (m, 2H), 0.90 (t, J=7.0, 6H), HPLC Rt=7.64 min.

The following compounds are prepared according to the procedure outlined for compound 346, substituting the appropriate amines in each of the two reaction step:

| Compound | HPLC ret. | MS m/z |
|---|---|---|
| 45 | 7.26 min. | 412 |
| 345 | 9.99 min. | 423 |
| 372 | 10.26 min. | 439 |
| 412 | 9.03 min. | 395 |

EXAMPLE 8

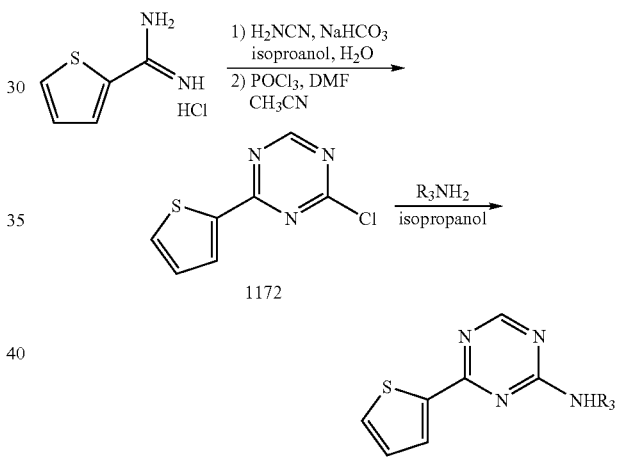

1172

By a similar procedure to examples 5–7, the commercially available amnidinethiophene hydrochloride may be converted to a variety of thiophenyl-[1,3,5]triazin-2-ylamines.

Amidinethiophene hydrochloride (2.6 g, 16 mmol) and cyanamide (1.3 g, 32 mmol) are stirred at room temperature in 20 ml isopropanol and 80 ml 5% aqueous sodium bicarbonate for five days. The resulting white precipitate is filtered and rinsed with a small amount of H$_2$O and isopropanol to provide the thiophene cyanoamidine intermediate. MS m/z=152 [M+H]$^+$; HPLC Rt=7.58 min. To a 0° C. solution of POCl$_3$ (550 µl, 6.0 mmol) and DMF (460 µl, 6.0 mmol) in 15 ml CH$_2$C$_2$ is added 750 mg (5.0 mmol) of this material. The stirring mixture is allowed to warm to room temperature. After an hour, 40 ml CH$_3$CN is added to better dissolve the suspended solids. After four additional hours, the mixture is concentrated and filtered through silica, the solids are dissolved with CHCl$_2$ and EtOAc and this solution is eluted with 5:1 hexaneslt-BuOMe to provide 860 mg white solid 2-chloro-4-thiophen-2-yl-[1,3,5]triazene 1172. MS m/z=198 [M+H]$^+$; HPLC Rt=13.16 min.

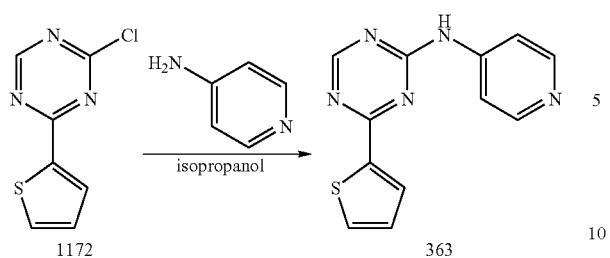

Compound 1172 (37 mg, 0.19 mmol) and 4-aminopyridine (21 mg, 0.22 mmol) are stirred overnight in 2.5 ml isopropanol at room temperature. 50 μl Et₃N is added. After stirring a few hours, the mixture is filtered and rinsed with isopropanol and t-BuOMe to provide compound 363 as a white solid. MS m/z.=256 [M+H]⁺; 1H NMR (300 MHz, DMSO-d6) 9.43 (br s, 1H), 9.33 (s, 1H), 9.24 (d, J=7.9, 2H), 8.41 (dd, J=3.7, 1.2, 1H), 8.12 (dd, J=4.9, 1.2, 1H), 7.36 (dd, J=4.9, 3.7, 1H), 7.06 (d, J=7.9, 2H); HPLC Rt=7.64 min.

Compound 217 is prepared from compound 1172 according to the procedure outlined for compound 363, substituting the amine 3,4,5-trimethoxyaniline. Compound 217: MS m/z=345 [M+H]⁺; 1H NMR (300 MHz, DMSO-d6) 10.15 (br s, 1H), 8.67 (s, 1H), 8.01 (dd, J=3.7, 1.2, 1H), 7.88 (dd, J=4.9, 1.2, 1H), 7.23 (dd, J=4.9, 3.7, 1H), 7.19 (br s, 2H), HPLC Rt=12.98 min.

Compounds below are prepared from compound 1172 according to the procedure outlined for compound 363, substituting the appropriate amine:

| Compound | HPLC ret. | MS m/z |
|---|---|---|
| 349 | 9.99 min. | 340 |
| 350 | 16.05 min. | 371 |
| 352 | 14.69 min. | 300 |
| 354 | 9.59 min. | 298 |
| 355 | 10.20 min. | 312 |
| 356 | 13.90 min. | 280 |
| 357 | 12.36 min. | 315 |
| 358 | 9.63 min. | 298 |
| 359 | 12.33 min. | 329 |
| 360 | 16.10 min. | 289 |
| 361 | 17.28 min. | 361 |
| 362 | 11.73 min. | 286 |
| 1072 | 13.47 min. | 299 |
| 1073 | 15.01 min. | 273 |

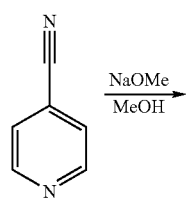

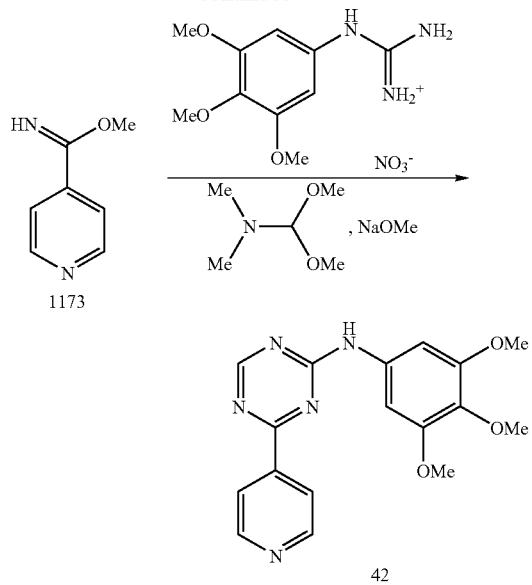

Compound 42 may be obtained by a procedure similar to that described in example 5–8, and also through a route extending from the work of Baldev Singh [*Heterocycles*, 34, 1929–935]. 4-Cyanopyridine is converted to imidate 1173 by base-catalyzed addition of methanol as described by Singh. One equivalent of trimethoxyphenylguanidine [Davis, P.; Moffat, D. F. C.; Davis, J. M.; Hutchings, M. C. WO 97/19065, 1997] is added to the methanolic solution, with no consumption of imidate at 42° C. overnight. One equivalent each of NaOMe and dimethylformamide, dimethyl acetal are added along with 1:1 isopropanol and toluene, and the mixture is heated at 65° C. for 1–2 days. After concentration, chromatography on silica gel (CH₂Cl₂/MeOH/NH₄OH), and purification by reverse-phase HPLC, compound 42 is obtained as an orange solid, trifluoroacetic acid salt. MS m/z=340 [M+H]⁺; 1H NMR (300 MHz, DMSO-d6) 10.37 (s, 1H), 8.88 (s, 1H), 8.83 (d, J=6.0, 2H), 8.25 (d, J=6.0, 2H), 7.16 (s, 2H); HPLC Rt=9.92 min.

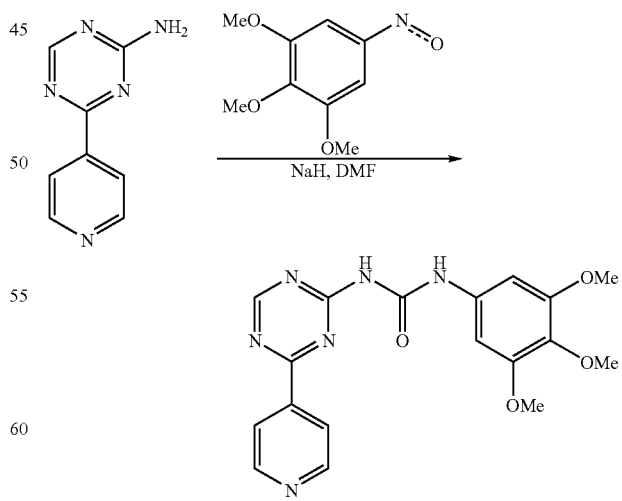

Preparation of compound 1118: 2-Amino-4-(4-pyridinyl)-1,3,5-triazine (200 mg, 1.2 mmol) [prepared according to B.

Singh *Heterocycles*, 34, 1992, 929–935] is stirred with trimethoxyphenylisocyanate (250 mg, 1.2 mmol) and 60% NaH/oil dispersion (47 mg, 1.2 mmol) in 20 mL DMF overnight. The mixture is concentrated and treated with water; the product is collected and recrystallized from DMSO. Compound 1118: MS m/z=383 [M+H]+; 1H NMR (300 MHz, DMSO-d6) 10.86 (s, 1H), 10.83 (s, 1H), 9.14 (s, 1H), 8.848.82 (m, 2H), 8.21–8.19 (m, 2H), 6.93 (s, 2H); HPLC Rt=8.26 min.

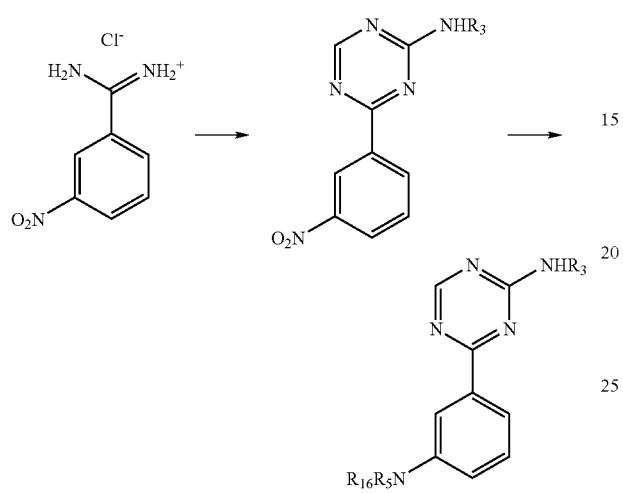

With use of the general procedure outlined in examples 5–8, commercially available 3-Nitroamidine provides entry to a variety of aryl substitutions. Reduction of the nitroarene to the amine may be followed, for example, by acylation, reductive amination, sulfonylation, or urea formation to provide compounds exemplified above with independent $R^5R^{16}$ as defined in the formulae herein.

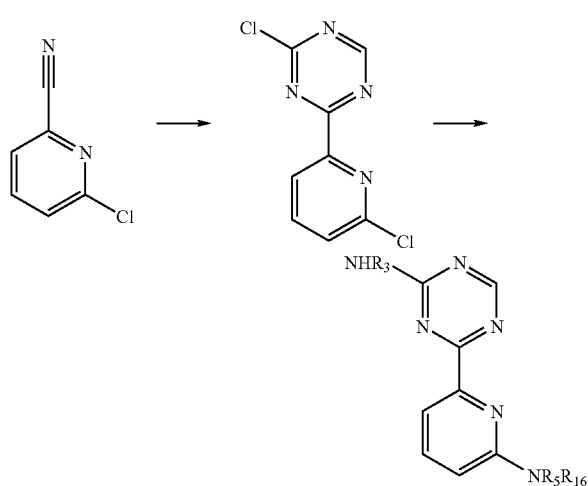

By the procedure outlined in examples 5–8, 6-chloro-pyridine-2-carbonitrile [Elman, B. *Tetrahedron*, 1985, 41, 4941–4948] may be functionalized to provide the pyridinyl [1,3,5]triazinylamines exemplified above with independent $R^5R^{16}$ as defined in the formulae herein.

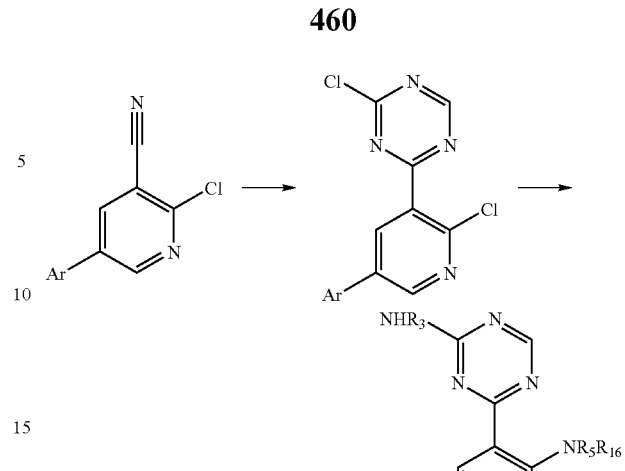

By the procedure outlined in examples 5–8, 2-chloro-4-aryl-3-pyridine-carbonitriles [Church, R.; Trust, R.; Albright, J. D.; Powell, D. W. *J. Org. Chem.* 1995, 60, 3750–3758] may be functionalized to provide the pyridinyl [1,3,5]-triazinylamines exemplified above with independent $R^5R^{16}$ as defined in the formulae herein.

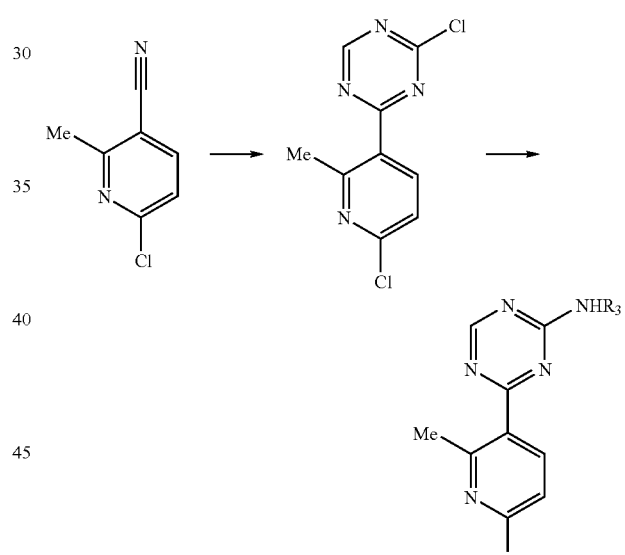

By the procedure outlined in examples 5–8, 6-chloro-2-methyl-3-pyridine-carbonitrile [Singh, B.; Lesher, G. Y.; Brundage, R. P. *Synthesis*, 1991, 894–8961 may be functionalized to provide the pyridinyl[1,3,5]triazinylamines exemplified above with independent $R^5R^{16}$ as defined in the formulae herein.

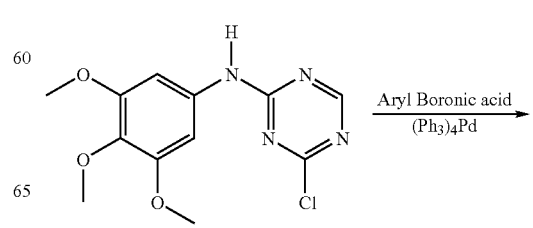

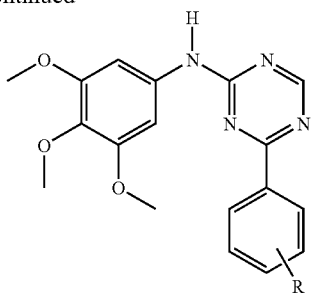

EXAMPLE 9

Compound 218: Compound 924 (214 mg, 0.72 mmol) is dissolved into toluene (25 mL) under air at room temperature. Tetrakis (triphenylphosphine) palladium(0) (25 mg, 0.02 mmol) is added, followed by addition of benzo[b] thiophene-2-boronic acid (141 mg, 0.79 mmol) as a solution in ethanol (2 mL), and sodium carbonate (2 M in water, 0.80 mL, 1.6 mmol). The reaction vessel is purged with argon, fitted with a reflux condenser and covered with aluminum foil to exclude light. The reaction is then heated to reflux for 18 hours, then quenched by cooling it to room temperature and adding excess water. This mixture is then extracted with ethyl acetate (3 times). The ethyl acetate extracts are then washed with brine, combined, dried over anhydrous sodium sulfate, filtered and concentrated under reduced pressure. The recovered material is then eluted through a 20×2.5 cm column of silica gel with a 20%, 40%, and 60% ethyl acetate: hexane step gradient. The recovered material is then applied to two 1000µ preparative TLC plates and developed one time with a 95:5:0.5 $CH_2Cl_2$:MeOH:$NH_4OH_{(a,q)}$ solvent system. The material that is recovered from these plates is then triturated with a 1:1 mixture of toluene:methanol giving 21 mg (7%) of a green solid: MS m/z=395 $[M+H]^+$; $^1$H NMR (300 MHz, DMSO-$d_6$) δ 10.31 (br s, 1H), 8.80 (s, 1H), 8.44 (s, 1H), 8.06 (dd, J=13.2, 7.5 Hz, 2H), 7.49 (m, 2H), 7.25 (br s, 2H), 3.87 (s, 6H), 3.67 (s, 3H); HPLC Rt=16.18 min.

Compound 219: Compound 924 (256 mg, 0.86 mmol) is reacted with 3-pyridyl boronic acid (117 mg, 0.95 mmol) in the manner described for Compound 218, but is kept at reflux under argon for 72 hours. The reaction is then quenched by cooling it to room temperature, diluting it with excess water, and extracting it with ethyl acetate (3 times). The ethyl acetate extracts are then washed with brine, combined, dried over anhydrous sodium sulfate, filtered and concentrated under reduced pressure. The recovered material is purified by applying it to two 1000µ preparative TLC plates and developing one time with a 95:5:0.5 $CH_2Cl_2$:$NH_4OH_{(aq)}$ solvent system. The material recovered from these plates is then applied to a set of two 500 µ preparative TLC plates and developed one time with a 7:7:7:1 MtBE:$CH_2Cl_2$:Hexane:MeOH solvent system. This gives 8 mg (2.7%) of a pale green solid: MS m/z=340 $[M+H]^+$; $^1$H NMR (300 MHz, CDCl$_3$) δ 9.67 (br s, 1H), 8.90 (br s, 1H), 8.80 (br s, 2H), 7.65 (br s, 1H), 7.39 (br s, 2H), 6.94 (br s, 2H), 3.90 (s, 6H), 3.85 (s, 3H); HPLC Rt=8.21 min.

Compound 220. Compound 924 (180 mg, 0.61 mmol) is reacted with 3-chlorophenyl boronic acid (104 mg, 0.67 mmol) in the manner described for example 218, but with an air atmosphere instead of argon. The reaction is then quenched by cooling it to room temperature, diluting it with excess water, and extracting it with ethyl acetate (3 times). The ethyl acetate extracts are then washed with brine, combined, dried over anhydrous sodium sulfate, filtered and concentrated under reduced pressure. The recovered material is purified by eluting it through a 17×2.5 cm column of silica gel with a 20%, 40%, and 80% ethyl acetate:hexane step gradient. The material from this column is then further purified by applying it to two 1000µ preparative TLC plates and developing one time with a 95:5:0.5 $CH_2Cl_2$:MeOH:$NH_4OH_{(aq)}$ solvent system. Final purification of the recovered material is accomplished with preparative HPLC giving 4 mg (1.7%) of a green solid: MS m/z 373 =$[M+H]^+$; $^1$H NMR (300 MHz, CDCl$_3$) δ 8.76 (br s, 1H), 8.46 (br s, 1H), 8.33 (br d, J=7.4 Hz, 1H), 7.51 (m, 1H), 7.42 (t, J=7.9 Hz, 1H), 6.99 (br s, 2H), 3.92 (s, 6H), 3.84 (s, 3H); HPLC Rt=16.23 min.

Compound 221: Compound 924 (88 mg, 0.30 mmol) is reacted with 4-methylphenyl boronic acid (44 mg, 0.33 mmol) in the manner described for example 218, but with an air atmosphere instead of argon, and with refluxing for 36 hours. The reaction is then quenched by cooling it to room temperature, diluting it with excess water, and extracting the mixture with ethyl acetate (3 times). The ethyl acetate extracts are then washed with brine, combined, dried over anhydrous sodium sulfate, filtered and concentrated under reduced pressure. The recovered material is then eluted through a 17×2.5 cm column of silica gel with a 20%, 40%, and 80% ethyl acetate:hexane step gradient. The recovered material is recrystallized from ethanol, and the recovered crystals are applied to two 500µ preparative TLC plates and developed one time with a 95:5:0.5 $CH_2Cl_2$:MeOH:$NH_4OH_{(aq)}$ solvent system giving 11 mg (10%) of a white solid: MS m/z=353 $[M+H]^+$; $^1$H NMR (300 MHz, CD$_3$OD) δ 8.69 (br s, 1H), 8.34 (d, J=8.4 Hz, 2H), 7.33 (d, J=7.7 Hz, 2H), 7.22 (br s, 2H), 3.89 (s, 6H), 3.77 (s, 3H), 2.43 (s 3H); HPLC Rt=14.61 min.

Compound 222: Compound 924 (106 mg, 0.36 mmol) is reacted with 4-fluorophenyl boronic acid (55 mg, 0.39 mmol) in the manner described for example 218, but with an air atmosphere instead of argon, and with refluxing for 60 hours. The reaction is then quenched by cooling it to room temperature, diluting it with excess water, and extracting the mixture with ethyl acetate (3 times). The ethyl acetate extracts are then washed with brine, combined, dried over anhydrous sodium sulfate, filtered and concentrated under reduced pressure. The recovered material is purified by trituration with diethyl ether, followed by $CH_2Cl_2$, followed by toluene, giving 28 mg (21%) of a gray solid: MS m/z=357 $[M+H]^+$; $^1$H NMR (300 MHz, DMS-$d_6$) δ 10.21 (br s, 1H), 8.82 (s, 1H), 8.45 (dd, J=8.7, 5.9 Hz, 1H), 7.41 (t, J=8.7 Hz, 1H), 7.22 (br s, 2H), 3.80 (s, 6H), 3.65 (s, 3H); HPLC Rt=14.60 min.

Compound 226: Compound 924 (212 mg, 0.71 mmol) is reacted with 3-thiophene boronic acid (101 mg, 0.78 mmol) in the manner described for example 218, but with refluxing for 36 days. The reaction is then quenched by cooling it to room temperature, diluting it with excess water, and extracting the mixture with ethyl acetate (3 times). The ethyl acetate extracts are then washed with brine, combined, dried over anhydrous sodium sulfate, filtered and concentrated under reduced pressure. The recovered material is purified by elution through a 20×2.5 cm column of silica gel with a 20%, 40%, and 60% ethyl acetate: hexane step gradient, followed by a 2.5% MeOH $CH_2Cl_2$ eluant. The material recovered from this column is then applied to two 500µ preparative TLC plates and developed one time with a 95:5:0.5 $CH_2Cl_2$:MeOH:$NH_4OH_{(aq)}$ solvent system. The material recovered from these plates is then finally purified by trituration with a 1:1 toluene:methanol solvent system giving 35 mg (14%) of a pale green solid: MS m/z=345 [M+H]+; 1H NMR (300 MHz, DMSO-$d_6$) δ 10.14 (br s, 1H), 8.76 (s, 1H), 8.49 (m, 1H), 7.79 (dd, J=5.04, 1.01 Hz, 1H), 7.71 (dd, J=5.04, 3.02 Hz, 1H), 7.22 (br s, 2H), 3.80 (s, 6H), 3.65 (s, 3H); HPLC Rt=12.66 min.

The following compounds are prepared according to Example 9 above:

| Cmpd # | HPLC Rt | MS | Cmpd # | HPLC Rt | MS |
|--------|---------|-----|--------|---------|-----|
| 230    | 11.73   | 399 | 611    | 13.91   | 389 |
| 232    | 14.04   | 369 |        |         |     |

EXAMPLE 10

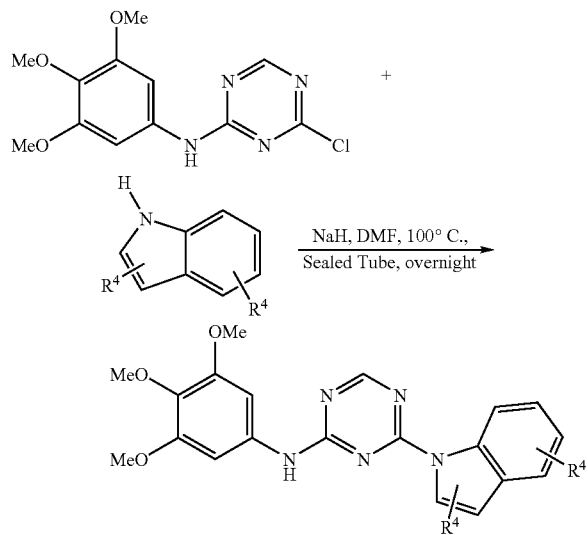

Compound 185: Indole (29 mg, 0.25 mmol) is dissolved into DUT (2 mL) under $N_2$ at room temperature. NaH (10 mg of a 60% suspension of NaH in-mineral oil, 0.25 mmol) is added producing a strong gas evolution. This mixture is stirred at room temperature for 30 minutes and Compound 924 (74 mg, 0.25 mmol) is added as a solution in DMF (1 mL), dropwise, via syringe, over a 5 minute period. The reaction is then heated to 100° C. for 7 days in a sealed tube under $N_2$. The reaction is then cooled to room temperature and quenched with water, which causes a precipitate to form. This mixture is then extracted with ethyl acetate (3 times). The ethyl acetate extracts are washed with brine, combined, dried over sodium sulfate, filtered and concentrated. The recovered material is then purified by elution through a 17×2.5 cm column of silica gel (15%, 30%, 60% EtOAc:Hexane step gradient, followed with 10% MeOH:$CH_2Cl_2$). The material recovered from the column is then further purified by applying it to two 500μ preparative TLC plates and developing one time with 95:5:0.5 $CH_2Cl_2$:MeOH:$NH_4OH_{(aq)}$. This gives 50 mg (53%) of a tan solid: MS m/z=378 [M+H]+, 1H NMR (300 MHz, DMSO-$d_6$) δ 10.26 (s, 1H), 8.71 (br s, 1H), 8.65 (br s, 1H), 8.20 (br s, 1H), 7.64 (m, 1H), 7.24 (m, 3H), 7.03 (br s, 1H), 6.83 (d, J=3.7 Hz, 1H), 3.78 (s, 6H), 3.68 (s, 3H); HPLC Rt=16.34 min.

Compound 198: 5-Chloroindole (38 mg, 0.25 mmol) is dissolved into DMF (2 mL) under air, at room temperature, in a sealed tube. NaH (10 mg of a 60% suspension of NaH in mineral oil, 0.25 mmol) is added producing a strong gas evolution, which is vented to the atmosphere. This mixture is allowed to sit for 15 minutes, then Compound 924 (1 mL of a 0.25 M solution in DMF, 0.25 mmol) is added. The tube is sealed and heated to 100° C. for 3 days. The reaction is then cooled to room temperature, and quenched with saturated $NH_4Cl_{(aq)}$. The resulting mixture is diluted with water and extracted 3 times with ethyl acetate. The ethyl acetate extracts are washed with brine, combined, dried over sodium sulfate, filtered and concentrated. The recovered material is then purified by elution through a 25×2.5 cm column of silica gel (20%, 40%, 60% and 80% EtOAc:Hexane step gradient). The material recovered from this column is then triturated with a 1:1 mixture of methanol:toluene giving 53 mg (52%) of a white solid: MS m/z=412 [M+H]+; 1H NMR (300 MHz, DMSO-$d_6$) δ 10.33 (br s, 1H), 8.90 (br s, 0.5H), 8.74 (br s, 1H), 8.65 (br s, 0.5H), 8.26 (br s, 1H), 7.74 (s, 1H), 7.50–7.10 (br m, 2H), 7.02 (br s, 1H), 6.83 (d, J=3.7 Hz, 1H), 3.79 (s, 6H), 3.68 (s, 3H); HPLC Rt=14.57 min.

Compound 238: 4-Methoxyindole (37 mg, 0.25 mmol) is reacted Compound 924 (1 mL of a 0.25 M solution in DMF, 0.25 mmol) in the manner described for compound 198. The reaction is heated to 100° C. for 3 days, then cooled to room temperature and quenched with saturated $NH_4Cl_{(aq)}$. The resulting mixture is diluted with water and extracted 3 times with ethyl acetate. The ethyl acetate extracts are washed with water and brine, combined, dried over sodium sulfate, filtered and concentrated. The recovered material is then purified by elution through a 20×2.5 cm column of silica gel (20%, 40%, 60% and 80% EtOAc:Hexane step gradient). The material recovered from this column is then triturated with a 1:1 mixture of methanol:toluene giving 40 mg (39%) of a white solid: MS m/z=408 [M+H]+; 1H NMR (300 MHz, DMSO-$d_6$) δ 10.26 (br s, 1H), 8.71 (br s, 1H), 8.53 (br s, 0.5H), 8.21 (br s, 0.5H), 8.03 (br s, 1H), 7.20 (br m, 2H), 7.01 (br s, 1H), 6.80 (br m, 2H), 3.90 (s, 3H), 3.78 (s, 6H), 3.67 (s, 3H); HPLC Rt=16.23 min.

Compound 239: 5,6-Dimethoxyindole (44 mg, 0.25 mmol) is reacted Compound 924 (1 mL of a 0.25 M solution in DMF, 0.25 mmol) in the manner described for compound 198. The reaction is heated to 100° C. for 3 days, then cooled to room temperature and quenched with saturated $NH_4Cl$ (aq). The-resulting mixture is diluted with water and extracted 3 times with ethyl acetate. The ethyl acetate extracts are washed with water and brine, combined, dried over sodium sulfate, filtered and concentrated. The recovered material is then purified by elution through a 25×2.5 cm column of silica gel (20%, 40%, 60% and 80% EtOAc:Hexane step gradient). The material recovered from the column is then further purified by applying it to two 500 μ preparative TLC plates and developing one time with 95:5:0.5 $CH_2Cl_2$: MeOH $NH_4OH_{(aq)}$. This gives 47 mg (43%) of a white solid: MS m/z=438 [M+H]+; 1H NMR (300 MHz, DMSO-$d_6$) δ 10.21 (br s, 1H), 8.69 (s, 1H), 8.40 (br s, 0.5H), 8.22 (br s, 0.5H), 8.04 (d, J=3.7 Hz, 1H), 7.17 (s, 1H), 7.06 (br m, 2H), 6.70 (d, J=3.3 Hz, 1H), 3.80 (s, 3H), 3.75 (s, 6H), 3.67 (s, 3H), 3.56 (br s, 3H); HPLC Rt=14.05 min.

Compound 327: 7-Azaindole (35 mg, 0.30 mmol) is reacted with Compound 924 (1 mL of a 0.30 M solution in DMF, 0.30 mmol) in the manner described for compound 198. The reaction is heated to 100° C. for 3 days, then cooled to room temperature and quenched with saturated $NH_4Cl$ $^{(aq)}$. The resulting mixture is diluted with water and extracted 3 times with ethyl acetate. The ethyl acetate extracts are washed with water and brine, combined, dried over sodium sulfate, filtered and concentrated. The recovered material is then applied to two 1000μ preparative TLC plates and developed one time with 95:5:0.5 CH$_2$Cl$_2$:MeOH:NH$_4$OH$_{(aq)}$. This gives 39 mg (34%) of a pale yellow solid: MS m/z=379 [M+H]$^+$; $^1$H NMR (300 MHz, DMSO-d$_6$) δ 10.35 (br s, 1H), 8.44 (dd, J=4.7, 1.7 Hz, 1H), 8.26 (d, J=4.0 Hz, 1H), 8.10 (dd, J=7.7, 1.7 Hz, 1H), 7.47 (br s, 2H), 7.33 (dd, J=7.7, 4.7 Hz, 1H), 6.84 (d. J=4.0 Hz, 1H), 3.80 (s, 6H), 3.66 (s, 3H); HPLC Rt=9.26 min.

Compound 339: Melatonin (46 mg, 0.2 mmol) is reacted with Compound 924 (1 mL of a 0.20 M solution in DMF, 0.20 mmol) in the manner described for compound 198. The reaction is heated to 80° C. for 3 days, then cooled to room temperature and quenched with saturated NH$_4$Cl$_{(aq)}$. A precipitate forms and is recovered by vacuum filtration, washed with cold water, suspended in methanol, vacuum filtered, and rinsed with fresh cold methanol to give 25 mg (25%) of a white solid: MS m/z=493 [M+H]$^+$; $^1$H NMR (300 MHz, DMSO-d$_6$) δ 10.20 (br s, 1H), 8.90–8.40 (brm, 2H), 8.02 (m, 2H), 7.18 (d, J=2.3Hz, 1H), 7.15–6.70 (br m, 3H), 3.82 (s, 3H), 3.79 (s, 6H), 3.68 (s, 3H), 3.35 (br m, 2H), 2.82 (br t, J=6.7 Hz, 2H), 1.79 (s 3H); HPLC Rt=12.61 min.

Compound 353: Indole-3-acetamide (35 mg, 0.2 mmol) is reacted with 2-chloro-4-(3',4',5'-trimethoxyanilino)-1,3,5-triazine (1 mL of a 0.20 M solution in DMF, 0.20 mmol) in the manner described for compound 198. The reaction is heated to 100° C. for 3 days, then cooled to room temperature and quenched with saturated NH$_4$Cl$_{(aq)}$. The resulting precipitate is recovered by vacuum filtration, washed with cold water, then triturated with a 1:1 mixture of methanol:CH$_2$Cl$_2$ and dried under high vacuum giving 16 mg (18%) of a brown solid: MS m/z=435 [M+H]$^+$; $^1$H NMR (300 MHz, DMSO-d$_6$) δ 10.24 (s, 1H), 9.00–8.50 (br m, 2H), 8.12 (s, 1H), 7.80–7.45 (m, 2H), 7.45–6.90 (m, 3H), 3.79 (s, 6H), 3.67 (s, 3H), 3.53 (s, 2H); HPLC Rt=11.46 min.

Compound 411: Ethyl 3-indole acetate (284 mg, 1.40 mmol) is reacted with

Compound 924 (166 mg, 0.56 mmol) in the manner described for compound 198 using 5 mL of DMF, 2.8 mmol of NaH, and adding solid Compound 924 instead of as a solution in DMF. The reaction is heated to 80° C. for 3 days, then cooled to room temperature and quenched with saturated NH$_4$Cl$_{(aq)}$. The resulting mixture is diluted with water and extracted 3 times with ethyl acetate. The ethyl acetate extracts are washed with water and brine, combined, dried over sodium sulfate, filtered and concentrated. The recovered material is then purified by elution through a 20×2.5 cm column of silica gel (20%, 40%, 60% and 80% EtOAc:Hexane step gradient). The material recovered from the column is then further purified by applying it to two 500μ preparative TLC plates and developing one time with 95:5:0.5 CH$_2$Cl$_2$:MeOH:NH$_4$OH$_{(aq)}$. The material recovered from these plates is then applied to a second set of two 500μ preparative TLC plates and developed one time with 7:7:7:1 MtBE:CH$_2$Cl$_2$:Hexane:MeOH. This gives 12 mg (5%) of a brown solid: MS m/z=464 [M+H]$^+$; $^1$H NMR (300 MHz, DMSO-d$_6$) δ 10.26 (s, 1H), 9.00–8.50 (br m, 2H), 8.18 (s, 1H), 7.60 (m, 1H), 7.50–6.90 (m, 4H), 4.11 (q, J=7.0 Hz, 2H), 3.85 (s, 2H), 3.79 (s, 6H), 3.68 (s, 3H), 1.20 (t, J=7.0 Hz, 3H); HPLC Rt=15.88 min.

The following compounds are prepared according to Example 9 above:

| Cmpd # | HPLC Rt | MS | Cmpd # | HPLC Rt | MS |
|---|---|---|---|---|---|
| 196 | 15.88 | 408 | 323 | 17.44 | 392 |
| 200 | 18.56 | 484 | 332 | 16.06 | 403 |
| 205 | 13.36 | 436 | 333 | 9.63 | 479 |
| 237 | 17.40 | 412 | 441 | 15.72 | 396 |
| 240 | 12.82 | 379 | | | |

EXAMPLE 11

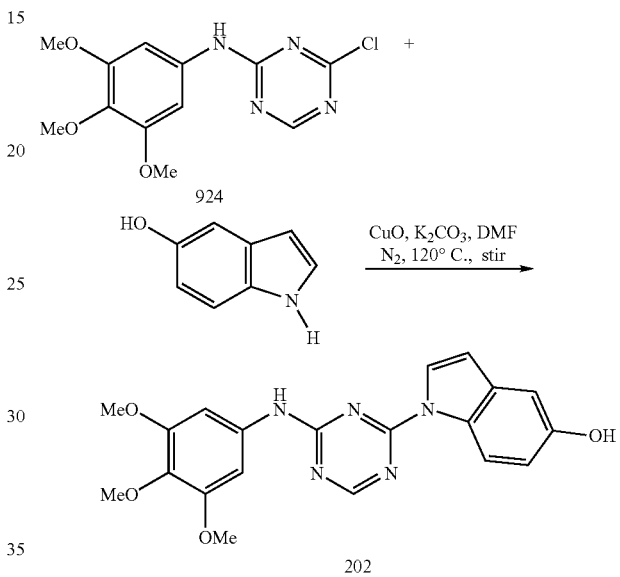

Reference: Khan, M. A.; Rocha, E. K. Chem. Pharm. Bull., 1977, 25 (11), 3110–3114.

Compound 202: Compound 924 (74 mg, 0.25 mmol), 5-hydroxyindole (33 mg, 0.25 mmol), and anhydrous K$_2$CO$_3$ (35 mg, 0.25 mmol) are dissolved in DMF (2 mL) in a sealed tube fitted with a magnetic stirrer, under N$_2$, at room temperature. A catalytic amount of copper(II) oxide is then added and the reaction heated to 120° C. for 18 hours. The reaction is then cooled to room temperature and quenched with water. This mixture is then extracted with ethyl acetate (3 times). The ethyl acetate extracts are washed with brine, combined, dried over sodium sulfate, filtered and concentrated. The recovered material is then purified by elution through a 17×2.5 cm column of silica gel (25%, 50% and 100% EtOAc:Hexane step gradient). The material recovered from the column is then triturated with a 1:1 mixture of methanol:CH$_2$Cl$_2$ and dried under high vacuum giving 39 mg (40%) of a brown solid: MS m/z=394 [M+H]$^+$; $^1$H NMR (300 MHz, DMSO-d$_6$) δ 10.18 (br s, 1H), 9.29 (s, 1H), 8.67 (br s, 1.5H), 8.38 (br s, 0.5H), 8.10 (d, J=3.4 Hz, 1H), 7.40–6.69 (m, 4H), 6.67 (d,J=3.7 Hz, 1H), 3.78 (s, 6H), 3.68 (s, 3H); HPLC Rt=12.02 min.

The following compounds are prepared according to the procedure of Example 11:

| Cmpd # | HPLC Rt | MS | Cmpd # | HPLC Rt | MS |
|---|---|---|---|---|---|
| 463 | 12.74 | 422 | 464 | 15.80 | 396 |

EXAMPLE 12

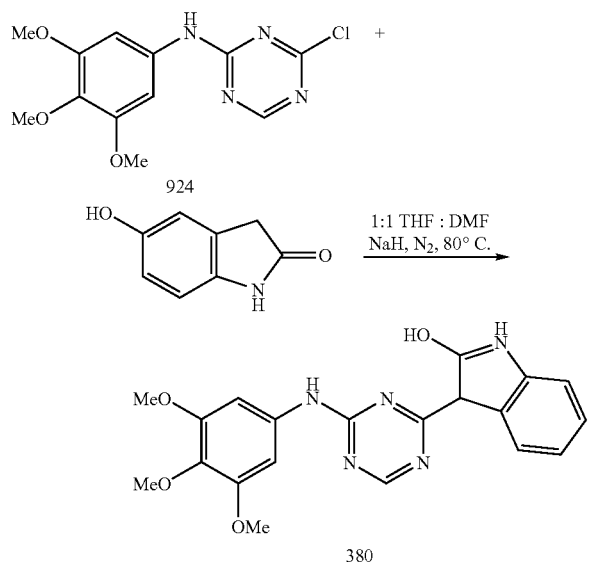

Reference: WO 99/10349

Compound 380

Oxindole (176 mg, 1.32 mmol) is dissolved into a 1:1 mixture of THF:DMF (4 mL), under $N_2$, at room temperature. NaH (53 mg of a 60% suspension in mineral oil, 1.32 mmol) is added, which produces a vigorous gas evolution. This mixture is stirred for 30 minutes at room temperature, then Compound 924 (156 mg, 0.53 mmol) is added and the reaction heated to 80° C. for 2 hours. The reaction is then cooled to room temperature, partially concentrated under reduced pressure, diluted with ethyl acetate, then extracted with water. The water extract is then back extracted two times with fresh ethyl acetate. All of the ethyl acetate extracts are washed with brine, combined, dried over sodium sulfate, filtered and concentrated. The recovered material is then purified by preparative HPLC (5 to 100% $CH_3CN:H_2O$ (0.1% TFA buffer) over 10 minutes at 20 mL/minute). Crystals form in the recovered eluant, which are recovered by vacuum filtration, washed with water, and dried under high vacuum giving 7 mg (7%) of a yellow solid: MS m/z=394 [M+H]$^+$; $^1$H NMR (300 MHz, DMSO-$d_6$) δ 13.0 (br s, 1H), 10.34 (s, 1H), 10.29 (s, 1H), 8.39 (br s, 1H), 7.77 (d, J=6.7 Hz, 1H), 7.08 (s, 2H), 6.91 (t, J=7.0 Hz, 1H), 6.81 (m, 2H), 3.80 (s, 6H), 3.69 (s, 3H); HPLC Rt=10.89 min.

Compound 465

Compound 924 (130 mg, 0.44 mmol) is reacted with N-methylindolin-2-one (162 mg, 1.1 mmol, prepared according to the procedure of Bordwell, F. G.; Fried, H. E., *J. Org. Chem.*, 1991, 56, 4218–4223, in 51% yield) in the manner described for Compound 380, and kept at 80° C. for 3 hours. The reaction is then cooled to room temperature, partially concentrated under reduced pressure, diluted with ethyl acetate, then extracted with water. The water extract is then back extracted two times with fresh ethyl acetate. All of the ethyl acetate extracts are washed with brine, combined, dried over sodium sulfate, filtered and concentrated. The recovered material is then purified by elution through a 17×2.5 cm column of silica gel (20%, 40%, 60% EtOAc:Hexane step gradient, followed by a 5% and 10% MeOH:$CH_2Cl_2$ step gradient). The material recovered from the column is then further purified by applying it to two 1000μ preparative TLC plates and developing one time with 7:7:7:1 MTBE:$CH_2Cl_2$:Hexane:MeOH. The material recovered from these plates is then applied to a set of two 500 μ preparative TLC plates and developed one time with 95:5:0.5 $CH_2Cl_2$:MeOH:$NH_4OH_{(aq)}$. This gives 52 mg (29%) of a yellow solid: MS m/z=408 [M+H]$^+$; $^1$H NMR (300 MHz, DMSO-$d_6$) δ 13.10 (br s, 1H), 10.33 (s, 1H), 8.41 (s, 1H), 7.82 (d, J=7.7 Hz, 1H), 7.08 (s, 2H), 6.99 (m, 2H), 6.88 (t, J=7.4 Hz, 1H), 3.80 (s, 6H), 3.70 (s, 3H), 3.28 (s, 3H); HPLC Rt=15.92 min.

Compound 517

Compound 924 (134 mg, 0.45 mmol) is reacted with 5-chlorooxindole (189 mg, 1.1 mmol) in the manner described for compound 380, and kept at 80° C. for 3 hours. The reaction is then cooled to room temperature, partially concentrated under reduced pressure, diluted with ethyl acetate, then extracted with water. The water extract is then back extracted two times with fresh ethyl acetate. All of the ethyl acetate extracts are washed with brine, combined, dried over sodium sulfate, filtered and concentrated. The recovered material is then purified by elution through a 17×2.5 cm column of silica gel (10%, 20%, and 50% acetone:$CH_2Cl_2$ step gradient, followed by a 10% and 15% MeOH:$CH_2Cl_2$ step gradient). The material recovered from the column is then further purified by trituration with acetone giving 5 mg (2.5%) of a yellow solid: MS m/z=428 [M+H]$^+$; $^1$H NMR (300 MHz, DMSO-$d_6$) δ 13.06 (br s, 1H), 10.41 (br s, 2H), 8.41 (s, 1H), 7.64 (s, 1H), 6 93 (s, 2H), 6.90 (m, 1H), 6.79 (d, J=8.0 Hz, 1H), 3.76 (s, 6H), 3.68 (s, 3H); HPLC Rt=11.47 min.

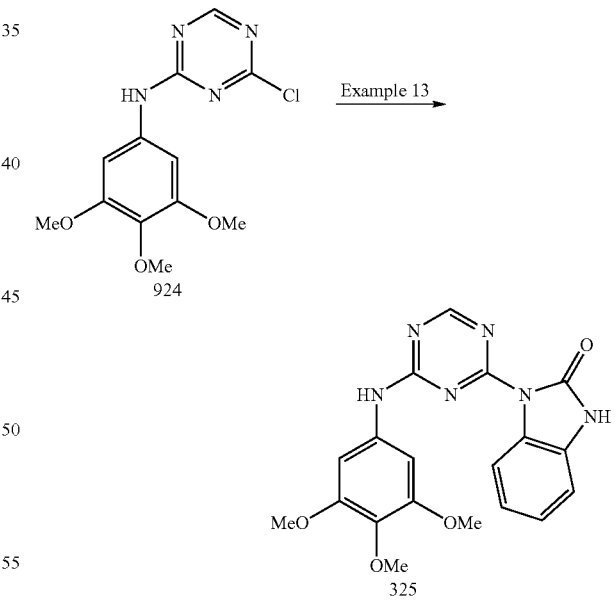

Compound 325

To a solution of 2-hydroxybenzimidazole (788 mg, 6 mmol) in dry DMF (12 mL) at 0° C. and under a nitrogen atmosphere is added NaH (60% in mineral oil, 252 mg, 6.30 mmol). The is stirred at 0° C. for 1.5 h and then a solution of chloride 924 (890 mg, 3.00 mmol) in dry DMF (3 mL) added dropwise. The reaction is allowed to warm to room temperature and then heated at 60–80° C. for 5–18 h. The mixture is poured onto water (15 volumes) and the precipitate collected, washed with water, ether and dried to give compound 325 as a white powder (1.09 g, 92%).

Compounds below are prepared according to the procedure for compound 325, substituting the appropriate reagents. Purification methods varied.

| Compound | MS m/z | HPLC Rt |
|---|---|---|
| 325 | 395.1 | 10.47 |
| 423 | 418.4 (M + Na) | 13.0 |
| 424 | 411.7 | 13.21 |
| 426 | 491.6 | 15.12 |
| 1032 | 393.9 (M − CO2Me) | 11.91 |

EXAMPLE 14a

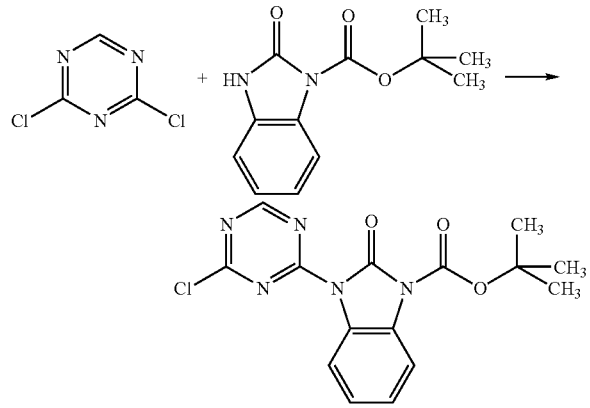

A mixture of 2,4-dichloro-1,3,5-triazine (0.64, 4.26 mmol) and solid $K_2CO_3$ (0.6 g, 4.34 mmol) is suspended in acetonitrile (10 mL) under nitrogen at room temperature followed by addition of 2,3-Dihydro-2-oxo-1H-benzimidazole-1-carboxylic acid, 1,1-dimethylethyl ester [Meanwell, N. A., Yuen, S. S., Gao, Q., St.Laurent, D. R., Balasubramanian, N., *J. Org Chem.*, 60,1565–82 (1995)] (1.0 g, 4.26 mmol). The mixture is allowed to stir at ambient temperature for 1.5 hours. The mixture is poured onto ice/water and the white solid formed is collected by suction filtration and dried under vacuum to give material identified as N3-[4-(2-Chloro-1,3,5-triazinyl)]-2,3-Dihydro-2-oxo-1H-benzimidazole-1-carboxylic acid, 1,1-dimethylethyl ester.

Compound 1277

EXAMPLE 14B

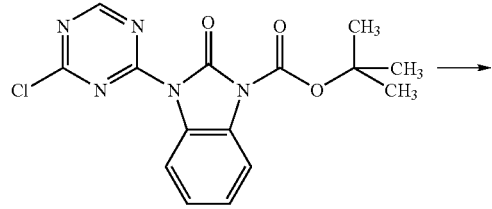

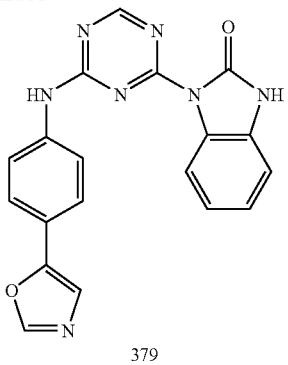

379

Compound 379

N3-[4-(2-Chloro-1,3,5-triazinyl)]-2,3-Dihydro-2-oxo-1H-benzimidazole-1-carboxylic acid, 1,1]-dimethylethyl ester Compound 1277 (75 mg, 0.22 mmol) is suspended in isopropanol (2 mL) in a sealed tube under air at room temperature. N,N-Diisopropylethylamine (0.2 mL, 0.0 mmol) is added, followed by addition of 4-aminophenyloxazole (15 mg, 0.17 mmol). The reaction mixture is then heated to 100° C. for 24 hours, during which everything goes into solution. The reaction is then cooled to room temperature and a white precipitate forms, and is recovered by vacuum filtration and washed with cold isopropanol. HPLC(Method A) Rt=8.49 min.; MS m/z 372; $^1H$ NMR (300 MHz, DMSO-$d_6$) 11.4 (m, 1H), 10.5 (m, 1H); 8.8 (m, 2H), 8.4 (s, 1H), 8.1 (s, 1H), 7.9 (m, 1H), 7.6 (m, 1H), 7.4 (m, 2H), 7.1 (t, 1H), 7.0 (d, 2H);

In a manner similar to that described in Example C, the following compounds of this example are prepared from the appropriately substituted amine and the chloride Compound 1277.

Compound 418: HPLC(Method A) Rt=8.47 min.; MS m/z=372; $^1H$ NMR (300 MHz, DMSO-$d_6$) δ 11.3 (s, 1H), 10.6 (s, 1H), 8.8 (s, 1H), 8.4 (s, 1H), 8.2 (m, 3H), 8.0 (bs, 1H), 7.6 (m, 3H), 7.1 (t, 1H), 7.0 (t, 1H).

Compound 419: HPLC Rt=8.22 min.; MS m/z=348; $^1H$ NMR (300 MHz, DMSO-$d_6$) δ 11.3 (s, 1H), 10.6 (s, 1H), 8.8 (s, 1H), 8.1 (d, 3H), 7.8 (d, 3H), 7.0–7.2 (m, 4H).

Compound 420: HPLC Rt=8.54 min.; MS m/z=348; $^1H$ NMR (300 MHz, DMSO-dd) δ 11.4 (s, 1H), 10.6 (s, 1H), 8.8 (s, 1H), 8.6 (s, 1H), 8.1 (d, 1H), 7.9 (s, 2H), 7.6 (s, 1H), 7.4(m, 2H), 7.0–7.2 (m, 3H).

Compound 422: In a manner similar to that described in Example C, the compound is prepared from the amine that is synthesized as described below. HPLC(Method A) Rt=9.7 min.; MS m/z=505; $^1H$ NMR (300 MHz, DMSO-$d_6$) 5 11.2 (s, 1H), 10.4 (m, 2H), 8.7 (s, 1H), 8.3 (d, 2H), 8.1 (d, 1H), 7.9 (d, 3H), 6.9–7.1 (m, 5H).

To a solution of N-(tert butoxycarbonyl)-phenylene-1,4-diamine (1.5 g, 7.20 mmol) and triethylamine (5 mL) in methylene chloride (50 mL) is added 4-nitrobenzene sulfonylchloride. The mixture is allowed to stir at room temperature for 18 hours. The reaction is diluted with methylene chloride and the organics washed with water. The organic extracts are dried over anh. Magnesium sulfate and concentrated under reduced pressure. The crude product is purified via medium pressure liquid chromatography using methylene chloride followed by 1:99 methanol/methylene chloride as the solvent system Ni -(tert butoxycarbonyl)-N4-(4-nitrophenylsulfonyl)-phenylene-1,4-diamine. The compound is dissolved in methylene chloride (15 mL) followed by addition of trifluoroacetic acid (5 mL) and allowed to stir for 2 hours at room temperature. The organics concentrated to dryness and the residue is taken up in a mixture of ethyl acetate and saturated sodium bicarbonate. The organics are separated, dried over anh. Magnesium sulfate and concentrated under reduced pressure to give N-(4-nitrophenylsulfonyl)-phenylene-1,4-diamine.

Compound 450: HPLC Rt=5.98 min.; MS m/z=316
Compound 451: HPLC Rt=8.85 min.; MS m/z=384
Compound 452: HPLC Rt=9.41 min.; MS m/z=425
Compound 453: In a manner similar to that described in Example C, the compound is prepared from the amine that is synthesized as described below. HPLC(Method A) Rt=9.91 min.; MS m/z=505;

To a solution of 1,4-phenylenediamine (3.0 g, 27.7 mmol) and triethylamine (10 mL) in methylene chloride (50 mL) is added 4-nitrobenzenesulfonylchloride. The mixture is allowed to stir at room temperature for 18 hours. The reaction is taken up in a mixture of ethyl acetate (IL) and saturated sodium bicarbonate (100 mL). The separated organics are dried over anh. Magnesium sulfate and concentrated under reduced pressure. The crude organics are purified via medium pressure liquid chromatography using methylene chloride followed by 2:98 methanol/methylene chloride followed by 0.5:5:995 Conc. NH$_{40}$H/methanol/methylene chloride as the solvent system N3-(4-nitrophenylsulfonyl)-phenylene-1,3-diamine.

Compound 0.454: In a manner similar to that described in Example C, the compound is prepared from the amine that is synthesized as described below. HPLC Rt=9.5 min.; MS m/z=434.

A mixture of 4-nitrophenylisocyanate (1.0 g, 6.09 mmol) and (S)-(+)-3-Hydroxytetrahydrofuran (1.0 mL, 11.3 mmol) is suspended in toluene (20 mL) under nitrogen. The mixture is allowed to stir at room temperature for 18 hours. The reaction is concentrated under reduced pressure. The crude compound is purified via medium pressure liquid chromatography using methylene chloride followed by 1:99 methanol/methylenechloride as the solvent system to give N-(S)-(+)-3-tetrahydrofuranyloxycarbonyl-4-nitroaniline. The compound is added to a suspension of 10% Pd/C (500 mg) and ethanol (20 mL). The mixture is stirred under a hydrogen gas atmosphere for 24 hours. The catalyst is removed by suction filtration and the organics concentrated under reduced pressure. The crude compound is purified via medium pressure liquid chromatography using methylene chloride followed by 1:99 methanol/methylene chloride followed by 5:95 methanol/methylenechloride as the solvent system to give N-(S)-(+)-3-tetrahydrofuranyloxycarbonyl-1,4-phenylenediamine.

Compound 455: In a manner similar to that described in Example C, the compound is prepared from amine that is synthesized as described below. HPLC Rt=9.7 min.; MS m/z=434.

A mixture of 3-nitrophenylisocyanate (1.0 g, 6.09 mmol) and (S)-(+)-3-hydroxytetrahydrofuran (1.0 mL, 11.3 mmol) is suspended in toluene (20 mL) under nitrogen. The mixture is allowed to stir at room temperature for 18 hours. The reaction is concentrated under reduced pressure. The crude compound is purified via medium pressure liquid chromatography using methylene chloride followed by 1:99 methanol/methylenechloride as the solvent system to give N-(S)-(+)-3-tetrahydrofuranyloxycarbonyl-3-nitroaniline. The compound is added to a suspension of 10% Pd/C (500 mg) and ethanol (20 mL). The mixture is stirred under a hydrogen gas atmosphere for 24 hours. The catalyst is removed by suction filtration and the organics concentrated under reduced pressure. The crude compound is purified via medium pressure liquid chromatography using methylene chloride followed by 1:99 methanol/methylenechloride followed by 5:95 methanol/methylenechloride as the solvent system to give N-(S)-(+)-3-tetrahydrofuranyloxycarbonyl-1,3-phenylenediamine.

The following compounds are synthesized in a manner similar to that described in Example C, substituting the appropriate amine.

| Compound | HPLC ret. | MS m/z |
|---|---|---|
| 456 | 7.8 min | 398 |
| 457 | (Method B) 3.47 min. | 339 |
| 458 | (Method B) 3.5 min. | 339 |
| 459 | 12.5 min. | 357 |
| 460 | (Method B) 3.28 min | 329 |
| 461 | (Method B) 3.79 min. | 389 |
| 462 | (Method B) 3.76 min. | 388 |
| 467 | (Method B) 3.19 min. | 350 |
| 482 | (Method B) 3.0 min. | 306 |
| 483 | (Method B) 3.7 min. | 419 |
| 484 | (Method B) 3.2 min. | 339 |
| 485 | (Method B) 3.1 min. | 330 |
| 486 | (Method B) 3.0 min. | 330 |
| 487 | (Method B) 1.9 min. | 306 |
| 488 | (Method B) 1.5 min. | 306 |
| 489 | (Method B) 2.6 min. | 336 |
| 490 | (Method B) 1.9 min. | 307 |
| 491 | (Method B) 2.5 min. | 367 |
| 492 | (Method B) 2.5 min. | 307 |
| 493 | (Method B) 3.2 min. | 349 |
| 494 | (Method B) 2.7 min. | 365 |
| 503 | 14.3 min. | 374 |
| 504 | (Method B) 3.6 min. | 374 |
| 505 | 13.4 min. | 372 |
| 506 | (Method B) 4.2 min. | 441 |
| 508 | (Method B) 2.86 min. | 356 |
| 681 | (Method B) 2.39 min. | 413 |
| 682 | (Method B) 2.3 min. | 321 |
| 683 | (Method B) 3.24 min. | 355 |
| 684 | (Method B) 3.56 min. | 355 |
| 685 | 8.22 min. | 344 |
| 686 | (Method B) 2.19 min. | 356 |

Compound 687: HPLC(Method B) Rt=2.28 min.; MS m/z 356; $^1$H NMR (300 MHz, DMSO-d$_6$) δ 11.2 (s, 1H), 11.0 (s, 1H), 9.6 (m, 1H), 9.0 (m, 2H), 8.7 (s, 1H), 7.8–8.2 (m, 4H), 7.0–7.2 (m, 2H).

Compound 688: HPLC(Method B) Rt=3.54 min.; MS m/z=356; $^1$H NMR (300 MHz, DMSO-d6) δ 11.4 (s, 1H), 10.0 (s, 1H), 9.0 (m, 3H), 8.5 (d, 1H), 8.2 (m, 1H), 7.7 (m, 3H), 7.0–7.2 (m, 3H).

Compound 689: HPLC(Method B) Rt=2.39 min.; MS m/z=356; $^1$H NMR (300 MHz, DMSO-d$_6$) δ 11.8 (s, 1H), 9.2 (s, 1H), 9.0 (m, 1H), 8.4 (m, 1H), 7.7–8.2 (m, 5H), 7.1–7.3 (m, 3H).

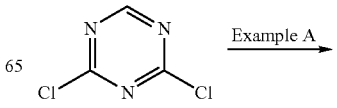

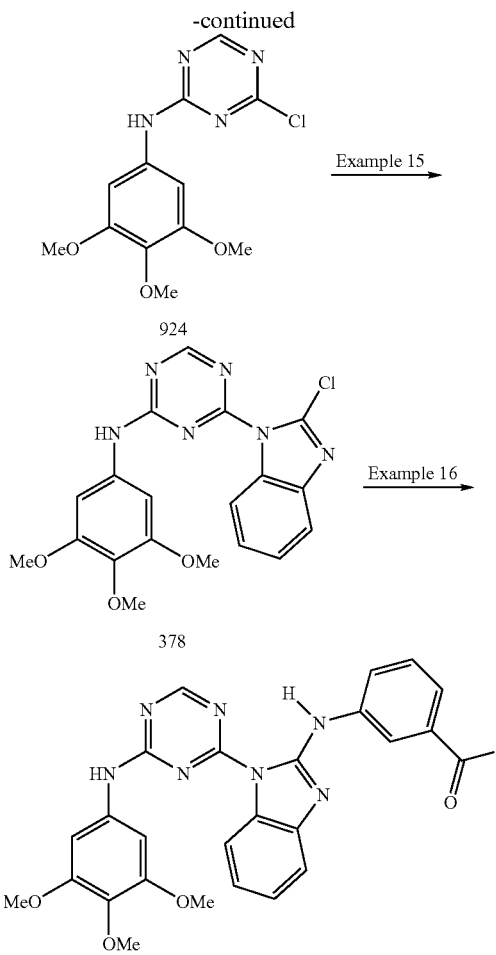

EXAMPLE 15

To a suspension of chlorotriazine 924 (2.97 g, 10 mmol) and chlorobenzimidazole (1.53 g, 10 mmol) in dry acetonitrile (100 mL) is added ground potassium carbonate (1.68 g, 12 mmol). The resulting mixture is heated at 50–90° C. for 2–12 h, cooled to temperature, concentrated in vacuo and purified by column chromatogrraphy (EtOAc/n-Hexanes) to provide compound 378 as a white powder (3.66 g, 89%).

EXAMPLE 16

A mixture of chloride 378 (41 mg, 0.10 mmol), 3-aminobenzamide (14 mg, 0.10 mmol) and diisopropylethylamine (Hunig's base) (16 mg, 0.12 mmol) in iPrOH (3.5 mL) is heated at 100–130° C. for 10–40 h. On cooling a precipitate formed which is collected, washed with iPrOH, ether and dried to give compound 377 as a yellow solid (41 mg, 80%).

Compounds below are synthesized according to the procedure outlined for Example 16, substituting the appropriate reagents.

| Compound | MS m/z | HPLC Rt |
|---|---|---|
| 336 | 470 | 12.40 |
| 371 | 484 | 12.09 |
| 375 | 504 | 14.37 |
| 376 | 509 | 11.94 |
| 377 | 513 | 10.22 |
| 378 | 413 | 13.48 |
| 381 | 495.0 | 15.59 |
| 382 | 496.1 | 13.85 |
| 383 | 528.3 | 13.18 |
| 384 | 484.0 | 11.59 |
| 385 | 484.0 | 12.12 |
| 386 | 483.8 | 12.49 |
| 387 | nd | 12.19 |
| 388 | 512.2 | 13.83 |
| 389 | 451.1 | 8.87 |
| 390 | 514.0 | 11.10 |
| 391 | 438.0 | 9.19 |
| 392 | 466.0 | 9.55 |
| 397 | 500 | 11.98 |
| 398 | 500 | 12.42 |
| 399 | 530 | 12.85 |
| 400 | 530 | 11.16 |
| 401 | 495[M + Na]+ | 10.91 |
| 402 | 560 | 11.61 |
| 403 | 436 | 10.59 |
| 404 | 510 | 10.26 |
| 405 | 422 | 11.40 |
| 406 | 510 | 10.83 |
| 407 | 450 | 9.33 |
| 413 | 485 | 8.50 |
| 414 | 485 | 9.73 |
| 415 | 500 | 12.23 |
| 416 | 485 | 8.53 |
| 417 | 408 | 9.73 |
| 509 | 498 | 11.86 |
| 510 | 499 | 8.60 |
| 511 | 498 | 12.05 |
| 512 | 502 | 11.77 |
| 513 | 502 | 11.93 |
| 514 | 502 | 11.89 |
| 515 | 498 | 12.32 |
| 516 | 498 | 12.45 |
| 549 | 491 | 10.64 |
| 561 | 500 | 10.39 |
| 569 | 512.3 | 12.2 |
| 571 | 568 | 13.15 |
| 572 | 529 | 11.88 |
| 574 | 434 | 10.54 |
| 579 | 526.0 | 11.28 |
| 579 | 526.0 | 11.13 |
| 583 | 474 | 8.96 |
| 585 | 556.2 | 13.12 |
| 586 | 544.3 | 12.24 |
| 587 | 524 | 12.61 |
| 587 | 524.2 | 12.67 |
| 588 | 521 | 13.87 |
| 591 | 528.6 | 11.15 |
| 592 | 512.1 | 12.34 |
| 593 | 527.1 | 8.93 |
| 595 | 528.4 | 11.54 |
| 596 | 544.1 | 11.19 |
| 597 | 532 | 12.93 |
| 598 | 552 | 12.96 |
| 605 | 515 | 12.05 |
| 606 | 536 | 12.72 |
| 940 | 563 | 12.63 |
| 941 | 499 | 10.27 |
| 943 | 518 | 12.08 |
| 944 | 518 | 12.42 |
| 945 | 512 | 12.58 |
| 946 | 563 | 12.50 |
| 947 | 499 | 8.33 |
| 948 | 499 | 8.36 |
| 949 | 518 | 12.32 |
| 950 | 490 | 11.47 |
| 951 | 536 | 12.52 |
| 952 | 529 | 11.87 |

-continued

| Compound | MS m/z | HPLC Rt |
|---|---|---|
| 954 | 524 | 9.95 |
| 1033 | 498.1 | 11.85 |
| 1034 | 498.1 | 11.88 |
| 1035 | 514.2 | 10.82 |
| 1036 | 514.2 | 10.85 |
| 1037 | 514.1 | 11.59 |
| 1042 | 514.0 | 12.08 |
| 1043 | 524 | 12.62 |
| 1044 | 510.2 | 12.20 |
| 1045 | 528.3 | 11.90 |
| 1046 | 528.3 | 11.97 |
| 1048 | 498 | 13.48 |
| 1049 | 512 | 13.40 |
| 1050 | 554 | 15.83 |
| 1051 | 513 | 10.70 |
| 1052 | ND | 16.15 |
| 1053 | 488 | 14.73 |
| 1054/1055 | ND | 13.94/14.11 |
| 1056/1057 | ND | 12.31/12.63 |
| 1058/1059 | ND | 10.11/10.44 |
| 1060/1061 | ND | 12.39/12.67 |
| 1062/1063 | 539/539 | 12.16/12.35 |
| 1064/1065 | 554 (M + Na)/532 | 12.04/12.74 |

Compound 558: HPLC(Method A) Rt=8.43 min.; MS m/z=514; $^1$H NMR (300 MHz, DMSO-d$_6$) δ 10.8 (m, 1H), 10.4 (s, 1H), 8.2–8.7 (m, 2H), 8.0–8.1 (m, 2H), 7.2 (d, 1H), 7.0 (m, 2H), 6.7 (m, 3H), 3.5–3.7 (m, 15H).

EXAMPLE 17

Aminobenzimidazole triazines can be prepared according to Examples B and C, substituting the appropriate amines, and according to the procedure shown below, which describes the preparation of Compound 525.

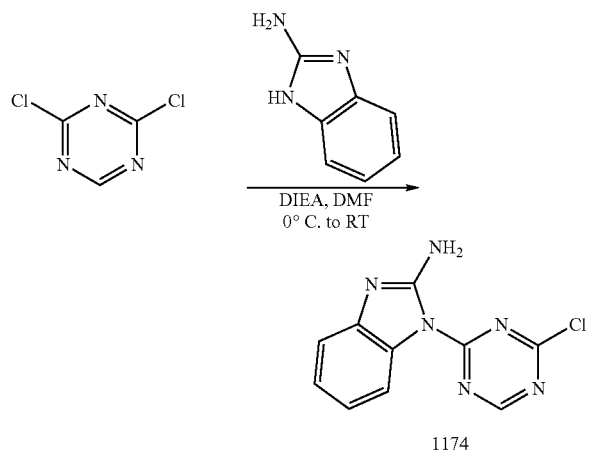

To 1.0 g (6.67 mmol) of 2,4-dichloro-1,3,5-triazine in 3 mL of DMF at 0° C. is added 1.16 mL (6.67 mmol) of DIEA. The resulting yellow solution is stirred at 0° C. for 10 min when 888 mg (6.67 mmol) of 2-aminobenzimidazole is added portionwise over 5 min, followed by an additional 1 mL of DMF. The resulting mixture is stirred at 0° C. for 1.9 h, then at RT for 3.25 h. At this point, the mixture is poured into 40 mL of stirring cold water with additional cold water rinses to a total volume of 100 mL. The light yellow solid is isolated by filtration, rinsed with cold water, and dried in vacuo, giving 1.36 g (83%) of 1-(4-chloro-[1,3,5]triazin-2-yl)-1H-benzoimidazol-2-ylamine (Compound 1174) as a light yellow solid: MS m/z=246 [M+H]$^+$; HPLC Rt=5.79 min.

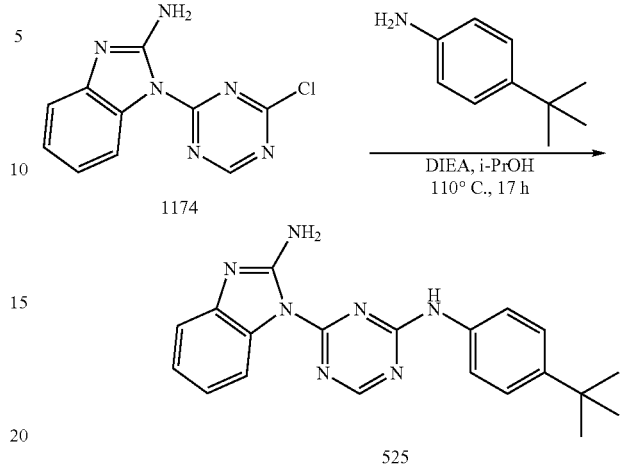

To a suspension of 100 mg (0.405 mmol) 1-(4-chloro[1,3,5]triazin-2-yl)-1H-benzoimidazol-2-ylamine (1174) in 2 mL of i-PrOH at RT in a sealed tube under air is added 0.106 mL (0.608 mmol) of DIEA, followed by 81.7 mg (0.446 mmol) of 4-tert-butylaniline. The resulting mixture is heated to 110° C. for 17 h, then cooled to room temperature. The yellowish precipitate is isolated by filtration, rinsed once each with i-PrOH and Et$_2$O and dried in vacuo, giving 61.8 mg (56.5%) of Compound 525 as a yellowish solid: MS m/z=360 [M+H]$^+$; $^1$H NMR (300 MHz, DMSO-d$_6$) δ 10.48 (s, 1H), 8.85–8.70 (m, 1H), 8.45 (d, 1H), 8.15–6.70 (m, 9H), 1.30 (m, 9H); HPLC Rt=12.87 min.

The following compounds are prepared according to Example 17, substituting the appropriate amine in the second step, corresponding to Example C:

| Cmpd # | HPLC Rt | MS | Cmpd # | HPLC Rt | MS |
|---|---|---|---|---|---|
| 289 | 9.65 | 394 | 527 | 7.13 | 347 |
| 395 | 7.78 | 347 | 528 | 12.07 | 372 |
| 396 | 7.77 | 347 | 646 | 6.85 | 228 |
| 438 | 9.87 | 371 | 647 | 12.03 | 388 |
| 439 | 9.60 | 371 | 648 | 9.01 | 335 |
| 440 | 8.69 | 425 | 651 | 10.19 | 304 |
| 285 | 9.66 | 364 | 479 | 8.58 | 389 |
| 286 | 8.89 | 350 | 480 | 12.54 | 380 |
| 287 | 9.87 | 408 | 524 | 9.38 | 378 |
| 299 | 11.36 | 392 | 526 | 9.95 | 348 |
| 302 | 9.93 | 452 | 654 | 10.41 | 334 |
| 324 | 8.89 | 445 | 655 | 11.72 | 332 |
| 445 | 7.64 | 493 | 656 | 10.16 | 334 |
| 466 | 7.78 | 493 | 657 | 11.78 | 332 |
| 473 | 8.50 | 347 | 658 | 6.47 | 305 |
| 474 | 11.24 | 338 | 659 | 7.39 | 305 |
| 475 | 8.21 | 361 | 662 | 10.68 | 318 |
| 476 | 10.55 | 422 | 663 | 10.74 | 348 |
| 477 | 10.38 | 364 | 664 | 11.52 | 352 |
| 478 | 11.20 | 338 | 923 | 8.27 | 383 |

Compound 700 is prepared according to Example 17, substituting amine 1175. Amine 1175 is prepared by the alkylation of 2-methoxy-5-nitrophenol with 4(2-chloroethyl)morpholine hydrochloride using K$_2$CO$_3$ in refluxing acetone/water as shown in the following scheme.

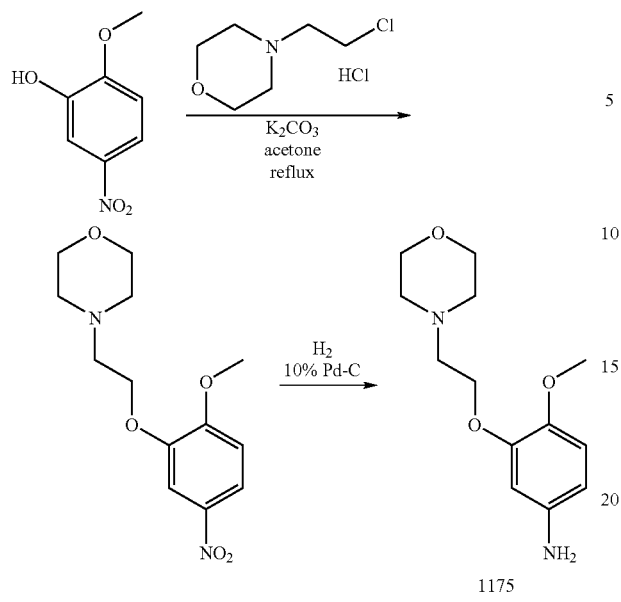

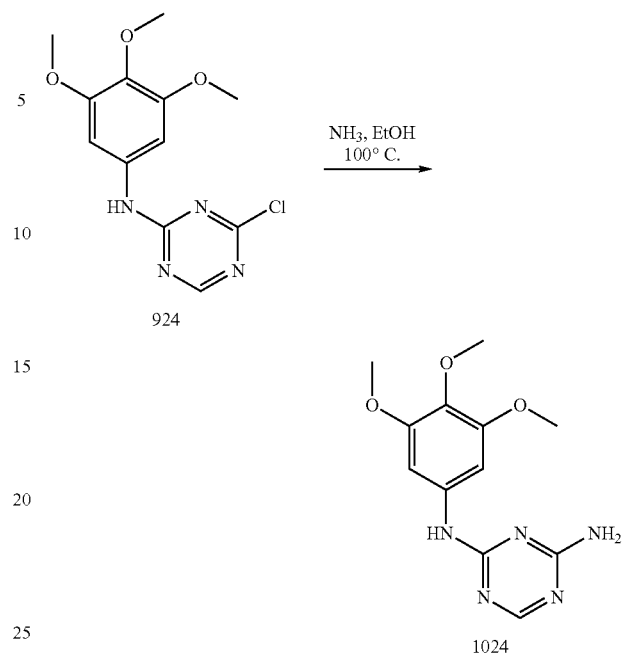

Standard acid/base workup give a yellow solid, which is purified by trituration with Et$_2$O. The resulting yellow solid is converted to the amine by standard hydrogenation using 10% Pd—C in MeOH and EtOAc at RT. Filtration through Celite™ and concentration of the filtrate gave the desired amine, which is then reacted with Compound 1174 under the conditions of Example C. Compound 700 is purified using preparative HPLC: MS m/z=463 [M+H]$^+$; HPLC Rt=7.65 min.

Compound 649 is prepared according to Example 17, substituting the appropriate amine, which is prepared according to the method described for Compound 1175, substituting 2-(diethylamino)ethyl chloride hydrochloride in the alkylation: MS m/z=449 [M+H]$^+$; HPLC Rt=7.91 min.

Compound 650 is prepared according to Example 17, substituting the appropriate amine, which is prepared according to the method described for Compound 1175, using 4-nitroguaiacol and 4-(2-chloroethyl)morpholine hydrochloride. The final solid is purified using preparative HPLC: MS m/z=463 [M+H]$^+$; HPLC Rt=7.48 min.

Compound 652 is prepared according to Example 17, substituting the appropriate amine, which is prepared according to the method described for Compound 1175, using 4-nitroguaiacol and 2-(diethylamino)ethyl chloride hydrochloride: MS m/z=449 [M+H]$^+$; HPLC Rt=7.88 min.

Compound 653 is prepared according Example 17, substituting the addition of potassium phthalimide in PhCH$_3$ and DMF at RT for the second step. Standard aqueous workup followed by flash chromatography (SiO$_2$, elution with EtOAc) gives Compound 653: MS m/z=358 [M+H]$^+$; HPLC Rt=11.14 min.

EXAMPLE 19

Aminotriazine compounds can be prepared by reacting the appropriate chlorotriazine with ammonia, according to the procedure shown below, which describes the preparation of Compound 1024.

1.0 g (3.37 mmol) of 2-chloro-4-(3',4',5'-trimethoxyanilino)-1,3,5-triazine (Compound 924) in 16.8 mL of NH$_3$ in EtOH (2.0 M) is heated at 100° C. for 22 h, then cooled to 0° C. The white solid is isolated by filtration, rinsed with EtOH, and dried in vacuo, giving 0.46 g (50%) of a white solid, which is N-(3,4,5-trimethoxy-phenyl)-[1,3,5]triazine-2,4-diamine (1024): MS m/z=278 [M+H]$^+$; HPLC Rt=6.75 min.

The following compounds are prepared according to Example 19, substituting the appropriate chlorotriazine:

| Cmpd # | HPLC Rt | MS  | Cmpd # | HPLC Rt | MS |
|--------|---------|-----|--------|---------|----|
| 665    | 9.12    | 318 |        |         |    |

EXAMPLE 20

Urea and thiourea compounds can be prepared by reacting the appropriate isocyanate or isothiocyanate with an aminotriazine such as Compound 1024, according to the procedure shown below, which describes the preparation of Compound 852.

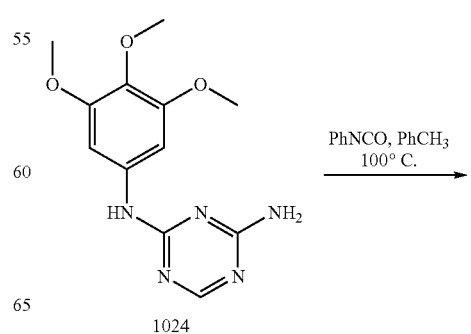

479
-continued

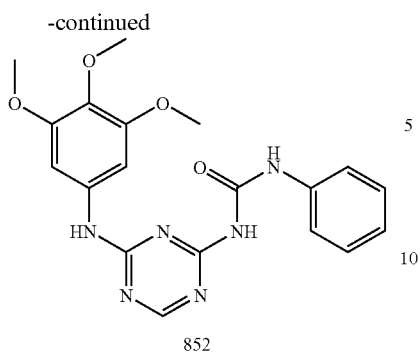

852

To a slurry of 300 mg (1.08 mmol) of N-(3,4,5-trimethoxy-phenyl)-[1,3,5]triazine-2,4-diamine (1024) in 2.5 mL of PhCH$_3$ at RT in a sealed tube under air is added 0.118 mL (1.08 mmol) of PhNCO. The resulting mixture is heated to 100° C. for 7 days, then cooled to room temperature. The white precipitate is isolated by filtration, rinsed once each with PhCH$_3$ and Et$_2$O and dried in vacuo. The slightly impure white solid is purified by trituration in refluxing i-PrOH, cooled to RT, and isolated by filtration, rinsed once each with i-PrOH and Et$_2$O and dried in vacuo giving 353.9 mg (82.5%) of Compound 852 as a white solid: MS m/z=397 [M+H]$^+$; HPLC Rt=11.44 min; $^1$H NMR (300 MHz, DMSO-d$_6$) δ 11.15 (br s, 1H), 10.27 (br s, 1H), 10.10 (s, 1H), 8.50 (s, 1H), 7.75–6.90 (m, 7H), 3.73 (br s, 6H), 3.64 (s, 3H).

The following compounds are prepared according to Example 20, substituting the appropriate amino triazine and either an isocyanate or isothiocyanate:

| Cmpd # | HPLC Rt | MS | Cmpd # | HPLC Rt | MS |
|---|---|---|---|---|---|
| 21 | 12.07 | 427 | 660 | 11.09 | 411 |
| 22 | 12.36 | 457 | 661 | 11.61 | 425 |

EXAMPLE 21

Amide and sulfonamide compounds can be prepared by reacting the appropriate carboxylic acid, acid chloride or sulfonyl chloride with an aminotriazine such as Compound 1024, according to the procedure shown below, which describes the preparation of Compound 679.

[structure of 1024]

PhCH$_2$COCl
pyridine, 100° C.

480
-continued

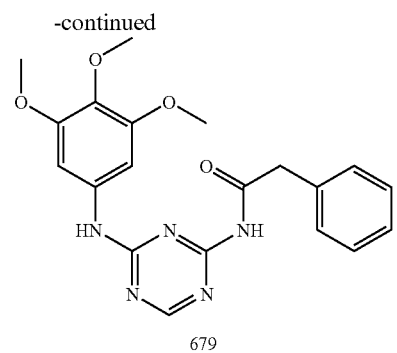

679

To a solution of 75 mg (0.27 mmol) of N-(3,4,5-trimethoxy-phenyl)-[1,3,5]triazine-2,4-diamine (1024) in 2 mL of pyridine at RT in a sealed tube under air is added 0.0.89 mL (0.68 mmol) of PhCH$_2$COCl. The resulting mixture is heated to 100° C. for 2.5 h, then cooled to room temperature, and poured into a stirring mixture of dil. aq. NaHCO$_3$ and EtOAc. The organic layer is washed with dil. NaHCO$_3$, brine, 1N HCl, brine, dried over Na$_2$SO$_4$ and concentrated. Chromatography (SiO$_2$, elution with 3:1 EtOAc-hexanes) gives 55.8 mg (52.1%) of Compound 679 as a yellowish solid: MS m/z=396 [M+H]$^+$; HPLC Rt=11.08 min; $^1$H NMR (300 MHz, DMSO-d$_6$) δ 10.93 (br s, 1H), 10.01 (br s, 1H), 8.53 (s, 1H), 7.40–7.20 (m, 7H), 3.80–3.70 (m, 8H), 3.62 (s, 3H).

Alternatively, amide and sulfonamide compounds can be prepared by reacting the appropriate amide with a substituted chlorotriazine, according to the procedure shown below, which describes the preparation of Compound 680.

[structure 701]

acrylamide
NaH, DMF
0° C.

[structure 680]

To a solution of 58.5 mg (0.823 mmol) of acrylamide in 1 mL of DMF at RT is added 32.9 mg (0.823 mmol) of NaH (60% dispersion in oil). The resulting foam is heated to 60° C. for 10 min, then cooled to 0° C. when a solution of 70 mg (0.274 mmol) of Compound 701 in 0.75 mL of DMF is added dropwise via syringe, followed by one 0.25 mL rinse. The resulting mixture is stirred at 0° for 1 h, then quenched with satd aq NH$_4$Cl and diluted with water and EtOAc. The organic layer is washed with brine and the combined aqueous layer and washing is extracted with EtOAc. The combined organics are dried and concentrated. Flash chromatography (SiO$_2$, elution with 3:1 EtOAc-hexanes, then EtOAc) gives 2.9 mg (3.6%) of a slightly impure product that could be purified to homogeneity by flash chromatography (SiO$_2$, elution with 2:1 EtOAc-hexanes) giving Compound 680: MS m/z=290 [M+H]$^+$; HPLC Rt=10.16 min.

EXAMPLE 22

Aminoindazole compounds can be prepared according to Examples B and C, substituting the appropriate amines, and according to the procedure shown below, which describes the preparation of Compound 554.

Preparation of 1-benzyl-1H-indazol-5-ylamine:

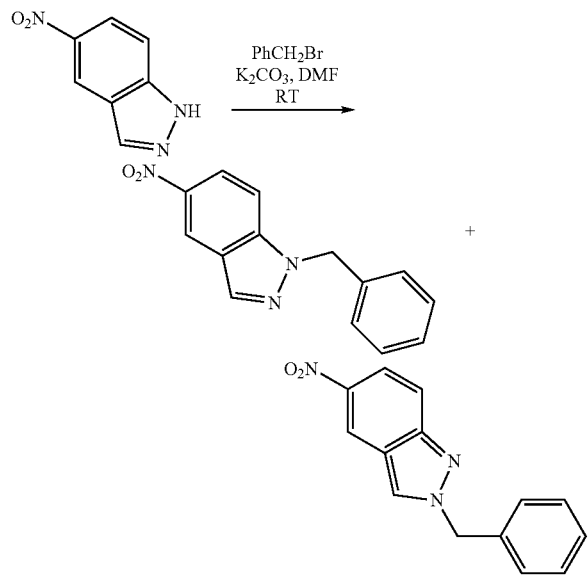

To a solution of 10 g (61.3 mmol) of 5-nitroindazole in 100 mL of DMP is added 12.7 g (91.9 mmol) of $K_2CO_3$ and 7.29 mL (61.3 mmol) of $PhCH_2Br$. The resulting mixture is stirred at RT for 3.5 days, then poured into 400 mL of water. The resulting slurry is filtered, rinsed once with water and dried in vacuo giving a beige solid. A 2.5 g portion of this crude material is purified by chromatography ($SiO_2$, elution with 1:2 EtOAc-hexanes) giving 906.4 mg of the faster eluting 1-substituted isomer and 518.4 mg of the slower eluting 2-substituted isomer.

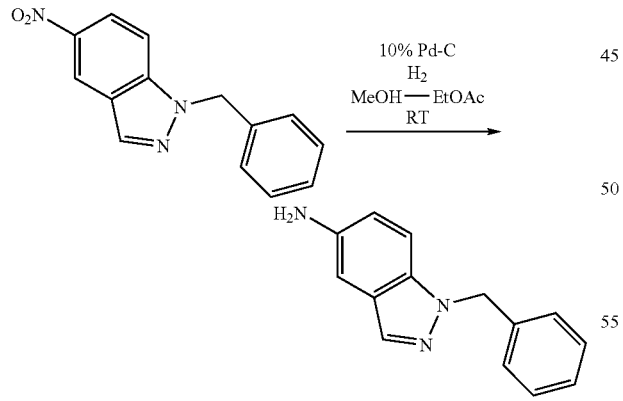

To 906.4 mg (3.58 mmol) of the 1-substituted isomer in 20 mL of MeOH and 5 mL of EtOAc at RT is added a slurry of 150 mg of 10% Pd-C in 5 mL of MeOH. The resulting slurry is then stirred under a balloon of $H_2$ for 1.2 h, filtered through Celite™, and rinsed with MeOH and EtOAc. Concentration of the filtrate gives 790.3 mg (98.9%) of 1-benzyl-1H-indazol-5-ylamine as a pinkish solid: MS m/z= 224 [M+H]$^+$.

Preparation of Compound 554:

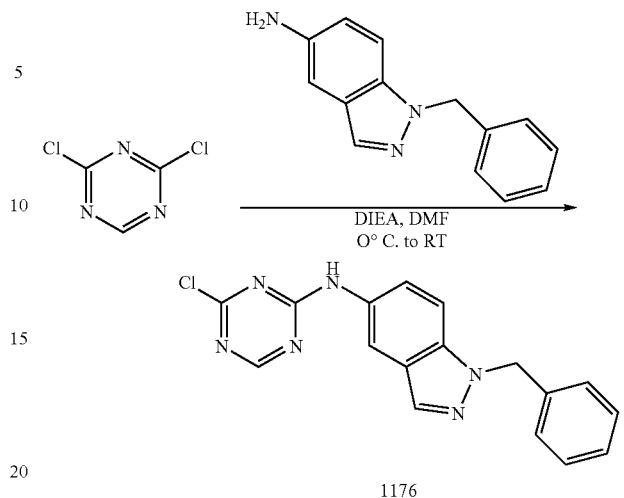

To 526.1 mg (3.51 mmol) of 2,4-dichloro-1,2,5-triazine in 15 mL of DMF at 0° C. is added 0.733 mL (4.21 mmol) of DIEA. The resulting yellow solution is stirred at 0° C. for 20 min when 783.5 mg (3.51 mmol) of 1-benzyl-1H-indazol-5-ylamine is added in one portion followed by 2×2.5 mL DMF flask rinses. The resulting mixture is stirred at 0° C. for 30 min, at RT for 4.5 h, then diluted with EtOAc. The organic layer is then washed twice with water and once with brine. The aqueous layer and washings are extracted once with EtOAc. The combined organics are dried, concentrated, and purified by chromatography ($SiO_2$, elution with 1:1 EtOAc-hexanes) to give a slightly impure pinikish solid. Trituration with $Et_2O$ gives 473 mg (40.1%) of Compound 1176 as a light pink solid: MS m/z=337 [M+H]$^+$; HPLC Rt=13.09 min.

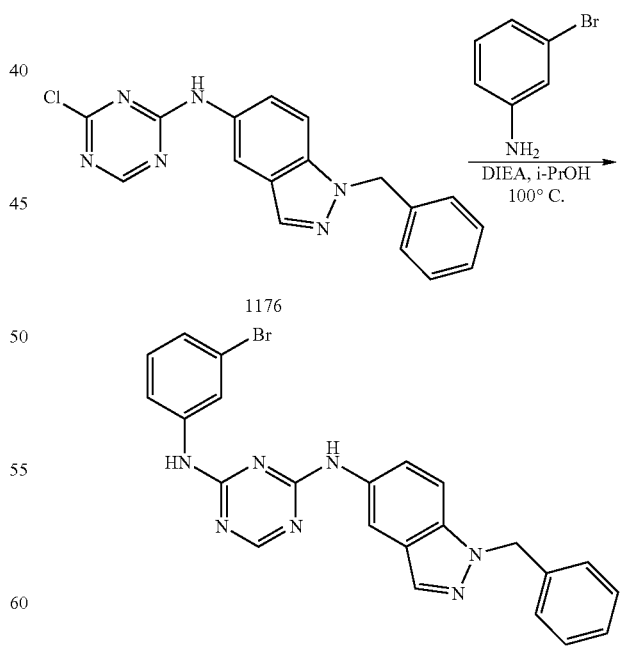

Compound 554 is prepared using Compound 1176 and 3-bromoaniline following Example C: MS m/z=473 [M+H]$^+$; HPLC Rt=13.801 min; $^1$H NMR (300 MHz, DMSO-d$_6$) δ 9.88 (br s, 2H), 8.35 (s, 1H), 8.15–7.90 (m, 4H), 7.70–7.50 (m, 4H), 7.35–7.10 (m, 5H), 5.64 (br s, 2H).

The following compounds are prepared according to Example 22, substituting the appropriate amine in the second step. The HPLC method for the compounds in the table are analyzed using Method A, except for Compound 553.

| Cmpd # | HPLC Rt | MS | Cmpd # | HPLC Rt | MS |
|---|---|---|---|---|---|
| 552 | 8.60 | ND | 871 | 4.31 | 415 |
| 553 | 12.79 | 408 | 872 | 8.38 | 497 |
| 559 | 9.15 | 583 | 873 | 6.97 | 482 |
| 726 | 8.46 | 530 | 900 | 6.41 | 451 |
| 727 | 7.50 | 414 | 901 | 6.51 | 486 |
| 728 | 6.56 | 398 | 902 | 7.33 | 430 |
| 729 | 6.39 | 479 | 903 | 8.26 | 477 |
| 730 | 6.62 | 436 | 904 | 7.01 | 424 |
| 731 | 6.60 | 433 | 905 | 6.83 | 424 |
| 732 | 6.34 | 468 | 906 | 7.91 | 478 |
| 733 | 4.25 | 389 | 907 | 7.88 | 478 |
| 734 | 7.02 | 422 | 908 | 6.25 | 466 |
| 735 | 5.67 | 477 | 909 | 7.86 | 492 |
| 736 | 6.21 | 501 | 910 | 7.64 | 434 |
| 737 | 6.56 | 460 | 911 | 8.05 | 463 |
| 738 | 5.49 | 396 | 912 | 6.94 | 419 |

Compound 676 is prepared according to Example 22 substituting the priate amine, which can be prepared according to Kume, M. et al. *J. Antibio.* 1993, 46, 177: MS m/z=475 [M+H]$^+$; HPLC Rt=10.72 min.

EXAMPLE 18

N-alkylated anilinotriazines can be prepared from the commercially available secondary amines according to Examples B and C, or from the alkylation of chlorotriazine intermediates such as Compound 1176 followed by Example C, according to the procedure shown below, which describes the preparation of Compound 566.

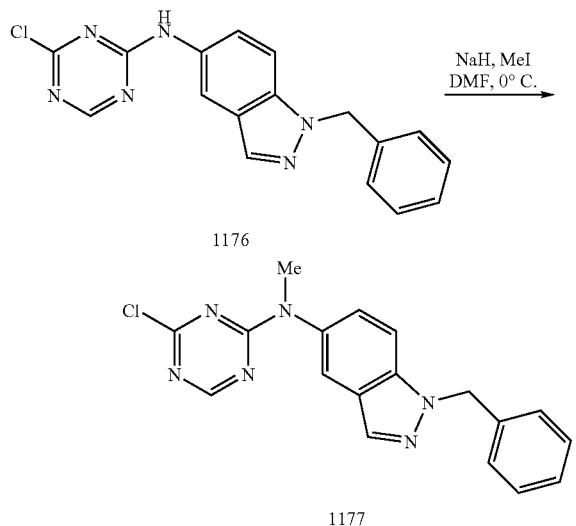

To 473 mg (1.40 mmol) of 1176 in 7.5 mL of DMF at 0° C. is added 0.262 mL (4.21 mmol) of MeI, followed by 67.4 mg (1.69 mmol) of NaH (60% dispersion in oil). The resulting mixture is stirred at 0° C. for 4.25 h (additional 10 mg NaH added after 3.1 h as TLC indicated remaining starting material). At this point, the reaction mixture is quenched with satd aq NH$_4$Cl and diluted with water and EtOAc. The organic layer is washed with water and brine. The aqueous layer and washings are extracted once with EtOAc. The combined organics are dried, concentrated and purified by chromatography (SiO$_2$, elution with 1:1 EtOAc-hexanes) to give Compound 1177 as a pale oil: MS m/z=351 [M+H]$^+$.

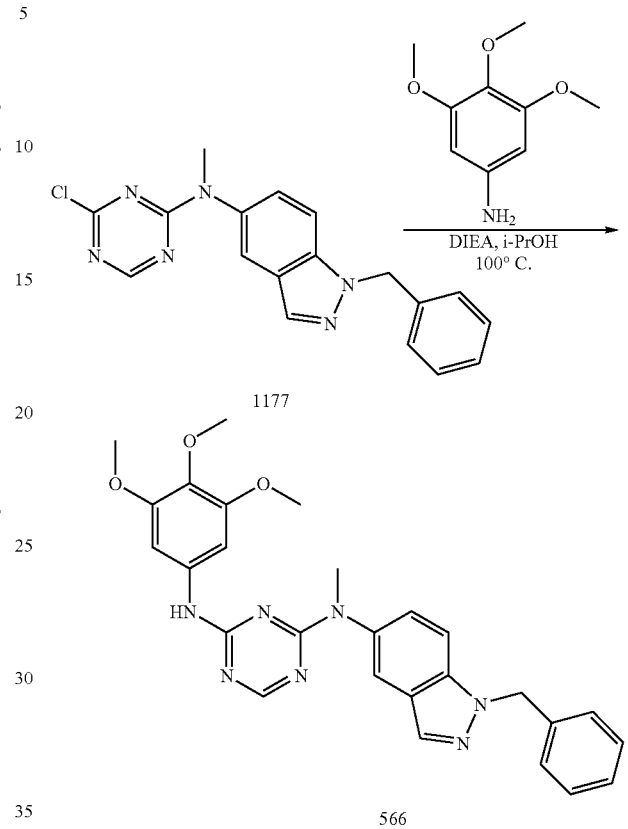

Compound 566 is prepared using Compound 1177 and 3,4,5-trimethoxyaniline following Example C: MS m/z=498 [M+H]$^+$; HPLC Rt=12.27 min; $^1$H NMR (300 MHz, DMSO-d$_6$) δ 9.60 (br s, 2H), 8.40–8.00 (m, 2H), 7.72 (br s, 2H), 7.50–6.60 (m, 7H), 5.68 (s, 2H), 4.00–2.80 (m, 12H).

The following compounds are prepared according to Example 18, substituting the appropriate amine and alkylating reagent for those used in the preparation of 1177, and the appropriate amine in the second step, following Example C. The preparation of the appropriate amines used for Compounds 670, 671, 677 are prepared according to Kume, M. et al. *J. Antibio.* 1993, 46, 177 and Koguro, K. et al. *Synthesis* 1998, 910:

| Cmpd # | HPLC Rt | MS | Cmpd # | HPLC Rt | MS |
|---|---|---|---|---|---|
| 666 | 14.42 | 371 | 670 | 10.83 | 439 |
| 667 | 14.89 | 487 | 671 | 10.92 | 490 |
| 668 | 13.68 | 422 | 677 | 11.48 | 489 |
| 669 | 12.12 | 468 | 51 | 15.67 | 459 |
| 972 | 13.87 | 428 | 310 | 12.95 | 482 |
| 973 | 14.92 | 472 | 309 | 13.52 | 512 |
| 291 | 15.63 | 446(–t – Bu) | 320 | 9.14 | 426 |
| 974 | 15.34 | 496(M + Na) | 319 | 9.74 | 478(M + Na) |
| 56 | 16.04 | 504 | | | |

The following compounds are prepared according to Examples B and C, substituting the appropriate amines, prepared either from the conversion of the commercially available nitrobenzene derivative to the corresponding aniline, as for Compound 1175, or as described in Examples 17, 18 and 22:

| Cmpd # | HPLC Rt | MS | Cmpd # | HPLC Rt | MS |
|---|---|---|---|---|---|
| 599 | 7.75 | 513 | 673 | 13.31 | 442 |
| 600 | 8.09 | 499 | 674 | 11.4 | 366 |
| 601 | 7.46 | 513 | 675 | 10.48 | 366 |
| 602 | 7.82 | 499 | 678 | 11.43 | 393 |
| 557 | 9.06 | 408 | 177 | 11.79 | 484 |
| 556 | 8.31 | 408 | 555 | 11.11 | 484 |
| 672 | 14.12 | 442 | | | |

Compound 539 is isolated during the preparation of Compound 666 resulting from the addition of 2 equivalents of 3-bromoaniline to 2,4-dichloro-1,2,5-triazine: MS m/z= 422 [M+H]$^+$; HPLC Rt=15.69 min.

EXAMPLE 23

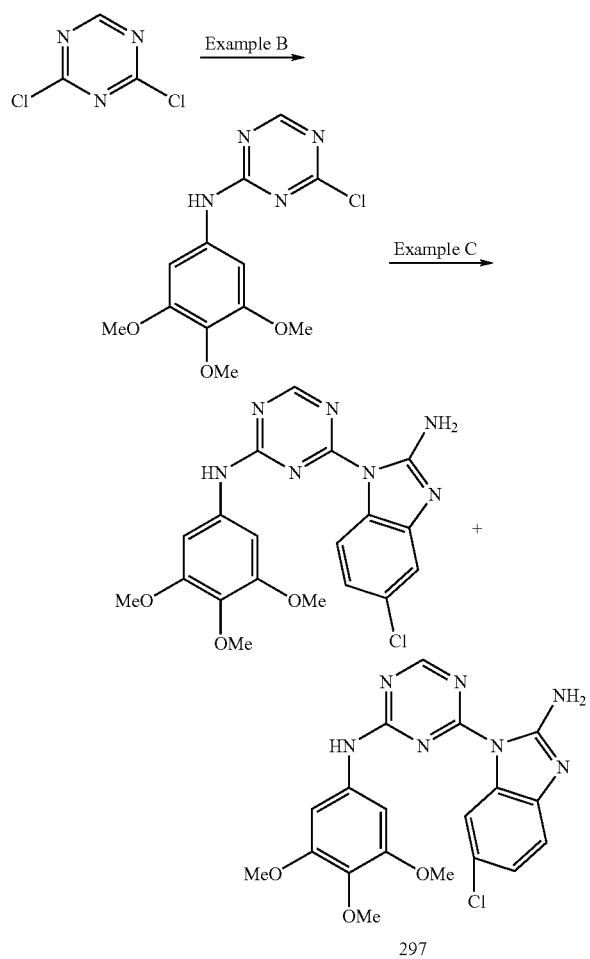

Compounds 296/297 are prepared by reacting chloride 924 with 2-amino-5-chlorobenzimidazole according to Example C to give a 1:1 mixture of 296/297 as a light brown solid (39%).

The following compounds are synthesized according to the procedure described in Example C. Purification methods vary. MS is [M +H]$^+$ except where noted. HPLC retention time is in minutes.

| Compound | MS m/z | HPLC Rt |
|---|---|---|
| 289, 575 | 394 | 9.58 |
| 292, 293 | 462, 462 | 11.20, 11.67 |
| 294, 295 | 439.0, 439.0 | 10.43, 10.77 |
| 296, 297 | 428.2, 428.2 | 10.46, 10.93 |
| 334 | Nd | 9.62 |
| 435 | 498 | 11.81 |
| 1030 | 454 | 9.63 |

EXAMPLE 24

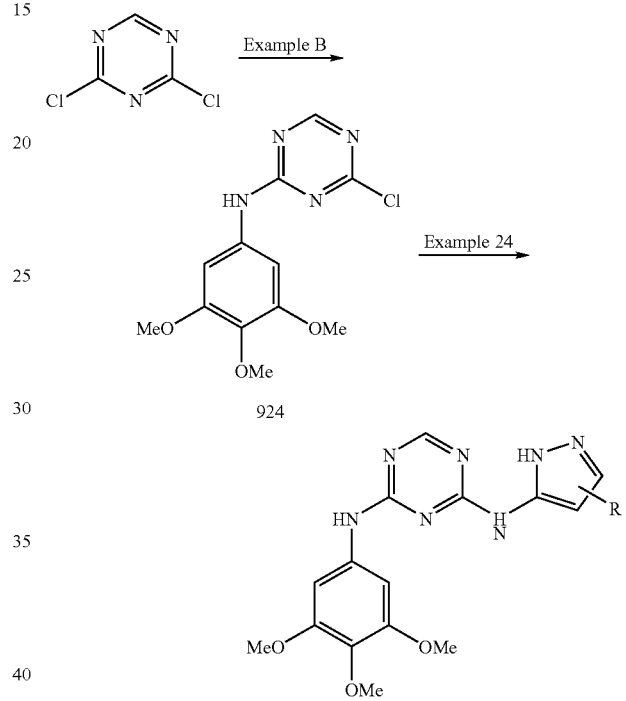

Compounds of example 24 below are synthesized in the same manner as Example C. Purification methods vary. Retention time is in minutes.

| Compound | MS m/z | HPLC Rt |
|---|---|---|
| 88 | 358 | 8.24 |
| 102, 447 | 420 | 10.53 |
| 308 | 410 | 9.65 |
| 313 | 399.8 | 10.05 |
| 318 | 425.9 | 10.29 |
| 367 | 454 | 11.9 |
| 368 | 426 | 12.18 |
| 369 | 420 | 12.54 |
| 393 | 372 | 8.19 |
| 394 | 433 | 11.1 |
| 999 | 454 | 10.26 |
| 470 | 480 | 8.65 |
| 495 | 476(M + Na) | 11.92 |
| 521 | 434 | 10.86 |
| 523 | 478 | 10.46 |
| 1000 | 488 | 12.1 |
| 1001 | 456(M + Na) | 10.99 |
| 1003 | 470 | 12.15 |
| 589 | 488 | 12.74 |

Compound 1178

In a manner similar to that described in Example B. 5.20 g (33.7 mmol) of 2,4-dichloro-1,3,5-triazine is dissolved in 75 mL of dry dimethylformamide and cooled to 0° C. To this solution are added diisopropylethylamine (6.46 mL, 37.1 mmol) and 3-amino-5-(4-carbomethoxyphenyl) pyrazole (7.67 g, 35.3 mmol; prepared as described below). The resulting mixture is stirred at 0° C. for three hours during which time a thick precipitate is formed. The precipitate is filtered under vacuum and washed with excess diethyl ether to provide pure product. MS m/z=331[M+H]$^+$; HPLC Rt=11.61 min.

The following compounds are made in a manner similar to that described above:

| Compound | MS m/z | HPLC Rt (Method B) |
|---|---|---|
| 975 | 253 | 10.38 |
| 976 | 273 | 11.08 |

3-Amino-5-(4-carbomethoxyphenyl) pyrazole used in the above example is prepared as follows: To a solution of 5 grams (24.6 mmol) of methyl 4-(cyanoacetyl)benzoate in 125 mL of absolute ethanol in a glass pressure vessel is added 3.8 mL (122 mmol) of hydrazine hydrate. The vessel is sealed and heated at 100° C. for 4.5 hours. After cooling the vessel is opened and cooling is continued at 0° C. for 45 minutes. The precipitate thus formed is filtered and washed with cold diethyl ether and utilized without further purification. Rt=7.33 min.

The following compounds are synthesized from 2,4-dichloro-1,3,5-triazine using the appropriate aminopyrazolotriazine and reacting it with the appropriate amine in isopropanol under conditions of Example C.

| Compound | MS m/z | HPLC Rt (Method B) |
|---|---|---|
| 338 | 416(M + Na) | 9.18 |
| 337 | 402(M + Na) | 9.15 |
| 340 | 405 | 8.55 |
| 342 | 363 | 7.89 |
| 341 | 385(M + Na) | 7.72 |
| 344 | 378 | 9.84 |
| 343 | 458(M + Na) | 11.17 |
| 364 | 376 | 9.34 |
| 366 | 376 | 10.95 |
| 365 | 380 | 10.71 |
| 429 | 350 | 8.26 |
| 430 | 350 | 7.85 |
| 432 | 406 | 10.46 |
| 431 | 449 | 11.05 |
| 499 | 339 | 8.64 |
| 501 | 339 | 8.16 |
| 500 | 353 | 8.15 |
| 502 | 353 | 7.83 |
| 977 | 390 | 9.61 |
| 978 | 404 | 9.61 |
| 979 | 368 | 8.96 |
| 980 | 390(M + Na) | 8.54 |
| 981 | 388 | 9.19 |
| 982 | 410(M + Na) | 8.94 |
| 983 | 400(M + Na) | 8.59 |
| 984 | 378 | 8.39 |
| 985 | 392(-t-Bu) | 11.09 |
| 986 | 459 | 11.61 |
| 987 | 439 | 11.25 |
| 604 | 445 | 9.47 |
| 573 | 387 | 8.14 |
| 577 | 445 | 8.99 |
| 578 | 387 | 8.64 |
| 988 | 418 | 9.56 |
| 989 | 418 | 9.3 |
| 990 | 431 | 9.08 |
| 991 | 470 | 9.63 |
| 992 | 460 | 10.07 |
| 994 | 364 | 9.96 |
| 995 | 335 | 6.47 |
| 996 | 352 | 10.18 |
| 997 | 424 | 9.37 |
| 998 | 476 | 9.57 |
| 481 | 549 | 10.73 |
| 437 | 349 | 6.88 |
| 443 | 391 | 7.9 |
| 821 | 418 | 6.96 |
| 822 | 394 | 5.43 |
| 823 | 408 | 5.59 |
| 824 | 387 | 5.52 |
| 825 | 400 | 4.33 |
| 826 | 377 | 4.86 |
| 827 | 420 | 7.20 |
| 884 | 421 | 4.57 |
| 885 | 435 | 4.63 |
| 886 | 390 | 5.24 |
| 887 | 392 | 5.37 |
| 888 | 427 | 5.29 |
| 889 | 311 | 4.12 |
| 891 | 404 | 6.00 |
| 913 | 362 | 5.63 |
| 914 | 412 | 7.12 |
| 915 | 403 | 5.11 |
| 916 | 371 | 4.56 |
| 917 | 362 | 5.61 |
| 918 | 377 | 5.36 |
| 919 | 356 | 6.34 |
| 920 | 402 | 7.13 |
| 921 | 360 | 6.64 |
| 805 | 392 | 5.98 |
| 806 | 455 | 6.30 |
| 807 | 473 | 5.82 |
| 808 | 425 | 3.95 |
| 809 | 403 | 4.42 |
| 810 | 424 | 6.90 |
| 811 | 457 | 7.44 |
| 812 | 432 | 6.67 |
| 813 | 460 | 6.62 |
| 814 | 420 | 6.37 |
| 815 | 432 | 6.41 |
| 816 | 370 | 5.32 |
| 817 | 446 | 6.36 |
| 818 | 370 | 4.78 |
| 819 | 397 | 4.69 |
| 820 | 424 | 4.74 |
| 877 | 408 | 6.18 |
| 878 | 439 | 5.17 |
| 879 | 432 | 6.48 |
| 880 | 470 | 6.03 |
| 881 |  | 6.02 |
| 882 | 468 | 5.11 |
| 883 | 495 | 5.69 |

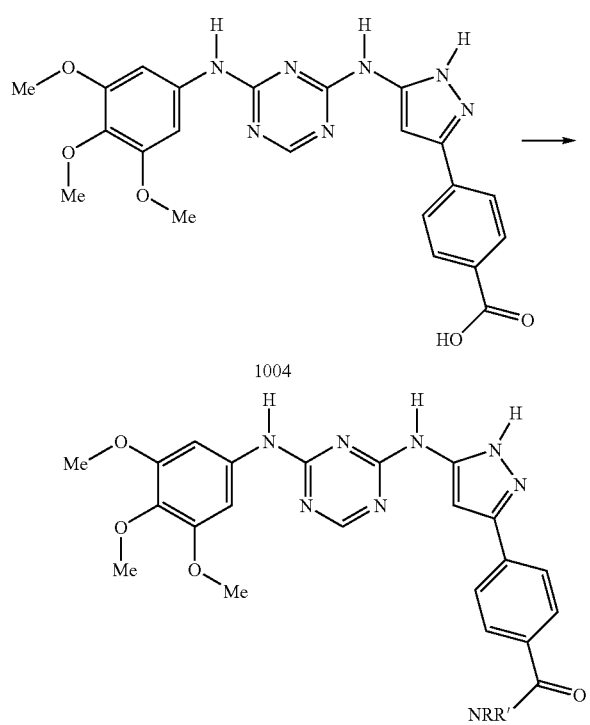

1004

Compound 1004

To a solution of 6 mL of a one to one mixture of 1N sodium hydroxide and MeOH is added 100 mg of Compound 523. The resulting solution is stirred for one hour at which time it is acidified to approximately pH 7 by the addition of 1.5 mL of 2M HCl. The resulting precipitate is filtered, washed with cold water and dried under high vacuum to provide compound 1004. MS m/z=464[M+H]$^+$; HPLC Rt=8.81 min.

Compound 993

To a solution of 82 mg (0.18 mmol) of Compound 1004 in 6 mL of dry dimethylformamide is added 37 mg (0.19 mmol) of 1-(3-dimethylaminopropyl)-3-ethylcarbodiimide hydrochloride, 97 µL (0.19 mmol) of dimethylamine (2M solution in THF), and 2 mg (0.016 mmol) of dimethylaminopyridine. The reaction is stirred for 3 hours, diluted with ethyl acetate and washed with water and dilute brine. The organic layer is then dried over magnesium sulfate, filtered and evaporated to dryness. The crude product is then applied to a 1000; preparative TLC plate and eluted with 10% methanol-dichloromethane. The product band is then scraped from the plate and washed with 10% methanol-dichloromethane. The methanol-dichloromethane wash is evaporated to yield pure 993. MS m/z=491[M+H]$^+$; HPLC Rt=8.86

The following compounds are made in a manner similar to that described above:

| Compound | MS m/z | HPLC Rt |
|---|---|---|
| 1005 | 503 | 8.96 |
| 1006 | 566 | 11.57 |

Compound 642

Reference: Tet. Lett. 1995, 36, 7115.

Compound 1004 (109 mg, 023 mmol) is suspended in dioxane (5 mL) and pyridine (0.5 mL) under N$_2$ at room temperature. Di-tert-butyl dicarbonate and ammonium bicarbonate are added and the reaction is vigorously stirred at room temperature for 45 hours. The reaction is quenched with water, and extracted three times with ethyl acetate. The ethyl acetate extracts are washed with brine, combined, dried over sodium sulfate, filtered, and concentrated under reduced pressure. The recovered material is dissolved into hot methanol to recrystallize. The cyrstals are recovered by vacuum filtration, washed with methanol, and dried under high vacuum giving 26 mg (24%) of a white solid: MS m/z=463 [M+H]$^+$; $^1$H NMR (300 MHz, DMSO-d$_6$) δ 12.98 (br s, 1H), 10.10 (br s, 1H), 9.92 (br s, 1H), 8.35 (br s, 1H), 8.20–7.50 (br m, 5H), 7.40 (s, 1H), 7.30–6.80 (br m, 2H), 3.79 (br s, 6H), 3.63 (s, 3H); HPLC Rt=8.01 min.

EXAMPLE 25

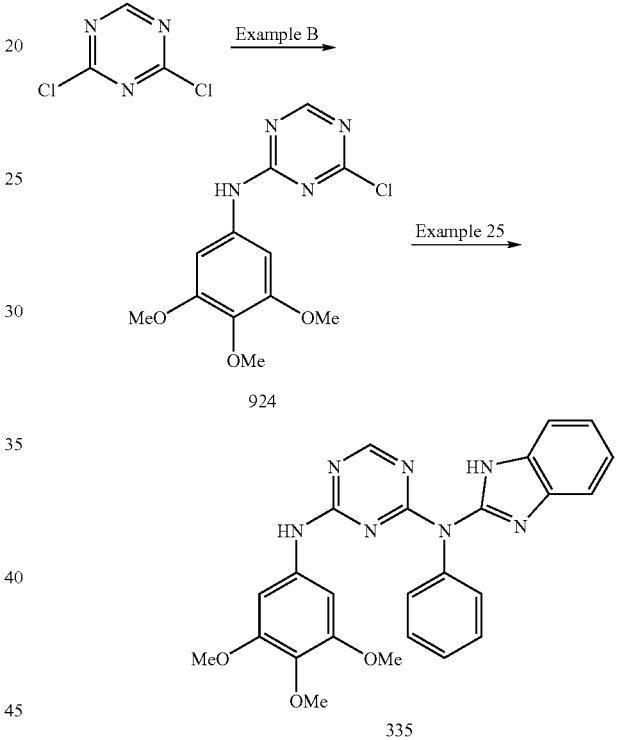

Compound 335

To a slurry of intermediate 924 (95.4 mg, 0.3216 mmol) in isopropanol (2 ml) are added diisopropylehylamine (56 µl, 0.3216 mmol) and 2-aminophenylbenzimidazole (67.3 mg, 0.3216 mmol) (2-Aminophenylbenzimidazole is prepared by protaecting 2-chlorobenzimidazole with a Boc group and subsequently displacing the chloride at 100° C. with aniline. The Boc group falls off during the displacement reaction). The mix is heated at 100° C. for 21 hours. The solution is then cooled to room temperature and concentrated under reduced pressure. The crude is eluted on silica gel preparative plate with 5% methanol/dichloromethane. The lower (minor) band is extracted with 15% methanol/dichloromethane and concentrated under reduced pressure, giving 30 mg (20%) of compound 335.

Compounds below are prepared according to the procedure outlined for compound 335, substitution the appropriate reagents. Purification methods vary. Retention time is in minutes.

| Compound | MS m/z | HPLC Rt |
|---|---|---|
| 256 | 464 | 8.54 |
| 311 | 420.4 | 11.42 |
| 312 | 481.1 | 12.20 |
| 315 | 418 | 14.05 |
| 317 | 429 | 12.0 |
| 335 | 470 | 10.85 |
| 373 | 484 | 9.62 |
| 374 | 504 | 11.85 |
| 938 | 408 | 9.83 |
| 442 | 383(M + Na) | 8.02 |
| 444 | 437 | 12.35 |
| 468 | 375 | 8.41 |
| 469 | | 11.18 |

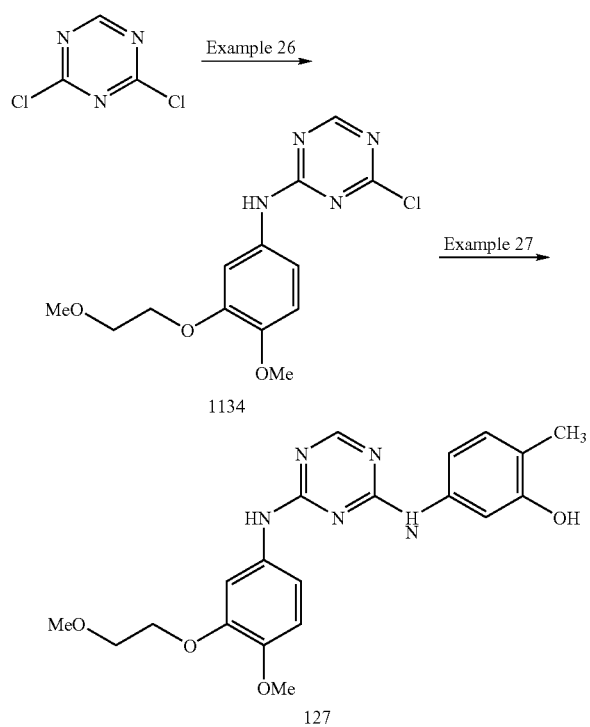

1134

127

EXAMPLE 26

2,4-Dichloro-1,3,5-triazine (89.1 mg, 0.5944 mmol) is dissolved into DMF (0.5 ml) and cooled to 0° C. To this solution are added diisopropylethylamine (104 μl,) and a solution of the appropriate aniline TFA salt (264 mg, ~0.59 mmol) (The starting aniline for intermediate 1134 is prepared from 5-amino-2-methoxyphenol using known procedures. The amine is Boc-protected, the phenol is alkylated with 2-bromoethylmethylether, and the Boc group is removed with trifluoroacetic acid, leaving the TFA salt of the desired aniline.) and 208 >l of diisopropylethylanine in 1 ml of DMF. The reaction mixture is kept at 0° C. for 15 to 30 minutes and then at room temperature for 15 minutes to 2 hours. The reaction mixture is then diluted with ethyl acetate and washed with brine. The organic layer is dried over sodium sulfate, filtered, and evaporated in vacuo, to give crude material identified as 1134. This intermediate is used as is for the next step. Intermediates 1129, 1131, 1132, 1133, and 1136 are prepared either from commercially available anilines or with anilines synthesized according to readily available literature procedures.

EXAMPLE 27

To a solution of intermediate 1134 in isopropanol (2 ml) are added diisopropylethylamine (79 μl, 0.453 mmol) and 5-amino-o-cresol (56 mg, 0.453 mmol). The mix is heated at 120° C. for 18 hours. The solution is then cooled to room temperature and sonicated. The precipitate is filtered and then dried under reduced pressure, giving 52.5 mg (22%) of 127.

Compounds below are prepared according to the procedure outlined for compound 127. Purification methods vary. HPLC retention times is in minutes.

| Compound | MS m/z | HPLC Rt |
|---|---|---|
| 111 | 338 | 10.05 |
| 113 | 376 | 11.68 |
| 114 | 367 | 7.01 |
| 115 | 363 | 9.19 |
| 116 | 348 | 10.78 |
| 117 | 421 | 12.13 |
| 118 | 403 | 11.61 |
| 119 | 354 | 9.35 |
| 121 | 382 | 11.03 |
| 123 | 398 | 9.61 |
| 125 | 442 | 9.72 |
| 127 | 398 | 9.67 |
| 321 | 451.1 | 9.41 |
| 322 | 444 | 11.50 |
| 328 | 468.1 | 9.53 |
| 929 | 416 | 12.69 |
| 953 | 503 | 8.99 |
| 181 | nd | 8.39 |
| 1039 | 494.3 | 8.45 |
| 1040 | 493.3 | 8.26 |
| 1184 | 355 | 10.76 |

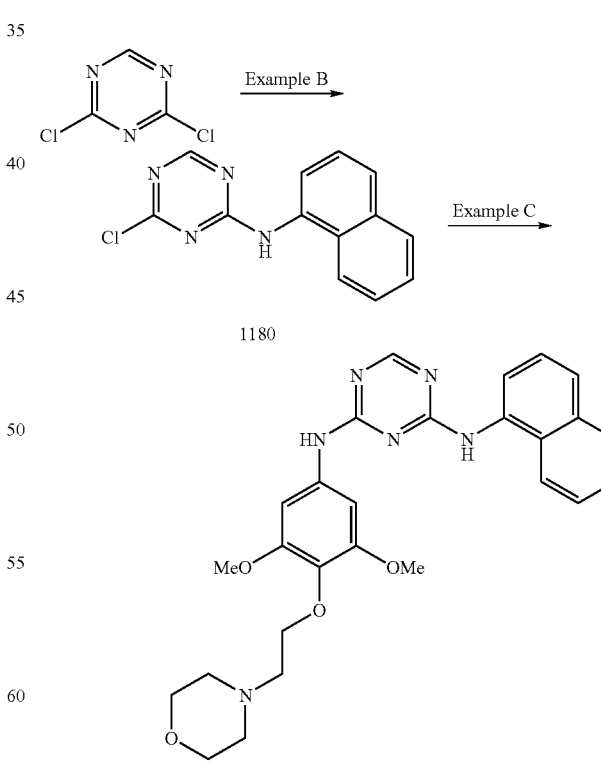

1180

1041

Compound 1180 is prepared by reacting dichlorotriazine with 1-Naphthylamine according to Example B. Crude product is purified by column chromatography (EtOAc/n-Heaxnes) to give chloride 1180 as off-white solid (86%).

Compound 1041 is prepared by reacting chloride 1180 with the appropriate aniline according to Example C. Product is isolated by filtration, washing with iPrOH and diethylether and finally dried to give compound 1041 as an off-white powder (34%).

| Compound | MS m/z | HPLC Rt |
|----------|--------|---------|
| 1180 | Nd | 12.5 |
| 1041 | 503 | 8.62 |
| 551 | Nd | 7.48 |

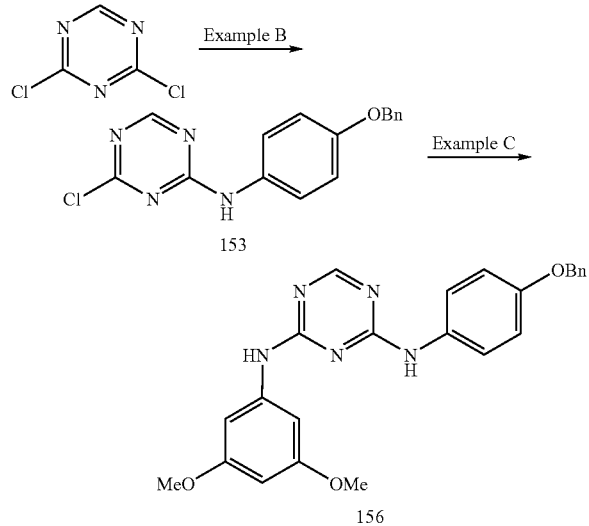

153

156

Compound 153 is prepared by reacting dichlorotriazine with 4-benzyloxyaniline according to Example B to give chloride 153 as a light brown solid (91%)

Compound 156 is prepared by reacting chloride 153 with 3,5-dimethoxyaniline according to Example C to give compound 156 as a white solid (51%)

| Compound | MS m/z | HPLC Rt |
|----------|--------|---------|
| 153 | 313 | 15.41 |
| 156 | 430 | 14.04 |
| 157 | 430 | 12.65 |
| 158 | 386 | 11.44 |
| 159 | 386 | 11.92 |
| 160 | 400 | 13.80 |
| 161 | 400 | 13.30 |
| 162 | 485 | 14.58 |
| 170 | 458 | 14.22 |
| 171 | 416 | 11.86 |

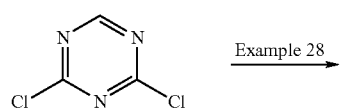

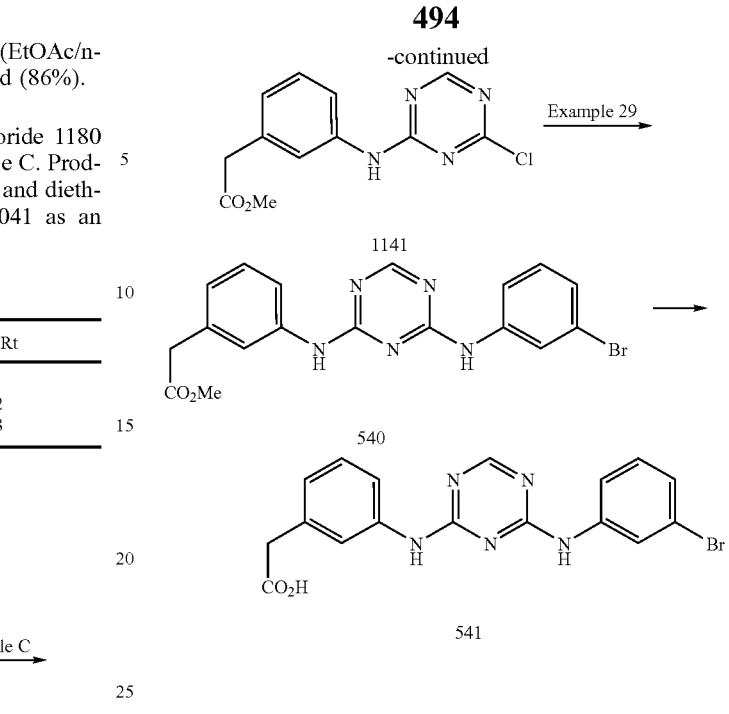

1141

540

541

EXAMPLE 28

The aniline used to prepare intermediate 1141 is prepared by reacting 3-aminophenylacetic acid with acetyl chloride in methanol to afford the corresponding methyl ester HCl salt, (3.09 g, 15.324 mmol) which is dissolved into DMF (5 ml) with diisopropylethylamine (2.67 ml, 15.324 mmol) and cooled to 0° C. To this solution is added dropwise a 0° C. solution of DMF (5 ml) containing 2,4-dichloro-1,3,5-triazine (2.297 g, 15.324 mmol) and diisopropylethylamine (2.67 ml, 15.324 mmol). The reaction is stirred at 0° C. for 15 to 40 minutes and then at room temperature for 15 minutes to 2 hours. The reaction mix is diluted with ethyl acetate and water. The layers are separated, and the aqueous layer is extracted two times with ethyl acetate. The combined organic layers are washed 4 times with brine and dried over sodium sulfate. The crude is then concentrated down and dried under reduced pressure, giving 4.3 g (100%) of intermediate 1141. HPLC Rt=11.71 min.

EXAMPLE 29

To a mixture of intermediate 1141 (279 mg, 1.001 mmol) in isopropanol (3 ml) are added diisopropylethylamine (175 l, 1.001 mmol) and 3-bromoaniline (172 mg, 1.001 mmol). The mix is heated at 100–120° C. for 4 to 18 hours. The solution is then cooled to room temperature and sonicated. The precipitate is filtered and then dried under reduced pressure, giving 254 mg (61%) of compound 540.

Compound 540 (142 mg, 0.3425 mmol) is dissolved into THF (34.5 ml) and 1N lithium hydroxide/water (6.85 ml). The reaction is stirred vigorously at room temperature for 2 to 20 hours. The organic solvent is evaporated off. The aqueous solution is acidified to pH 3, whereupon a white precipitate is formed. The precipitate is filtered and dried under vacuum, giving 130 mg (95%) of Compound 541.

EXAMPLE 28

2,4-Dichloro-1,3,5-triazine (173.7 mg, 1.158 mmol) is dissolved into DMF (1 ml). To the stirring solution cooled to 0° C. is added diisopropylethylamine (202 µl, 1.158 mmol). This solution is added dropwise to a 0° C. mix of DMF (1 ml) and 3-aminophenyl acetamide (prepared from 3-nitrophenylacetic acid via literature preparation (Pozdnev, V. F., et al.; *Tetrahedron Letters*; 1995; 36; 7115), followed by reduction of nitro to amine). The reaction is stirred at 0° C. for 15 minutes to 40 minutes and then at room temperature for 20 minutes to 2 hours. The reaction mix is then diluted with ethyl acetate and water. The layers are separated, and the aqueous layer is extracted 2 times with ethyl acetate. The combined organic layer is washed 3 times with brine, dried over sodium sulfate, and concentrated under reduced pressure, giving 175 mg (57%) of compound 1143. HPLC Rt=7.61 min.

EXAMPLE 29

To a mixture of intermediate 1143 (36.6 mg, 0.1388 mmol) in isopropanol (1 ml) are added diisopropylethylamine (27 μl, 0.1527 mmol) and 3-bromoaniline (26.3 mg, 0.1527 mmol). The mix is heated at 100–120° C. for 4 to 18 hours. The solution is then cooled to room temperature and sonicated. The precipitate is filtered and then dried under reduced pressure, giving 39.1 mg (70%) of compound 966.

Compound 1147

2,4-Dichloro-1,3,5-triazine (405.8 mg, 2.7065 mmol) is dissolved into DMF (2 ml). To the stirring solution cooled to 0° C. is added diisopropylethylamine (471 μl, 2.7065 mmol). This solution is added dropwise to a 0° C. mix of DMF (2 ml) and 471.5 mg (2.7065 mmol) of the appropriate aniline (prepared from 3-nitrobenzylbromide and 1H-1,2,3-triazole, followed by separation of regioisomers and reduction of nitro to amine). The reaction is stirred at 0° C. for 15 minutes to 40 minutes and then at room temperature for 20 minutes to 2 hours. The reaction mix is then diluted with ethyl acetate and water. The layers are separated, and the aqueous layer is extracted 2 times with ethyl acetate. The combined organic layer is washed 3 times with brine, dried over sodium sulfate, and concentrated under reduced pressure, giving 696.3 mg (89%) of a white foam named compound 1147. HPLC Rt=9.34 min.

Compound 961

To a mixture of intermediate 1147 (64.8 mg, 0.2252 mmol) in isopropanol (1 ml) are added diisopropylethylamine (39 μl, 0.225 mmol) and 3-bromoaniline (38.7 mg, 0.2252 mmol). The mix is heated at 100–120° C. for 4 to 18 hours. The solution is then cooled to room temperature and sonicated. The precipitate is filtered and then dried under reduced pressure, giving 34.3 mg (36%) of 961.

The following compounds are prepared according to the procedures of examples 28 and 29.

| Compound | MS m/z | HPLC Rt |
|---|---|---|
| 107 | 294 | 9.20 |
| 108 | 338 | 10.65 |
| 109 | 357 | 14.12 |
| 110 | nd | 10.64 |
| 120 | 318 | 9.05 |
| 540 | 415 | 13.01 |
| 541 | 401 | 10.95 |
| 542 | 366 | 10.22 |
| 543 | 352 | 8.68 |
| 544 | 362 | 9.02 |
| 546 | 376 | 10.22 |
| 955 | 361 | 8.13 |
| 956 | 452 | 7.63 |
| 960 | 385 | 9.10 |
| 961 | 424 | 11.44 |

-continued

| Compound | MS m/z | HPLC Rt |
|---|---|---|
| 966 | 400 | 9.80 |
| 968 | 374 | 10.79 |

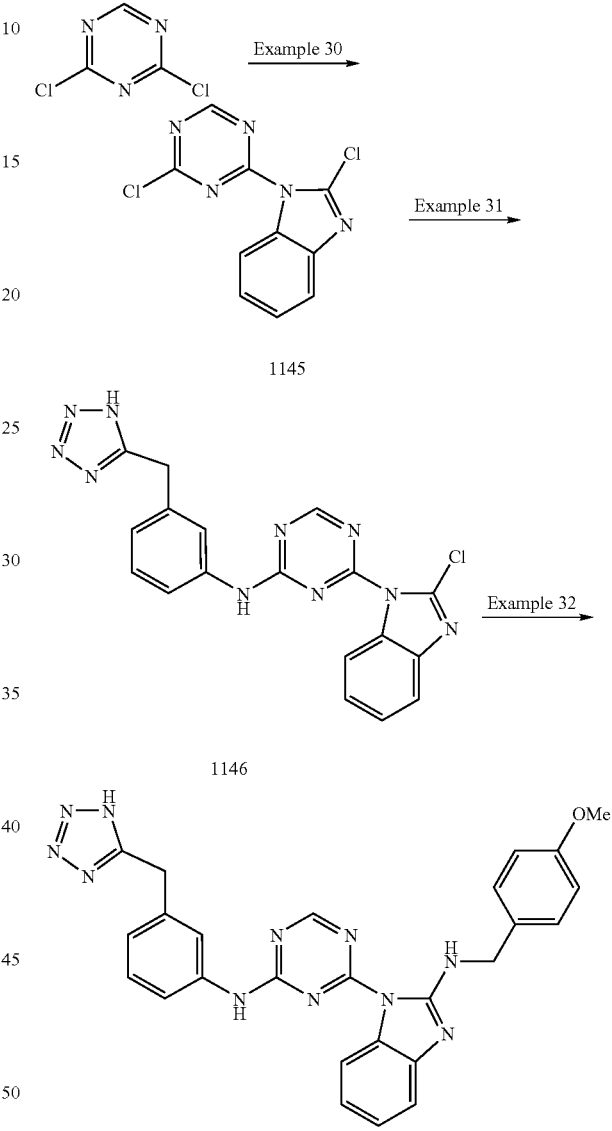

EXAMPLE 30

2,4-Dichloro-1,3,5-triazine (327.5 mg, 2.1845 mmol) is dissolved into DMF (2 ml) and cooled to 0° C. To this solution are added diisopropylethylamine (381 μl, 2.184 mmol) and 2-chlorobenzimidazole (333.3 g, 2.1845 mmol). The reaction mixture is kept at 0° C. for 15 to 30 minutes and then at room temperature for 15 minutes to 2 hours. The crude compound 1145 is used as is for the next step.

EXAMPLE 31

To crude reaction mix 1145 are added diisopropylethylamine (381μl, 2.184 mmol) and then a solution of DMF (1 ml) and 382.7 mg (2.1845 mmol) of the appropriate aniline (prepared from 3-nitrophenylacetonitrile according to Koguro, K., et al. (*Synthesis*; 1998; 910), followed by reduction of nitro to amine). The reaction is heated at 60–75° C. for 4 to 20 hours. The reaction is then cooled to room temperature and concentrated to a small volume. The crude is eluted on a silica gel column with a methanol/dichloromethane elution gradient, giving 120 mg (14%) of intermediate 1146. HPLCRt=11.43 min.

EXAMPLE 32

Intermediate 1146 (40 mg, 0.0988 mmol), 4-methoxybenzylamine (19.4 µl, 0.148 mmol), and diisopropylethylamine (17.2 µl, 0.0988 mmol) are combined with isopropanol (1 ml) and heated at 100–120° C. for 30 minutes to 20 hours. The reaction is cooled to room temperature and diluted into water. The aqueous solution is then acidified to pH 3. The precipitate is filtered and dried, giving 33.5 mg (67%) of 959.

| Compound | MS m/z | HPLC Rt |
|---|---|---|
| 957 | 476 | 10.74 |
| 958 | 477 | 8.80 |
| 959 | 506 | 10.89 |

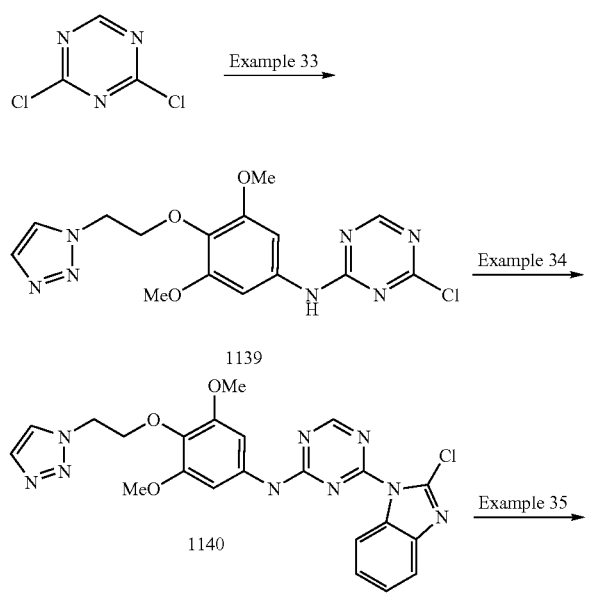

1139

1140

942

EXAMPLE 33

2,4-Dichloro-1,3,5-triazine (204 mg, 1.362 mmol) is dissolved into DMF (2 mL) and cooled to 0° C. To this solution are added diisopropylethylamine (238 µl, 1.362 mmol) and the appropriate aniline (360 mg, 1.362 mmol) (The aniline is prepared the following way. 2,6-Dimethoxy-4-nitrophenol is prepared according to known sources (Tepe, Jetze J. et al.; *J. Med. Chem.*; 39; 11; 1996; 2188–2196) and then is reacted via Mitsunobu with 2-(1-triazolyl)ethanol (prepared according to Kume, Masaharu et al., *Journal of Antibiotics*; 1993; 46; 177–195). The Mitsunobu product is then reduced to the aniline via palladium on carbon.) dissolved in DMF (2 mL). The reaction mixture is kept at 0° C. for 15 to 30 minutes and then at room temperature for 15 minutes to 2 hours. The reaction mix is then added to water, whereupon the product precipitates out of solution. The precipitate is filtered and dried under vacuum, giving 425 mg (83%) of 1139. HPLC Rt=9.79 min. Intermediates 1135 and 1136 are prepared in a similar fashion.

EXAMPLE 34

Intermediate 1139 (407 mg, 1.076 mmol) is combined with 2-chlorobenzimidazole (164 mg, 1.076 mmol) and potassium carbonate (179 mg, 1.292 mmol) in acetonitrile (10 ml) and heated at 65 to 75° C. for 4 to 20 hours. The mix is concentrated down under reduced pressure and treated with water. A white precipitate is formed. The precipitate is filtered and dried under vacuum, giving 393 mg (74%) of intermediate 1140. HPLC Rt=12.08 min. Intermediates 1137 and 1138 are prepared in a similar fashion.

EXAMPLE 35

Intermediate 1140 (377 mg, 0.763 mmol) is combined with 2-aminomethylpyridine (107 mg, 0.993 mmol) and diisopropylethylamine (173 µl, 0.993 mmol) in isopropanol (3 ml). The mix is heated at 100–120° C. for 30 minutes to 20 hour. The reaction mix is cooled to room temperature and added to about 40 ml of water. The precipitate is filtered and dried under vacuum, giving 376 mg (87%) of compound 942.

The following compounds are prepared according to the method outlined for compound 942.

| Compound | MS | HPLC Rt |
|---|---|---|
| 507 | 584 | 7.91 |
| 519 | 584 | 7.78 |
| 942 | 566 | 9.02 |

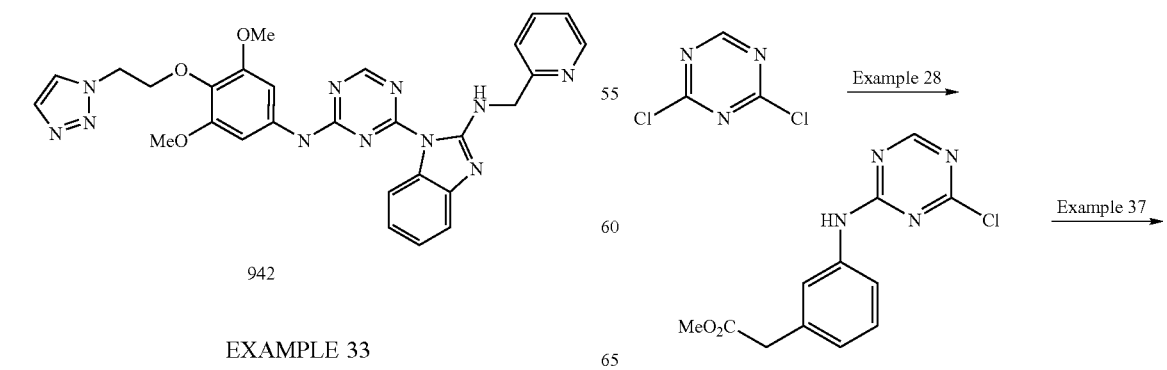

1141

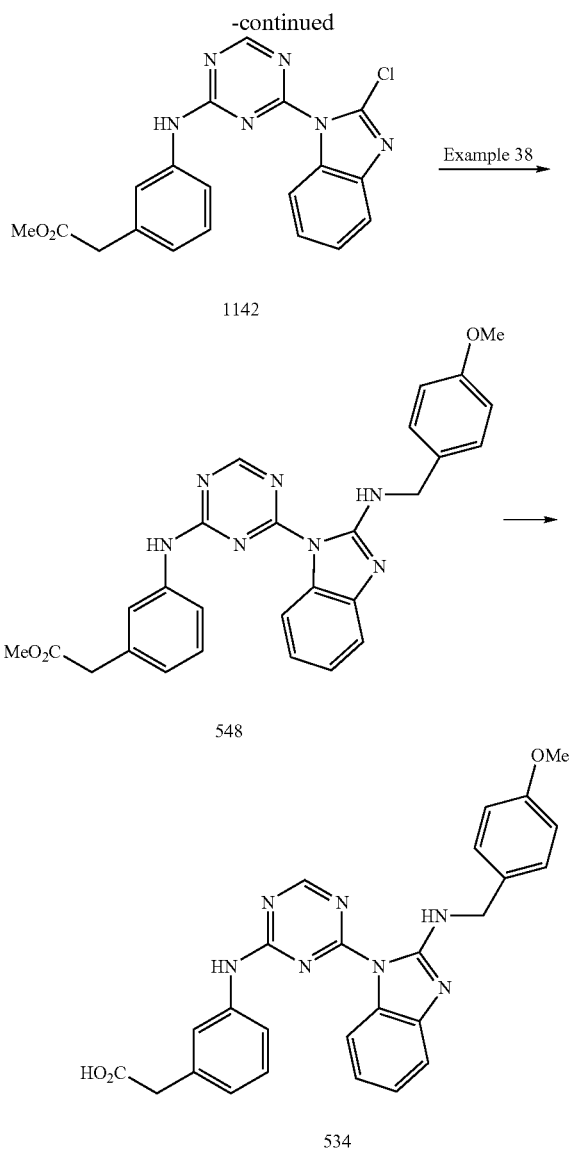

EXAMPLE 37

Intermediate 1141 (3.530 g, 12.67 mmol) is combined with 2-chlorobenzimidazole (1.933 g, 12.67 mmol) and potassium carbonate (2.101 g, 15.20 mmol) in acetonitrile (50 ml) and heated at 65–75° C. for 2 to 20 hours. The reaction mix is then cooled to room temperature. The inorganic salts are filtered off. The acetonitrile solution is then concentrated down under reduced pressure. The crude is then purified on a silica gel column with an ethyl acetate/hexane elution gradient, giving 530 mg (10%) of intermediate 1142 along with several more grams of product requiring further purification. HPLC Rt=14.52 min.

EXAMPLE 38

Intermediate 1142 (169.8 mg, 0.4301 mmol), 4-methoxybenzylamine (84 µl, 0.6451 mmol), and diisopropylethylamine (150 µl, 0.8602 mmol) are combined with isopropanol (2 ml) and heated at 100–120° C. for 30 minutes to 20 hours. The reaction mix is cooled to room temperature and added to water. The precipitate is filtered and dried, giving 188 mg (88%) of compound 548.

Compound 548 (123 mg, 0.248 mmol) is dissolved into THF (25.5 ml) and 1N lithium hydroxide/water (5 ml). The reaction is stirred vigorously at room temperature for 1 to 20 hours. The organic solvent is evaporated off. The aqueous solution is acidified to pH 3, whereupon a white precipitate is formed. The precipitate is filtered and dried under vacuum, giving 120 mg (100%) of compound 534.

Compound 1144

Intermediate 1143 (136.5 mg, 0.5177 mmol) is combined with 2-chlorobenzimidazole (86.9 mg, 0.5177 mmol) and potassium carbonate (93 mg, 0.673 mmol) in acetonitrile (5 ml) and heated at 65–75° C. for 2 to 20 hours. The reaction mix is then cooled to room temperature. The inorganic salts are filtered off. The acetonitrile solution is then concentrated down under reduced pressure. The crude is then purified on a silica gel column with an ethyl acetate/hexane to methanol/dichloromethane elution gradient, giving 29 mg (15%) of Compound 1144. HPLC Rt=10.61 min.

Compound 967

Intermediate 1144 (27.9 mg, 0.0735 mmol), benzylamine (11 µl, 0.103 mmol), and diisopropylethylamine (20µl, 0.110 mmol) are combined with isopropanol (1 ml) and heated at 100–120° C. for 30 minutes to 20 hours. The reaction mix is cooled to room temperature and sonicated. The precipitate is filtered and dried, giving 20.7 mg (62%) of compound 967.

Compound 1148

Intermediate 1147 (552.7 mg, 1.921 mmol) is combined with 2-chlorobenzimidazole (381 mg, 2.497 mmol) and potassium carbonate (372 mg, 2.689 mmol) in acetonitrile (10 ml) and heated at 65–75° C. for 2 to 20 hours. The reaction mix is then cooled to room temperature and diluted with methanol and dichloromethane. The inorganic salts are filtered off. The organic solution is then concentrated down under reduced pressure. The crude is then treated with 5–8 ml of acetonitrile. The precipitate is filtered and dried, giving 330 mg (42%) of intermediate 1148. HPLCRt=12.329 min.

Compound 964

Intermediate 1148 (62.0 mg, 0.1535 mmol), 3-fluorobenzylamine (24.5 µl, 0.2149 mmol), and diisopropylethylamine (38µl, 0.2149 mmol) are combined with isopropanol (1 ml) and heated at 100–120° C. for 30 minutes to 20 hours. The reaction mix is cooled to room temperature and sonicated. The precipitate is filtered and dried, giving 43.4 mg (57%) of compound 964.

Compound 1149

2,4-Dichloro-1,3,5-triazine (122.7 mg, 0.8182 mmol) is dissolved into DMF (1 ml). To the stirring solution cooled to 0° C. is added diisopropylethylamine (150 µl, 0.861 mmol). This solution is added dropwise to a 0° C. mix of DMF (2 ml), diisopropylethylamine (150 µl, 0.861 mmol) and 340 mg (0.8182 mmol) of the appropriate aniline (prepared from 3-nitrophenylacetonitrile to yield the imidazoline (Amemiya, Yoshiya et al.; J. Med. Chem.; 1992; 35, 750–755), which is then oxidized to the imidazole (Amemiya, Yoshiya, et al.; Synthetic Communications; 20(16); 2483–2489), trityl-protected and finally reduced from nitro to amine). The reaction is stirred at 0° C. for 15 minutes to 40 minutes and then at room temperature for 20 minutes to 2 hours. The reaction mix is then diluted with ethyl acetate and water. The layers are separated, and the aqueous layer is extracted 2 times with ethyl acetate. The combined organic layer is washed 3 times with brine, dried over sodium sulfate, and concentrated under reduced pressure. The crude is eluted on a silica gel column with ethyl acetate: hexane (1:1), giving 333 mg (77%) of a white solid named 1149. HPLC Rt=13.87 min.

Compound 1150

Intermediate 1149 (331 mg, 0.6256 mmol) is combined with 2-chlorobenzimidazole (114.6 mg, 0.7508 mmol) and potassium carbonate (190 mg, 1.376 mmol) in acetonitrile (5 ml) and heated at 65–75° C. for 2 to 20 hours. The reaction mix is then cooled to room temperature. The product apparently precipitates out of acetonitrile, which is filtered off. The crude solid is then treated with water. The precipitate is filtered and dried, giving 264 mg (65%) of intermediate 1150. HPLC Rt=15.52 min.

Compound 969

Compound 1150 (103.3 mg, 0.1601 mmol), benzylamine (23μl, 0.208 mmol), and diisopropylethylamine (42 μl, 0.240 mmol) are combined with isopropanol (1 ml) and heated at 100–120° C. for 30 minutes to 20 hours. The reaction mix is cooled to room temperature and sonicated. The precipitate is filtered and dried, giving 69.5 mg (60%) of Compound 1151. HPLC Rt=13.53 min.

Compound 1151 (68 mg, 0.0950 mmol) is heated at 60–75° C. in a mix of methanol (3.8 ml), dichloromethane (1 ml), and acetic acid (0.20 ml) for 1 to 6 hours. The reaction mix is cooled to room temperature and concentrated down. The crude is purified on a silica gel column with a methanol/dichloromethane elution gradient, giving about 30 mg (67%) of Compound 969.

| Compound | MS m/z | HPLC Rt |
|---|---|---|
| 531 | 452 | 11.26 |
| 533 | 453 | 9.20 |
| 534 | 482 | 11.16 |
| 545 | 466 | 12.64 |
| 547 | 467 | 10.60 |
| 548 | 496 | 12.79 |
| 962 | 498[M + Na]+ | 9.28 |
| 963 | 500 | 11.31 |
| 964 | 493 | 11.57 |
| 965 | 475 | 11.27 |
| 967 | 451 | 10.21 |
| 969 | 474 | 9.07 |
| 1066 | 381 | 14.95 |
| 1067 | 451 | 13.0 |
| 1068 | 482 | 12.92 |
| 1069 | 438 | 11.12 |
| 1070 | 468 | 11.20 |
| 1185 | nd | 12.05 |

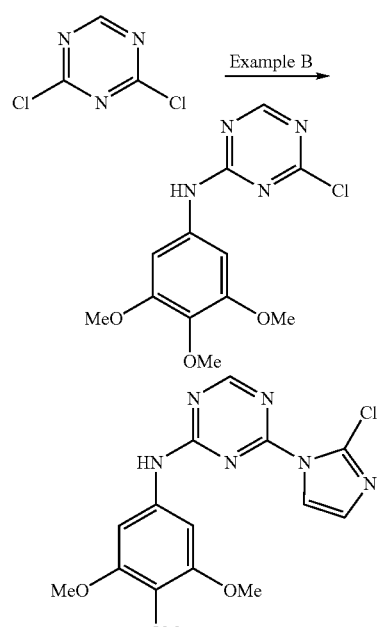

1071

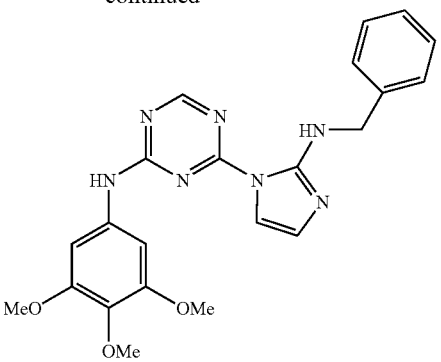

Compound 1186 is prepared by reacting chlorotriazine with 3-chloroindazole according to Example 39 to give an off-white solid (78%). MS m/z=413[M+H]+; HPLC Rt=16.07 minutes.

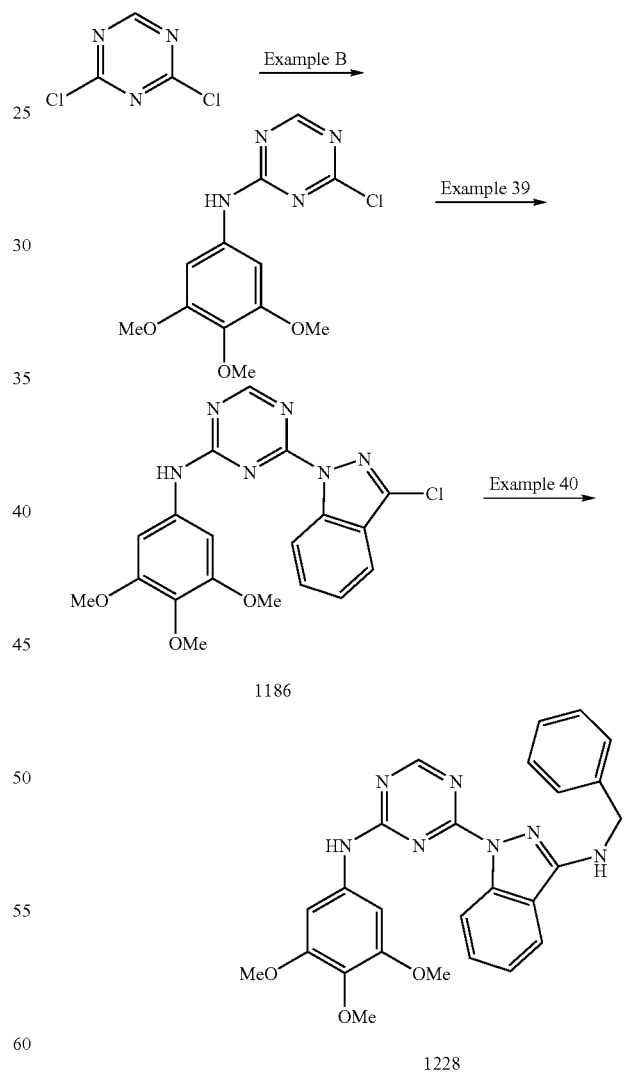

1186

1228

Compound 1071 is prepared by reacting chloride 924 with 2-chloroimidazole (prepared according to literature procedure: "Facile Synthesis of 2-Substituted Imidazoles", K. L. Kirk, J. Org. Chem. 43 (22), 1978, 4381–4383) according to EXAMPLE 15 to give compound 1071.

Compound 1296 is prepared by reacting 1071 with benzylamine according to Example 42 to give Compound 1296

| Compound | MS m/z | HPLC Rt |
|---|---|---|
| 1071 | 363 | 11.24 min |
| 1296 | 434 | (Method A) 7.8 min |

Compound 701

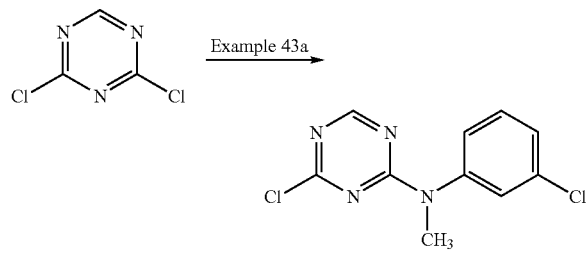

A mixture of the compound 2,4-dichloro-1,3,5-triazine (Example A) (2.5 g, 16.7 mmol) and solid $K_2CO_3$ (6.9 g, 49.9 mmol) is suspended in acetonitrile (50 mL) under nitrogen at 0° C. followed by addition of N-methyl-3-chloroaniline (2.5 g, 17.7 mmol). The mixture is allowed to stir at 0° C. for 2 hours. The reaction is quenched by pouring onto ice/water. The white solid formed is collected by suction filtration and dried under vacuum to give material identified as N-methyl-2-chloro-4-(3-chloroanilino)-1,3,5-triazine. HPLC(Method A) Rt=8.63 min.; MS m/z=256; $^1$H NMR (300 MHz, DMSO-$d_6$) δ 8.4 (bs, 1H), 7.1–7.4 (m, 5H), 3.2 (s, 3H).

In a manner similar to that described in Example C, the following compounds of this example are prepared from the appropriately substituted amine and the chloride described in Compound 701.

EXAMPLE 43b

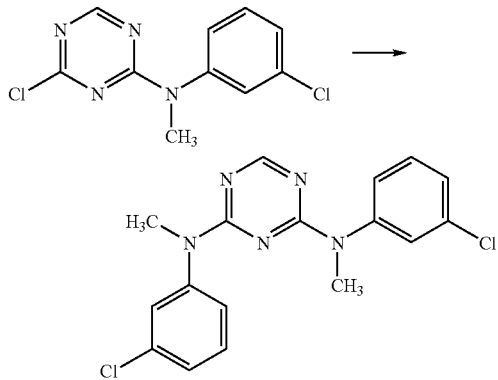

Compound 702: HPLC(Method A) Rt=9.60 min.; MS m/z=361; $^1$H NMR (300 MHz, DMSO-$d_6$) δ 8.0 (bs, 1H), 7.0–7.3 (m, 8H), 3.1 (s, 6H).

Compound 703: HPLC(Method A) Rt=9.7 min.; MS m/z=365; $^1$H NMR (300 MHz, DMSO-$d_6$) δ 9.0 (bs, 1H), 8.2 (s, 1H), 7.0 (s, 1H), 7.7 (bs, 1H), 7.0–7.2 (m, 5H), 3.1 (s, 3H).

Compound 705: HPLC(Method A) Rt=7.33 min; MS m/z 370; $^1$H NMR (300 MHz, DMSO-$d_6$) δ 12.0 (bs, 1H), 9.6 (s, 1H), 8.1 (s, 1H), 7.2–7.4 (m, 3H), 6.8 (m, 1H), 6.6 (d, 2H), 6.3 (d, 2H), 4.8 (bs, 1H), 3.1 (s, 3H).

Compound 706: HPLC(Method A) Rt=7.5 min.; MS m/z=370; $^1$H NMR (300 MHz, DMSO-$d_6$) δ 11.0 (bs, 1H), 9.5 (s, 1H), 8.0 (s, 1H), 7.0–7.4 (m, 6H), 6.9 (s, 1H), 6.8 (s, 1H), 6.2 (s, 1H).

Compound 707: HPLC(Method A) Rt=10.1 min.; MS m/z=391; $^1$H NMR (300 MHz, DMSO-$d_6$) δ 9.8 (s, 1H), 8.1 (s, 1H), 7.7 (s, 1H), 6.8–7.4 (m, 7H), 3.1 (s, 3H).

Compound 708: HPLC(Method A) Rt=10.6 min.; MS m/z=381; $^1$H NMR (300 MHz, DMSO-$d_6$) δ 9.9 (s, 1H), 8.1 (s, 1H), 7.7 (s, 1H), 7.0–7.4 (m, 5H), 3.1 (s, 3H).

Compound 709: HPLC(Method A) Rt=9.6 min.; MS m/z=326; $^1$H NMR (300 MHz, DMSO-$d_6$) δ 9.5 (s, 1H), 8.1 (s, 1H), 7.0–7.4 (m, 6H), 6.8 (m, 1H), 6.6 (m, 1H), 3.1 (s, 3H), 2.0 (s, 3H).

Compound 711: HPLC Rt=18.36 min.; MS m/z=372; $^1$H NMR (300 MHz, DMSO-d6) δ 9.9 (s, 1H), 8.2 (s, 1H), 6.8–7.5 (m, 7H), 3.2 (s, 3H).

Compound 712: HPLC Rt=13.86 min.; MS m/z=372; $^1$H NMR (300 MHz, DMSO-$d_6$) δ 9.5 (s, 1H), 8.0 (s, 1H), 7.0–7.4 (m, 4H), 6.7 (s, 2H), 5.9 (s, 1H), 3.5(s, 6H), 3.0(s, 3H).

Compound 714: HPLC(Method A) Rt=7.14 min.; MS m/z=351; $^1$H NMR (300 MHz, DMSO-$d_6$) δ 10.7 (s, 1H), 9.4 (s, 1H), 8.1 (s, 1H), 7.6 (s, 1H), 6.9–7.4 (m, 6H), 6.0 (s, 1H), 3.1 (s, 3H).

Compound 716: HPLC(Method A) Rt=6.26 min.; MS m/z=353; $^1$H NMR (300 MHz, DMSO-$d_6$) δ 9.6 (s, 1H), 8.1 (s, 1H), 7.7 (s, 1H), 7.6 (s, 1H). 7.0–7.4 (m, 4H), 3.1 (s, 3H).

Compound 718: HPLC(Method A) Rt=6.59 min.; MS m/z=352; $^1$H NMR (300 MHz, DMSO-$d_6$) δ 9.7 (s, 1H), 8.1 (s, 1H), 7.8 (s, 1H), 7.7 (s, 1H), 7.5 (s, 1H), 7.0–7.4 (m, 4H), 6.3 (s, 1H), 5.0 (s, 1H), 3.2 (s, 3H).

Compound 720: In a manner similar to that described in Example C, the compound of this example is prepared from the appropriately substituted amine prepared from 3-nitrophenylacetonitrile according to Koguro, K., et al. (*Synthesis*; 1998; 910), followed by reduction of nitro to amine. HPLC(Method A) Rt=6.28 min.; MS m/z=394; $^1$H NMR (300 MHz, DMSO-$d_6$) δ 9.6 (s, 1H), 8.1 (s, 1H), 7.1–7.4 (m, 7H), 6.9 (m, 1H), 6.6 (m, 1H), 4.0 (s, 2H), 3.2 (s, 3H).

Compound 721; HPLC(Method A) Rt=8.21 min.; MS m/z=455; $^1$H NMR (300 MHz, DMSO-$d_6$) δ 9.6 (s, 1H), 8.1 (s, 1H), 7.5 (m, 1H), 7.1–7.3 (m, 5H), 7.0 (m, 1H), 6.7 (m, 1H), 6.2 (m, 1H), 4.9 (m, 2H), 3.8 (m, 2H), 3.6 (m, 4H), 1.6 (m, 1H).

| Compound | HPLC ret. | MS m/z |
|---|---|---|
| 739 | (Method A) 6.48 min. | 320 |
| 740 | (Method A) 4.26 min. | 347 |
| 741 | (Method A) 3.62 min. | 342 |
| 742 | (Method A) 8.56 min. | 398 |
| 743 | (Method A) 7.40 min. | 342 |
| 744 | (Method A) 8.48 min. | 380 |
| 745 | (Method A) 4.19 min. | 335 |
| 746 | (Method A) 5.34 min. | 324 |
| 747 | (Method A) 7.01 min. | 416 |
| 748 | (Method A) 7.66 min. | 312 |
| 749 | (Method A) 6.63 min. | 390 |
| 750 | (Method A) 7.80 min. | 427 |
| 751 | (Method A) 6.31 min. | 433 |
| 752 | (Method A) 4.78 min. | 409 |

-continued

| Compound | HPLC ret. | MS m/z |
|---|---|---|
| 753 | (Method A) 6.70 min. | 368 |
| 754 | (Method A) 8.17 min. | 359 |
| 755 | (Method A) 5.00 min. | 395 |
| 756 | (Method A) 4.24 min. | 313 |
| 757 | (Method A) 5.26 min. | 314 |
| 804 | (Method A) 9.44 min | 416 |
| 874 | (Method A) 8.67 min. | 396 |
| 875 | (Method A) 8.71 min. | 396 |
| 876 | (Method A) 8.58 min. | 392 |

Compound 704

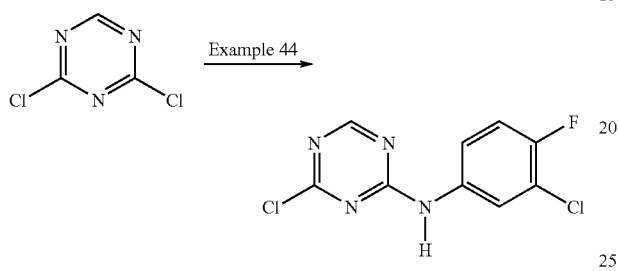

In a manner similar to that described in Example B, the compound of this example is prepared from the appropriately substituted amine and the chloride described in Example A to give material identified as 2-Chloro-4-(3-chloro-4-fluoroanilino)-1,3,5-triazine. HPLC Rt=13.89 min.; $^1$H NMR (300 MHz, DMSO-d$_6$) δ 10.7 (s, 1H), 8.5 (s, 1H), 7.8 (m, 1H), 7.4 (s, 1H), 7.3 (s, 1H).

In a manner similar to that described in Example C, the following compounds of this example is prepared from the appropriately substituted amine and the chloride described in Compound 704.

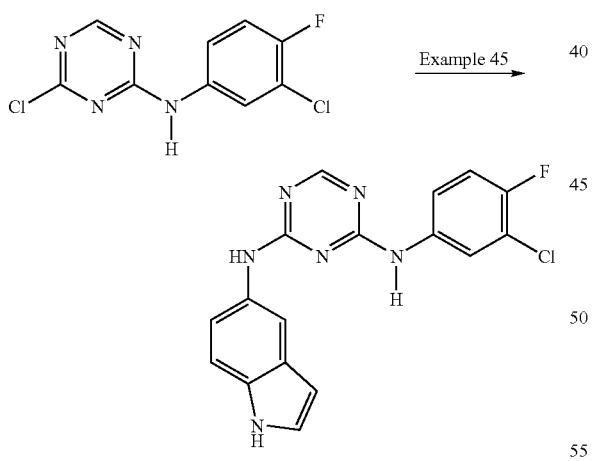

Compound 715 HPLC(Method A) Rt=6.91 min.; MS m/z=355; $^1$H NMR (300 MHz, DMSO-d$_6$) δ 10.8 (s, 1H), 9.6 (s, 1H), 9.4 (s, 1H), 8.1 (s, 1H), 7.8 (s, 1H), 7.6 (s, 1H), 7.4 (s, 1H), 6.9–7.2 (m, 6H), 6.2 (s, 1H), 3.1(s, 3H).

Compound 717 HPLC(Method A) Rt=6.02 min.; MS m/z=356; $^1$H NMR (300 MHz, DMSO-d$_6$) δ 9.6 (m, 2H), 8.2 (s, 1H), 7.8 (s, 3H), 7.3 (m, 2H), 7.1 (m, 2H), 3.1 (s, 2H), Compound 719 HPLC(Method A) Rt=6.37 min.; MS m/z=356; $^1$H NMR (300 MHz, DMSO-d$_6$) δ 9.8 (s, 1H), 7.8 (m, 2H), 7.5 (m, 2H), 7.2 (m, 2H), 6.3 (m, 2H), 5.0 (m, 2H), 3.1 (s, 3H).

Compound 710

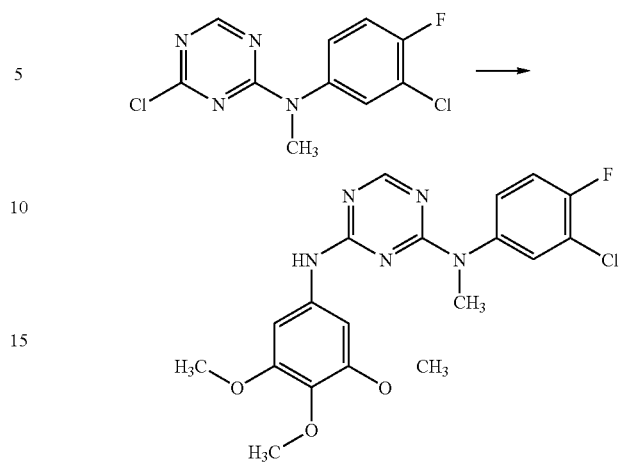

In a manner similar to that described in Example C, the compound of this example is prepared from the appropriately substituted amine and the following described chloride. HPLC Rt=12.9 min.; MS m/z=420; $^1$H NMR (300 MHz, DMSO-d$_6$) δ 9.4 (s, 1H), 8.0 (s, 1H), 7.5 (s, 1H), 7.2 (m, 2H), 6.8 (s, 2H), 3.5 (s, 6H), 3.4 (s, 3H), 3.1 (s, 3H).

Compound 1152

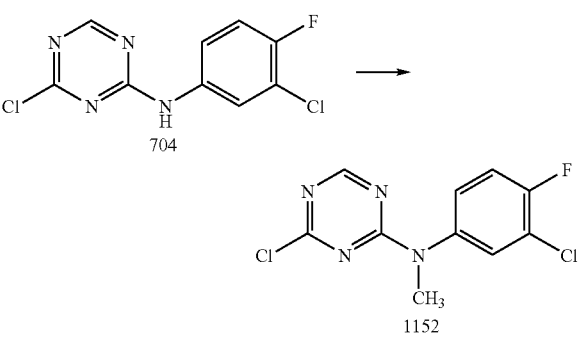

A mixture of the compound of Compound 704 (1.7 g, 6.56 mmol) and methyl iodide (1.5 mL) in DMF (20 mL) under a nitrogen atmosphere is added sodium hydride (60% dispersion, 0.53 mg, 13.3 mmol). The mixture is allowed to stir for 3 hours. The reaction is quenched by the addition of water and the organic extracts are taken up in ethyl acetate dried over anh. magnesium sulfate and concentrated under reduced pressure. The crude product is purified via medium pressure liquid chromatography using methylene chloride as the solvent system to give N-methyl-2-chloro-4-(3 chloro-4-fluoroanilino)-1,3,5-triazine.

Compound 713 HPLC Rt=16.1 min.; MS m/z 409; $^1$H NMR (300 MHz, DMSO-d$_6$) δ 9.7 (s, 1H), 8.1 (s, 1H), 7.7 (bs, 1H), 7.5 (m, 1H), 7.2 (m, 3H)) 6.9 (m, 2H), 3.1 (s, 3H).

Compound 722

In a manner similar to that described in Example C, the compound of this example is prepared from the appropriately substituted amine and the following described chloride. HPLC(Method A) Rt=9.8 min.; MS m/z=398

Compound 1154

In a manner similar to that described in Compound 710, the chloride of this example is prepared from the allyl bromide and 2-Chloro-4-(3-chloroanilino)-1,3,5-triazine described in Compound 1153.

Compound 134

In a manner similar to that described in Example C, the compound of this example is prepared from the appropriately substituted amine and the chloride described in Compound 1153. HPLC (Method A) Rt=6.00 min.; MS m/z=338; $^1$H NMR (300 MHz, DMSO-$d_6$) δ 9.8 (s, 1H), 9.7 (s, 1H), 8.2 (s, 1H), 7.9 (s, 1H), 7.8 (s, 1H), 7.7 (s, 1H), 7.2 (m, 3H), 7.1 (m, 1H), 6.9 (d, 1H), Compound 723

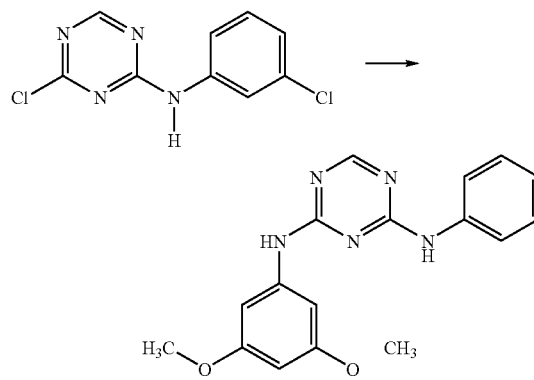

In a manner similar to that described in Example C, the compound of this example is prepared from the appropriately substituted amine and 2-Chloro-4-(3-chloroanilino)-1,3,5-triazine (Compound 1153). HPLC(Method A) Rt=7.60 min.; MS m/z=358; $^1$H NMR (300 MHz, DMSO-$d_6$) δ 9.8 (s, 1H), 9.6 (s, 1H), 8.2 (s, 1H), 7.8 (s, 1H), 7.5 (s, 1H), 7.2 (t, 1H), 6.9 (d, 1H), 6.8 (s, 2H), 6.1 (s, 1H), 3.6(s, 6H).

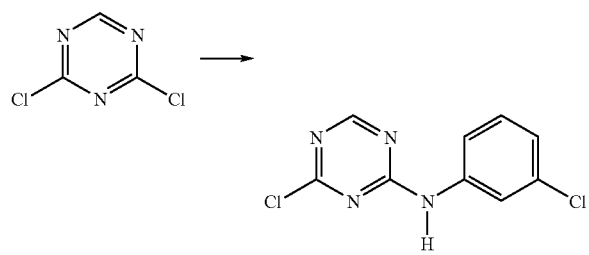

Compound 1153

In a manner similar to that described in Compound 701, the chloride of this example is prepared from the appropriately substituted amine and the chloride described in Example A to give material identified as 2-Chloro-4-(3-chloroanilino)-1,3,5-triazine Compound 724

In a manner similar to that described in Example B, the compound of this example is prepared from the appropriately substituted amine and Compound 1155. HPLC (Method A) Rt=8.1 min.; MS m/z=386; $^1$H NMR (300 MHz, DMSO-$d_6$) 59.5 (s, 1H), 8.1 (s, 1H), 7.1–7.4 (m, 4H), 6.8 (s, 2H), 6.0 (s, 1H), 3.8 (q, 2H), 3.5 (s, 6H), 1.0 (t, 3H).

Compound 1155

In a manner similar to that described in Compound 710, the chloride of this example is prepared from ethyl iodide and 2-Chloro-4-(3-chloroanilino)-1,3,5-triazine described in Compound 1153.

Salts of Compound 414

Compound 414, Hydrochloric Acid Salt

To a solution of Compound 414 (100.0 mg 0.21 mmol) in absolute ethanol (2 mL) is added a saturated solution of HCl in ethanol (1 mL). The solid formed is collected by suction filtration and dried under vacuum. HPLC Rt=9.6 min.

Compound 414, Oxalic Acid Salt

To a solution of Compound 414 (100.0 mg 0.21 mmol) in absolute ethanol (2 mL) is added Oxalic acid (18.6 mg 0.21 mmol). The mixture is heated to 60° C. for 3 hours. The solid formed is collected by suction filtration and dried under vacuum. HPLC Rt=9.6 min.

Compound 414, Methane Sulfonic c Acid Salt

To a solution of Compound 414 (100.0 mg 0.21 mmol) in absolute ethanol (2 mL) is added Methane sulfonic acid (19.8 mg 0.21 mmol). The mixture is heated to 60° C. for 3 hours. The solid formed is collected by suction filtration and dried under vacuum. HPLC Rt=9.6 min.

Compound 414, Fumaric Acid Salt

To a solution of Compound 414 (100.0 mg 0.21 mmol) in absolute ethanol (2 mL) is added fumaric acid (24 mg 0.21 mmol). The mixture is heated to 60° C. for 3 hours. The solid formed is collected by suction filtration and dried under vacuum. HPLC Rt=9.6 min.

Compound 414, Ascorbic Acid Salt

To a solution of Compound 414 (100.0 mg 0.21 mmol) in absolute ethanol (2 mL) is added ascorbic acid (36.3 mg 0.21 mmol). The mixture is heated to 60° C. for 3 hours. The solid formed is collected by suction filtration and dried under vacuum. HPLC Rt=9.6 min.

Compound 414, Citric Acid Salt

To a solution of Compound 414 (100.0 mg 0.21 mmol) in absolute ethanol (2 mL) is added citric acid (40.3 mg 0.21 mmol). The mixture is heated to 60° C. for 3 hours. The solid formed is collected by suction filtration and dried under vacuum. HPLC Rt=9.6 min.

Compound 414, Acetic Acid Salt

To a solution of Compound 414 (100.0 mg 0.21 mmol) in absolute ethanol (2 mL) is added acetic acid (18 μL 0.21 mmol). The mixture is heated to 60° C. for 3 hours. The solid formed is collected by suction filtration and dried under vacuum. HPLC Rt=9.6 min.

Compound 414, Tartaric Acid Salt

To a solution of Compound 414 (100.0 mg 0.21 mmol) in absolute ethanol (2 mL) is added tartaric acid (31 mg 0.21 mmol). The mixture is heated to 60° C. for 3 hours. The solid formed is collected by suction filtration and dried under vacuum. HPLC Rt=9.6 min.

Compound 414, Malic Acid Salt

To a solution of Compound 414 (100.0 mg 0.21 mmol) in absolute ethanol (2 mL) is added L-Malic acid (28.0 mg 0.21 mmol). The mixture is heated to 60° C. for 3 hours. The solid formed is collected by suction filtration and dried under vacuum. HPLC Rt=9.6 min.

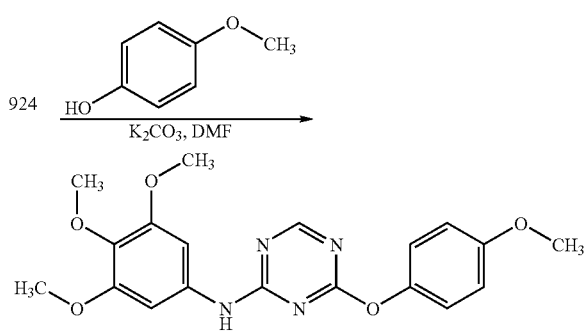

EXAMPLE 46a

To a stirred mixture of 924 (50 mg, 0.169 mmol) and powdered potassium carbonate (51 mg, 0.37 mmol) in dry DMF (2.0 mL) is added p-methoxyphenol (46 mg, 0.37 mmol). The mixture is stirred at room temperature for 18–24 h, diluted with water (3 volumes) and brine (3 volumes) and extracted with EtOAc (3×10 mL). Combined organic extracts are dried, concentrated in vacuo and the resulting solid purified by column chromatography (EtOAc/n-Hexanes) to provide compound 174 as a white solid (37 mg, 57%).

| Compound | HPLC ret. | MS m/z |
|---|---|---|
| 174 | 12.57 min. | 385 |
| 175 | 14.28 min. | 401 |
| 421 | 9.16 min. | 293 |

EXAMPLE 46b

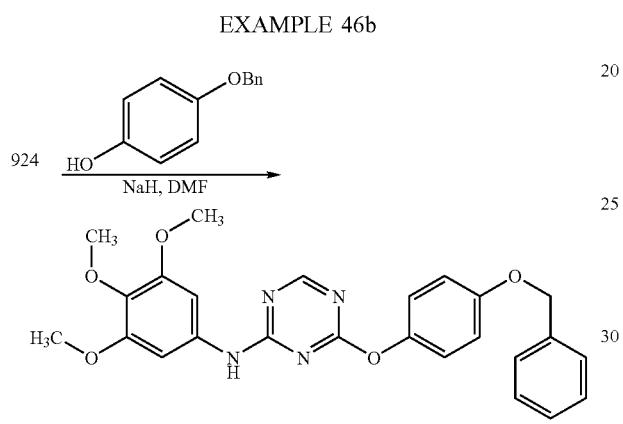

To a mixture of 4-benzyloxyphenol (200 mg, 1.0 mmol) in DMF under a nitrogen atmosphere is added sodium hydride (60% dispersion, 40 mg, 1.0 mmol). The mixture is allowed to stir for 0.75 hours followed by addition of 2-chloro-4-(3',4',5'-trimethoxyanilino)-1,3,5-triazine. The reaction is allowed to stir for 18 hrs, diluted with water and extracted with ethyl acetate (100 mL), dried over anh. magnesium sulfate and concentrated in vacuo. The crude product is purified via medium pressure liquid chromatography using methylene chloride followed by 1:99 methano/methylenechloride as the solvent system to afford compound 530. HPLC(Method A) Rt=9.12 min.; MS m/z=461; $^1$H NMR (300 MHz, DMSO-d$_6$) 10.0 (s, 1H), 8.3 (s, 1H), 6.6–7.4 (m, 13H), 4.8 (s, 2H), 3.0–3.6 (m, 9H).

Compound 1121: HPLC ret time=13.48 min; MS m/z=437; $^1$H NMR (300 MHz, DMSO-d$_6$) δ 9.9–10.1 (broad d, 1H), 8.4 (s, 1H), 7.5 (d, 1H), 7.2 (d, 1H), 6.9 (s, 1H), 6.7 (s, 2H), 3.3–3.5 (m, 9H).

Compound 1122: HPLC ret time=11.47 min; MS m/z=415; $^1$H NMR (300 MHz, DMSO-d$_6$) δ 9.83–10.1(broad d, 1H), 8.4 (s, 1H), 6.7–6.9 (m, 4H), 6.6 (d, 1H), 3.3–3.7 (m, 5H).

Compound 1123: HPLC ret time 13.05 min; MS m/z=431; $^1$H NMR (300 MHz, DMSO-d$_6$) δ 9.8–10.1 (broad s, 1H), 8.26 (s, 1H), 7.0 (s, 2H), 6.9 (s, 2H), 6.7 (s, 1H), 3.34–3.7 (m, 15H).

Compound 1124: HPLC ret time=9.78 min; MS m/z=398; $^1$H NMR (300 MHz, DMSO-d$_6$) δ 9.9–10.1(broad d, 1H), 8.4 (s, 1H), 7.03 (t, 1H), 6.94 (broad s, 1H), 6.78 (broad s, 1H), 6.4 (d, 2H), 6.3 (s, 1H), 3.3–3.4 (m, 9H), 2.7 (s, 6H).

| Compound | HPLC ret. | MS m/z |
|---|---|---|
| 1119 | 13.48 min. | 437 |
| 1120 | 9.81 min. | 356 |

EXAMPLE 47

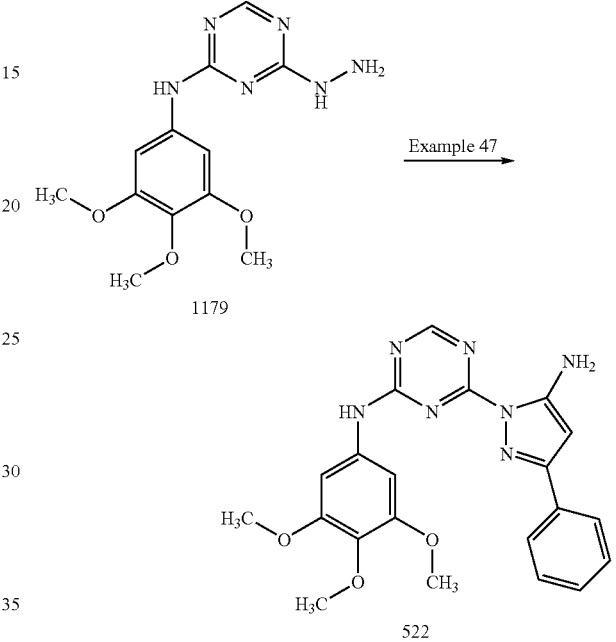

Compound 522

Compound 924 (300 mg, 1 mmol) is dissolved in hydrazine monohydrate (0.630 mL, 20 mmol) and heated at 120° C. for 25 minutes. The resulting white solid is filtered and dried to provide intermediate 1179. This intermediate (40 mg, 0.14 mmol) is then reacted with benzoyl acetonitrile (20 mg, 0.14 mmol) in refluxing absolute ethanol (1 mL). The resulting product is purified by silica gel chromatography. MS m/z=442[M+Na]$^+$; HPLC Rt=12.25

Compound 520, the related regioisomer, can be prepared as above by using formyl phenylacetonitrile as the condensing reagent. MS m/z 442[M+Na]$^+$; HPLC Rt=11.76

EXAMPLE 49

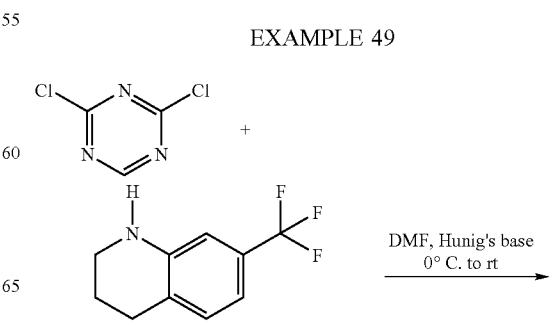

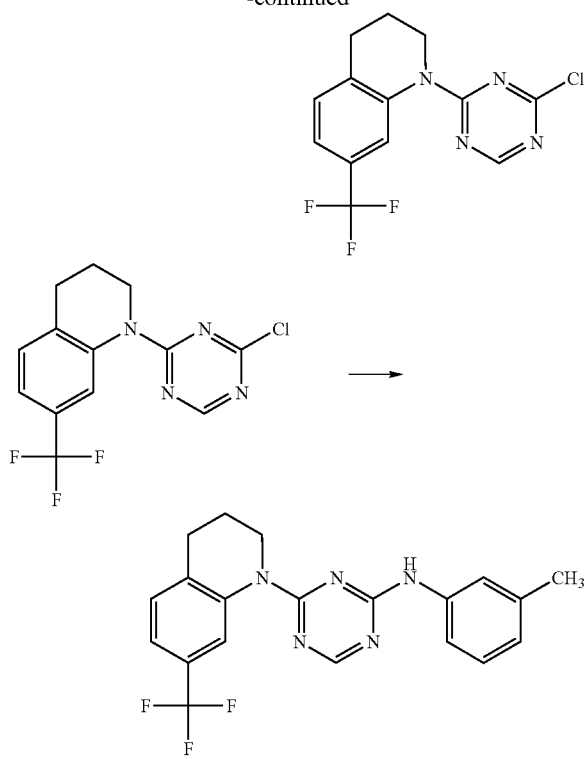

7-(Trifluoromethyl)-1,2,3,4-tetrahydroquinoline (440 mg, 2.2 mmol) is dissolved into DMF (10 mL) under $N_2$ at room temperature. N,N-Diisopropylethylamine (284 mg, 2.2 mmol) is added, and the reaction solution is cooled to 0° C. 2,4-Dichloro-1,3,5-triazine is then added, and reaction is stirred with gradual warming to room temperature. The reaction is quenched after 3 hours with water, which causes a fine precipitate to form, which is not filterable. This mixture is extracted 3 times with ethyl acetate. The ethyl acetate extracts are then washed brine, combined, dried over sodium sulfate, filtered, concentrated, and dried under high vacuum giving 800 mg (>100%) of a yellow oil that is used without further purification.

Compound 1288

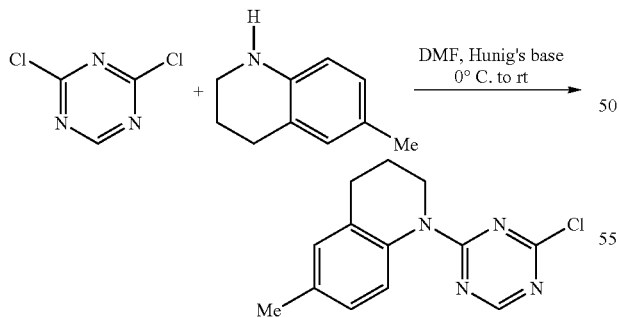

2,4-Dichloro-1,3,5-triazine (1.95 g, 13 mmol) is dissolved into DMF (50 mL) under $N_2$ and cooled to 0° C. N,N-Diisopropylethylamine (1.68 g, 13 mmol) is added, followed by the addition of 6-methyl-1,2,3,4-tetrahydroquinoline (1.91 g, 13 mmol). The reaction solution is then stirred with gradual warming to room temperature. The reaction is quenched after 3 hours with water, which causes a sticky precipitate to form. The mixture is extracted 3 times with ethyl acetate. The ethyl acetate extracts are then washed brine, combined, dried over sodium sulfate, filtered, and concentrated, then dried under high vacuum to remove residual traces of DMF. The recovered material is then purified by elution through a 17×2.5 cm column of silica gel (5%, 10%, 20% and 40% EtOAc:Hexane step gradient) giving 1.98 g (58%) of a white solid: $^1$H NMR 300 MHz, DMSO-$d_6$) δ 8.57 (s, 1H), 7.57 (d, J=7.7 Hz, 1H), 7.00 (m, 2H), 3.93 (t, J=6.7 Hz, 2H), 2.71 (t, J=6.7 Hz, 2H), 1.92 (m, 2H). In a manner similar to that described in Example C, the following compounds of this example are prepared from the appropriately substituted amine and the chloride described previously.

| Compound | HPLC ret. | MS m/z |
|---|---|---|
| 759 | (Method A) 6.92 min. | 326 |
| 760 | (Method A) 6.50 min. | 375 |
| 761 | (Method A) 7.16 min. | 328 |
| 762 | (Method A) 6.77 min. | 314 |
| 763 | (Method A) 7.27 min. | 374 |
| 764 | (Method A) 6.93 min. | 401 |
| 765 | (Method A) 7.38 min | 397 |
| 766 | (Method A) 6.31 min | 308 |
| 767 | (Method A) 9.09 min. | 382 |
| 768 | (Method A) 7.81 min | 385 |
| 769 | (Method A) 5.95 min. | 333 |
| 770 | (Method A) 6.81 min. | 348 |
| 771 | (Method A) 7.47 min. | 406 |
| 772 | (Method A) 4.43 min. | 350 |
| 773 | (Method A) 7.50 min. | 375 |
| 774 | (Method A) 7.65 min. | 385 |
| 775 | (Method A) 5.22 min. | 347 |
| 776 | (Method A) 4.38 min. | 355 |
| 777 | (Method A) 5.88 min. | 333 |
| 778 | (Method A) 8.86 min. | 366 |
| 779 | (Method A) 5.50 min. | 389 |
| 853 | (Method A) 6.61 min. | 376 |
| 854 | (Method A) 8.58 min. | 382 |
| 892 | (Method A) 8.59 min. | 362 |
| 893 | (Method A) 8.59 min. | 354 |

EXAMPLE 50

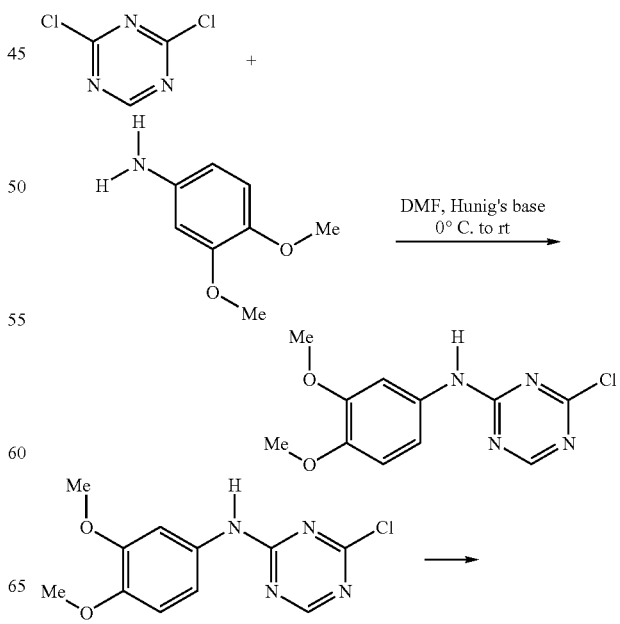

-continued

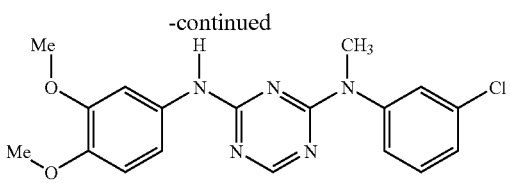

2,4-Dichloro-1,3,5-triazine (12.6 g, 84 mmol) is dissolved into DMF (100 mL) under $N_2$ and cooled to 0° C. N,N-Diisopropylethylamine (11.7 g, 90 mmol) is added, followed by the addition of 4-aminoveratrole (13.35 g, 87 mmol). The reaction solution is then stirred with gradual warming to room temperature. The reaction is quenched after 3.5 hour with water, which causes a gray precipitate to form. This precipitate is recovered by vacuum filtration, washed with cold water, dried under high vacuum, then eluted through a 28×4.5 cm column of silica gel (0.1% $NH_4OH_{(aq)}$ buffered 1%, 2%, 3%, 4%, and 5% $MeOH:CH_2Cl_2$ step gradient) giving 4.16 g (18%) of an off white solid: $^1H$ NMR (300 MHz, DMSO-$d_6$) δ 10.57 (s, 1H), 8.57 (br s, 1H), 7.27 (br s, 1H), 7.14 (br s, 1H), 6.95 (br s, 1H), 3.74 (br s, 6H).

In a manner similar to that described in Example C, the following compounds of this example are prepared from the appropriately substituted amine and the chloride described previously.

| Compound | HPLC ret. | MS m/z |
|---|---|---|
| 758 | (Method A) 7.53 min. | 406 |
| 780 | (Method A) 5.24 min. | 368 |
| 781 | (Method A) 7.68 min. | 359 |
| 782 | (Method A) 3.41 min. | 387 |
| 783 | (Method A) 6.50 min. | 368 |
| 784 | (Method A) 3.71 min. | 333 |
| 785 | (Method A) 5.48 min. | 348 |
| 786 | (Method A) 1.62 min. | 388 |
| 787 | (Method A) 4.54 min | 301 |
| 788 | (Method A) 4.44 min. | 320 |
| 789 | (Method A) 5.47 min. | 416 |
| 790 | (Method A) 4.81 min. | 332 |
| 791 | (Method A) 6.74 min. | 386 |
| 792 | (Method A) 6.39 min. | 372 |
| 793 | (Method A) 6.74 min. | 386 |
| 794 | (Method A) 6.53 min. | 360 |
| 795 | (Method A) 7.05 min. | 372 |
| 796 | (Method A) 7.01 min. | 344 |
| 797 | (Method A) 6.38 min. | 338 |
| 798 | (Method A) 4.29 min. | 418 |
| 799 | (Method A) 6.82 min. | 352 |
| 800 | (Method A) 6.81 min. | 352 |
| 801 | (Method A) 6.74 min | 374 |
| 802 | (Method A) 4.46 min. | 421 |
| 803 | (Method A) 7.09 min. | 366 |
| 855 | (Method A) 5.76 min. | 421 |
| 856 | (Method A) 5.85 min. | 407 |
| 857 | (Method A) 5.56 min. | 366 |
| 858 | (Method A) 6.57 min. | 441 |
| 859 | (Method A) 7.06 min | 420 |
| 860 | (Method A) 5.43 min. | 382 |
| 861 | (Method A) 3.14 min. | 359 |
| 862 | (Method A) 6.64 min | 383 |
| 863 | (Method A) 6.31 min. | 368 |
| 864 | (Method A) 6.46 min. | 396 |
| 865 | (Method A) 6.77 min. | 372 |
| 866 | (Method A) 7.50 min. | 422 |
| 867 | (Method A) 7.23 min. | 422 |
| 868 | (Method A) 5.76 min. | 382 |
| 869 | (Method A) 3.99 min. | 367 |
| 870 | (Method A) 3.79 min. | 361 |
| 894 | (Method A) 5.41 min. | 380 |
| 895 | (Method A) 5.44 min. | 381 |
| 896 | (Method A) 6.81 min. | 364 |
| 897 | (Method A) 6.01 min. | 349 |
| 898 | (Method A) 7.30 min. | 392 |
| 899 | (Method A) 4.43 min. | 407 |

EXAMPLE 51

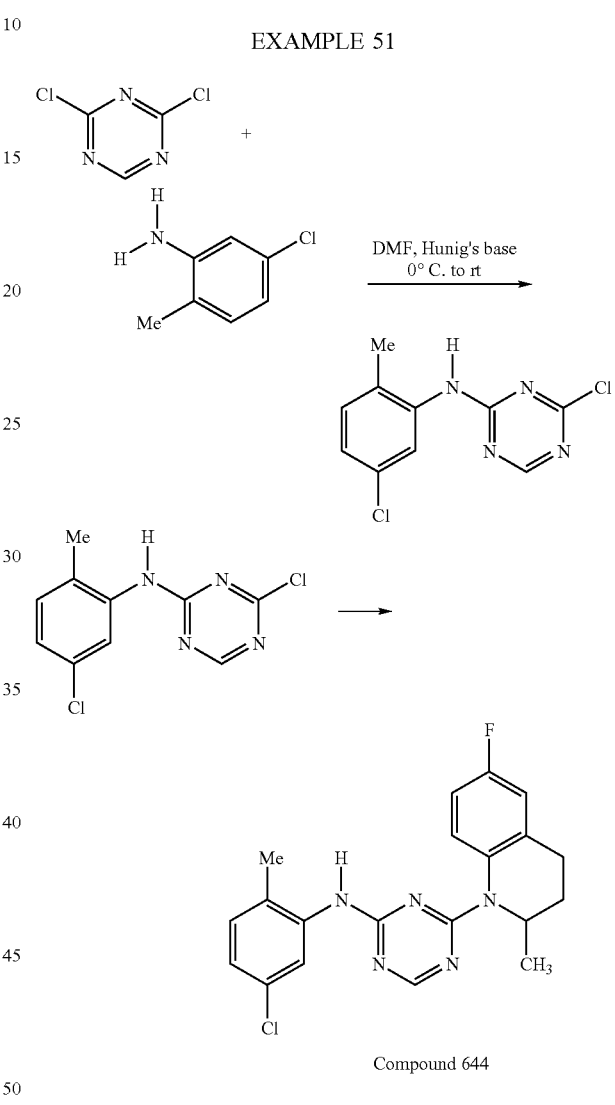

Compound 644

2,4-Dichloro-1,3,5-triazine (3 g, 20 mmol) is dissolved into DMF (20 mL) under $N_2$ and cooled to 0° C. N,N-Diisopropylethylamine (2.58 g, 20 mmol) is added, followed by the addition of 3-chloro-6-methylaniline (2.83 g, 20 mmol). The reaction solution is then stirred with gradual warming to room temperature. The reaction is quenched after 3 hours with water, then extracted 3 times with ethyl acetate. The ethyl acetate extracts are then washed brine, combined, dried over sodium sulfate, filtered, and concentrated, then eluted through a 17×2.5 cm column of silica gel (25%, 40%, 60% EtOAc:Hexane step gradient) giving 169 mg (3.3%) of the desired compound as a white solid: $^1H$ NMR (300 MHz, DMSO-$d_6$) δ 10.34 (s, 1H), 8.55 (br s, 1H), 7.45 (s, 1H), 7.29 (, 2H), 2.18 (s, 3H). A by-product of the reaction recovered from the silica gel column is the bis-addition product, Example 638, giving 601 mg (11%) of a white solid: MS m/z 360 =[M+H]+; 1H NMR (300 MHz, DMSO-d6) δ 9.12 (s, 2H), 8.24 (s, 1H), 7.45 (s, 2H), 7.23 (d, J=8.0 Hz, 2H), 7.13 (d, J=8.0 Hz, 2H), 2.19 (s, 6H); HPLC Rt=14.32 min.

Compound 1291

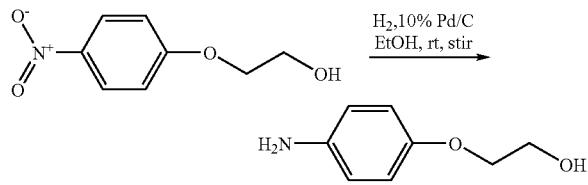

2-(4-Nitrophenoxy)ethanol (1.83 g, 10 mmol) is dissolved into ethanol (100 mL) under air at room temperature. A catalytic amount of 10% Palladium on carbon is added. The air is then replaced with a H2(g) atmosphere and the reaction is stirred vigorously for 18 hours. The reaction is quenched by filtering it through celite with ethanol. The filtrate is concentrated under reduced pressure and the recovered material purified by eluting it through a 17×2.5 cm column of silica gel (5% and 10% MeOH:CH2Cl2 step gradient) giving 1.18 g (77%) of a black solid: MS m/z 154 =[M+H]+; 1H NMR (300 MHz, DMSO-d6) δ 6.64 (d, J=8.7 Hz, 2H), 6.49 (d, J=9.0 Hz, 2H), 4.76 (t, J=5.5 Hz, 1H), 4.58 (br s, 2H), 3.81 (t, J=5.0 Hz, 2H), 3.63 (q, J=5.4 Hz, 2H).

Compound 1292:

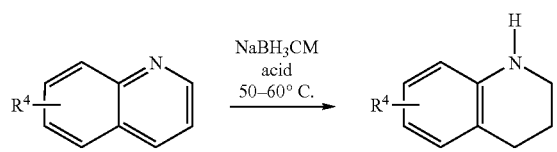

Reference: Gribble, G. W.; Heald, P. W. *Synthesis*, 1975, 650–652.

6-Methoxyquinoline (1.26 g, 7.9 mmol) is dissolved into glacial acetic acid (20 mL) under N2 at room temperature. Solid sodium cyanoborohydride (2 g, 32 mmol) is then added in small portions over a 45 minute period. The reaction is then heated to 50° C. for 8 hours, then cooled to room temperature and stirred overnight. The reaction is then quenched by cooling it to 0° C., and adjusting the pH of the solution to 14 with 2 N NaOH(aq). This solution is then extracted 3 times with ethyl acetate. The ethyl acetate extracts are then washed brine, combined, dried over sodium sulfate, filtered, and concentrated, then eluted through a 17×2.5 cm column of silica gel (5% and 10% EtOAc:Hexane step gradient) giving 750 mg (58%) of a red oil. This material is then used without further purification.

Compound 1293:

Reference: Rauckman, B. S.; Tidwell, M. Y.; Johnson, J. V.; Roth, B. *J. Med. Chem.*, 1989, 32, 1927–1935.

5-Chloroquinoline (1.01 g, 6.2 mmol) is dissolved into anhydrous ethanol (30 mL) under N2 at-room temperature. Concentrated hydrochloric acid (2.14 mL, 24.8 mmol) is added, followed by the addition of the sodium cyanoborohydride (1.56 g, 24.8 mmol). This produces a vigorous gas and heat evolution. The reaction is then heated to 60° C. for 2 hours, then cooled and stirred at room temperature for an additonal 18 hours. The reaction is then quenched by adjusting the pH to approximately 9 with 2 N NaOH(aq). This mixture is then extracted 3 times with ethyl acetate. The ethyl acetate extracts are then washed brine, combined, dried over sodium sulfate, filtered, and concentrated, then eluted through a 17×2.5 cm column of silica gel (5%, 10%, 15%, 40% and 50% EtOAc:Hexane step gradient) giving 725 mg (69%) of a green oil: MS m/z 168 =[M+H]+; 1H NMR (300 MHz, DMSO-d6) δ 6.83 (t, J=7.9 Hz, 1H), 6.48 (d, J=8.0 Hz, 1H), 6.39 (d, J=8.1 Hz, 1H), 5.99 (br s, 1H), 3.13 (m, 2H), 2.64 (t, J=0.6.4 Hz, 2H), 1.81 (m, 2H).

Compound 1294

Reference: Rauckman, B. S.; Tidwell, M. Y.; Johnson, J. V.; Roth, B. *J. Med. Chem.*, 1989, 32, 1927–1935

4,7-Dichloroquinoline (1.02 g, 5.1 mmol) is dissolved into anhydrous ethanol (30 mL) under N2 at room temperature. Concentrated hydrochloric acid (1.76 mL, 20.4 mmol) is added, followed by the addition of the sodium cyanoborohydride (1.28 g, 20.4 mmol). This produces a vigorous gas and heat evolution. The reaction is then heated to 60° C. for 2 hours, then cooled and stirred at room temperature for an additonal 18 hours. The reaction is then quenched by adjusting the pH to approximately 9 with 2 N NaOH(aq). This mixture is then extracted 3 times with ethyl acetate. The ethyl acetate extracts are then washed brine, combined, dried over sodium sulfate, filtered, and concentrated, then eluted through a 30×2.5 cm column of silica gel (3.75% EtOAc:Hexane) giving 134 mg (13%) of an orange solid: MS m/z 168 =[M+H]+; 1H NMR (300 MHz, DMSO-d6) δ 6.80 (d, J=8.0 Hz, 1H), 6.42 (s, 1H), 6.36 (d, J=7.7 Hz, 1H), 5.95 (br s, 1H), 3.15 (t, J=5.5 Hz, 2H), 2.60 (t, J=6.2 Hz, 2H), 1.75 (m, 2H).

Compound 1295

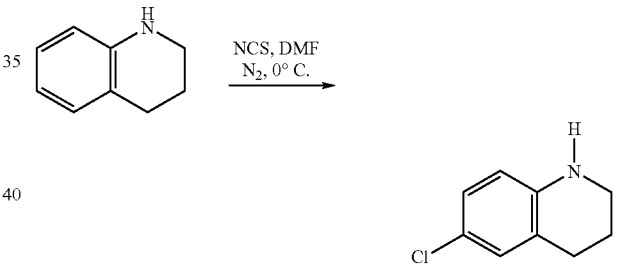

Reference: Nagata, R.; Tanno, N.; Kodo, T.; Ae, N.; Yamaguchi, H.; Nishimura, T.; Antoku, F.; Tatsuno, T.; Kato, T.; Tanaka, Y.; Nakamura, M.; Ogita, K.; Yoneda, Y. *J. Med. Chem.*, 1994, 37, 3956–3968.

1,2,3,4-Tetrahydroquinoline (1.33 g, 10 mmol) is dissolved into DMF (15 mL) under N2 and cooled to 0° C. N-Chlorosuccinimide (1.35 g, 10 mmol) is dissolved into DMF (10 mL) under N2 and is then added to the tetrahydroquinoline solution dropwise, via pressure equalizing dropping funnel, over a 45 minute period. The reaction is then stirred at 0° C. for 3 hours, then quenched by pouring it into water (100 mL). This mixture is then extracted one time with a 5:1 mixture of ethyl acetate toluene, then two more times with ethyl acetate. All of the organic extracts are then washed with brine, combined, dried over sodium sulfate, filtered, and concentrated, then eluted through a 17×2.5 cm column of silica gel (5%, 10% and 15% EtOAc Hexane step gradient) giving 830 mg (49%) of a green oil: 1H NMR (300 MHz, DMSO-d6) δ 6.83 (m, 1H), 6.40 (d, J=9.0 Hz, 1H), 5.81 (br s, 1H), 3.14 (t, J=5.5 Hz, 2H), 2.63 (t, J=6.4 Hz, 2H), 1.74 (m, 2H).

EXAMPLE 36

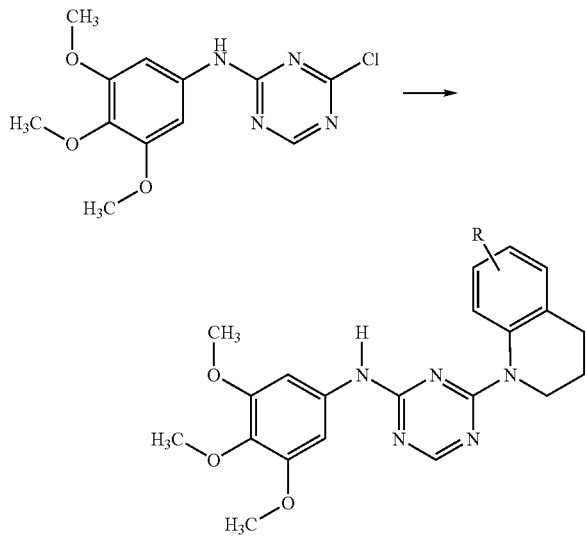

Compound 207: 2-Chloro-4-(3',4',5'-trimethoxyanilino)-1,3,5-triazine (51 mg, 0.17 mmol) is suspended in ethanol (2 mL) in a sealed tube under air at room temperature. N,N-Diisopropylethylamine (22 mg, 0.17 mmol) is added, followed by addition of piperidine (15 mg, 0.17 mmol). The reaction mixture is then heated to 100° C. for 30 minutes, during which everything goes into solution. The reaction is then cooled to room temperature and a white precipitate forms, and is recovered by vacuum filtration and washed with cold ethanol. The recovered solid is then dissolved into hot ethanol to re-crystallize. The recovered crystals are then applied to two 500 l preparative TLC plates and developed one time with 40% EtOAc: Hexanes giving 12 mg (20%) of a white solid: MS m/z=346 [M+H]$^+$; $^1$H NMR (300 MHz, DMSO-d$_6$) δ 9.48 (br s, 1H), 8.20 (s, 1H), 7.14 (s, 2H), 3.76 (br s, 4H), 3.74 (s, 6H), 3.61 (s, 3H), 1.63 (br s, 2H), 1.52 (br s, 4H); HPLC Rt=10.44 min.

Compound 208: 2-Chloro-4-(3',4',5'-trimethoxyanilino)-1,3,5-triazine (43 mg, 0.14 mmol) is reacted with 4-hydroxypiperidine (15 mg, 0.14 mmol) in the manner described for compound 207, and kept at 100° C. for 4 days. A solid does form when the reaction is cooled to room temperature, and is allowed to settle to the bottom of the reaction vessel and recovered by decantation of the solvent. This solid is then washed with methanol and dried under high vacuum giving 36 mg (72%) of a white solid: MS m/z=362 [M+H]$^+$; $^1$H NMR (300 MHz, DMSO-d$_6$) δ 9.49 (br s, 1H), 8.20 (s, 1H), 7.12 (s, 2H), 4.78 (d, J=4.0 Hz, 1H), 4.20 (br d, J=13.8 Hz, 2H), 3.74 (s, 6H), 3.61 (s, 3H), 3.39 (br m, 2H), 1.75 (br m, 2H), 1.35 (br s, 1H); HPLC Rt=7.50 min.

Compound 209: 2-Chloro-4-(3',4',5'-trimethoxyanilino)-1,3,5-triazine (56 mg, 0.19 mmol) is reacted with morpholine (16 mg, 0.19 mmol) in the manner described for compound 207, and kept at 100° C. for 30 minutes. A white precipitate forms when the reaction is cooled to room temperature and is recovered by vacuum filtration, then washed with cold ethanol. The recovered material is then dissolved into hot ethanol to re-crystallize. The recovered crystals are then applied to two 500 l preparative TLC plates and developed one time with 95:5:0.5 CH$_2$Cl$_2$: MeOH NH$_4$OH$_{(aq)}$ giving 31 mg (460%) of a white solid: MS m/z=348 [M+H]$^+$; $^1$H NMR (300 MHz, DMSO-d$_6$) δ 9.55 (br s, 1H), 8.24 (s, 1H), 7.11 (s, 2H), 3.76 (s, 4H), 3.73 (s, 6H), 3.64 (s, 4H), 3.61 (s, 4H); HPLC Rt=8.59 min.

Compound 211: 2-Chloro-4-(3',4',5'-trimethoxyanilino)-1,3,5-triazine (110 mg, 0.37 mmol) is reacted with tert-butyl 1-piperazine carboxylate (69 mg, 0.37 mmol) in the manner described for compound 207, and kept at 100° C. for 3 hours. A white precipitate forms when the reaction is cooled to room temperature and is recovered by vacuum filtration, then washed with cold ethanol and dried under high vacuum giving 43 mg (26%) of a white solid: MS m/z=447 [M+H]$^+$; $^1$H NMR (300 MHz, DMSO-d$_6$) δ 9.57 (br s, 1H), 8.24 (s, 1H), 7.11 (s, 2H), 3.75 (br s, 10H), 3.61 (s, 3H), 3.40 (br s, 4H), 1.42 (s 9H); HPLC Rt=11.99 min.

Compound 212: 2-Chloro-4-(3',4',5'-trimethoxyanilino)-1,3,5-triazine (53 mg, 0.18 mmol) is reacted with 1-methylpiperazine (18 mg, 0.18 mmol) in the manner described for compound 207, and kept at 100° C. for 18 hours. A white precipitate forms when the reaction is cooled to room temperature and is recovered by vacuum filtration, then washed with cold ethanol. The recovered solid is then applied to two 500 μ preparative TLC plates and developed one time with 95:5:0.5 CH$_2$Cl$_2$: MeOH: NH$_4$OH$_{(aq)}$ giving 16 mg (25%) of a white solid: MS m/z=361 [M+H]$^+$; $^1$H NMR (300 MHz, DMSO-d$_6$) δ 9.55 (br s, 1H), 8.22 (s, 1H), 7.12 (s, 2H), 3.77 (br s, 4H), 3.74 (s, 6H), 3.61 (s, 3H), 2.36 (br s, 4H), 2.21 (s 3H); HPLC Rt=6.62 min.

Compound 213: 2-Chloro-4-(3',4',5'-trimethoxyanilino)-1,3,5-triazine (62 mg, 0.21 mmol) is reacted with 1-(2-pyridyl)piperazine (34 mg, 0.21 mmol) in the manner described for compound 207, and kept at 100° C. for 1 hour. A white precipitate forms when the reaction is cooled to room temperature and is recovered by vacuum filtration, washed with cold ethanol, then dried under high vacuum giving 61 mg (68%) of a white solid: MS m/z=424 [M+H]$^+$; $^1$H NMR (300 MHz, DMSO-d$_6$) δ 9.56 (br s, 1H), 8.26 (s, 1H), 8.13 (dd, J=5.0, 1.9 Hz, 1H), 7.56 (m, 1H), 7.15 (s, 2H), 6.89 (d, J=8.7 Hz, 1H), 6.67 (dd, J=7.0, 5.0 Hz, 1H), 3.90 (br s, 4H), 3.78 (s, 6H), 3.62 (s, 3H), 3.61 (br s, 4H); HPLC Rt=7.48 min.

Compound 298: 2-Chloro-4-(3',4',5'-trimethoxyanilino)-1,3,5-triazine (56 mg, 0.19 mmol) is reacted with 6-fluoro-2-methyl-1,2,3,4-tetrahydroquinoline (31 mg, 0.19 mmol) in the manner described for compound 207, and kept at 100° C. for 18 hours. The reaction mixture is then cooled to room temperature and concentrated under reduced pressure. The recovered material is then applied to two 1000μ preparative TLC plates and developed one time with 95:5:0.5 CH$_2$Cl$_2$:MeOH:NH$_4$OH$_{(aq)}$. The recovered material is then applied to two 500) preparative TLC plates and developed one time with 95:5:0.5 CH$_2$Cl$_2$:MeOH:NH$_{40}$H$_{(aq)}$ giving 38 mg (47%o) of a glassy white solid: MS m/z=426 [M+H]$^+$; $^1$H NMR (300 MHz, DMSO-d$_6$) δ 9.64 (br s, 1H), 8.28 (s, 1H), 7.59 (dd, J=9.1, 5.4 Hz, 1H), 7.05 (m, 3H), 6.99 (t, J=9.0 Hz, 1H), 5.13 (q, J=6.7 Hz, 1H), 3.68 (s, 6H), 3.61 (s, 3H), 2.73 (m, 1H), 2.65 (m, 1H), 2.27 (m, 1H), 1.48 (m, 1H), 1.13 (d, J=6.4 Hz, 3H); HPLC Rt=13.41 min.

Compound 326: 2-Chloro-4-(3',4',5'-trimethoxyanilino)-1,3,5-triazine (54 mg, 0.18 mmol) is reacted with 1,2,3,4-tetrahydroisoquinoline (24 mg, 0.18 mmol) in the manner described for compound 207, and kept at 100° C. for 3 days. A precipitate forms when the reaction is cooled to room temperature and is recovered by vacuum filtration, then washed with cold methanol and dried under high vacuum giving 54 mg (76%) of yellow needles: MS n/z=394 [M+H]$^+$; $^1$H NMR (300 MHz, CDCl$_3$) δ 9.60 HPLC(Method A) Rt=7.14 min.; MS m/z=351; $^1$H 8.26 (br s, 1H), 7.30–7.10 (m, 6H), 4.90 (br d, J=6.6 Hz, 2H), 4.00 (br d, J=5.1 Hz, 2H), 3.82 (s, 3H), HPLC(Method A) Rt=6.26 min.; MS m/z=353; $^1$H 3.63 (s, 3H), 2.89 (m, 2H); HPLC Rt=12.16 min.

Compound 498: 2-Chloro-4-3',4',5'-trimethoxyanilino)-1,3,5-triazine (74 mg, 0.25 mmol) is reacted with 6-methyl-1,2,3,4-tetrahydroquinoline (44 mg, 0.3 mmol) in the manner described for compound 207, except for using 1.5 equivalents of N,N-diisopropylethylamine, and kept at 100° C. for 3 days. A white precipitate forms when the reaction is cooled to 0° C., and is recovered by vacuum filtration, then washed with cold isopropanol. The recovered solid is then applied to two 1000 µ preparative TLC plates and developed one time with 95:5:0.5 $CH_2Cl_2$:MeOH $NH_4OH_{(aq)}$. The recovered material is then applied to a set of two 500 µ preparative TLC plates and developed one time with 7:7:7:1 MtBE:$CH_2Cl_2$:Hexane:MeOH giving 20 mg (20%) of a white solid: MS m/z 408 [M+H]$^+$; $^1$H NMR (300 MHz, DMSO-d6) δ 9.64 (br s, 1H), 8.29 (s, 1H), 7.60 (d, J=8.4 Hz, 1H), 7.10 (s, 2H), 6.97 (s, 1H), 6.93 (d, J=8.7 Hz, 1H), 3.98 (t, J=6.0 Hz, 2H), 3.66 (s, 6H), 3.61 (s, 3H), 2.71 (t, J=6.0 Hz, 2H), 2.25 (s, 3H), 1.90 (m, 2H); HPLC Rt=12.77 min.

Compound 518: 2-Chloro-4-(3',4',5'-trimethoxyanilino)-1,3,5-triazine (74 mg, 0.25 mmol) is reacted with 7-(trifluoromethyl)-1,2,3,4-tetrahydroquinoline (60 mg, 0.3 mmol) in the manner described for compound 207, except for using 1.5 equivalents of N,N-diisopropylethylamine, and kept at 100° C. for 3 days. A white precipitate forms when the reaction is cooled to 0° C., and is recovered by vacuum filtration, then washed with cold isopropanol. The recovered solid is then applied to two 1000 µ preparative TLC plates and developed one time with 7:7:7:1 MtBE:$CH_2Cl_2$:Hexane:MeOH. The recovered material is then applied to a set of two 500 µ preparative TLC plates and developed one time with 95:5:0.5 $CH_2Cl_2$:MeOH $NH_4OH_{(aq)}$ giving 36 mg (31%) of a white solid: MS m/z=462 [M+H]$^+$; $^1$H NMR (300 MHz, DMSO-d$_6$) δ 9.81 (br s, 1H), 8.36 (s, 1H), 8.11 (s, 1H), 7.38 (m, 2H), 7.09 (s, 2H), 4.04 (m, 2H), 3.65 (s, 6H), 3.61 (s, 3H), 2.83 (m, 2H), 1.90 (m, 2H); HPLC Rt=14.40 min.

Compound 535: 2-Chloro-4-(3',4',-dimethoxyanilino)-1,3,5-triazine (130 mg, 0.49 mmol) is reacted with 7-(trifluoromethyl)-1,2,3,4-tetrahydroquinoline (98 mg, 0.49 mmol) in the manner described for compound 207, except for using isopropanol (4 mL) as the solvent, then kept at 100° C.0.18 hours. A white precipitate forms when the reaction is cooled to room temperature, and is removed by vacuum filtration. The filtrate is then concentrated under reduced pressure, and eluted through a 17×2.5 cm column of silica gel with a 10%, 20%, 40%, 60%, and 80% EtOAc:Hexane step gradient, giving a white solid that is then triturated with methanol giving 58 mg (27%) of a white solid: MS m/z 432 [M+H]$^+$; $^1$H NMR (300 MHz, DMSO-d$_6$) δ 9.73 (br s, 1H), 8.34 (s, 1H), 8.10 (s, 1H), 7.45–7.20 (m, 3H), 7.14 (br s, 1H), 6.81 (br s, 1H), 4.02 (t, J=6.2 Hz, 2H), 3.70 (s, 3H), 3.64 (s, 3H), 2.84 (t, J=6.4 Hz, 2H), 1.94 (m, 2H); HPLC Rt=14.27 min.

Compound 567: 2-Chloro-4-(6'-methyl-1',2',3',4'-tetrahydroquinolino)-1,3,5-triazine (108 mg, 0.41 mmol) is reacted with 4-aminoveratrole (63 mg, 0.41 mmol) in the manner described for compound 207, except for using isopropanol (4 mL) as the solvent, then kept at 100° C. 18 hours. A white precipitate forms when the reaction is cooled to room temperature, and is recovered by vacuum filtration, washed with cold isopropanol, and dried under high vacuum giving 147 mg (94%) of a white solid: MS m/z=378 [M+H]$^+$; $^1$H NMR (300 MHz, DMSO-d$_6$) δ 9.62 (br s, 1H), 8.29 (s, 1H), 7.62 (d, J=8.1 Hz, 1H), 7.43 (s, 1H), 7.14 (m, 1H), 6.96 (m, 3H), 6.86 (d, J=8.7 Hz, 1H), 3.98 (t, J=6.1 Hz, 2H), 3.73 (s, 3H), 3.65 (s, 3H), 2.72 (t, J=6.7 Hz, 2H), 2.28 (s, 3H), 1.91 (m, 2H); HPLC Rt=12.19 min Compound 582: 2-Chloro-4-(7'-(trifluoromethyl)-1',2',3',4'-tetrahydroquinolino)-1,3,5-triazine (168 mg, 0.53 mmol) is reacted with 3-methylaniline (57 mg, 0.53 mmol) in the manner described for compound 207, except for using isopropanol (5 mL) as the solvent, then kept at 100° C. 18 hours. The reaction is then concentrated under reduced pressure, and applied to two 1000µ preparative TLC plates and developed one time with 7:7:7:1 MtBE:$CH_2Cl_2$:Hexane:MeOH. The recovered material is then applied to a second set of two 1000µ preparative TLC plates and developed one time with 30% EtOAc:Hexanes giving 53 mg (25%) of a clear glassy solid: MS m/z=386 [M+H]$^+$; $^1$H NMR (300 MHz, DMSO-d$_6$) δ 9.82 (br s, 1H), 8.38 (s, 1H), 8.09 (s, 1H), 7.5–7.3 (m, 4H), 7.09 (t, J=7.1 Hz, 1H), 6.80 (d, J=7.1 Hz, 1H), 4.01 (t, J=6.2 Hz, 2H), 2.84 (t, J=6.2 Hz, 2H), 2.20 (s, 3H), 1.95 (m, 2H); HPLC Rt=16.02 min.

Compound 609: 2-Chloro-4-(3',4',5'-trimethoxyanilino)-1,3,5-triazine (56 mg, 0.19 mmol) is reacted with 1,2,3,4-tetrahydroquinoline (25 mg, 0.19 mmol) in the manner described for compound 207, then kept at 100° C. 15 hours. A white precipitate forms when the reaction is cooled to room temperature, and is recovered by vacuum filtration, washed with cold ethanol, and dried under high vacuum giving 49 mg (65%) of a white solid: MS m/z=394 [M+H]$^+$; $^1$H NMR (300 MHz, DMSO-d$_6$) δ 9.66 (br s, 1H), 8.31 (s, 1H), 7.72 (d, J=8.0 Hz, 1H), 7.18–7.00 (m, 5H), 4.00 (t, J=6.2 Hz, 2H), 3.67 (s, 6H), 3.61 (s, 3H), 2.75 (t, J=6.7 Hz, 2H), 1.92 (m, 2H); HPLC Rt=12.50 min.

Compound 610: 2-Chloro-4-(3',4',-dimethoxyanilino)-1,3,5-triazine (73 mg, 0.25 mmol) is reacted with 2-methylindoline (33 mg, 0.25 mmol) in the manner described for compound 207, except for using isopropanol (4 mL) as the solvent, then kept at 100° C. 3 days. The reaction is cooled to room temperature, and then concentrated under reduced pressure. The recovered material is then eluted through a 17×2.5 cm column of silica gel with a 20%, 40%, 60%, and 80% EtOAc:Hexane step gradient. The material recovered from the column is then applied to two 1000µ preparative TLC plates and developed one time with 95:5:0.5 $CH_2Cl_2$:MeOH:$NH_4OH_{(aq)}$ giving 42 mg (42%) of a white solid: MS m/z=394 [M+H]$^+$; $^1$H NMR (300 MHz, DMSO-d$_6$) δ 9.69 (br s, 1H), 8.42 (s, 1H), 8.31 (br s, 1H), 7.27 (d, J=7.0 Hz, 1H), 7.15 (m, 3H), 7.00 (t, J=7.4 Hz, 1H), 4.96 (br s, 1H), 3.76 (s, 6H), 3.64 (s, 3H), 3.39 (m, 1H), 2.70 (d, J=16 Hz, 1H), 1.27 (d, J=6.0 Hz, 3H); HPLC Rt=12.77 min.

Compound 621: 2-Chloro-4-(3',4',-dimethoxyanilino)-1,3,5-triazine (97 mg, 0.36 mmol) is reacted with 3-chloro-N-methylaniline (51 mg, 0.36 mmol) in the manner described for compound 207, except for using isopropanol (4 mL) as the solvent, then kept at 100° C. 18 hours. The reaction is cooled to room temperature, and then concentrated under reduced pressure. The recovered material is then applied to two 1000µ preparative TLC plates and developed one time with 95:5:0.5 $CH_2Cl_2$:MeOH:$NH_4OH_{(aq)}$. The material recovered from these plates is then applied to a second set of two 1000µ preparative TLC plates and developed one time with 7:7:7:1 MtBE:$CH_2Cl_2$:Hexane:MeOH giving 80 mg (59%) of a white solid: MS m/z=372 [M+H]$^+$; $^1$H NMR (300 MHz, DMSO-d$_6$) δ 9.62 (br s, 1H), 8.23 (s, 1H), 7.55–7.30 (m, 5H), 7.10 (br s, 1H), 6.78 (br s, 1H), 3.70 (s, 3H), 3.62 (s, 3H), 3.46 (s, 3H); HPLC Rt=11.49 min.

Compound 631: 2-Chloro-4-(3',4',5'-trimethoxyanilino)-1,3,5-triazine (120 mg, 0.40 mmol) is reacted with 6-methoxy-1,2,3,4-tetrahydroquinoline (65 mg, 0.40 mmol) in the manner described for compound 207, except for using isopropanol (6 mL) as the solvent, then kept at 100° C. 3 days. The reaction is cooled to room temperature, and then concentrated under reduced pressure. The recovered material is then applied to two 1000 μ preparative TLC plates and developed one time with 95:5:0.5 $CH_2Cl_2$:MeOH:$NH_4OH_{(aq)}$. The material recovered from these plates is then applied to two 500 μ preparative TLC plates and developed one time with 7:7:7:1 MtBE:$CH_2Cl_2$:Hexane:MeOH giving 15 mg (8%) of a white solid: MS m/z=424 [M+H]$^+$; $^1$H NMR (300 MHz, DMSO-$d_6$) δ 9.65 (br s, 1H), 8.27 (s, 1H), 7.61 (d, J=8.7 Hz, 1H), 7.10 (s, 2H), 6.74 (m, 2H), 3.98 (t, J=6.2 Hz, 2H), 3.74 (s, 6H), 3.67 (s, 3H), 3.61 (s, 3H), 2.73 (t, J=6.4 Hz, 2H), 1.91 (m, 2H); HPLC Rt=12.16 min.

Compound 640: 2-Chloro-4-(3'-chloro-N-methylanilino)-1,3,5-triazine (175 mg, 0.68 mmol) is reacted with 3,4-diethoxyaniline hydrochloride (149 mg, 0.68 mmol) in the manner described for compound 207, except for using isopropanol (4 mL) as the solvent, two equivalents of N,N-diisopropylethylamine, and then heating at 100° C. 3 days. The reaction is cooled to room temperature, and then concentrated under reduced pressure. The recovered material is then applied to two 1000 μ preparative TLC plates and developed one time with 95:5:0.5 $CH_2Cl_2$:MeOH $NH_4OH_{(aq)}$. The material recovered from these plates is then applied to a second set of two 1000μ preparative TLC plates and developed one time with 7:7:7:1 MtBE:$CH_2Cl_2$:Hexane:MeOH. The material isolated from these plates is then applied to a third set of 1000 μ preparative TLC plates and developed one more time with 95:5:0.5 $CH_2Cl_2$:MEOH:$NH_4OH_{(aq)}$. The material from this set of plates is then triturated with diethyl ether giving 25 mg (9%) of a clear, glassy solid: MS m/z=432 [M+H]$^+$; $^1$H NMR (300 MHz, DMSO-$d_6$) δ 9.60 (br s, 1H), 8.23 (s, 1H), 7.55–7.30 (m, 5H), 7.07 (br s, 1H), 6.78 (br s, 1H), 3.94 (q, J=7.0 Hz, 2H), 3.80 (br s, 2H), 3.46 (s, 3H), 1.28 (m, 6H); HPLC Rt=14.27 min.

The following compounds are prepared according to Examples B and C according to the procedures shown above:

| Cmpd # | HPLC Rt | MS | Cmpd # | HPLC Rt | MS |
|---|---|---|---|---|---|
| 181 | 9.02 | 332 | 615 | ND | 445 |
| 184 | 12.72 | 380 | 616 | 11.97 | 402 |
| 187 | 14.91 | 425 | 622 | 16.66 | ND |
| 191 | 13.81 | 425 | 626 | 12.09 | 374 |
| 214 | 9.39 | 425 | 634 | 13.24 | 432 |
| 314 | 13.01 | 400 | 635 | 11.26 | 400 |
| 536 | 11.30 | 382 | 637 | 9.12 | 398 |
| 537 | 12.14 | 396 | 639 | 14.47 | 428 |
| 538 | 12.20 | 396 | 641 | 10.13 | 372 |
| 603 | 12.15 | 402 | 643 | 14.71 | 428 |
| 607 | 12.05 | 418 | 644 | 15.86 | 384 |
| 612 | 12.43 | 408 | 645 | 14.44 | 428 |

EXAMPLE 48

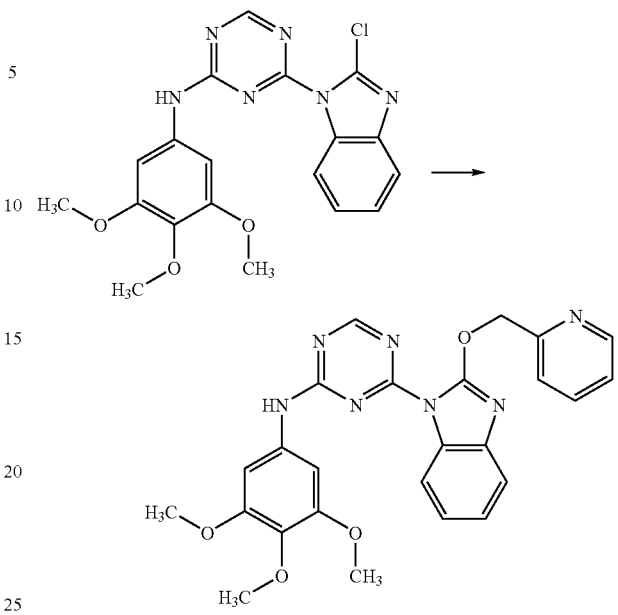

Compound 690

A mixture of 2-pyridylcarbinol (79 mg, 0.72 mmol) in DMF under a nitrogen atmosphere is added sodium hydride (60% dispersion, 30 mg, 0.75 mmol). The mixture is allowed to stir for 0.75 hours followed by addition of the compound of Compound 378. The reaction is quenched by the addition of water and the organics taken up in ethyl acetate (100 mL) dried over anh. Magnesium sulfate and concentrated under reduce pressure. The crude product is purified via medium pressure liquid chromatography using methylene chloride followed by 1:99 methanol/methylenechloride as the solvent system. HPLC(Method A) Rt=6.36 min., MS m/z=486.

EXAMPLE 52

The inhibitor compounds described herein are screened in the following manner. Kinases suitable for use in the following protocol to determine kinase activity of the compounds described herein include, -but are not limited to: Lck, Lyn, Src, Fyn, Syk, Zap-70, Itk, Tec, Btk, EGFR, ErbB2, Kdr, Flt-1, Flt-3, Tek, c-Met, InsR, and AKT.

Kinases are expressed as either kinase domains or full length constructs fused to glutathione S-transferase (GST) or polyHistidine tagged fusion proteins in either E. coli or Baculovirus-High Five expression systems. They are purified to near homogeneity by affinity chromatography essentially as previously described (Lehr et al., 1996; Gish et al., 1995). In some instances, kinases are co-expressed or mixed with purified or partially purified regulatory polypeptides prior to measurement of activity.

Kinase activity and inhibition are measured essentially by established protocols (Braunwalder et al., 1996). Briefly, The transfer of $^{33}PO_4$ from ATP to the synthetic substrates poly(Glu, Tyr) 4:1 or poly(Arg, Ser) 3:1 attached to the bioactive surface of microtiter plates serves as the basis to evaluate enzyme activity. After an incubation period, the amount of phosphate transferred is measured by first washing the plate with 0.5% phosphoric acid, adding liquid scintillant, and then counting in a liquid scintillation detector. The $IC_{50}$ is determined by the concentration of compound that causes a 50% reduction in the amount of $^{133}P$ incorporated onto the substrate bound to the plate.

Other similar methods whereby phosphate is transferred to peptide or polypeptide substrate containing tyrosine, serine, threonine, or histidine, either alone, in combination, or in combination with other amino acids, in solution or immobilized (i.e., solid phase) are also useful. For example, transfer of phosphate to a peptide or polypeptide can also be detected using scintillation proximity (Wu et al., 2000), ELISA (Cleaveland et al., 1990), Fluorescence Polarization (Seethala and Menzel, 1998), and homogeneous time-resolved fluorescence (HTRF, Kolb et al., 1998). Alternatively, kinase activity can be measured using antibody-based methods whereby an antibody or polypeptide is used as a reagent to detect phosphorylated target polypeptide. The compounds of the invention described herein are potent and selective kinase inhibitors as demonstrated by representative compounds described herein that inhibit kinases with $IC_{50}$ values at between about 10 nM and about 5 µM or greater.

References:

Braunwalder A F, Yarwood D R, Hall T, Missbach M, Lipson K E, Sills M A. (1996). A solid-phase assay for the determination of protein tyrosine kinase activity of c-src using scintillating microtitration plates. *Anal. Biochem.* 234(1):23–26.

Cleaveland J S, Kiener P A, Hammond D J, Schacter B Z. (1990). A microtiter-based assay for the detection of protein tyrosine kinase activity. *Anal Biochem.* 190(2):249–53.

Gish G, McGlone M L, Pawson T, Adams J A. (1995). Bacterial expression, purification and preliminary kinetic description of the kinase domain of v-fps. *Protein Eng.* 8(6):609–614.

Kolb, A. J., Kaplita, P. V., Hayes, D. J., Park, Y.-W., Pernell, C., Major, J. S., Mathis, G. (1998). Tyrosine kinase assays adapted to homogeneous time-resolved fluorescence. *Drug Discov. Today*. 3:333–342.

Lehr R V, Ma Y G, Kratz D, Brake P G, Wang S, Faltynek C R, Wang X M, Stevis P E (1996). Production, purification and characterization of non-myristylated human T-cell protein tyrosine kinase in a baculovirus expression system. *Gene* 169(2):27527–9.

Seethala R, Menzel R. (1998). A fluorescence polarization competition immunoassay for tyrosine kinases. *Anal Biochem.* 255(2):257–62.

Wu J J, Yarwood D R, Sills M A, Chaudhuri B, Muller L, Zurini M, Sills M A. (2000). Measurement of cdk4 kinase activity using an affinity peptide-tagging technology. *Comb Chem High Throughput Screen*. 3(1):27–36.

EXAMPLE 53

The cellular activities of the inhibitor compounds described herein may be assessed in a number of assays known to those skilled in the art, some of which are exemplified as described below. Typical sources for cells include, but are not limited to, human bone marrow or peripheral blood lymphocytes, fibroblasts, tumors, immortalized cell lines, in-vitro transformed cell lines, rodent spleen cells, or their equivalents. Tumor cells and transformed cell lines that have been reported as cytokine- and growth factor-dependent cells are available from standard cell banks such as The American Type Culture Collection (Bethesda, Md.). Cells genetically manipulated to express a particular kinase or kinases are also suitable for use in assaying cellular activity and can be made using standard molecular biology methods. These cells are grown in various standard tissue culture media available from suppliers such as GIBCO/BRL (Grand Island, N.Y.) supplemented with fetal bovine serum. Cellular activity may also be measured using bacterial, yeast, or virally infected mammalian cells. Standard inhibitors (or reference compounds) of cellular activities measured in cellular assays, include mycophenolic acid (SIGMA, St. Louis, Mo.), staurosporine (Calbiochem, San Diego, Calif.), wortmannin (Calbiochem), cyclosporine, FK-506, and steroids (e.g., corticosteroids).

The compound(s) are tested for activity in cellular assays of T or B cell activation. For example, the receptor-induced production of cytokines and/or cell proliferation is a useful measure. This assay is performed similarly to techniques described in the literature (1,2), and involves antibody-, antigen-, mitogen-, or antigen presenting cell-mediated crosslinking of the T cell or B cell receptor with or without engagement of co-stimulatory receptors.

The compound(s) are tested for activity in cellular assays of allergic mediator release. For example, the receptor-induced degranulation in mast cells or basophils leading to histamine release and the production of cytokines is a useful measure. This assay is performed similarly to techniques described in the literature (3), and involves signalling via specific cell surface receptors for I, E, or other immunoglobulin (e.g., IgG) following crosslinking of antigen-specific IgE on cells or immunune complex binding leading to degranulation and or cytokine production.

The compound(s) are tested for activity in cellular assays of growth factor effects. For example, growth factor receptor-induced signaling in a cell leading to intracellular signaling events such as kinase autophosphorylation, phosphorylation of relevant kinase substrates, phosphorylation of MAP kinases, induction of gene expression, or protein expression. Also, for example, growth factor-induced functional events in cells such as DNA synthesis, proliferation, migration, or apoptosis. These assays are performed similarly to techniques described in the literature (4–7), and involve addition of growth factor to responsive cells followed by monitoring of signaling or functional events.

The compound(s) are tested for activity in cellular assays of lymphokine, chemokine, cytokine, growth factor, or hormone, activation. For example, cytokine-induced intracellular signaling events and/or DNA synthesis and/or cell proliferation and/or cytokine or chemokine production are a useful measure. These assays are performed similarly to techniques described in the literature (8), and involves addition of cytokine to responsive cells followed by monitoring intracellular signaling events and/or cell proliferation and/or cytokine production.

References:

1. Shuji, K., et al. Activation of p21-CDC42/Rac-activated kinases by CD28 signaling: p21-activated kinase (PAK) and MEK kinase 1 (MEKK1) may mediate the interplay between CD3 and CD28 signals. *J. Immunol.* 160: 4182–4189 (1998).
2. Satterthwaite, A. B., et al., Independent and opposing roles for Btk and Lyn in B cell and myeloid signaling pathways. *J. Exp. Med.* 188: 833–844 (1998).
3. Stephan, V., et al. FcεFR1-induced protein tyrosine phosphorylation of pp72 in rat basophilic leukemia cells (RBL-2H3). *J. Biol. Chem.* 267 (8): 5434–5441 (1992).
4. Olayioye, M. A., et al. ErbB-1 and ErbB-2 acquire distinct signaling properties dependent upon their dimerization partner. *Molecular and Cellular Biology*. 18(9): 5042–5051 (1998).
5. Buchdunger, E., et al. Inhibition of the Ab1 protein-tyrosine kinase in vitro and in vivo by a 2-phenylaminopyrimidine derivative. *Cancer Res.* 56;101–104 (1996).

6. Yoshida, A. et al., Differential endothelial migration and proliferation to basic fibroblast growth factor and vascular endothelial growth factor. *Growth Factors*. 13:57–64 (1996).
7. Brunet, A., et al., Akt promotes cell survival by phosphorylating and inhibiting a forkhead transcription factor. *Cell*. 96:857–868 (1999).
8. Liu, K. D., et al. Janus kinases in interleukin-2-mediated signaling: JAK1 and JAK3 are differentially regulated by tyrosine phosphorylation. *Current Biology*. 7 (11): 817–826 (1997).

Representative compounds tested under the following example protocols exhibit cellular activities consistent with their observed enzyme inhibition activities.

EXAMPLE 54

Vascular endothelial growth factor (VEGF)-induced Kdr auto-phosphorylation.

Human umbilical vein endothelial cells (HUVEC) are plated out in flat-well plates in complete media and allowed to adhere overnight. The cells are then starved in medium containing 0.1% fetal calf serum (FCS), pre-incubated with or without dilutions of compound, then activated for 15 minutes with 50 ng/ml VEGF. The cells are lysed and Kdr is immunoprecipitated using an anti-Kdr antibody. The immunoprecipitated Kdr protein is separated by sodium dodecyl sulfate-polyacrylamide gel electrophoresis (SDS-PAGE) and the level of phosphotyrosine is determined by western blotting with an anti-phosphotyrosine-specific antibody. $IC_{50}$'s are determined by comparing the level of phosphotyrosine found in the presence of compound compared to controls.

EXAMPLE 55

Vascular endothelial growth factor (VEGF)-induced extracellular signal regulated kinase (Erk) 1/2-phosphorylation.

Human umbilical vein endothelial cells (HUVEC) are plated out in flat-well plates in complete media and allowed to adhere overnight. The cells are then starved in medium containing 0.1% fetal calf serum (FCS), pre-incubated with or without dilutions of compound, then activated for 15 minutes with 50 ng/ml VEGF. The cells are lysed and proteins are separated by SDS-PAGE. The level of phosphotyrosine on Erk1/2 is determined by western blotting with an anti-phospho-Erk1/2-specific antibody. $IC_{50}$'s are determined by comparing the level of phosphotyrosine found in the presence of compound compared to controls.

EXAMPLE 56

Vascular endothelial growth factor (VEGF)-induced proliferation. Human umbilical vein endothelial cells (HUVEC) are plated out in flat-well plates in complete media and allowed to adhere overnight. The cells are then starved in medium containing 0.1% fetal calf serum (FCS), pre-incubated with or without dilutions of compound, then activated for 72 hours with 50 ng/ml VEGF. Proliferation is determined by the level of $^{13}$H-thymidine incorporation into DNA. $IC_{50}$'s are determined by comparing the level of thymidine incorporation found in the presence of compound compared to controls.

EXAMPLE 57

Growth factor-induced DNA synthesis. A rat fibroblast cell line is plated out in flat-well plates in complete medium and allowed to adhere overnight. The cells are then starved in medium containing 0.1% bovine serum albumin (BSA), pre-incubated with or without dilutions of compound, then activated overnight with 50 ng/ml platelet derived growth factor (PDGF), 1 ng/ml epidermal growth factor (EGF), 3 ng/ml fibroblast growth factor (FGF), or 10 ng/ml insulin-like growth factor-1 (IGF-1). Proliferation is determined by the level of $^{13}$H-thymidine incorporation into DNA. $IC_{50}$'s are determined by comparing the level of thymidine incorporation found in the presence of compound compared to controls.

EXAMPLE 58

Platelet-derived growth factor (PDGF)-induced PDGF receptor (PDGF-R) auto-phosphorylation. A mouse fibroblast cell line is plated out in flat-well plates in complete medium and allowed to adhere overnight. The cells are then starved in medium containing 0.1% bovine serum albumin (BSA), pre-incubated with or without dilutions of compound, then activated with 50 ng/ml platelet derived growth factor (PDGF) for 5 minutes. The cells are lysed and proteins are separated by SDS-PAGE. The level of phosphotyrosine on PDGF-R is determined by western blotting with an anti-phospho-tyrosine-specific antibody. $IC_{50}$'s are determined by comparing the level of phosphotyrosine found in the presence of compound compared to controls.

EXAMPLE 59

Epidermal growth factor (EGF)-induced EGF receptor (EGF-R) auto-pbosphorylation. Human epidermoid carcinoma cells (A43 1) are plated out in flat-well plates in complete media and allowed to adhere overnight. The cells are then starved in medium containing 0.5% fetal calf serum (FCS), pre-incubated with or without dilutions of compound, then activated for 3 minutes with 50 ng/ml EGF. The cells are lysed and proteins are separated by SDS-PAGE. The level of phosphotyrosine on EGF-R is determined by western blotting with an anti-phospho-EGF-R-specific antibody. $IC_{50}$'s are determined by comparing the level of phosphotyrosine found in the presence of compound compared to controls.

EXAMPLE 60

Heregulin-β1 (NRG)-induced ErbB2 iuto-phosphorylation. Human breast carcinoma cells (ZR-75) are plated out in flat-well plates in complete media and allowed to adhere overnight. The cells are then starved in medium containing 0.5% fetal calf serum (FCS), pre-incubated with or without dilutions of compound, then activated for 5 minutes with 50 ng/ml NRG. The cells are lysed and proteins are separated by SDS-PAGE. The level of phosphotyrosine on ErbB2 is determined by western blotting with an anti-phospho-ErbB2-specific antibody. $IC_{50}$'s are determined by comparing the level of phosphotyrosine found in the presence of compound compared to controls.

EXAMPLE 61

Hepatocyte growth factor (HGF) receptor (Met) auto-pbosphorylation. Human gastric carcinoma cells (MKN-45), which overexpress and constitutively auto-phosphorylate Met, are plated out in flat-well plates in complete media and allowed to adhere overnight. The cells are then incubated with or without dilutions of compound for 1 hour. The cells are lysed and proteins are separated by SDS-PAGE. The level of phosphotyrosine on Met is determined by western blotting with an anti-phospho-tyrosine-specific antibody. $IC_{50}$'s are determined by comparing the level of phosphotyrosine found in the presence of compound compared to controls.

EXAMPLE 62

Anti-CD3/CD28-induced IL-2 secretion and proliferation. Purified T cells are obtained from human peripheral blood lymphocytes. T cells are pre-incubated incubated with or without dilutions of compound for 30 minutes. The T cells and compounds are then transferred to a plate containing captured anti-CD3-specific antibody. Anti-CD28-specific antibody is then added and the cells are incubated for 20 hours. T cell supernatants are measured for the presence of interleukin-2 by commercially available ELISA. $IC_{50}$'s are determined by comparing the level of IL-2 secretion found in the presence of compound compared to controls. The cells are then pulsed with $^3$H-thymidine and incubated for an additional 24 hours to determine cellular proliferation. $IC_{50}$'s are determined by comparing the level of thymidine incorporation found in the presence of compound compared to controls.

EXAMPLE 63

Anti-CD3-induced T cell receptor ζ-chain (TCRζ) phosphorylation. The human T cell line, Jurkat, is pre-incubated with or without compounds, then incubated with anti-CD3-specific antibody at 4° C. Cells are washed, then incubated at 4° C. with a secondary anti-immunoglobulin antibody for crosslinking. Cells are activated by transfer to a 37° C. water bath for 1 minute. The cells are lysed and proteins are separated by SDS-PAGE. The level of phosphotyrosine on TCRζ is determined by western blotting with an anti-phospho-tyrosine-specific antibody. $IC_{50}$'s are determined by comparing the level of phosphotyrosine found in the presence of compound compared to controls.

TABLE 2

| Compound Number | EGFR-1 | IGFR-1 | AKT3-1 | Met-1 |
| --- | --- | --- | --- | --- |
| 1014 | E | ND | ND | E |
| 1015 | E | ND | ND | E |
| 1016 | E | ND | ND | E |
| 1017 | E | ND | ND | E |
| 1018 | E | ND | ND | E |
| 1019 | E | ND | ND | E |
| 271 | E | ND | ND | E |
| 272 | E | ND | ND | E |
| 1020 | E | ND | ND | E |
| 1021 | E | ND | ND | E |
| 1022 | E | ND | ND | E |
| 273 | E | ND | ND | E |
| 1023 | E | ND | ND | E |
| 1024 | E | ND | ND | E |
| 1025 | D | ND | E | E |
| 1027 | E | ND | ND | E |
| 970 | E | E | E | E |
| 36 | D | E | E | E |
| 182 | E | ND | ND | D |
| 275 | E | ND | ND | D |
| 274 | E | ND | ND | E |
| 276 | E | ND | ND | E |
| 277 | E | ND | ND | E |
| 11 | E | E | E | E |
| 12 | E | E | E | E |
| 13 | E | E | E | E |
| 14 | E | E | E | E |
| 15 | E | E | E | E |
| 17 | E | E | E | E |
| 16 | E | E | E | E |
| 18 | E | E | E | E |
| 19 | E | C | E | E |
| 20 | E | E | E | E |
| 21 | E | B | E | D |
| 8 | E | E | E | E |
| 971 | E | E | E | E |
| 924 | E | E | E | E |
| 925 | E | E | E | E |
| 61 | A | A | E | E |
| 926 | B | E | E | D |
| 29 | A | C | E | D |
| 27 | C | A | E | D |
| 28 | B | B | E | E |
| 852 | E | A | E | C |
| 151 | E | E | E | E |
| 1028 | E | E | E | E |
| 153 | E | E | E | E |
| 63 | E | E | E | E |
| 62 | A | B | E | D |
| 40 | E | E | E | E |
| 39 | E | E | E | E |
| 65 | A | B | E | E |
| 64 | A | A | E | C |
| 67 | C | D | E | E |
| 66 | E | A | E | B |
| 69 | E | E | E | E |
| 68 | A | A | E | D |
| 927 | C | E | E | E |
| 70 | B | B | E | E |
| 928 | A | A | D | C |
| 232 | C | E | E | E |
| 1118 | B | E | E | E |
| 77 | B | B | E | E |
| 73 | E | E | E | E |
| 76 | D | B | E | E |
| 72 | B | A | E | D |
| 75 | A | A | D | D |
| 74 | A | A | E | D |
| 33 | E | A | E | E |
| 78 | A | B | E | E |
| 79 | A | A | E | C |
| 80 | E | E | E | E |
| 81 | E | E | E | E |
| 82 | B | B | E | E |
| 83 | A | B | E | E |
| 289 | E | A | E | B |
| 86 | E | A | E | E |
| 85 | B | B | E | E |
| 88 | D | B | E | B |
| 87 | B | A | E | E |
| 90 | B | B | E | E |
| 89 | B | B | E | E |
| 91 | B | B | E | E |
| 92 | B | B | D | B |
| 93 | E | E | E | E |
| 94 | A | C | E | E |
| 95 | E | B | E | E |
| 96 | B | A | E | E |
| 97 | E | E | E | E |
| 98 | A | E | E | E |
| 99 | B | A | E | D |
| 100 | D | C | C | E |
| 101 | E | E | E | E |
| 102 | B | A | E | A |
| 154 | E | B | E | E |
| 155 | E | E | E | E |
| 207 | E | E | E | E |
| 251 | B | E | B | B |
| 22 | E | E | E | E |
| 278 | E | ND | ND | E |
| 279 | E | ND | ND | E |
| 280 | E | ND | ND | E |
| 281 | E | ND | ND | E |
| 282 | E | ND | ND | C |
| 283 | E | ND | ND | E |
| 284 | E | ND | ND | E |
| 156 | A | E | E | D |
| 157 | B | E | D | D |
| 158 | B | C | B | B |
| 159 | A | D | B | B |
| 160 | B | E | D | D |
| 161 | E | E | C | E |
| 162 | E | E | D | E |
| 209 | E | E | D | E |
| 183 | E | E | E | E |
| 253 | C | E | E | E |
| 221 | E | A | E | E |
| 252 | B | A | E | E |
| 256 | E | E | E | E |

TABLE 2-continued

| Compound Number | EGFR-1 | IGFR-1 | AKT3-1 | Met-1 |
|---|---|---|---|---|
| 103 | E | C | B | E |
| 104 | B | C | E | E |
| 105 | B | E | E | B |
| 106 | B | C | E | B |
| 220 | E | E | E | E |
| 107 | A | B | B | C |
| 108 | A | C | E | E |
| 109 | A | E | E | E |
| 110 | A | B | E | D |
| 929 | A | D | E | A |
| 111 | A | A | E | E |
| 114 | E | C | E | E |
| 113 | B | A | E | E |
| 116 | A | B | E | E |
| 115 | A | B | B | E |
| 118 | A | B | E | E |
| 41 | A | B | E | C |
| 117 | C | E | C | D |
| 119 | A | C | E | E |
| 163 | E | E | E | E |
| 164 | E | E | E | E |
| 165 | E | E | E | E |
| 1029 | E | E | E | E |
| 285 | E | A | E | E |
| 299 | C | C | B | B |
| 286 | C | A | C | B |
| 214 | E | E | E | C |
| 213 | E | E | E | E |
| 181 | E | E | E | E |
| 184 | E | E | E | D |
| 255 | E | E | E | E |
| 185 | E | B | E | D |
| 191 | E | E | E | E |
| 211 | E | E | E | E |
| 254 | E | E | E | E |
| 42 | E | E | E | E |
| 922 | B | B | B | C |
| 186 | D | B | E | B |
| 208 | E | E | E | D |
| 121 | B | E | E | D |
| 123 | A | B | E | E |
| 125 | B | B | E | E |
| 127 | A | B | E | E |
| 120 | A | A | C | C |
| 170 | B | E | B | C |
| 171 | A | E | B | E |
| 287 | D | A | E | E |
| 222 | E | E | E | E |
| 51 | A | E | E | B |
| 212 | E | E | E | E |
| 250 | A | A | E | E |
| 200 | E | E | E | D |
| 218 | E | E | E | E |
| 187 | E | E | E | E |
| 930 | A | B | E | D |
| 931 | A | B | E | E |
| 932 | B | B | E | C |
| 933 | A | B | E | E |
| 934 | B | A | E | E |
| 935 | A | B | E | E |
| 1030 | E | A | E | A |
| 174 | C | E | E | E |
| 175 | E | B | E | B |
| 972 | A | C | E | B |
| 609 | A | E | E | B |
| 936 | A | A | E | E |
| 937 | A | A | E | C |
| 938 | E | C | E | E |
| 135 | A | A | E | B |
| 226 | E | E | E | E |
| 973 | B | E | E | E |
| 291 | B | E | E | E |
| 292/293 | E | A | E | A |
| 294/295 | E | A | E | B |
| 296/297 | E | A | B | A |
| 178 | A | B | D | C |
| 302 | E | A | E | E |
| 300 | A | A | E | C |
| 303 | B | B | E | E |
| 304 | A | A | E | B |
| 305 | B | C | E | D |
| 196 | D | B | E | E |
| 298 | B | C | E | A |
| 306 | A | A | E | C |
| 974 | A | E | E | E |
| 56 | A | D | E | E |
| 310 | B | B | E | E |
| 309 | C | E | E | E |
| 311 | E | E | E | B |
| 312 | E | E | E | E |
| 313 | B | A | E | A |
| 238 | E | E | E | E |
| 239 | D | E | E | E |
| 198 | E | E | E | E |
| 237 | D | A | E | C |
| 240 | E | E | E | E |
| 314 | A | E | E | B |
| 315 | E | E | E | D |
| 316 | B | A | E | E |
| 317 | E | B | E | B |
| 318 | A | A | D | A |
| 308 | A | A | D | A |
| 320 | B | E | E | C |
| 319 | B | E | E | E |
| 321 | A | C | E | E |
| 322 | E | E | E | E |
| 323 | E | E | E | D |
| 324 | E | A | E | E |
| 328 | B | A | C | A |
| 325 | D | E | E | E |
| 327 | E | C | E | E |
| 326 | E | E | E | E |
| 338 | B | A | E | B |
| 337 | B | A | E | A |
| 336 | E | E | E | E |
| 335 | A | E | E | E |
| 334 | E | A | C | E |
| 219 | E | E | E | E |
| 333 | E | E | E | E |
| 332 | E | C | E | C |
| 331 | E | E | E | E |
| 330 | E | D | E | E |
| 339 | E | E | E | E |
| 340 | C | A | C | A |
| 342 | A | B | E | B |
| 341 | C | B | E | B |
| 344 | E | B | E | B |
| 343 | E | B | E | D |
| 345 | E | B | E | B |
| 346 | E | E | E | E |
| 217 | E | E | E | D |
| 1072 | E | E | E | D |
| 1073 | E | E | E | E |
| 349 | E | E | D | D |
| 350 | E | E | E | E |
| 352 | E | E | E | E |
| 205 | E | E | E | E |
| 353 | E | E | E | E |
| 354 | E | E | E | E |
| 356 | E | E | E | E |
| 355 | E | E | E | E |
| 358 | E | E | E | E |
| 357 | E | E | E | E |
| 359 | E | E | E | E |
| 360 | E | E | E | E |
| 362 | E | E | E | E |
| 361 | E | E | E | E |
| 363 | E | E | E | E |
| 364 | B | B | E | B |
| 366 | E | B | E | E |
| 365 | B | A | C | A |
| 367 | C | A | E | A |
| 368 | E | E | E | E |
| 369 | E | E | E | E |

TABLE 2-continued

| Compound Number | EGFR-1 | IGFR-1 | AKT3-1 | Met-1 |
|---|---|---|---|---|
| 180 | E | E | E | E |
| 372 | E | E | E | E |
| 373 | C | E | E | E |
| 371 | C | E | E | E |
| 374 | A | E | E | B |
| 375 | E | E | E | E |
| 376 | D | B | E | C |
| 378 | E | B | E | B |
| 377 | E | C | E | D |
| 379 | E | E | E | E |
| 380 | E | C | E | E |
| 382 | E | B | E | E |
| 381 | E | E | E | D |
| 383 | E | E | E | E |
| 384 | D | E | E | D |
| 386 | E | E | E | E |
| 385 | E | E | E | E |
| 387 | E | E | E | D |
| 388 | E | E | E | E |
| 389 | E | A | E | E |
| 390 | D | E | B | D |
| 391 | E | E | E | E |
| 392 | E | E | E | E |
| 393 | D | E | E | E |
| 394 | D | B | E | E |
| 396 | C | A | C | B |
| 395 | E | B | D | B |
| 397 | E | ND | E | E |
| 398 | E | ND | E | E |
| 399 | E | ND | D | E |
| 400 | E | ND | E | E |
| 402 | E | ND | E | E |
| 401 | B | ND | E | B |
| 403 | E | ND | E | E |
| 404 | D | ND | D | E |
| 406 | E | ND | E | E |
| 405 | E | ND | E | E |
| 407 | E | ND | E | E |
| 393 | E | ND | E | E |
| 409 | E | ND | E | E |
| 45 | E | ND | E | E |
| 412 | E | ND | E | E |
| 411 | E | ND | E | A |
| 413 | E | ND | E | E |
| 414 | E | E | E | E |
| 416 | E | ND | E | E |
| 415 | E | ND | E | E |
| 417 | E | ND | E | E |
| 418 | B | ND | B | E |
| 419 | E | ND | E | E |
| 420 | E | ND | E | E |
| 422 | B | ND | B | E |
| 421 | E | ND | E | E |
| 423 | B | ND | C | E |
| 424 | E | ND | E | E |
| 426 | E | ND | E | E |
| 425 | B | ND | E | E |
| 427 | E | ND | E | E |
| 428 | A | B | E | E |
| 202 | E | ND | D | B |
| 429 | B | ND | B | A |
| 430 | B | ND | B | B |
| 432 | B | ND | E | B |
| 431 | B | ND | C | E |
| 433 | E | ND | E | E |
| 434 | E | ND | E | E |
| 436 | D | ND | E | E |
| 435 | E | ND | E | E |
| 437 | B | ND | E | B |
| 438 | B | ND | C | B |
| 439 | B | ND | B | B |
| 440 | B | ND | B | B |
| 441 | E | ND | E | E |
| 442 | E | ND | E | E |
| 443 | B | ND | E | B |
| 444 | E | ND | E | E |
| 445 | E | ND | E | B |
| 446 | E | ND | E | E |
| 448 | E | ND | E | E |
| 449 | E | ND | E | E |
| 450 | E | ND | E | E |
| 452 | E | ND | E | E |
| 451 | E | ND | D | E |
| 453 | B | ND | C | C |
| 454 | E | ND | E | C |
| 456 | E | ND | E | E |
| 455 | C | ND | E | E |
| 457 | C | ND | E | E |
| 458 | E | ND | E | C |
| 459 | E | ND | E | C |
| 460 | B | ND | E | C |
| 461 | E | ND | E | E |
| 462 | E | ND | E | D |
| 464 | E | ND | E | E |
| 463 | E | ND | E | E |
| 465 | E | ND | E | E |
| 466 | E | ND | E | B |
| 467 | E | ND | E | E |
| 468 | B | ND | E | E |
| 469 | E | ND | E | E |
| 999 | E | ND | E | E |
| 470 | D | ND | E | E |
| 471 | E | ND | E | E |
| 472 | E | ND | E | E |
| 1074 | E | ND | E | E |
| 473 | E | C | E | D |
| 474 | B | B | B | B |
| 476 | E | B | E | E |
| 475 | E | ND | E | C |
| 477 | E | ND | E | E |
| 478 | B | ND | B | B |
| 479 | D | A | E | C |
| 480 | B | ND | B | B |
| 481 | E | ND | E | E |
| 482 | E | ND | E | E |
| 484 | B | ND | E | C |
| 483 | B | ND | E | E |
| 486 | E | ND | E | E |
| 485 | E | ND | E | E |
| 487 | E | ND | E | E |
| 488 | E | ND | E | E |
| 489 | E | ND | E | E |
| 490 | E | ND | E | E |
| 492 | C | ND | E | C |
| 491 | E | ND | E | E |
| 493 | E | ND | E | D |
| 494 | C | ND | E | E |
| 495 | B | ND | E | B |
| 923 | E | ND | E | B |
| 497 | E | ND | E | E |
| 498 | A | E | E | A |
| 499 | B | ND | E | B |
| 501 | B | ND | E | A |
| 500 | B | ND | E | B |
| 502 | B | ND | B | B |
| 503 | E | ND | E | E |
| 504 | E | ND | E | E |
| 505 | E | ND | E | E |
| 506 | E | ND | E | E |
| 508 | E | ND | E | E |
| 507 | E | ND | E | E |
| 509 | B | E | E | E |
| 510 | E | E | E | E |
| 511 | E | E | E | E |
| 512 | E | E | E | E |
| 513 | D | D | E | E |
| 514 | E | E | E | E |
| 515 | E | E | E | E |
| 516 | E | E | E | E |
| 517 | C | B | E | D |
| 518 | A | E | E | E |
| 519 | E | B | E | E |
| 520 | E | B | E | E |
| 522 | C | B | E | C |

TABLE 2-continued

| Compound Number | EGFR-1 | IGFR-1 | AKT3-1 | Met-1 |
|---|---|---|---|---|
| 521 | B | A | E | A |
| 523 | B | A | E | A |
| 524 | E | A | E | C |
| 526 | B | ND | C | B |
| 525 | E | ND | E | D |
| 528 | B | ND | B | B |
| 527 | C | ND | E | B |
| 975 | E | ND | E | E |
| 976 | E | ND | E | E |
| 977 | B | A | E | A |
| 978 | B | A | E | A |
| 979 | B | ND | E | B |
| 980 | B | ND | B | D |
| 610 | B | B | E | B |
| 681 | E | ND | E | E |
| 682 | B | ND | E | C |
| 683 | E | ND | E | E |
| 684 | E | ND | E | E |
| 685 | E | ND | E | E |
| 686 | E | ND | E | E |
| 687 | D | ND | E | E |
| 688 | E | ND | E | E |
| 689 | B | ND | E | C |
| 1031 | A | B | E | E |
| 1032 | E | ND | E | E |
| 570 | D | ND | E | E |
| 570 | A | ND | E | E |
| 1033 | C | E | E | E |
| 1034 | E | ND | E | D |
| 1035 | E | ND | E | E |
| 1036 | B | D | E | E |
| 1037 | E | E | E | E |
| 700 | E | B | E | E |
| 646 | E | ND | B | E |
| 611 | E | ND | E | E |
| 230 | D | ND | E | E |
| 612 | B | C | E | A |
| 940 | E | ND | E | E |
| 941 | E | ND | E | E |
| 942 | E | C | E | E |
| 943 | E | E | E | E |
| 944 | E | D | E | E |
| 1000 | C | B | D | C |
| 1001 | B | A | E | A |
| 1002 | E | ND | E | E |
| 1003 | C | ND | E | B |
| 945 | E | ND | E | E |
| 946 | D | C | E | D |
| 947 | E | ND | E | E |
| 948 | E | ND | E | E |
| 949 | E | D | E | D |
| 981 | A | A | E | A |
| 982 | B | ND | D | B |
| 983 | A | B | D | A |
| 984 | A | ND | E | B |
| 1075 | E | ND | E | E |
| 1076 | E | E | E | E |
| 1077 | E | E | E | E |
| 1078 | E | ND | E | E |
| 647 | B | ND | E | E |
| 1038 | E | ND | E | E |
| 177 | A | B | C | B |
| 690 | E | ND | E | E |
| 648 | E | ND | E | E |
| 649 | E | A | E | E |
| 650 | E | A | E | D |
| 651 | E | A | E | B |
| 652 | E | A | E | B |
| 691 | C | A | E | B |
| 985 | B | ND | E | C |
| 986 | C | ND | E | B |
| 987 | E | ND | E | E |
| 1039 | E | ND | E | E |
| 613 | B | D | E | E |
| 614 | A | A | E | E |
| 950 | B | E | E | E |
| 1079 | E | ND | E | E |
| 1080 | E | ND | E | E |
| 1081 | E | ND | E | E |
| 1082 | B | C | E | D |
| 653 | E | ND | E | E |
| 654 | C | A | E | C |
| 655 | B | A | E | B |
| 656 | C | A | E | B |
| 657 | B | B | C | C |
| 615 | E | E | E | E |
| 658 | C | A | E | E |
| 951 | D | E | E | E |
| 952 | E | B | E | E |
| 692 | B | B | E | C |
| 693 | B | ND | E | B |
| 694 | B | ND | E | E |
| 695 | C | ND | E | E |
| 696 | E | ND | E | E |
| 697 | B | B | E | E |
| 698 | C | ND | E | E |
| 699 | B | B | E | E |
| 616 | A | B | E | A |
| 1004 | B | A | E | A |
| 1083 | B | E | E | E |
| 1084 | E | E | E | C |
| 1085 | E | E | E | E |
| 953 | A | C | E | E |
| 954 | E | D | E | D |
| 1086 | E | E | E | E |
| 1087 | E | E | E | E |
| 1088 | E | E | E | E |
| 1089 | E | E | E | E |
| 1040 | C | D | E | E |
| 1041 | A | B | E | E |
| 659 | E | B | E | E |
| 660 | B | E | E | E |
| 661 | E | E | E | E |
| 599 | D | E | E | E |
| 600 | E | E | E | E |
| 601 | B | E | E | E |
| 602 | B | E | E | E |
| 604 | B | B | C | A |
| 603 | A | B | E | B |
| 617 | C | C | E | E |
| 606 | E | D | E | E |
| 605 | E | E | E | E |
| 598 | E | E | E | E |
| 597 | D | D | C | E |
| 607 | A | E | E | E |
| 559 | A | B | E | E |
| 592 | B | E | E | E |
| 591 | E | E | E | E |
| 1042 | E | D | E | E |
| 593 | C | A | E | E |
| 596 | C | E | E | E |
| 595 | E | E | C | E |
| 1043 | D | D | E | E |
| 1044 | C | E | E | E |
| 618 | A | A | D | C |
| 579 | E | E | E | E |
| 579 | A | E | E | E |
| 414 | E | D | E | E |
| 589 | C | A | E | D |
| 583 | E | B | E | E |
| 584 | C | E | E | D |
| 619 | D | E | D | E |
| 620 | B | E | E | C |
| 581 | B | E | E | E |
| 582 | A | E | E | D |
| 585 | E | E | E | D |
| 584 | E | E | E | E |
| 1045 | E | E | E | E |
| 587 | C | D | E | D |
| 662 | C | D | E | E |
| 663 | E | E | E | E |
| 664 | B | B | C | B |
| 587 | D | E | E | E |
| 573 | B | A | C | B |

TABLE 2-continued

| Compound Number | EGFR-1 | IGFR-1 | AKT3-1 | Met-1 |
|---|---|---|---|---|
| 569 | E | E | E | E |
| 571 | E | E | E | D |
| 1046 | E | E | E | E |
| 574 | E | B | E | E |
| 572 | E | E | E | D |
| 588 | E | D | E | E |
| 561 | E | E | E | E |
| 577 | D | A | E | A |
| 578 | A | A | E | A |
| 562 | A | C | E | E |
| 563 | A | B | E | C |
| 565 | E | E | E | E |
| 564 | C | E | E | E |
| 566 | A | D | E | B |
| 549 | C | E | E | E |
| 567 | A | E | E | B |
| 621 | A | C | E | B |
| 1047 | E | E | E | E |
| 551 | E | E | E | D |
| 552 | E | E | E | E |
| 554 | A | E | D | C |
| 553 | A | D | C | B |
| 622 | C | E | E | E |
| 555 | A | A | C | C |
| 557 | B | A | E | E |
| 556 | B | A | E | E |
| 576 | B | A | E | A |
| 558 | E | E | E | C |
| 701 | E | E | E | E |
| 702 | B | E | E | E |
| 703 | A | E | E | E |
| 530 | E | E | E | E |
| 704 | E | E | E | E |
| 665 | B | E | E | E |
| 539 | A | C | D | D |
| 546 | C | A | D | C |
| 540 | A | A | E | C |
| 542 | B | B | E | D |
| 544 | E | A | E | E |
| 541 | A | B | E | D |
| 543 | A | E | E | E |
| 545 | B | E | E | E |
| 547 | E | E | E | E |
| 548 | E | E | E | E |
| 1007 | A | A | E | B |
| 531 | A | E | E | D |
| 623 | B | B | E | D |
| 533 | E | E | E | E |
| 534 | E | E | E | E |
| 535 | A | E | E | B |
| 536 | A | B | E | A |
| 537 | A | B | E | B |
| 538 | A | A | E | A |
| 666 | A | E | E | C |
| 988 | B | B | E | B |
| 989 | B | D | E | D |
| 990 | E | B | E | C |
| 955 | E | A | E | B |
| 705 | A | E | E | E |
| 706 | A | E | E | B |
| 707 | A | E | E | E |
| 708 | E | E | E | E |
| 709 | A | E | E | B |
| 1048 | A | E | E | E |
| 1049 | E | E | E | B |
| 1050 | C | E | E | C |
| 1051 | E | C | E | E |
| 1052 | E | E | E | E |
| 1005 | E | B | E | C |
| 624 | A | E | E | E |
| 625 | A | B | E | E |
| 626 | D | E | E | B |
| 627 | B | A | E | D |
| 956 | E | A | E | D |
| 710 | A | C | E | B |
| 711 | A | E | E | E |
| 712 | A | E | E | B |
| 713 | E | E | E | E |
| 1006 | E | A | E | A |
| 628 | B | B | E | E |
| 629 | B | A | E | C |
| 957 | A | B | B | B |
| 958 | B | B | C | B |
| 959 | B | B | B | B |
| 1053 | C | E | E | E |
| 1090 | E | D | E | D |
| 1091 | E | E | C | D |
| 630 | A | D | E | E |
| 714 | A | B | E | B |
| 715 | A | B | D | C |
| 716 | A | A | D | B |
| 717 | A | B | E | B |
| 718 | A | E | D | E |
| 719 | A | E | E | E |
| 631 | B | B | E | A |
| 632 | A | B | E | E |
| 720 | A | E | E | A |
| 721 | A | D | E | B |
| 1009 | A | A | E | E |
| 1011 | B | A | B | B |
| 1012 | A | A | B | B |
| 726 | A | E | E | E |
| 727 | E | E | E | D |
| 728 | B | B | E | B |
| 729 | A | B | D | B |
| 730 | A | B | C | B |
| 731 | A | B | D | B |
| 732 | D | D | E | E |
| 733 | B | E | E | E |
| 734 | E | C | E | D |
| 735 | A | D | C | D |
| 736 | B | B | B | B |
| 737 | B | B | D | C |
| 738 | B | B | E | E |
| 739 | B | E | E | E |
| 740 | C | E | E | E |
| 741 | A | E | E | E |
| 742 | B | E | E | E |
| 743 | A | E | E | E |
| 744 | B | E | E | E |
| 745 | B | E | E | E |
| 746 | E | E | E | E |
| 747 | C | E | E | E |
| 748 | A | C | E | B |
| 749 | A | E | E | B |
| 750 | A | E | E | C |
| 751 | A | E | E | E |
| 752 | B | E | E | E |
| 753 | A | B | E | B |
| 754 | E | E | E | E |
| 755 | E | E | E | E |
| 756 | A | E | E | B |
| 757 | A | E | E | E |
| 758 | A | C | E | A |
| 759 | E | E | E | E |
| 760 | A | E | E | B |
| 761 | E | E | E | E |
| 762 | D | E | E | E |
| 763 | A | E | E | B |
| 764 | A | E | E | A |
| 765 | E | E | E | E |
| 766 | B | B | E | B |
| 767 | E | E | E | E |
| 768 | E | E | E | C |
| 769 | E | E | E | E |
| 770 | A | D | E | A |
| 771 | E | E | E | E |
| 772 | E | E | E | E |
| 773 | B | B | E | A |
| 774 | A | C | B | A |
| 775 | E | E | E | E |
| 776 | E | E | E | E |
| 777 | E | E | E | E |
| 778 | C | E | B | B |

TABLE 2-continued

| Compound Number | EGFR-1 | IGFR-1 | AKT3-1 | Met-1 |
|---|---|---|---|---|
| 779 | E | E | E | E |
| 780 | D | E | E | E |
| 781 | E | E | E | E |
| 782 | E | E | E | E |
| 783 | E | B | E | E |
| 784 | E | E | E | E |
| 785 | E | E | E | E |
| 786 | E | E | E | E |
| 787 | E | E | E | E |
| 788 | E | E | E | E |
| 789 | E | B | E | E |
| 790 | E | E | E | E |
| 791 | E | E | E | E |
| 792 | B | E | E | E |
| 793 | E | E | E | E |
| 794 | B | C | E | D |
| 795 | A | D | E | A |
| 796 | A | E | E | B |
| 797 | A | C | E | B |
| 798 | E | E | E | D |
| 799 | A | B | E | B |
| 800 | A | D | E | B |
| 801 | A | E | E | B |
| 802 | E | E | E | E |
| 803 | B | E | E | E |
| 804 | E | E | E | E |
| 805 | E | C | E | C |
| 806 | B | B | E | B |
| 807 | D | B | E | A |
| 808 | C | E | E | E |
| 809 | E | C | D | C |
| 810 | E | D | E | E |
| 811 | E | C | E | E |
| 812 | E | B | E | B |
| 813 | E | E | E | E |
| 814 | E | E | E | E |
| 815 | E | E | E | E |
| 816 | E | D | E | E |
| 817 | E | E | E | E |
| 818 | E | E | E | E |
| 819 | E | E | E | E |
| 820 | E | D | E | E |
| 821 | B | B | C | B |
| 822 | B | B | E | C |
| 823 | E | C | B | B |
| 824 | A | A | A | A |
| 825 | A | B | B | B |
| 826 | A | B | E | B |
| 827 | A | B | D | B |
| 828 | E | E | E | E |
| 829 | D | E | E | E |
| 830 | E | E | E | B |
| 831 | E | E | E | C |
| 832 | E | E | E | B |
| 833 | E | E | E | E |
| 834 | E | E | E | E |
| 835 | E | E | E | E |
| 836 | E | E | E | E |
| 837 | E | E | E | E |
| 383 | D | E | B | D |
| 839 | E | E | E | E |
| 840 | E | E | E | E |
| 841 | E | E | E | E |
| 842 | E | E | E | D |
| 843 | E | E | E | E |
| 844 | E | C | E | E |
| 845 | E | E | B | E |
| 846 | C | E | E | E |
| 847 | E | E | E | E |
| 848 | E | E | E | E |
| 849 | D | E | E | E |
| 850 | E | E | E | E |
| 851 | E | E | E | E |
| 667 | A | E | E | D |
| 668 | A | E | E | C |
| 669 | A | E | E | D |
| 670 | A | E | E | A |
| 671 | A | C | E | A |
| 633 | B | E | E | E |
| 634 | A | E | D | C |
| 1013 | B | A | B | B |
| 1008 | B | A | E | B |
| 635 | A | E | E | A |
| 636 | B | E | E | E |
| 637 | A | E | E | C |
| 960 | C | A | E | D |
| 961 | A | B | E | E |
| 991 | B | B | C | A |
| 992 | B | A | C | A |
| 993 | B | A | E | A |
| 962 | C | D | E | E |
| 963 | C | C | D | B |
| 964 | B | E | E | E |
| 672 | B | E | E | E |
| 673 | A | E | E | B |
| 674 | A | E | E | B |
| 675 | A | C | E | B |
| 1092 | E | E | E | E |
| 1093 | B | D | E | B |
| 1094 | B | E | E | B |
| 1095 | E | E | E | E |
| 1096 | E | E | D | D |
| 1097 | E | E | E | C |
| 1098 | C | E | C | C |
| 638 | A | D | E | E |
| 994 | E | E | E | E |
| 639 | A | E | E | A |
| 995 | B | C | E | E |
| 996 | D | B | E | E |
| 997 | E | E | E | E |
| 965 | A | E | E | E |
| 966 | A | A | E | E |
| 967 | A | E | D | C |
| 968 | B | D | E | D |
| 1010 | B | A | B | A |
| 1099 | A | E | E | B |
| 1100 | B | E | E | D |
| 1101 | B | E | E | C |
| 1102 | C | E | E | E |
| 1103 | B | E | D | E |
| 1104 | E | E | D | E |
| 1105 | E | E | E | E |
| 1106 | E | E | E | E |
| 1104 | B | D | E | E |
| 1108 | B | C | B | E |
| 1127 | E | A | E | A |
| 1128 | D | A | E | B |
| 1109 | B | B | E | C |
| 722 | A | D | E | B |
| 1054/1055 | E | B | E | E |
| 1056/1057 | B | E | E | E |
| 1058/1059 | E | C | E | E |
| 1060/1061 | E | E | E | E |
| 1062/1063 | E | A | C | D |
| 1064/1065 | C | E | E | E |
| 640 | A | E | E | B |
| 641 | A | B | E | A |
| 642 | B | A | E | A |
| 853 | E | E | E | E |
| 854 | B | E | E | E |
| 855 | E | E | E | E |
| 856 | E | C | E | E |
| 857 | C | E | E | E |
| 858 | C | E | E | E |
| 859 | B | C | B | B |
| 860 | E | C | E | B |
| 861 | E | E | E | E |
| 862 | B | E | E | A |
| 863 | A | E | E | B |
| 864 | E | E | E | A |
| 865 | A | E | E | B |
| 866 | B | E | E | B |
| 867 | B | E | B | A |
| 723 | A | A | B | C |

TABLE 2-continued

| Compound Number | EGFR-1 | IGFR-1 | AKT3-1 | Met-1 |
|---|---|---|---|---|
| 134 | A | A | B | A |
| 676 | A | B | C | B |
| 677 | A | C | E | A |
| 1110 | B | E | E | E |
| 1111 | B | E | E | E |
| 1112 | B | E | E | B |
| 1113 | B | E | E | B |
| 1114 | D | E | E | D |
| 1115 | B | E | E | B |
| 1116 | B | B | D | B |
| 1117 | D | E | E | B |
| 1066 | C | E | C | C |
| 1067 | B | E | E | E |
| 1068 | E | E | E | E |
| 868 | B | E | E | E |
| 869 | B | E | E | D |
| 870 | E | E | E | E |
| 871 | E | E | E | E |
| 872 | B | B | B | B |
| 873 | E | E | E | E |
| 874 | B | E | E | E |
| 875 | A | E | E | C |
| 876 | A | E | E | E |
| 877 | C | D | E | B |
| 878 | E | C | E | D |
| 879 | B | C | E | B |
| 880 | B | E | E | B |
| 881 | B | B | E | B |
| 882 | B | B | C | B |
| 883 | C | C | E | A |
| 884 | B | B | B | B |
| 885 | B | B | D | B |
| 886 | A | B | B | A |
| 887 | A | A | B | A |
| 888 | B | A | B | A |
| 889 | B | B | E | B |
| 890 | E | E | E | E |
| 891 | B | A | B | A |
| 892 | A | E | E | B |
| 893 | B | E | B | B |
| 894 | C | E | E | E |
| 895 | B | A | E | E |
| 896 | B | B | C | B |
| 897 | A | E | E | E |
| 898 | C | C | E | E |
| 899 | B | C | C | B |
| 900 | A | B | A | A |
| 901 | A | E | B | B |
| 902 | A | C | B | B |
| 903 | A | E | E | C |
| 904 | A | C | D | B |
| 905 | A | E | E | B |
| 906 | B | C | B | B |
| 907 | A | E | E | C |
| 678 | A | E | E | A |
| 643 | A | E | E | B |
| 644 | B | E | E | B |
| 724 | A | B | E | B |
| 645 | A | E | E | E |
| 1069 | A | E | E | E |
| 1070 | E | E | C | E |
| 1071 | B | B | E | E |
| 679 | B | E | E | E |
| 1125 | A | A | E | B |
| 1126 | B | A | E | B |

TABLE 3

| Compound Number | KDR-1 | Zap-1 | Lck-1 | Itk-1 |
|---|---|---|---|---|
| 1014 | E | E | E | E |
| 1015 | E | E | E | E |
| 1016 | E | E | E | E |
| 1017 | E | E | E | E |

TABLE 3-continued

| Compound Number | KDR-1 | Zap-1 | Lck-1 | Itk-1 |
|---|---|---|---|---|
| 1018 | E | E | E | E |
| 1019 | C | E | E | E |
| 271 | E | B | E | E |
| 272 | E | C | E | E |
| 1020 | E | E | E | E |
| 1021 | E | E | E | E |
| 1022 | E | E | E | E |
| 273 | E | E | E | E |
| 1023 | C | E | D | C |
| 1024 | E | E | E | E |
| 1025 | C | D | E | E |
| 1027 | E | E | E | E |
| 970 | A | E | E | E |
| 36 | A | E | B | E |
| 182 | A | E | C | E |
| 275 | B | E | E | E |
| 274 | B | E | E | E |
| 276 | B | E | E | E |
| 277 | B | E | E | E |
| 11 | B | E | C | E |
| 12 | D | E | E | E |
| 13 | E | E | E | E |
| 14 | E | D | E | E |
| 15 | E | D | E | E |
| 17 | E | E | E | E |
| 16 | E | E | E | E |
| 18 | C | E | C | E |
| 19 | C | C | E | E |
| 20 | E | E | E | E |
| 21 | B | D | B | E |
| 8 | C | E | E | E |
| 971 | E | E | E | E |
| 924 | B | E | E | E |
| 925 | E | E | B | E |
| 61 | A | E | A | E |
| 926 | A | C | B | E |
| 29 | A | E | A | E |
| 27 | A | E | B | E |
| 28 | A | E | B | E |
| 852 | C | D | E | E |
| 151 | D | E | E | E |
| 1028 | E | E | E | E |
| 153 | D | E | E | E |
| 63 | B | E | E | E |
| 62 | B | E | B | E |
| 40 | E | E | E | E |
| 39 | E | E | E | E |
| 65 | B | E | D | E |
| 64 | B | D | B | E |
| 67 | B | E | B | E |
| 66 | B | C | B | E |
| 69 | B | E | B | E |
| 68 | A | E | A | E |
| 927 | B | E | C | E |
| 70 | A | E | B | D |
| 928 | A | E | A | C |
| 232 | B | E | B | E |
| 1118 | E | E | E | E |
| 77 | A | E | B | D |
| 73 | E | E | E | E |
| 76 | B | E | B | E |
| 72 | A | E | B | E |
| 75 | B | D | B | E |
| 74 | B | E | B | E |
| 33 | B | E | D | E |
| 78 | A | E | B | B |
| 79 | A | E | A | A |
| 80 | E | E | E | E |
| 81 | B | E | B | E |
| 82 | A | E | B | E |
| 83 | A | E | A | B |
| 289 | A | E | A | B |
| 86 | A | E | B | E |
| 85 | A | E | A | B |
| 88 | A | E | B | B |
| 87 | B | D | B | E |
| 90 | A | E | B | D |

TABLE 3-continued

| Compound Number | KDR-1 | Zap-1 | Lck-1 | Itk-1 |
|---|---|---|---|---|
| 89 | A | E | B | E |
| 91 | B | E | B | E |
| 92 | B | D | E | E |
| 93 | E | E | E | E |
| 94 | A | E | A | E |
| 95 | B | D | B | E |
| 96 | B | D | B | E |
| 97 | A | E | D | E |
| 98 | A | E | A | E |
| 99 | A | E | B | E |
| 100 | B | B | E | E |
| 101 | B | E | C | E |
| 102 | A | E | A | B |
| 154 | B | E | E | E |
| 155 | E | E | E | E |
| 207 | B | E | D | E |
| 251 | A | C | C | E |
| 22 | E | E | E | E |
| 278 | E | E | E | E |
| 279 | E | E | E | E |
| 280 | E | E | E | E |
| 281 | E | E | E | E |
| 282 | E | E | E | E |
| 283 | E | E | E | E |
| 284 | D | E | E | E |
| 156 | C | E | D | E |
| 157 | B | C | E | E |
| 158 | B | B | D | E |
| 159 | C | C | E | E |
| 160 | E | E | E | E |
| 161 | B | E | E | E |
| 162 | C | E | E | E |
| 209 | E | E | E | E |
| 183 | C | E | E | E |
| 253 | B | E | D | E |
| 221 | B | E | E | E |
| 252 | A | E | A | C |
| 256 | D | E | E | E |
| 103 | E | E | E | E |
| 104 | B | E | C | E |
| 105 | B | E | E | E |
| 106 | A | E | C | E |
| 220 | E | E | E | E |
| 107 | B | E | B | B |
| 108 | C | E | D | E |
| 109 | C | C | E | E |
| 110 | A | E | B | C |
| 929 | B | C | B | B |
| 111 | B | E | B | E |
| 114 | A | E | E | E |
| 113 | E | E | E | E |
| 116 | C | E | D | E |
| 115 | B | E | B | D |
| 118 | E | E | D | B |
| 41 | A | E | C | D |
| 117 | B | D | C | E |
| 119 | A | E | B | D |
| 163 | E | E | E | E |
| 164 | E | E | E | E |
| 165 | E | E | E | E |
| 1029 | D | C | E | E |
| 285 | A | E | B | E |
| 299 | B | B | D | E |
| 286 | A | E | B | B |
| 214 | B | E | E | E |
| 213 | B | E | E | E |
| 181 | E | E | E | E |
| 184 | A | E | B | E |
| 255 | A | E | E | E |
| 185 | A | E | C | E |
| 191 | C | E | E | E |
| 211 | C | E | E | E |
| 254 | E | E | E | E |
| 42 | B | E | B | E |
| 922 | A | C | B | E |
| 186 | A | E | B | E |
| 208 | B | E | E | E |
| 121 | A | E | B | D |
| 123 | A | E | B | C |
| 125 | A | E | B | C |
| 127 | A | E | B | E |
| 120 | B | D | D | C |
| 170 | B | C | E | E |
| 171 | E | E | E | E |
| 287 | A | E | B | C |
| 222 | D | E | E | E |
| 51 | B | E | B | E |
| 212 | E | E | E | E |
| 250 | C | E | B | E |
| 200 | C | E | D | E |
| 218 | E | E | E | E |
| 187 | B | E | E | E |
| 930 | A | E | B | E |
| 931 | A | E | B | E |
| 932 | A | E | B | E |
| 933 | B | E | B | E |
| 934 | B | E | E | E |
| 935 | A | E | B | C |
| 1030 | A | E | C | B |
| 174 | A | E | E | E |
| 175 | A | E | B | E |
| 972 | A | E | B | E |
| 609 | A | E | A | E |
| 936 | B | E | B | C |
| 937 | A | E | B | E |
| 938 | A | E | E | E |
| 135 | A | D | B | C |
| 226 | C | D | D | E |
| 973 | E | E | C | E |
| 291 | C | E | C | E |
| 292/293 | B | E | B | B |
| 294/295 | C | E | C | E |
| 296/297 | A | E | B | C |
| 178 | B | B | B | E |
| 302 | B | E | E | E |
| 300 | A | E | B | C |
| 303 | B | E | B | E |
| 304 | A | E | A | D |
| 305 | A | E | B | E |
| 196 | A | E | E | E |
| 298 | A | D | B | B |
| 306 | A | E | B | E |
| 974 | B | E | C | E |
| 56 | B | E | C | E |
| 310 | D | E | B | E |
| 309 | D | E | D | E |
| 311 | B | E | E | E |
| 312 | E | E | E | E |
| 313 | B | E | B | C |
| 238 | B | E | E | E |
| 239 | B | E | E | E |
| 198 | B | E | E | E |
| 237 | A | D | B | E |
| 240 | B | E | B | E |
| 314 | A | E | A | B |
| 315 | A | D | D | E |
| 316 | A | E | E | E |
| 317 | B | E | B | E |
| 318 | A | E | B | C |
| 308 | A | E | B | B |
| 320 | C | D | C | E |
| 319 | E | E | E | E |
| 321 | A | E | D | E |
| 322 | B | E | E | E |
| 323 | A | D | D | E |
| 324 | A | E | E | B |
| 328 | A | E | B | B |
| 325 | A | E | E | E |
| 327 | E | E | B | B |
| 326 | E | E | E | E |
| 338 | B | E | B | E |
| 337 | A | E | B | B |
| 336 | A | E | B | E |
| 335 | A | E | B | E |

TABLE 3-continued

| Compound Number | KDR-1 | Zap-1 | Lck-1 | Itk-1 |
|---|---|---|---|---|
| 334 | B | E | D | B |
| 219 | B | E | E | E |
| 333 | E | E | E | E |
| 332 | B | E | D | E |
| 331 | E | E | E | E |
| 330 | E | E | E | E |
| 339 | A | E | E | E |
| 340 | A | E | B | E |
| 342 | A | E | B | B |
| 341 | A | E | C | C |
| 344 | A | E | B | E |
| 343 | B | E | E | E |
| 345 | A | E | B | E |
| 346 | B | E | E | E |
| 217 | C | E | B | E |
| 1072 | C | E | E | E |
| 1073 | E | E | E | E |
| 349 | D | E | B | E |
| 350 | E | E | E | E |
| 352 | E | E | E | E |
| 205 | C | E | E | E |
| 353 | A | E | D | B |
| 354 | E | E | E | E |
| 356 | E | E | E | E |
| 355 | E | E | E | E |
| 358 | E | E | E | E |
| 357 | E | E | E | E |
| 359 | E | E | E | E |
| 360 | E | E | E | E |
| 362 | E | E | E | E |
| 361 | E | E | E | E |
| 363 | E | E | E | E |
| 364 | A | E | C | C |
| 366 | E | C | C | E |
| 365 | A | B | B | B |
| 367 | A | E | B | B |
| 368 | E | E | D | E |
| 369 | E | E | C | D |
| 180 | B | E | B | E |
| 372 | E | E | E | E |
| 373 | B | E | E | E |
| 371 | A | E | B | E |
| 374 | A | E | A | E |
| 375 | B | E | C | E |
| 376 | A | E | A | B |
| 378 | A | E | C | E |
| 377 | B | B | B | D |
| 379 | D | E | E | E |
| 380 | A | E | E | E |
| 382 | B | E | B | E |
| 381 | C | E | D | E |
| 383 | B | E | C | C |
| 384 | A | E | A | E |
| 386 | A | E | C | E |
| 385 | A | E | B | E |
| 387 | A | E | B | E |
| 388 | B | E | B | E |
| 389 | E | E | E | E |
| 390 | B | E | A | E |
| 391 | B | E | D | E |
| 392 | B | E | C | E |
| 393 | E | E | B | E |
| 394 | A | E | B | E |
| 396 | A | E | B | A |
| 395 | A | E | C | B |
| 397 | A | E | A | E |
| 398 | C | E | E | E |
| 399 | B | E | D | E |
| 400 | A | E | E | E |
| 402 | B | E | E | E |
| 401 | A | B | B | A |
| 403 | A | E | A | E |
| 404 | A | E | B | B |
| 406 | B | E | B | E |
| 405 | B | E | E | E |
| 407 | A | E | A | E |
| 393 | C | E | E | E |
| 409 | E | E | D | E |
| 45 | E | E | B | E |
| 412 | B | E | A | E |
| 411 | A | E | D | E |
| 413 | A | E | E | E |
| 414 | A | E | E | E |
| 416 | A | E | B | E |
| 415 | A | E | C | E |
| 417 | A | E | A | E |
| 418 | A | E | B | D |
| 419 | B | E | E | E |
| 420 | B | E | E | E |
| 422 | B | E | E | E |
| 421 | E | E | E | E |
| 423 | B | E | B | E |
| 424 | C | E | E | E |
| 426 | E | E | E | E |
| 425 | D | E | E | E |
| 427 | E | E | E | E |
| 428 | C | E | A | E |
| 202 | A | E | A | A |
| 429 | A | E | B | B |
| 430 | A | E | B | B |
| 432 | B | E | E | D |
| 431 | B | E | D | C |
| 433 | E | E | E | E |
| 434 | E | E | E | E |
| 436 | D | E | E | E |
| 435 | E | E | E | E |
| 437 | A | E | B | B |
| 438 | B | D | B | B |
| 439 | A | C | B | B |
| 440 | B | B | B | D |
| 441 | A | E | C | E |
| 442 | C | E | E | E |
| 443 | A | E | E | B |
| 444 | E | E | E | E |
| 445 | A | E | A | B |
| 446 | E | E | E | E |
| 448 | C | E | B | E |
| 449 | E | E | E | E |
| 450 | E | E | E | E |
| 452 | B | E | E | E |
| 451 | B | E | B | E |
| 453 | B | E | E | E |
| 454 | B | E | B | E |
| 456 | E | E | E | E |
| 455 | B | E | E | E |
| 457 | B | E | D | E |
| 458 | B | E | E | E |
| 459 | B | E | E | E |
| 460 | B | E | D | E |
| 461 | E | E | E | E |
| 462 | E | C | D | E |
| 464 | B | E | C | E |
| 463 | A | E | E | E |
| 465 | B | E | E | E |
| 466 | A | E | A | C |
| 467 | B | C | E | E |
| 468 | B | E | E | E |
| 469 | B | E | E | E |
| 999 | E | E | E | E |
| 470 | E | E | C | B |
| 471 | E | E | E | E |
| 472 | B | E | E | E |
| 1074 | B | E | C | E |
| 473 | D | D | C | E |
| 474 | B | C | B | B |
| 476 | D | E | E | E |
| 475 | A | E | B | B |
| 477 | A | E | B | B |
| 478 | B | B | B | B |
| 479 | B | E | B | C |
| 480 | B | B | B | D |
| 481 | B | E | E | D |
| 482 | A | E | E | E |
| 484 | E | E | E | E |

TABLE 3-continued

| Compound Number | KDR-1 | Zap-1 | Lck-1 | Itk-1 |
|---|---|---|---|---|
| 483 | B | B | C | E |
| 486 | B | E | B | E |
| 485 | B | E | E | E |
| 487 | E | E | E | E |
| 488 | B | E | E | E |
| 489 | E | E | E | E |
| 490 | E | E | E | E |
| 492 | C | D | E | E |
| 491 | D | E | E | E |
| 493 | E | E | E | E |
| 494 | A | E | C | E |
| 495 | D | E | C | E |
| 923 | A | E | D | B |
| 497 | A | E | D | E |
| 498 | A | E | A | E |
| 499 | B | E | B | B |
| 501 | B | E | B | B |
| 500 | B | E | B | B |
| 502 | B | E | B | B |
| 503 | E | D | D | E |
| 504 | E | E | E | E |
| 505 | E | D | E | E |
| 506 | E | E | D | E |
| 508 | B | E | B | C |
| 507 | A | E | B | E |
| 509 | A | E | B | C |
| 510 | A | E | B | B |
| 511 | A | E | A | E |
| 512 | A | E | B | E |
| 513 | A | E | B | E |
| 514 | A | E | E | E |
| 515 | A | E | A | E |
| 516 | A | E | C | E |
| 517 | A | E | B | D |
| 518 | D | E | E | E |
| 519 | A | E | B | E |
| 520 | E | E | B | B |
| 522 | C | E | B | B |
| 521 | A | E | A | B |
| 523 | E | E | A | D |
| 524 | B | E | C | D |
| 526 | A | B | B | B |
| 525 | C | E | C | C |
| 528 | B | B | B | B |
| 527 | A | E | B | B |
| 975 | E | E | E | E |
| 976 | E | C | E | E |
| 977 | A | E | A | E |
| 978 | B | E | B | C |
| 979 | C | E | E | E |
| 980 | E | E | E | D |
| 610 | A | E | A | B |
| 681 | B | E | E | E |
| 682 | B | E | C | D |
| 683 | E | E | E | E |
| 684 | C | E | E | E |
| 685 | E | E | E | E |
| 686 | E | E | E | E |
| 687 | B | E | B | D |
| 688 | E | C | E | E |
| 689 | C | B | C | E |
| 1031 | C | E | B | E |
| 1032 | B | E | E | E |
| 570 | E | E | E | E |
| 570 | E | E | B | E |
| 1033 | A | E | A | E |
| 1034 | A | E | B | E |
| 1035 | A | E | E | E |
| 1036 | A | E | A | E |
| 1037 | A | E | E | E |
| 700 | A | E | B | D |
| 646 | B | E | E | C |
| 611 | B | E | B | D |
| 230 | A | E | B | D |
| 612 | A | D | A | B |
| 940 | A | E | D | E |
| 941 | E | E | E | E |
| 942 | A | E | C | E |
| 943 | A | C | B | E |
| 944 | A | E | E | E |
| 1000 | B | E | B | E |
| 1001 | B | E | A | B |
| 1002 | D | E | E | E |
| 1003 | B | C | B | B |
| 945 | B | E | D | E |
| 946 | B | E | B | E |
| 947 | A | E | E | C |
| 948 | B | E | C | C |
| 949 | A | E | A | E |
| 981 | A | E | B | B |
| 982 | A | B | B | B |
| 983 | A | C | C | B |
| 984 | A | D | B | B |
| 1075 | D | E | E | E |
| 1076 | A | E | A | E |
| 1077 | A | E | B | E |
| 1078 | B | E | E | E |
| 647 | B | E | E | E |
| 1038 | E | E | B | E |
| 177 | B | C | A | D |
| 690 | A | E | E | E |
| 648 | B | E | E | E |
| 649 | B | E | B | D |
| 650 | A | E | B | E |
| 651 | A | E | B | B |
| 652 | A | E | A | B |
| 691 | A | E | B | C |
| 985 | B | E | B | C |
| 986 | B | E | E | C |
| 987 | E | E | B | E |
| 1039 | A | E | B | E |
| 613 | C | E | B | E |
| 614 | D | E | B | E |
| 950 | A | E | A | E |
| 1079 | E | E | E | E |
| 1080 | A | E | C | E |
| 1081 | A | E | B | E |
| 1082 | A | B | B | E |
| 653 | E | E | E | E |
| 654 | A | E | B | B |
| 655 | A | E | B | B |
| 656 | A | E | B | C |
| 657 | B | B | C | C |
| 615 | E | E | D | D |
| 658 | B | E | E | B |
| 951 | A | E | B | E |
| 952 | A | E | C | D |
| 692 | A | B | A | B |
| 693 | B | E | B | C |
| 694 | B | E | B | C |
| 695 | A | E | A | B |
| 696 | E | E | E | E |
| 697 | B | E | A | E |
| 698 | A | E | A | B |
| 699 | B | E | A | B |
| 616 | A | E | A | E |
| 1004 | B | E | A | D |
| 1083 | A | E | B | D |
| 1084 | B | E | A | C |
| 1085 | A | E | B | E |
| 953 | B | E | A | D |
| 954 | D | E | D | C |
| 1086 | A | E | C | E |
| 1087 | B | E | C | E |
| 1088 | A | E | C | E |
| 1089 | A | E | A | C |
| 1040 | A | E | B | B |
| 1041 | A | E | A | B |
| 659 | C | E | C | B |
| 660 | E | E | B | E |
| 661 | B | E | E | E |
| 599 | C | E | B | E |
| 600 | B | E | A | E |
| 601 | C | E | B | E |

TABLE 3-continued

| Compound Number | KDR-1 | Zap-1 | Lck-1 | Itk-1 |
|---|---|---|---|---|
| 602 | D | E | B | E |
| 604 | B | C | B | B |
| 603 | A | E | A | E |
| 617 | B | E | B | E |
| 606 | A | E | C | E |
| 605 | A | E | B | E |
| 598 | B | E | E | E |
| 597 | B | E | B | E |
| 607 | A | E | A | E |
| 559 | B | E | A | C |
| 592 | A | E | B | E |
| 591 | A | E | A | E |
| 1042 | A | E | B | E |
| 593 | B | E | B | E |
| 596 | D | E | E | E |
| 595 | B | E | D | E |
| 1043 | B | E | C | E |
| 1044 | B | E | C | E |
| 618 | B | E | B | D |
| 579 | B | E | B | E |
| 579 | A | E | B | E |
| 414 | A | E | B | E |
| 589 | B | E | B | C |
| 583 | C | E | B | B |
| 584 | B | E | B | E |
| 619 | C | E | C | E |
| 620 | D | D | B | E |
| 581 | D | E | B | E |
| 582 | C | E | C | E |
| 585 | A | E | C | E |
| 584 | B | E | D | E |
| 1045 | B | E | B | E |
| 587 | A | E | B | E |
| 662 | B | E | C | E |
| 663 | C | E | E | E |
| 664 | B | C | B | C |
| 587 | B | E | B | E |
| 573 | A | C | A | B |
| 569 | A | E | A | E |
| 571 | E | E | E | E |
| 1046 | A | E | E | E |
| 574 | A | E | A | E |
| 572 | A | E | B | E |
| 588 | C | E | E | E |
| 561 | A | E | A | E |
| 577 | B | E | B | B |
| 578 | A | E | A | A |
| 562 | C | E | A | E |
| 563 | B | E | A | E |
| 565 | C | E | B | E |
| 564 | A | E | A | E |
| 566 | A | E | A | E |
| 549 | A | E | B | E |
| 567 | A | E | B | E |
| 621 | B | E | B | E |
| 1047 | E | E | E | E |
| 551 | E | E | E | E |
| 552 | E | E | E | E |
| 554 | B | D | C | E |
| 553 | B | C | E | D |
| 622 | E | E | E | E |
| 555 | B | D | A | D |
| 557 | B | E | A | D |
| 556 | B | E | A | B |
| 576 | A | E | A | B |
| 558 | A | C | C | E |
| 701 | E | E | E | E |
| 702 | E | E | E | E |
| 703 | E | E | E | E |
| 530 | E | E | E | E |
| 704 | E | E | E | E |
| 665 | E | E | E | E |
| 539 | B | B | D | D |
| 546 | A | D | B | B |
| 540 | C | E | B | D |
| 542 | A | E | B | B |
| 544 | A | E | E | E |

TABLE 3-continued

| Compound Number | KDR-1 | Zap-1 | Lck-1 | Itk-1 |
|---|---|---|---|---|
| 541 | B | E | E | D |
| 543 | A | E | C | E |
| 545 | A | E | B | E |
| 547 | A | E | E | E |
| 548 | A | E | E | E |
| 1007 | B | E | B | B |
| 531 | A | E | B | E |
| 623 | B | E | A | B |
| 533 | A | E | E | E |
| 534 | A | E | D | E |
| 535 | B | E | B | E |
| 536 | A | E | B | E |
| 537 | A | E | A | D |
| 538 | A | E | B | D |
| 666 | E | E | C | E |
| 988 | E | E | C | B |
| 989 | D | E | E | D |
| 990 | E | E | E | C |
| 955 | A | E | B | B |
| 705 | D | E | E | E |
| 706 | A | E | E | E |
| 707 | E | E | E | E |
| 708 | E | C | E | E |
| 709 | E | E | C | E |
| 1048 | A | E | B | E |
| 1049 | A | E | B | E |
| 1050 | B | E | E | E |
| 1051 | A | E | A | C |
| 1052 | B | E | E | E |
| 1005 | E | E | D | E |
| 624 | C | E | B | E |
| 625 | B | E | A | E |
| 626 | B | E | B | D |
| 627 | B | E | A | B |
| 956 | A | E | C | B |
| 710 | B | E | A | E |
| 711 | C | E | E | E |
| 712 | B | E | B | E |
| 713 | B | E | E | E |
| 1006 | E | E | B | C |
| 628 | C | E | B | E |
| 629 | B | C | A | B |
| 957 | A | C | B | B |
| 958 | A | C | B | B |
| 959 | A | B | B | B |
| 1053 | A | E | B | E |
| 1090 | A | E | A | E |
| 1091 | A | E | B | D |
| 630 | C | E | B | E |
| 714 | B | E | B | E |
| 715 | B | C | E | D |
| 716 | B | E | B | B |
| 717 | B | B | B | B |
| 718 | E | D | E | E |
| 719 | B | E | E | E |
| 631 | A | E | A | E |
| 632 | D | E | B | E |
| 720 | B | C | B | E |
| 721 | B | E | B | E |
| 1009 | E | E | E | B |
| 1011 | B | E | B | B |
| 1012 | B | D | B | B |
| 726 | D | E | E | E |
| 727 | D | C | E | E |
| 728 | B | B | E | E |
| 729 | B | C | B | C |
| 730 | B | B | C | B |
| 731 | B | C | B | B |
| 732 | E | D | E | E |
| 733 | E | E | E | E |
| 734 | B | C | E | E |
| 735 | B | C | E | D |
| 736 | B | B | B | B |
| 737 | B | D | C | B |
| 738 | E | E | E | B |
| 739 | E | E | E | E |
| 740 | E | E | E | E |

TABLE 3-continued

| Compound Number | KDR-1 | Zap-1 | Lck-1 | Itk-1 |
|---|---|---|---|---|
| 741 | E | E | C | E |
| 742 | E | E | E | E |
| 743 | E | E | E | E |
| 744 | E | E | E | E |
| 745 | E | E | E | E |
| 746 | E | E | E | E |
| 747 | E | E | E | E |
| 748 | C | E | B | E |
| 749 | C | E | B | E |
| 750 | E | E | B | E |
| 751 | B | E | C | E |
| 752 | E | E | E | E |
| 753 | B | B | B | B |
| 754 | E | E | E | E |
| 755 | E | E | E | E |
| 756 | E | E | B | E |
| 757 | E | E | E | E |
| 758 | B | E | A | E |
| 759 | E | E | E | E |
| 760 | B | E | B | E |
| 761 | E | E | E | E |
| 762 | E | E | E | E |
| 763 | B | E | C | E |
| 764 | E | E | E | E |
| 765 | E | E | E | E |
| 766 | B | E | B | A |
| 767 | E | E | E | E |
| 768 | D | E | E | E |
| 769 | E | E | E | E |
| 770 | B | E | A | E |
| 771 | C | E | E | E |
| 772 | E | E | E | D |
| 773 | B | E | B | B |
| 774 | B | E | B | B |
| 775 | E | E | E | E |
| 776 | E | E | E | E |
| 777 | E | E | E | D |
| 778 | C | E | E | E |
| 779 | E | E | E | E |
| 780 | E | E | C | E |
| 781 | E | E | E | E |
| 782 | E | E | E | E |
| 783 | D | E | B | E |
| 784 | E | E | E | E |
| 785 | E | E | E | E |
| 786 | E | E | E | E |
| 787 | E | E | E | E |
| 788 | E | E | E | E |
| 789 | E | E | B | E |
| 790 | E | E | E | E |
| 791 | E | E | E | E |
| 792 | E | E | B | E |
| 793 | E | E | E | E |
| 794 | C | D | B | D |
| 795 | B | E | B | E |
| 796 | D | E | A | C |
| 797 | B | E | B | E |
| 798 | B | E | E | E |
| 799 | B | E | B | E |
| 800 | B | E | B | E |
| 801 | C | E | B | E |
| 802 | E | E | E | E |
| 803 | E | E | B | E |
| 804 | E | E | E | E |
| 805 | E | E | E | C |
| 806 | B | E | B | B |
| 807 | E | E | E | C |
| 808 | E | E | E | E |
| 809 | E | E | E | B |
| 810 | E | E | E | E |
| 811 | E | E | E | E |
| 812 | D | E | B | D |
| 813 | E | E | E | B |
| 814 | E | E | E | E |
| 815 | D | E | E | E |
| 816 | E | E | E | C |
| 817 | E | E | E | E |
| 818 | E | E | E | E |
| 819 | E | E | E | E |
| 820 | E | E | E | D |
| 821 | B | B | B | B |
| 822 | D | C | E | B |
| 823 | B | D | D | B |
| 824 | A | B | B | A |
| 825 | A | C | D | B |
| 826 | A | E | B | B |
| 827 | B | B | B | B |
| 828 | E | E | E | E |
| 829 | A | E | E | E |
| 830 | B | E | E | E |
| 831 | E | E | E | E |
| 832 | B | E | E | E |
| 833 | A | E | A | E |
| 834 | B | E | E | E |
| 835 | E | E | E | E |
| 836 | E | E | E | E |
| 837 | E | E | E | E |
| 383 | A | E | E | E |
| 839 | E | E | E | E |
| 840 | C | E | E | E |
| 841 | E | E | E | E |
| 842 | B | D | E | E |
| 843 | A | E | A | E |
| 844 | A | E | E | E |
| 845 | A | E | B | E |
| 846 | B | E | B | E |
| 847 | E | E | E | E |
| 848 | A | E | D | E |
| 849 | A | E | E | E |
| 850 | B | E | E | E |
| 851 | E | E | E | E |
| 667 | E | E | E | E |
| 668 | C | E | C | E |
| 669 | B | E | B | E |
| 670 | B | E | B | E |
| 671 | B | E | D | D |
| 633 | D | E | B | E |
| 634 | A | E | B | E |
| 1013 | A | C | B | B |
| 1008 | B | E | B | B |
| 635 | A | D | C | E |
| 636 | A | E | A | E |
| 637 | B | E | B | E |
| 960 | A | E | B | B |
| 961 | B | E | C | C |
| 991 | C | D | C | C |
| 992 | B | B | A | B |
| 993 | B | E | A | C |
| 962 | A | E | B | E |
| 963 | A | D | B | C |
| 964 | A | E | C | D |
| 672 | E | E | E | E |
| 673 | C | D | C | E |
| 674 | B | E | B | E |
| 675 | B | E | B | E |
| 1092 | A | E | E | E |
| 1093 | A | E | B | C |
| 1094 | A | C | E | E |
| 1095 | A | E | E | E |
| 1096 | B | E | B | C |
| 1097 | B | C | B | E |
| 1098 | B | E | B | B |
| 638 | D | E | E | E |
| 994 | E | E | E | E |
| 639 | A | E | B | E |
| 995 | C | E | E | D |
| 996 | E | E | E | E |
| 997 | E | E | E | E |
| 965 | A | E | B | C |
| 966 | B | E | C | E |
| 967 | A | E | A | D |
| 968 | A | E | E | E |
| 1010 | B | E | B | C |
| 1099 | A | E | B | E |

TABLE 3-continued

| Compound Number | KDR-1 | Zap-1 | Lck-1 | Itk-1 |
|---|---|---|---|---|
| 1100 | A | E | D | E |
| 1101 | A | E | C | C |
| 1102 | A | D | E | E |
| 1103 | A | D | B | E |
| 1104 | A | E | E | E |
| 1105 | A | E | E | E |
| 1106 | B | E | E | E |
| 1104 | A | E | B | D |
| 1108 | A | C | C | C |
| 1127 | E | E | E | E |
| 1128 | B | E | B | B |
| 1109 | A | C | B | A |
| 722 | A | E | B | A |
| 1054/1055 | B | E | E | E |
| 1056/1057 | A | E | B | E |
| 1058/1059 | A | E | B | E |
| 1060/1061 | A | E | E | E |
| 1062/1063 | A | E | B | E |
| 1064/1065 | A | E | B | E |
| 640 | B | E | B | E |
| 641 | B | E | B | E |
| 642 | B | E | A | B |
| 853 | E | E | E | E |
| 854 | E | E | E | E |
| 855 | E | E | E | E |
| 856 | E | E | E | E |
| 857 | E | E | E | E |
| 858 | E | E | E | E |
| 859 | C | B | E | B |
| 860 | C | E | E | E |
| 861 | E | E | E | E |
| 862 | E | E | E | E |
| 863 | B | E | B | E |
| 864 | B | E | E | E |
| 865 | C | E | B | E |
| 866 | B | E | C | E |
| 867 | D | E | B | E |
| 723 | B | B | B | D |
| 134 | A | B | B | A |
| 676 | B | E | B | B |
| 677 | A | E | B | C |
| 1110 | C | E | A | E |
| 1111 | A | E | A | E |
| 1112 | A | E | B | D |
| 1113 | B | B | C | E |
| 1114 | B | D | B | D |
| 1115 | A | E | B | E |
| 1116 | C | E | B | E |
| 1117 | A | E | E | E |
| 1066 | C | E | E | E |
| 1067 | A | E | E | E |
| 1068 | A | E | E | E |
| 868 | E | E | E | B |
| 869 | D | E | E | C |
| 870 | E | E | E | E |
| 871 | E | E | E | C |
| 872 | B | E | E | B |
| 873 | E | E | E | E |
| 874 | E | E | E | E |
| 875 | C | E | E | D |
| 876 | E | E | E | D |
| 877 | E | E | E | B |
| 878 | E | E | E | D |
| 879 | E | E | E | D |
| 880 | C | E | E | E |
| 881 | B | E | E | B |
| 882 | B | E | C | B |
| 883 | E | E | E | E |
| 884 | A | C | E | B |
| 885 | A | C | E | B |
| 886 | A | B | B | A |
| 887 | A | E | B | C |
| 888 | A | E | C | A |
| 889 | B | E | E | B |
| 890 | D | E | E | E |
| 891 | A | B | C | B |
| 892 | B | E | B | D |

TABLE 3-continued

| Compound Number | KDR-1 | Zap-1 | Lck-1 | Itk-1 |
|---|---|---|---|---|
| 893 | E | E | E | E |
| 894 | B | E | E | D |
| 895 | B | E | B | B |
| 896 | C | E | E | C |
| 897 | E | E | E | C |
| 898 | E | E | E | E |
| 899 | B | E | B | B |
| 900 | A | C | B | B |
| 901 | B | E | B | B |
| 902 | E | E | E | E |
| 903 | E | E | E | E |
| 904 | C | E | B | D |
| 905 | B | E | E | B |
| 906 | B | E | E | E |
| 907 | E | E | E | E |
| 678 | B | E | B | B |
| 643 | B | E | E | E |
| 644 | B | E | E | D |
| 724 | B | E | B | B |
| 645 | E | E | E | E |
| 1069 | A | E | E | E |
| 1070 | B | E | E | E |
| 1071 | D | E | D | B |
| 679 | D | E | B | E |
| 1125 | B | E | A | A |
| 1126 | C | E | A | B |

TABLE 4

| Compound Number | PDGFRB-1 | Tek-1 | ErbB2-2 |
|---|---|---|---|
| 1021 | ND | E | ND |
| 1024 | ND | E | ND |
| 1025 | ND | E | ND |
| 970 | C | E | ND |
| 36 | A | D | ND |
| 182 | E | ND | ND |
| 11 | ND | E | ND |
| 12 | ND | E | ND |
| 13 | ND | E | ND |
| 14 | ND | E | ND |
| 15 | ND | E | ND |
| 18 | ND | E | ND |
| 19 | ND | E | ND |
| 61 | A | ND | ND |
| 926 | A | D | ND |
| 29 | B | E | ND |
| 27 | E | ND | ND |
| 852 | D | ND | C |
| 63 | B | E | ND |
| 62 | ND | E | ND |
| 65 | A | E | ND |
| 64 | D | E | B |
| 67 | B | E | ND |
| 66 | E | C | ND |
| 68 | B | E | ND |
| 927 | ND | E | ND |
| 70 | A | E | ND |
| 928 | A | E | A |
| 232 | ND | E | ND |
| 77 | A | E | ND |
| 76 | ND | E | ND |
| 72 | A | E | B |
| 75 | E | E | ND |
| 74 | ND | E | ND |
| 33 | D | E | ND |
| 78 | A | E | ND |
| 79 | B | E | ND |
| 80 | ND | E | ND |
| 81 | ND | E | ND |
| 82 | A | E | ND |
| 83 | A | D | A |
| 289 | A | B | E |
| 86 | B | E | B |

TABLE 4-continued

| Compound Number | PDGFRB-1 | Tek-1 | ErbB2-2 |
|---|---|---|---|
| 85 | A | E | ND |
| 88 | ND | E | ND |
| 87 | A | E | A |
| 90 | A | E | ND |
| 89 | A | E | ND |
| 91 | A | E | B |
| 92 | B | C | ND |
| 93 | ND | E | ND |
| 94 | B | E | ND |
| 95 | ND | E | ND |
| 96 | B | E | A |
| 97 | A | E | E |
| 98 | E | E | A |
| 99 | B | E | ND |
| 100 | ND | E | ND |
| 101 | ND | D | ND |
| 102 | C | C | B |
| 154 | ND | E | ND |
| 155 | ND | E | ND |
| 207 | E | E | ND |
| 251 | E | E | ND |
| 22 | ND | D | ND |
| 156 | D | E | B |
| 157 | ND | C | ND |
| 158 | ND | C | ND |
| 159 | ND | C | ND |
| 160 | ND | E | ND |
| 161 | ND | C | ND |
| 252 | B | E | ND |
| 256 | ND | E | ND |
| 103 | ND | E | ND |
| 104 | B | E | B |
| 105 | ND | E | ND |
| 106 | A | E | ND |
| 220 | ND | E | ND |
| 107 | B | E | ND |
| 108 | B | E | ND |
| 109 | E | E | C |
| 110 | A | E | A |
| 929 | E | E | ND |
| 111 | ND | E | ND |
| 114 | E | E | ND |
| 113 | ND | E | ND |
| 116 | E | E | ND |
| 115 | E | E | ND |
| 118 | ND | E | ND |
| 41 | B | D | ND |
| 117 | ND | E | ND |
| 119 | A | E | ND |
| 285 | E | E | E |
| 299 | ND | C | ND |
| 286 | B | B | ND |
| 184 | A | E | ND |
| 255 | ND | E | ND |
| 185 | A | E | E |
| 922 | B | B | ND |
| 186 | A | D | ND |
| 208 | ND | E | ND |
| 121 | A | E | ND |
| 123 | A | D | ND |
| 125 | A | E | ND |
| 127 | A | E | ND |
| 120 | A | C | B |
| 170 | E | C | ND |
| 171 | ND | E | ND |
| 287 | E | E | ND |
| 222 | ND | E | ND |
| 51 | ND | B | ND |
| 212 | ND | E | ND |
| 250 | ND | E | ND |
| 200 | B | E | ND |
| 218 | ND | E | ND |
| 187 | E | E | ND |
| 930 | A | E | B |
| 931 | A | D | B |
| 932 | ND | C | ND |
| 935 | A | E | ND |
| 1030 | B | E | ND |
| 174 | ND | E | ND |
| 175 | A | B | ND |
| 972 | A | D | ND |
| 609 | A | D | ND |
| 936 | A | E | ND |
| 937 | A | E | ND |
| 938 | B | E | ND |
| 135 | A | C | A |
| 226 | ND | D | ND |
| 973 | ND | E | ND |
| 291 | ND | D | ND |
| 292/293 | B | C | B |
| 294/295 | C | D | D |
| 296/297 | A | B | ND |
| 178 | C | C | A |
| 302 | E | E | ND |
| 300 | A | D | ND |
| 303 | ND | B | ND |
| 304 | A | E | B |
| 305 | A | E | ND |
| 196 | A | E | ND |
| 298 | A | B | ND |
| 306 | A | E | ND |
| 974 | E | E | ND |
| 56 | E | E | ND |
| 310 | ND | E | ND |
| 309 | ND | E | ND |
| 311 | E | E | ND |
| 312 | ND | E | ND |
| 313 | B | E | ND |
| 238 | B | E | ND |
| 239 | E | E | ND |
| 198 | A | E | ND |
| 237 | E | E | ND |
| 240 | A | E | ND |
| 314 | B | B | ND |
| 315 | B | E | ND |
| 316 | A | E | ND |
| 317 | ND | D | ND |
| 318 | A | C | ND |
| 308 | A | C | ND |
| 320 | E | E | ND |
| 319 | E | E | ND |
| 321 | B | E | B |
| 322 | ND | E | ND |
| 323 | A | E | ND |
| 324 | E | B | ND |
| 328 | B | C | ND |
| 325 | A | E | ND |
| 337 | B | E | ND |
| 336 | A | E | ND |
| 335 | D | E | ND |
| 334 | B | E | ND |
| 339 | A | E | ND |
| 340 | D | D | ND |
| 342 | B | E | ND |
| 341 | A | E | ND |
| 344 | C | E | ND |
| 353 | A | E | ND |
| 364 | C | E | ND |
| 366 | ND | E | ND |
| 365 | C | E | ND |
| 367 | E | D | ND |
| 368 | ND | E | ND |
| 369 | ND | E | ND |
| 180 | D | E | ND |
| 372 | ND | E | ND |
| 373 | ND | B | ND |
| 371 | A | E | E |
| 374 | B | B | ND |
| 375 | ND | E | ND |
| 376 | A | B | C |
| 378 | B | D | ND |
| 377 | A | D | ND |
| 379 | ND | E | ND |
| 380 | A | E | ND |

TABLE 4-continued

| Compound Number | PDGFRB-1 | Tek-1 | ErbB2-2 |
|---|---|---|---|
| 383 | ND | C | ND |
| 384 | A | E | ND |
| 386 | B | E | ND |
| 385 | A | E | ND |
| 387 | A | E | ND |
| 388 | B | E | ND |
| 389 | ND | E | ND |
| 390 | B | C | ND |
| 394 | B | E | ND |
| 396 | B | B | ND |
| 395 | B | B | ND |
| 397 | A | E | ND |
| 398 | ND | D | ND |
| 399 | ND | E | ND |
| 400 | E | E | ND |
| 402 | ND | E | ND |
| 401 | A | B | ND |
| 403 | A | E | ND |
| 404 | A | E | ND |
| 406 | B | E | ND |
| 405 | ND | E | ND |
| 407 | A | E | ND |
| 412 | C | E | ND |
| 411 | A | E | ND |
| 413 | A | E | ND |
| 414 | A | E | E |
| 416 | A | E | ND |
| 415 | A | E | ND |
| 417 | A | E | ND |
| 418 | ND | D | ND |
| 422 | ND | D | ND |
| 425 | B | E | ND |
| 427 | ND | E | ND |
| 428 | B | E | B |
| 202 | A | C | ND |
| 429 | A | D | ND |
| 430 | B | B | ND |
| 432 | ND | E | ND |
| 431 | ND | C | ND |
| 437 | A | C | ND |
| 438 | ND | B | ND |
| 439 | A | B | ND |
| 440 | B | C | ND |
| 441 | A | E | ND |
| 442 | ND | E | ND |
| 443 | B | E | ND |
| 444 | ND | E | ND |
| 445 | A | D | ND |
| 462 | ND | C | ND |
| 464 | ND | E | ND |
| 463 | A | E | ND |
| 465 | ND | E | ND |
| 466 | A | D | ND |
| 467 | ND | C | ND |
| 473 | ND | E | D |
| 474 | B | B | B |
| 476 | ND | E | C |
| 478 | ND | B | ND |
| 479 | C | E | C |
| 480 | ND | B | ND |
| 483 | ND | B | ND |
| 492 | ND | C | ND |
| 491 | ND | B | ND |
| 493 | ND | C | ND |
| 494 | ND | E | ND |
| 495 | ND | E | ND |
| 923 | ND | E | ND |
| 497 | ND | E | ND |
| 498 | A | D | B |
| 504 | ND | B | ND |
| 505 | ND | C | ND |
| 506 | ND | C | ND |
| 508 | ND | C | ND |
| 507 | ND | D | ND |
| 509 | B | D | C |
| 510 | C | E | E |
| 511 | A | D | D |
| 512 | A | E | C |
| 513 | A | E | D |
| 514 | A | E | E |
| 515 | A | D | E |
| 516 | D | E | E |
| 517 | B | C | C |
| 518 | E | D | B |
| 519 | A | E | E |
| 520 | E | E | E |
| 522 | C | D | D |
| 521 | ND | E | B |
| 523 | E | E | D |
| 524 | ND | E | C |
| 526 | ND | B | ND |
| 525 | ND | C | ND |
| 528 | ND | B | ND |
| 977 | E | E | B |
| 978 | E | E | B |
| 979 | ND | E | ND |
| 980 | ND | E | ND |
| 610 | A | C | B |
| 689 | ND | C | ND |
| 1031 | A | E | B |
| 1033 | A | E | D |
| 1034 | ND | E | ND |
| 1035 | ND | E | ND |
| 1036 | A | C | B |
| 1037 | E | E | E |
| 700 | B | B | ND |
| 646 | ND | E | ND |
| 611 | ND | C | ND |
| 230 | ND | D | ND |
| 612 | B | B | B |
| 940 | ND | E | ND |
| 941 | ND | E | ND |
| 942 | A | E | E |
| 943 | A | D | E |
| 944 | B | E | E |
| 1000 | ND | E | C |
| 1001 | ND | E | B |
| 1002 | ND | E | ND |
| 1003 | ND | B | ND |
| 945 | ND | E | ND |
| 946 | A | E | E |
| 947 | ND | E | ND |
| 948 | ND | E | ND |
| 949 | A | E | E |
| 981 | B | B | B |
| 982 | ND | B | ND |
| 983 | B | C | E |
| 984 | ND | E | ND |
| 1075 | ND | E | ND |
| 1076 | A | E | E |
| 1077 | A | E | E |
| 1078 | ND | E | ND |
| 647 | ND | E | ND |
| 1038 | ND | E | ND |
| 177 | A | B | A |
| 690 | ND | E | ND |
| 648 | ND | E | ND |
| 649 | B | C | ND |
| 650 | B | D | ND |
| 651 | B | C | ND |
| 652 | B | B | C |
| 691 | A | E | E |
| 985 | ND | C | ND |
| 986 | ND | D | ND |
| 613 | A | E | A |
| 614 | B | D | B |
| 950 | A | C | B |
| 1082 | B | B | E |
| 653 | ND | E | ND |
| 654 | B | B | B |
| 655 | B | C | B |
| 656 | B | B | C |
| 657 | C | B | B |
| 615 | E | E | E |

TABLE 4-continued

| Compound Number | PDGFRB-1 | Tek-1 | ErbB2-2 |
|---|---|---|---|
| 658 | E | E | E |
| 951 | A | C | E |
| 952 | B | C | C |
| 692 | A | B | A |
| 693 | ND | E | ND |
| 694 | ND | D | ND |
| 695 | ND | C | ND |
| 696 | ND | E | ND |
| 697 | A | D | B |
| 698 | ND | D | ND |
| 699 | A | D | A |
| 616 | A | B | B |
| 1004 | B | B | B |
| 1083 | B | B | E |
| 1084 | B | E | E |
| 1085 | B | E | E |
| 953 | A | B | B |
| 954 | E | E | C |
| 1086 | E | D | D |
| 1087 | C | E | E |
| 1088 | A | E | E |
| 1089 | A | E | E |
| 1040 | A | E | C |
| 1041 | A | B | A |
| 659 | E | ND | E |
| 660 | E | ND | C |
| 661 | E | ND | E |
| 599 | B | ND | C |
| 600 | B | ND | C |
| 601 | B | ND | B |
| 602 | B | ND | B |
| 604 | B | ND | B |
| 603 | B | ND | A |
| 617 | B | ND | E |
| 606 | B | ND | D |
| 605 | A | ND | E |
| 598 | E | ND | D |
| 597 | C | ND | B |
| 607 | B | ND | B |
| 559 | A | ND | A |
| 592 | A | ND | B |
| 591 | A | ND | C |
| 1042 | A | ND | E |
| 593 | B | ND | C |
| 596 | C | ND | B |
| 595 | D | ND | B |
| 1043 | C | ND | B |
| 1044 | D | ND | B |
| 618 | B | ND | C |
| 579 | E | ND | C |
| 579 | E | ND | A |
| 414 | A | ND | E |
| 589 | E | ND | C |
| 583 | B | ND | E |
| 584 | E | ND | C |
| 619 | E | ND | D |
| 620 | E | ND | D |
| 581 | C | ND | E |
| 582 | E | ND | B |
| 585 | B | ND | C |
| 584 | E | ND | B |
| 1045 | B | ND | E |
| 587 | B | ND | B |
| 662 | E | ND | C |
| 663 | E | ND | E |
| 664 | D | ND | B |
| 587 | E | ND | C |
| 573 | B | ND | C |
| 569 | A | ND | E |
| 571 | E | ND | C |
| 1046 | E | ND | E |
| 574 | A | ND | E |
| 572 | A | ND | D |
| 588 | B | ND | B |
| 561 | A | ND | E |
| 577 | B | ND | D |
| 578 | B | ND | B |
| 562 | C | ND | C |
| 563 | B | ND | B |
| 565 | B | ND | E |
| 564 | A | ND | E |
| 566 | B | ND | A |
| 549 | A | ND | B |
| 567 | B | ND | C |
| 621 | B | ND | A |
| 1047 | E | ND | E |
| 551 | E | ND | E |
| 552 | E | ND | E |
| 554 | D | ND | C |
| 553 | B | ND | B |
| 622 | D | ND | C |
| 555 | B | ND | B |
| 557 | A | ND | A |
| 556 | A | ND | A |
| 576 | E | ND | E |
| 558 | B | ND | D |
| 701 | E | ND | E |
| 702 | E | ND | E |
| 703 | E | ND | D |
| 530 | E | ND | E |
| 704 | E | ND | E |
| 665 | E | ND | B |
| 539 | D | ND | B |
| 546 | B | ND | C |
| 540 | D | ND | B |
| 542 | B | ND | B |
| 544 | B | ND | E |
| 541 | B | ND | A |
| 543 | B | ND | B |
| 545 | A | ND | D |
| 547 | E | ND | E |
| 548 | E | ND | E |
| 1007 | E | ND | B |
| 531 | A | ND | A |
| 623 | A | ND | B |
| 533 | B | ND | E |
| 534 | B | ND | E |
| 535 | C | ND | A |
| 536 | B | ND | B |
| 537 | B | ND | B |
| 538 | B | ND | B |
| 666 | D | ND | B |
| 988 | E | ND | B |
| 989 | E | ND | E |
| 990 | E | ND | E |
| 955 | B | ND | B |
| 705 | E | ND | B |
| 706 | C | ND | A |
| 707 | E | ND | E |
| 708 | E | ND | E |
| 709 | C | ND | B |
| 1048 | D | ND | B |
| 1049 | B | ND | E |
| 1050 | B | ND | C |
| 1051 | B | ND | B |
| 1052 | C | ND | C |
| 1005 | E | ND | E |
| 624 | B | ND | A |
| 625 | A | ND | A |
| 626 | B | ND | E |
| 627 | A | ND | B |
| 956 | C | ND | E |
| 710 | B | ND | A |
| 711 | E | ND | E |
| 712 | B | ND | A |
| 713 | E | ND | E |
| 1006 | E | ND | C |
| 628 | B | ND | E |
| 629 | A | ND | B |
| 957 | A | ND | A |
| 958 | B | ND | B |
| 959 | B | ND | C |
| 1053 | A | ND | E |
| 1090 | A | ND | E |

TABLE 4-continued

| Compound Number | PDGFRB-1 | Tek-1 | ErbB2-2 |
|---|---|---|---|
| 1091 | A | ND | B |
| 630 | B | ND | C |
| 714 | B | ND | A |
| 715 | B | ND | B |
| 716 | A | ND | A |
| 717 | A | ND | B |
| 718 | C | ND | E |
| 719 | E | ND | C |
| 631 | A | ND | B |
| 632 | B | ND | B |
| 720 | B | ND | A |
| 721 | B | ND | B |
| 1009 | D | ND | E |
| 1011 | B | ND | B |
| 1012 | B | ND | C |
| 726 | E | ND | E |
| 727 | E | ND | E |
| 728 | E | ND | E |
| 729 | B | ND | B |
| 730 | B | ND | B |
| 731 | B | ND | A |
| 732 | E | ND | E |
| 733 | E | ND | E |
| 734 | E | ND | C |
| 735 | E | ND | B |
| 736 | B | ND | B |
| 737 | C | ND | B |
| 738 | E | ND | C |
| 739 | E | ND | E |
| 740 | E | ND | E |
| 741 | C | ND | B |
| 742 | E | ND | E |
| 743 | E | ND | E |
| 744 | E | ND | E |
| 745 | E | ND | E |
| 746 | E | ND | E |
| 747 | E | ND | E |
| 748 | B | ND | B |
| 749 | B | ND | B |
| 750 | E | ND | C |
| 751 | B | ND | E |
| 752 | E | ND | E |
| 753 | B | ND | B |
| 754 | E | ND | E |
| 755 | E | ND | E |
| 756 | B | ND | E |
| 757 | E | ND | E |
| 758 | A | ND | A |
| 759 | E | ND | E |
| 760 | B | ND | B |
| 761 | E | ND | E |
| 762 | E | ND | E |
| 763 | C | ND | B |
| 764 | A | ND | E |
| 765 | E | ND | E |
| 766 | B | ND | B |
| 767 | E | ND | E |
| 768 | E | ND | D |
| 769 | E | ND | E |
| 770 | A | ND | A |
| 771 | E | ND | E |
| 772 | D | ND | E |
| 773 | A | ND | B |
| 774 | A | ND | A |
| 775 | E | ND | E |
| 776 | E | ND | E |
| 777 | E | ND | E |
| 778 | E | ND | C |
| 779 | E | ND | E |
| 780 | D | ND | E |
| 781 | B | ND | E |
| 782 | C | ND | E |
| 783 | C | ND | C |
| 784 | E | ND | E |
| 785 | E | ND | E |
| 786 | E | ND | E |
| 787 | E | ND | E |
| 788 | D | ND | E |
| 789 | C | ND | ND |
| 790 | D | ND | B |
| 791 | E | ND | C |
| 792 | E | ND | C |
| 793 | E | ND | ND |
| 794 | B | ND | B |
| 795 | A | ND | A |
| 796 | B | ND | C |
| 797 | C | ND | B |
| 798 | B | ND | E |
| 799 | B | ND | B |
| 800 | E | ND | B |
| 801 | B | ND | D |
| 802 | B | ND | E |
| 803 | E | ND | C |
| 804 | D | ND | E |
| 805 | E | ND | E |
| 806 | E | ND | B |
| 807 | E | ND | B |
| 808 | B | ND | E |
| 809 | D | ND | D |
| 810 | E | ND | E |
| 811 | E | ND | E |
| 812 | E | ND | C |
| 813 | B | ND | E |
| 814 | B | ND | E |
| 815 | B | ND | B |
| 816 | A | ND | C |
| 817 | B | ND | B |
| 818 | B | ND | E |
| 819 | B | ND | E |
| 820 | E | ND | E |
| 821 | B | ND | B |
| 822 | B | ND | C |
| 823 | B | ND | C |
| 824 | A | ND | A |
| 825 | B | ND | B |
| 826 | B | ND | B |
| 827 | B | ND | A |
| 828 | E | ND | E |
| 829 | B | ND | B |
| 830 | E | ND | E |
| 831 | A | ND | E |
| 832 | E | ND | E |
| 833 | A | ND | E |
| 834 | A | ND | E |
| 835 | E | ND | E |
| 836 | E | ND | E |
| 837 | E | ND | E |
| 383 | A | ND | C |
| 839 | C | ND | B |
| 840 | B | ND | B |
| 841 | E | ND | E |
| 842 | C | ND | D |
| 843 | A | ND | D |
| 844 | B | ND | B |
| 845 | B | ND | C |
| 846 | B | ND | C |
| 847 | E | ND | E |
| 848 | A | ND | E |
| 849 | B | ND | B |
| 850 | E | ND | E |
| 851 | E | ND | E |
| 667 | E | ND | B |
| 668 | D | ND | A |
| 669 | B | ND | A |
| 670 | B | ND | A |
| 671 | B | ND | A |
| 633 | C | ND | B |
| 634 | D | ND | B |
| 1013 | A | ND | B |
| 1008 | E | ND | E |
| 635 | B | ND | A |
| 636 | A | ND | B |
| 637 | C | ND | C |
| 960 | D | ND | C |

TABLE 4-continued

| Compound Number | PDGFRB-1 | Tek-1 | ErbB2-2 |
|---|---|---|---|
| 961 | D | ND | A |
| 991 | B | ND | B |
| 992 | B | ND | B |
| 993 | B | ND | B |
| 962 | A | ND | D |
| 963 | A | ND | B |
| 964 | A | ND | C |
| 672 | C | ND | D |
| 673 | B | ND | C |
| 674 | B | ND | B |
| 675 | B | ND | A |
| 1092 | A | ND | E |
| 1093 | A | ND | E |
| 1094 | A | ND | C |
| 1095 | A | ND | E |
| 1096 | A | ND | E |
| 1097 | A | ND | E |
| 1098 | B | ND | E |
| 638 | B | ND | D |
| 994 | E | ND | E |
| 639 | A | ND | C |
| 995 | B | ND | E |
| 996 | E | ND | E |
| 997 | E | ND | E |
| 965 | A | ND | B |
| 966 | A | ND | E |
| 967 | A | ND | B |
| 968 | A | ND | C |
| 1010 | B | ND | B |
| 1099 | A | ND | B |
| 1100 | A | ND | B |
| 1101 | A | ND | E |
| 1102 | A | ND | E |
| 1103 | A | ND | D |
| 1104 | A | ND | E |
| 1105 | A | ND | E |
| 1106 | B | ND | E |
| 1104 | A | ND | B |
| 1108 | A | ND | E |
| 1127 | E | ND | E |
| 1128 | E | ND | B |
| 1109 | A | ND | B |
| 722 | B | ND | B |
| 1054/1055 | ND | ND | E |
| 1056/1057 | ND | ND | B |
| 1058/1059 | ND | ND | E |
| 1060/1061 | ND | ND | E |
| 1062/1063 | ND | ND | C |
| 1064/1065 | ND | ND | E |
| 640 | ND | ND | A |
| 641 | ND | ND | B |
| 642 | ND | ND | B |
| 856 | ND | ND | B |
| 857 | ND | ND | C |
| 858 | ND | ND | E |
| 859 | ND | ND | B |
| 860 | ND | ND | D |
| 861 | ND | ND | C |
| 862 | ND | ND | E |
| 863 | ND | ND | C |
| 864 | ND | ND | E |
| 865 | ND | ND | B |
| 723 | ND | ND | A |
| 134 | ND | ND | B |
| 676 | ND | ND | A |
| 677 | ND | ND | A |
| 1110 | ND | ND | E |
| 1111 | ND | ND | C |
| 1112 | ND | ND | B |
| 1113 | ND | ND | B |
| 1067 | ND | ND | B |
| 1068 | ND | ND | C |
| 868 | B | ND | E |
| 869 | B | ND | D |
| 870 | E | ND | E |
| 871 | D | ND | E |
| 872 | B | ND | B |
| 873 | E | ND | E |
| 874 | E | ND | E |
| 875 | B | ND | B |
| 876 | E | ND | B |
| 877 | B | ND | E |
| 878 | B | ND | E |
| 879 | B | ND | E |
| 880 | B | ND | C |
| 881 | B | ND | B |
| 882 | B | ND | B |
| 883 | C | ND | E |
| 884 | A | ND | B |
| 885 | B | ND | B |
| 886 | E | ND | B |
| 887 | B | ND | B |
| 888 | B | ND | B |
| 889 | B | ND | B |
| 890 | B | ND | E |
| 891 | A | ND | A |
| 892 | A | ND | B |
| 893 | B | ND | E |
| 894 | A | ND | E |
| 895 | A | ND | C |
| 896 | A | ND | B |
| 897 | A | ND | E |
| 898 | D | ND | E |
| 899 | A | ND | B |
| 900 | B | ND | A |
| 901 | A | ND | B |
| 902 | E | ND | B |
| 903 | C | ND | C |
| 904 | B | ND | B |
| 905 | B | ND | B |
| 906 | E | ND | B |
| 907 | E | ND | B |
| 678 | A | ND | A |
| 643 | A | ND | B |
| 644 | B | ND | E |
| 724 | B | ND | B |
| 645 | E | ND | A |
| 1069 | A | ND | A |
| 1070 | B | ND | E |
| 1071 | B | ND | E |
| 679 | D | ND | C |
| 1125 | B | ND | B |
| 1126 | B | ND | B |

TABLE 5

| Compound Number | EPHB4-1 | ErbB4-1 | FGFR1-1 | Flt-1 | Fyn-1 |
|---|---|---|---|---|---|
| 970 | E | ND | E | C | D |
| 36 | D | ND | E | A | E |
| 182 | ND | ND | E | E | ND |
| 61 | A | E | E | A | A |
| 926 | E | E | B | B | C |
| 29 | E | B | A | A | A |
| 27 | E | ND | B | A | B |
| 28 | B | ND | ND | ND | B |
| 852 | E | E | E | E | E |
| 62 | E | E | ND | ND | ND |
| 40 | E | ND | ND | ND | ND |
| 39 | E | ND | ND | ND | ND |
| 65 | C | E | E | B | E |
| 64 | B | E | E | E | B |
| 67 | C | ND | E | D | D |
| 66 | D | ND | E | E | E |
| 69 | E | ND | ND | ND | ND |
| 68 | B | E | E | A | E |
| 927 | E | ND | ND | ND | ND |
| 70 | B | B | B | A | E |
| 928 | A | B | B | A | E |
| 232 | E | ND | ND | ND | E |
| 1118 | E | ND | ND | ND | ND |

TABLE 5-continued

| Compound Number | EPHB4-1 | ErbB4-1 | FGFR1-1 | Flt-1 | Fyn-1 |
|---|---|---|---|---|---|
| 77 | B | ND | B | B | B |
| 73 | E | ND | ND | ND | ND |
| 76 | B | ND | ND | ND | B |
| 72 | B | B | A | A | ND |
| 75 | A | E | D | E | B |
| 74 | A | E | ND | ND | E |
| 33 | E | ND | C | E | C |
| 78 | A | B | A | A | A |
| 79 | A | B | C | B | B |
| 80 | E | ND | ND | ND | ND |
| 81 | E | ND | ND | ND | ND |
| 82 | B | ND | B | A | ND |
| 83 | B | B | A | A | A |
| 289 | B | E | A | A | B |
| 86 | E | B | E | E | D |
| 85 | B | B | A | A | A |
| 88 | B | ND | ND | ND | B |
| 87 | E | D | C | D | B |
| 90 | B | ND | B | B | A |
| 89 | E | ND | E | A | B |
| 91 | C | ND | C | A | A |
| 92 | C | ND | C | C | E |
| 93 | E | ND | ND | ND | ND |
| 94 | B | B | E | D | A |
| 95 | D | ND | ND | ND | B |
| 96 | E | B | E | D | D |
| 97 | E | E | C | C | C |
| 98 | E | E | C | E | B |
| 99 | A | ND | B | B | B |
| 100 | B | ND | ND | ND | ND |
| 101 | E | ND | ND | ND | B |
| 102 | A | A | B | A | A |
| 154 | D | ND | ND | ND | ND |
| 155 | E | ND | ND | ND | ND |
| 207 | E | ND | E | B | ND |
| 251 | E | ND | E | D | E |
| 22 | E | ND | ND | ND | ND |
| 156 | E | C | B | C | C |
| 157 | B | E | ND | ND | ND |
| 158 | B | ND | ND | ND | ND |
| 159 | C | E | ND | ND | ND |
| 253 | E | ND | ND | ND | E |
| 221 | B | ND | ND | ND | ND |
| 252 | B | ND | B | A | B |
| 256 | E | ND | ND | ND | ND |
| 103 | B | ND | ND | ND | ND |
| 104 | A | ND | E | B | B |
| 105 | E | ND | ND | ND | ND |
| 106 | B | C | B | A | ND |
| 220 | E | ND | ND | ND | ND |
| 107 | B | C | B | A | A |
| 108 | E | D | B | E | B |
| 109 | E | E | ND | ND | ND |
| 110 | D | B | A | A | A |
| 929 | E | B | E | E | ND |
| 111 | E | E | ND | ND | ND |
| 114 | E | ND | E | E | ND |
| 113 | C | ND | ND | ND | ND |
| 116 | E | E | E | E | E |
| 115 | D | E | C | B | C |
| 118 | B | E | ND | ND | ND |
| 41 | B | E | C | B | B |
| 117 | D | ND | ND | ND | ND |
| 119 | E | B | B | A | A |
| 285 | E | E | D | E | E |
| 299 | E | ND | ND | ND | ND |
| 286 | C | ND | A | A | E |
| 184 | C | ND | C | A | B |
| 255 | E | ND | ND | ND | ND |
| 185 | E | E | E | B | E |
| 922 | C | A | B | C | B |
| 186 | E | E | E | B | E |
| 208 | E | ND | ND | ND | ND |
| 121 | E | B | B | A | A |
| 123 | E | B | B | A | B |
| 125 | E | D | B | A | B |
| 127 | D | B | B | A | A |
| 120 | B | B | B | B | B |
| 170 | C | D | E | E | E |
| 171 | C | E | ND | ND | ND |
| 287 | E | E | B | E | E |
| 222 | E | ND | ND | ND | ND |
| 51 | B | C | ND | ND | ND |
| 212 | E | ND | ND | ND | ND |
| 250 | E | B | ND | ND | ND |
| 200 | E | C | D | E | E |
| 218 | E | ND | ND | ND | ND |
| 187 | E | C | E | E | E |
| 930 | C | B | C | C | A |
| 931 | B | B | B | A | A |
| 932 | E | B | ND | ND | ND |
| 933 | C | B | ND | ND | ND |
| 934 | B | E | ND | ND | ND |
| 935 | B | B | B | B | A |
| 1030 | B | E | C | B | B |
| 174 | E | ND | ND | ND | ND |
| 175 | B | E | E | C | B |
| 972 | B | B | B | B | B |
| 609 | E | E | A | A | A |
| 936 | A | B | B | B | A |
| 937 | B | C | E | D | B |
| 938 | E | C | B | B | E |
| 135 | A | C | B | E | A |
| 226 | E | ND | ND | ND | ND |
| 973 | C | ND | ND | ND | ND |
| 291 | D | ND | ND | ND | ND |
| 292 | B | E | D | B | C |
| 294 | B | E | E | E | E |
| 296 | A | D | B | B | C |
| 178 | C | E | D | D | B |
| 302 | E | E | B | E | E |
| 300 | B | B | C | E | B |
| 303 | D | ND | ND | ND | ND |
| 304 | B | A | B | B | A |
| 305 | B | B | B | B | A |
| 196 | E | E | C | B | E |
| 298 | B | B | A | A | B |
| 306 | B | E | B | B | B |
| 974 | E | E | C | E | E |
| 56 | E | E | C | C | E |
| 310 | E | ND | ND | ND | ND |
| 309 | E | ND | ND | ND | ND |
| 311 | E | E | E | E | E |
| 312 | E | ND | ND | ND | ND |
| 313 | B | A | B | C | B |
| 238 | E | E | E | E | E |
| 239 | E | E | E | E | E |
| 198 | E | E | E | B | E |
| 237 | D | E | C | D | E |
| 240 | E | E | C | B | B |
| 314 | E | B | C | B | B |
| 315 | E | B | E | E | E |
| 316 | D | E | E | D | D |
| 317 | C | ND | ND | ND | ND |
| 318 | A | A | B | A | A |
| 308 | A | B | A | A | A |
| 320 | E | E | E | E | E |
| 319 | E | E | E | E | E |
| 321 | E | E | E | E | E |
| 322 | E | ND | ND | ND | ND |
| 323 | E | ND | E | C | E |
| 324 | E | ND | A | A | E |
| 328 | E | ND | B | A | C |
| 325 | E | B | E | A | C |
| 338 | C | ND | ND | ND | ND |
| 337 | B | B | A | A | B |
| 336 | E | E | A | A | E |
| 335 | B | E | D | B | E |
| 334 | C | E | B | B | E |
| 332 | B | ND | ND | ND | ND |
| 330 | C | ND | ND | ND | ND |
| 339 | E | E | E | E | E |
| 340 | B | B | B | A | B |
| 342 | B | B | A | A | B |

TABLE 5-continued

| Compound Number | EPHB4-1 | ErbB4-1 | FGFR1-1 | Flt-1 | Fyn-1 |
|---|---|---|---|---|---|
| 341 | B | E | A | A | E |
| 344 | B | E | A | C | E |
| 343 | B | ND | ND | ND | ND |
| 353 | E | E | B | A | D |
| 364 | B | E | B | B | E |
| 366 | B | ND | ND | ND | ND |
| 365 | B | C | B | B | B |
| 367 | B | E | C | B | B |
| 368 | E | ND | ND | ND | ND |
| 369 | E | ND | ND | ND | ND |
| 180 | E | E | E | E | C |
| 372 | E | ND | ND | ND | ND |
| 373 | E | ND | ND | ND | ND |
| 371 | A | E | A | A | A |
| 374 | A | B | A | B | B |
| 375 | E | ND | ND | ND | ND |
| 376 | D | D | A | A | B |
| 378 | E | E | A | B | C |
| 377 | B | E | A | A | E |
| 379 | E | ND | ND | ND | ND |
| 380 | E | B | A | A | B |
| 382 | E | ND | ND | ND | ND |
| 381 | B | ND | ND | ND | ND |
| 383 | E | ND | ND | ND | ND |
| 384 | B | E | B | E | B |
| 386 | E | E | A | A | E |
| 385 | E | E | A | A | E |
| 387 | E | E | B | A | E |
| 388 | E | E | C | E | E |
| 390 | E | D | C | B | B |
| 394 | C | E | B | A | B |
| 396 | B | B | A | A | B |
| 395 | E | E | A | A | C |
| 397 | ND | E | A | A | E |
| 400 | ND | E | E | B | E |
| 401 | ND | B | A | A | B |
| 403 | ND | E | A | B | B |
| 404 | ND | E | A | A | B |
| 406 | ND | E | A | C | B |
| 407 | ND | E | A | A | A |
| 412 | ND | E | E | E | E |
| 411 | ND | E | A | B | E |
| 413 | ND | E | A | B | B |
| 414 | ND | E | A | A | B |
| 416 | ND | E | A | B | D |
| 415 | ND | E | A | B | E |
| 417 | ND | E | A | B | C |
| 425 | ND | E | C | E | D |
| 428 | ND | B | C | E | B |
| 202 | ND | B | A | A | A |
| 429 | ND | B | A | A | B |
| 430 | ND | B | A | B | B |
| 437 | ND | B | A | A | B |
| 439 | ND | B | A | A | B |
| 440 | ND | B | B | B | B |
| 441 | ND | E | E | B | B |
| 443 | ND | B | B | B | C |
| 445 | ND | E | A | A | B |
| 463 | ND | E | A | A | A |
| 466 | ND | E | A | B | B |
| 479 | ND | D | B | B | E |
| 498 | ND | B | A | B | A |
| 509 | ND | B | B | B | E |
| 510 | ND | E | B | B | E |
| 511 | ND | B | A | A | E |
| 512 | ND | B | A | B | E |
| 513 | ND | C | A | A | D |
| 514 | ND | E | A | A | E |
| 515 | ND | E | A | B | E |
| 516 | ND | E | A | C | E |
| 517 | ND | B | A | A | C |
| 518 | ND | E | E | E | C |
| 519 | ND | E | A | B | E |
| 610 | ND | B | A | A | B |
| 1031 | ND | E | B | E | E |
| 1033 | ND | B | A | A | A |
| 1036 | ND | C | A | A | B |
| 1037 | ND | E | B | C | E |
| 612 | ND | B | A | A | B |
| 942 | ND | E | A | A | E |
| 943 | ND | D | B | B | E |
| 944 | ND | E | B | B | E |
| 946 | ND | E | A | B | E |
| 949 | ND | B | A | A | E |
| 1076 | ND | E | B | B | B |
| 1077 | ND | E | A | A | E |
| 177 | ND | A | C | B | A |
| 652 | ND | E | A | B | E |
| 613 | ND | B | B | E | E |
| 950 | ND | B | A | A | B |
| 1082 | ND | B | E | E | E |
| 655 | ND | C | B | A | E |
| 656 | ND | C | B | B | D |
| 951 | ND | E | A | E | E |
| 952 | ND | E | B | B | C |
| 616 | ND | B | B | B | B |
| 1084 | ND | E | E | E | E |
| 953 | ND | B | B | B | A |
| 1086 | ND | E | E | C | E |
| 1087 | ND | E | D | E | E |
| 1088 | ND | E | A | E | E |
| 1089 | ND | E | E | E | B |
| 1040 | ND | C | B | B | B |
| 1041 | ND | B | B | C | B |
| 600 | ND | B | E | B | B |
| 602 | ND | B | E | E | B |
| 603 | ND | D | B | B | B |
| 606 | ND | E | B | C | E |
| 605 | ND | E | A | B | E |
| 607 | ND | B | B | D | B |
| 559 | ND | A | B | E | A |
| 592 | ND | C | A | B | B |
| 591 | ND | D | A | A | A |
| 1042 | ND | E | A | B | E |
| 579 | ND | A | B | B | E |
| 582 | ND | E | B | E | E |
| 585 | ND | E | A | B | E |
| 587 | ND | B | A | B | E |

TABLE 6

| Compound Number | Hck-1 | Lyn-1 | Ret-1 | Src-1 |
|---|---|---|---|---|
| 970 | E | E | E | E |
| 36 | E | E | E | E |
| 61 | E | A | E | A |
| 926 | E | B | D | B |
| 29 | E | A | A | A |
| 27 | E | B | B | B |
| 28 | E | B | ND | B |
| 852 | E | E | C | E |
| 65 | E | B | B | B |
| 64 | E | A | E | A |
| 67 | E | A | E | B |
| 66 | E | B | E | A |
| 68 | E | A | B | A |
| 70 | E | B | B | A |
| 928 | E | A | A | A |
| 232 | E | E | ND | E |
| 77 | E | A | B | B |
| 76 | E | B | ND | A |
| 72 | ND | ND | A | ND |
| 75 | E | A | E | E |
| 74 | E | A | ND | B |
| 33 | E | B | E | B |
| 78 | B | A | A | A |
| 79 | E | A | A | A |
| 82 | ND | ND | B | ND |
| 83 | B | A | A | A |
| 289 | E | C | B | B |
| 86 | E | E | B | B |

TABLE 6-continued

| Compound Number | Hck-1 | Lyn-1 | Ret-1 | Src-1 |
|---|---|---|---|---|
| 85 | E | A | B | A |
| 88 | D | B | ND | B |
| 87 | E | B | B | B |
| 90 | B | A | B | B |
| 89 | E | B | B | C |
| 91 | E | B | B | B |
| 92 | E | B | E | D |
| 94 | E | A | E | B |
| 95 | E | C | ND | E |
| 96 | D | B | C | C |
| 97 | E | B | B | E |
| 98 | E | B | E | E |
| 99 | D | D | B | B |
| 101 | E | C | ND | B |
| 102 | C | A | B | A |
| 251 | E | B | E | E |
| 156 | E | C | E | E |
| 253 | E | E | ND | A |
| 221 | ND | ND | ND | ND |
| 252 | E | A | E | A |
| 104 | E | E | E | C |
| 106 | ND | ND | B | ND |
| 107 | D | A | B | A |
| 108 | E | A | ND | B |
| 110 | C | A | B | A |
| 929 | ND | ND | C | ND |
| 114 | ND | ND | B | ND |
| 116 | E | E | E | E |
| 115 | E | C | B | C |
| 41 | E | A | A | B |
| 119 | E | B | A | B |
| 285 | E | E | C | E |
| 286 | E | E | A | D |
| 184 | E | B | E | B |
| 185 | E | E | E | E |
| 922 | E | A | B | B |
| 186 | E | D | E | E |
| 121 | E | A | A | A |
| 123 | C | A | A | A |
| 125 | D | A | B | A |
| 127 | B | A | A | A |
| 120 | B | A | A | B |
| 170 | E | E | ND | E |
| 287 | E | E | E | E |
| 200 | E | E | E | E |
| 187 | E | E | E | E |
| 930 | C | A | B | A |
| 931 | B | A | A | A |
| 935 | C | A | ND | A |
| 1030 | E | B | A | B |
| 175 | E | C | C | B |
| 972 | E | A | ND | B |
| 609 | E | A | A | A |
| 936 | C | A | ND | A |
| 937 | E | A | A | B |
| 938 | E | E | E | E |
| 135 | E | A | B | A |
| 292 | E | B | B | B |
| 294 | E | E | B | E |
| 296 | E | B | A | B |
| 178 | E | A | C | B |
| 302 | E | E | E | E |
| 300 | E | A | B | A |
| 304 | C | A | A | A |
| 305 | C | A | A | A |
| 196 | E | C | E | E |
| 298 | B | A | A | B |
| 306 | D | A | A | B |
| 974 | E | C | E | E |
| 56 | E | B | E | E |
| 311 | E | E | E | E |
| 313 | C | A | B | A |
| 238 | E | E | E | E |
| 239 | E | E | E | E |
| 198 | E | E | E | E |
| 237 | E | C | C | E |
| 240 | E | B | C | D |
| 314 | C | A | E | B |
| 315 | E | E | E | E |
| 316 | E | B | B | D |
| 318 | B | A | A | A |
| 308 | B | A | A | A |
| 320 | E | E | E | E |
| 319 | E | E | E | E |
| 321 | E | A | B | B |
| 323 | E | E | E | E |
| 324 | E | E | A | E |
| 328 | C | B | B | B |
| 325 | E | D | E | E |
| 337 | E | B | A | B |
| 336 | E | B | A | E |
| 335 | E | B | A | C |
| 334 | E | E | B | E |
| 219 | ND | ND | ND | ND |
| 339 | E | E | A | E |
| 340 | E | B | A | E |
| 342 | C | B | A | E |
| 341 | E | E | A | E |
| 344 | E | E | B | E |
| 353 | E | E | A | E |
| 364 | E | D | B | E |
| 365 | E | A | ND | B |
| 367 | E | B | ND | B |
| 180 | E | B | ND | E |
| 371 | E | A | ND | B |
| 374 | D | A | ND | A |
| 376 | E | A | ND | E |
| 378 | E | B | ND | C |
| 377 | E | E | ND | E |
| 379 | ND | ND | ND | ND |
| 380 | E | B | ND | E |
| 384 | E | A | ND | E |
| 386 | E | E | ND | E |
| 385 | E | B | ND | E |
| 387 | E | B | ND | E |
| 388 | E | B | ND | E |
| 390 | E | B | ND | C |
| 394 | E | A | ND | B |
| 396 | C | B | ND | E |
| 395 | E | D | ND | D |
| 397 | E | E | ND | E |
| 400 | E | E | ND | E |
| 401 | B | B | ND | B |
| 403 | E | A | ND | B |
| 404 | D | B | ND | C |
| 406 | E | B | ND | E |
| 407 | E | A | ND | A |
| 412 | E | A | ND | E |
| 411 | E | B | ND | B |
| 413 | E | B | ND | B |
| 414 | E | E | ND | E |
| 416 | E | B | ND | C |
| 415 | E | E | ND | E |
| 417 | E | B | ND | B |
| 425 | E | A | ND | B |
| 428 | E | A | ND | B |
| 202 | E | A | ND | A |
| 429 | E | A | ND | A |
| 430 | E | B | ND | B |
| 437 | D | B | ND | B |
| 439 | B | B | ND | B |
| 440 | C | C | ND | E |
| 441 | E | E | ND | E |
| 443 | E | B | ND | C |
| 445 | E | B | ND | B |
| 463 | E | B | ND | B |
| 466 | E | A | ND | B |
| 479 | E | D | B | E |
| 498 | E | A | A | A |
| 509 | E | B | A | E |
| 510 | E | E | B | E |

TABLE 6-continued

| Compound Number | Hck-1 | Lyn-1 | Ret-1 | Src-1 |
|---|---|---|---|---|
| 511 | E | B | A | E |
| 512 | E | A | A | E |
| 513 | E | B | A | D |
| 514 | E | E | A | E |
| 515 | E | E | A | E |
| 516 | E | E | A | E |
| 517 | E | D | C | E |
| 518 | E | B | D | E |
| 519 | E | D | A | E |
| 610 | E | A | A | B |
| 1031 | E | B | B | C |
| 1033 | E | A | A | B |
| 1036 | E | A | A | B |
| 1037 | E | E | B | E |
| 612 | D | B | B | B |
| 942 | E | A | A | E |
| 943 | E | B | A | E |
| 944 | E | C | A | E |
| 946 | E | A | B | E |
| 949 | E | B | A | E |
| 1076 | E | E | A | B |
| 1077 | E | B | A | D |
| 177 | B | A | A | A |
| 652 | E | B | A | B |
| 613 | E | C | B | E |
| 950 | E | A | A | B |
| 1082 | E | C | A | E |
| 655 | E | C | A | C |
| 656 | C | C | B | C |
| 951 | E | E | A | E |
| 952 | D | A | A | D |
| 616 | C | B | A | A |
| 1084 | E | A | A | E |
| 953 | B | A | B | A |
| 1086 | E | E | D | E |
| 1087 | E | E | B | E |
| 1088 | E | E | A | E |
| 1089 | E | A | A | B |
| 1040 | E | E | C | B |
| 1041 | B | A | B | A |
| 600 | E | A | B | B |
| 602 | E | B | E | B |
| 603 | D | B | A | B |
| 606 | E | C | B | E |
| 605 | E | B | A | E |
| 607 | B | A | A | B |
| 559 | C | A | A | A |
| 592 | E | B | A | B |
| 591 | B | B | A | A |
| 1042 | ND | E | A | E |
| 579 | ND | C | A | E |
| 582 | ND | E | C | E |
| 585 | ND | E | A | E |
| 587 | ND | B | A | E |

The Tables herein utilize the following designations:

A<0.4 ug/mL

B>0.4 and <2.4 ug/mL

C>2.4 and <3.5 ug/mL

D>3.5 and <4.5 ug/mL

E>4.5 ug/mL

ND-Not Determined

While we have described a number of embodiments of this invention, it is apparent that our basic examples may be altered to provide other embodiments that utilize the products and processes of this invention. Therefore, it will be appreciated that the scope of this invention is to be defined by the claims rather than by the specific embodiments that have been represented by way of example.

What is claimed is:
1. A compound having the formula:

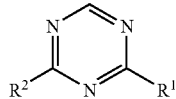

wherein,
$R^1$ is

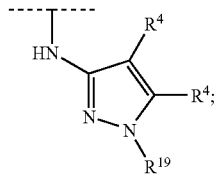

wherein
$R^{19}$ is independently H or C1–C6 alkyl;
$R^2$ is —$NHR^3$, —$NHR^5$, —$NHR^6$, —$NR^5R^5$ or —$NR^5R^6$;
$R^3$ is independently aryl, phenyl optionally substituted with 1–5 independent $R^4$ on each ring, or heteroaryl optionally substituted with 1–4 independent $R^4$ on each ring;
$R^4$ is independently selected from H, C1–C10 alkyl, C2–C10 alkenyl, C2–C10 alkynyl, C3–C10 cycloalkyl, C4–C10 cycloalkenyl, aryl, $R^8$, halo, $CF_3$, $SR^5$, $OR^5$, $OC(O)R^5$, $NR^5R^5$, $NR^5R^6$, $NR^5R^{16}$, $COOR^5$, $NO_2$, CN, $C(O)R^5$, $C(O)C(O)R^5$, $C(O)NR^5R^5$, $S(O)_nR^5$, $S(O)_nNR^5R^5$, $NR^5C(O)NR^5R^5$, $NR^5C(O)C(O)R^5$, $NR^5C(O)R^5$, $NR^5(COOR^5)$, $NR^5C(O)R^8$, $NR^5S(O)_nNR^5R^5$, $NR^5S(O)_nR^5$, $NR^5S(O)_nR^8$, $NR^5C(O)C(O)NR^5R^5$, $NR^5C(O)C(O)NR^5R^6$, $OC(O)NR^5R^5$, $OS(O)_nNR^5R^5$, $NR^5S(O)_nOR^5$, $P(O)(OR^5)_2$,
C1–C10 alkyl substituted with 1–3 independent aryl, $R^7$ or $R^8$, or
C2–C10 alkenyl substituted with 1–3 independent aryl, $R^7$ or $R^8$;
n is independently 1 or 2;
$R^5$ is independently H, C1–C10 alkyl, C2–C10 alkenyl, C2–C10 alkynyl, C3–C10 cycloalkyl, C4–C10 cycloalkenyl, aryl, $R^9$, haloalkyl,
C1–C10 alkyl substituted with 1–3 independent aryl, $R^7$ or $R^9$ groups,
C3–C10 cycloalkyl substituted with 1–3 independent aryl, $R^7$ or $R^9$ groups, or
C2–C10 alkenyl substituted with 1–3 independent aryl, $R^7$ or $R^9$,
$R^6$ is independently $C(O)R^5$, $COOR^5$, $C(O)NR^5R^5$, $C(=NR^5)NR^5R^5$, or $S(O)_nR^5$;
$R^7$ is independently halo, $CF_3$, $SR^{10}$, $OR^{10}$, $OC(O)R^{10}$, $NR^{10}R^{10}$, $NR^{10}R^{11}$, $NR^{11}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$, $S(O)_nNR^{10}R^{10}$, $NR^{10}S(O)_nNR^{10}R^{10}$, $NR^{10}S(O)_nR^{10}$ or $P(O)(OR^5)_2$;
$R^8$ is independently a 3–8 membered monocyclic, 7–12 membered bicyclic, or 11–14 membered tricyclic ring system having 1–3 heteroatoms if monocyclic, 1–6 heteroatoms if bicyclic, or 1–9 heteroatoms if tricyclic, said heteroatoms independently selected from O, N, or S, which may be saturated or unsaturated, and wherein 0, 1, 2, 3 or 4 atoms of each ring may be substituted by a substituent independently selected from C1–C10 alkyl, C2–C10 alkenyl, C2–C10 alkynyl, C3–C10 cycloalkyl, C4–C10 cycloalkenyl, aryl, $R^9$, halo, sulfur, oxygen, $CF_3$, $SR^5$, $OR^5$, $OC(O)R^5$, $NR^5R^5$, $NR^5R^6$, $NR^6R^6$, $COOR^5$, $NO_2$, CN, $C(O)R^5$, $C(O)NR^5R^5$, $S(O)_nNR^5R^5$, $NR^5C(O)NR^5R^5$, $NR^5C(O)R^9$, $NR^5S(O)_nNR^5R^5$, $NR^5S(O)_nR^9$, C1–C10 alkyl substituted with 1–3 independent $R^7$, $R^9$ or aryl, or C2–C10 alkenyl substituted with 1–3 independent $R^7$, $R^9$ or aryl;

$R^9$ is independently a 3–8 membered monocyclic, 7–12 membered bicyclic, or 11–14 membered tricyclic ring system having 1–3 heteroatoms if monocyclic, 1–6 heteroatoms if bicyclic, or 1–9 heteroatoms if tricyclic, said heteroatoms independently selected from O, N, or S, which may be saturated or unsaturated, and wherein 0, 1, 2 or 3 atoms of each ring may be substituted by a substituent independently selected from C1–C10 alkyl, C2–C10 alkenyl, C2–C10 alkynyl, C3–C10 cycloalkyl, C4–C10 cycloalkenyl, halo, sulfur, oxygen, $CF_3$, $SR^{10}$, $OR^{10}$, $NR^{10}R^{10}$, $NR^{10}R^{10}$, $NR^{10}R^{11}$, $COOR^{10}$, $NO_2$, CN, $C(O)R^{10}$, $S(O)_nR^{10}$, $S(O)_nNR^{10}R^{10}$ or $C(O)NR^{10}R^{10}$;

$R^{10}$ is independently H, C1–C10 alkyl, C2–C10 alkenyl, C2–C10 alkynyl, C3–C10 cycloalkyl, C4–C10 cycloalkenyl, haloalkyl, C1–C10 alkyl optionally substituted with 1–3 independent substituents selected from C1–C10 alkyl, C2–C10 alkenyl, C2–C10 alkynyl, C3–C10 cycloalkyl, C4–C10 cycloalkenyl, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NR^{12}C(O)R^{12}$, $N(R^{12})(COOR^{12})$, $S(O)_nNR^{12}R^{12}$ or $OC(O)R^{12}$, or phenyl optionally substituted with 1–3 independent substituents selected from C1–C10 alkyl, C2–C10 alkenyl, C2–C10 alkynyl, C3–C10 cycloalkyl, C4–C10 cycloalkenyl, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NR^{12}C(O)R^{12}$, $N(R^{12})(COOR^{12})$, $S(O)_nNR^{12}R^{12}$ or $OC(O)R^{12}$;

$R^{11}$ is independently $C(O)R^{10}$, $COOR^{10}$, $C(O)NR^{10}R^{10}$ or $S(O)_nR^{10}$;

$R^{12}$ is independently H, C1–C10 alkyl, C2–C10 alkenyl, C2–C10 alkynyl, C3–C10 cycloalkyl, C4–C10 cycloalkenyl, C1–C10 alkyl substituted with 1–3 independent substituents selected from C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NR^{13}C(O)R^{13}$ or $OC(O)R^{13}$, or phenyl optionally substituted with 1–3 independent substituents selected from C1–C10 alkyl, C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NR^{13}C(O)R^{13}$ or $OC(O)R^{13}$;

$R^{13}$ is independently H, C1–C10 alkyl, C2–C10 alkenyl, C2–C10 alkynyl, C3–C10 cycloalkyl, C4–C10 cycloalkenyl, C1–C10 alkyl optionally substituted with halo, $CF_3$, $OR^{14}$, $SR^{14}$, $NR^{14}R^{14}$, $COOR^{14}$, $NO_2$ or CN, or phenyl optionally substituted with halo, $CF_3$, $OR^{14}$, $SR^{14}$, $NR^{14}R^{14}$, $COOR^4$, $NO_2$ or CN;

$R^{14}$ is independently H, C1–C10 alkyl, C3–C10 cycloalkyl or phenyl;

$R^{16}$ is independently H, C1–C10 alkyl, C2–C10 alkenyl, C2–C10 alkynyl, C3–C10 cycloalkyl, C4–C10 cycloalkenyl, aryl, $R^8$, halo, $CF_3$, $COOR^5$, $C(O)R^5$, $C(O)C(O)R^5$, $C(O)NR^5R^5$, $S(O)_nR^5$; $S(O)_nNR^5R^5$, C1–C10 alkyl substituted with 1–3 independent aryl, $R^7$ or $R^8$, or phenyl optionally substituted with substituted with 1–4 independent $R^{23}$, or C2–C10 alkenyl substituted with 1–3 independent aryl, $R^7$ or $R^8$; and $R^{23}$ is independently selected from H, C1–C10 alkyl, C2–C10 alkenyl, C2–C10 alkynyl, C3–C10 cycloalkyl, C4–C10 cycloalkenyl, aryl, $R^8$, halo, $CF_3$, $SR^5$, $OR^5$, $OC(O)R^5$, $NR^5R^5$, $NR^5R^6$, $COOR^5$, $NO_2$, CN, $C(O)R^5$, $C(O)C(O)R^5$, $C(O)NR^5R^5$, $S(O)_nR^5$, $S(O)_nNR^5R^5$, $NR^5C(O)NR^5R^5$, $NR^5C(O)C(O)R^5$, $NR^5C(O)R^5$, $NR^5(COOR^5)$, $NR^5C(O)R^8$, $NR^5S(O)_nNR^5R^5$, $NR^5S(O)_nR^5$, $NR^5S(O)_nR^8$, $NR^5C(O)C(O)NR^5R^5$, $NR^5C(O)C(O)NR^5R^6$, $OC(O)NR^5R^5$, $OS(O)_nNR^5R^5$, $NR^5S(O)_nOR^5$, $P(O)(OR^5)_2$, C1–C10 alkyl substituted with 1–3 independent aryl, $R^7$ or $R^8$, or C2–C10 alkenyl substituted with 1–3 independent aryl, $R^7$ or $R^8$.

2. Compound of claim 1 and a pharmaceutically acceptable salt thereof selected from

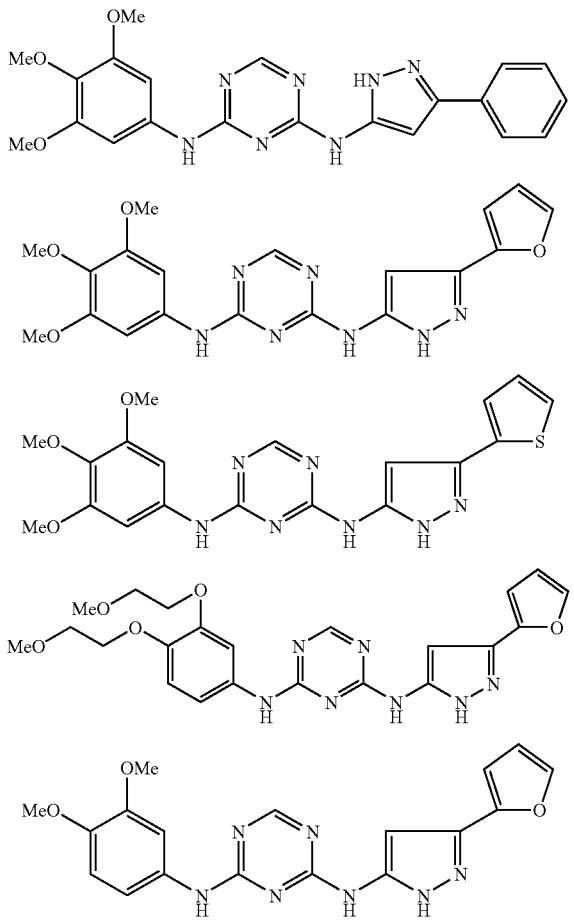

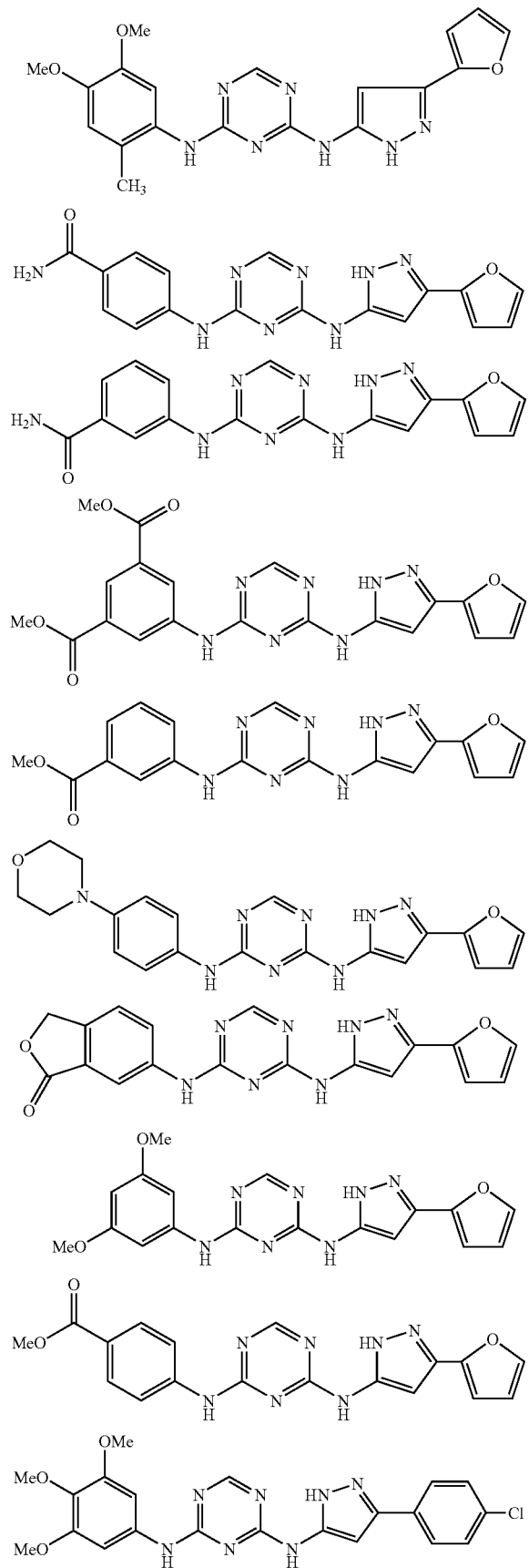
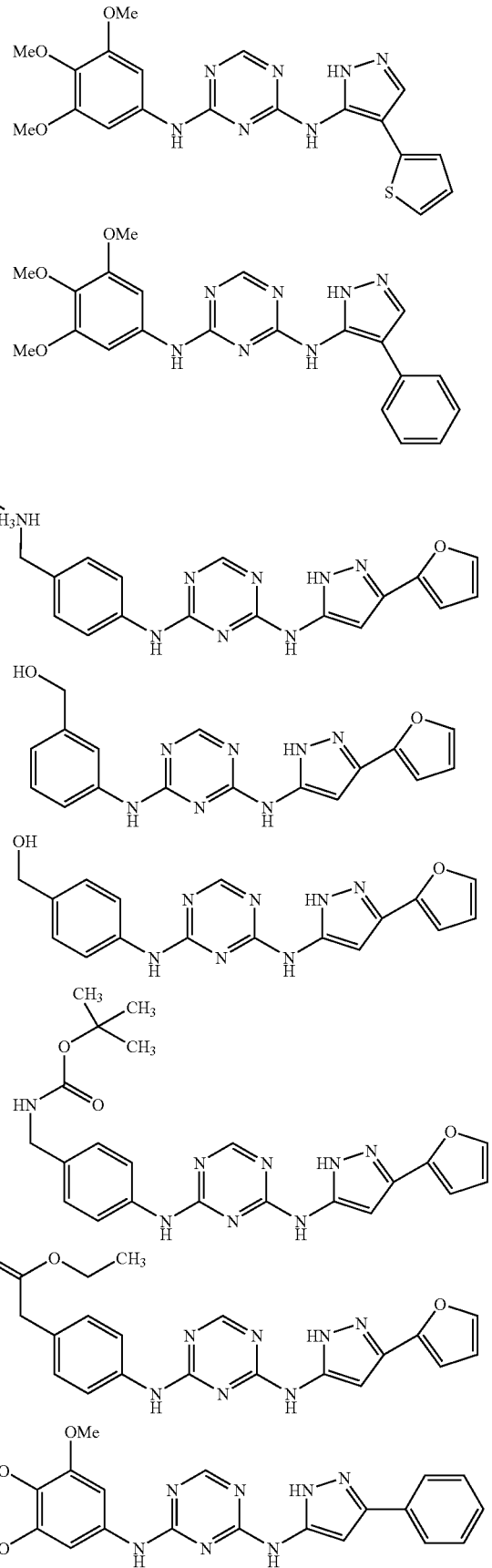

575
-continued
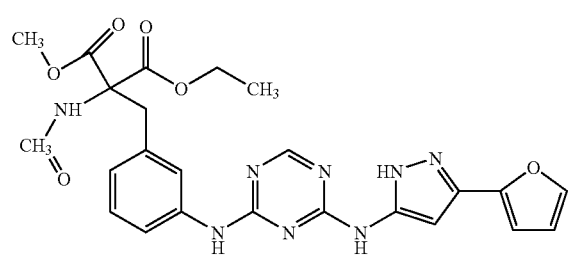
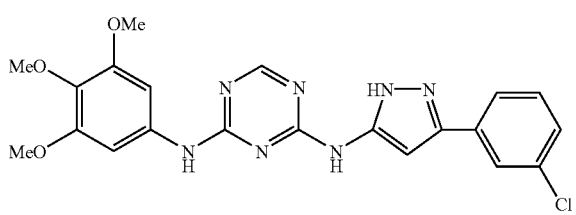
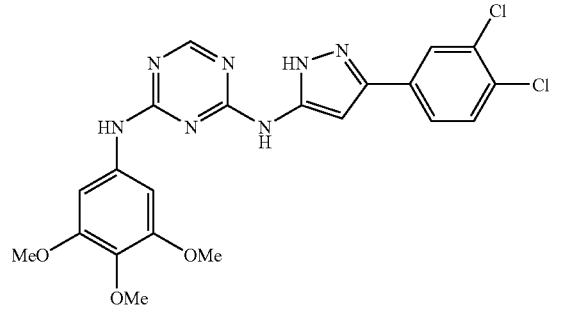
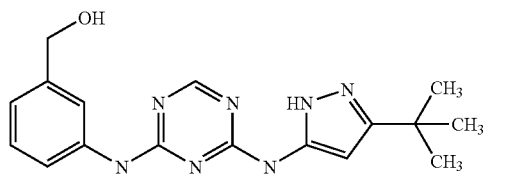
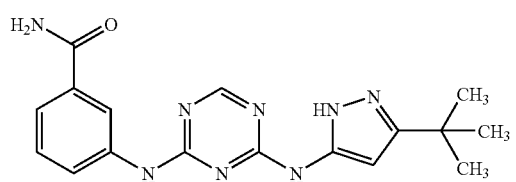
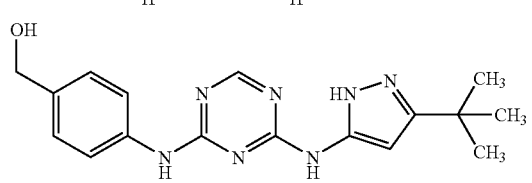
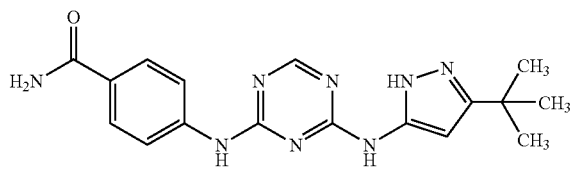
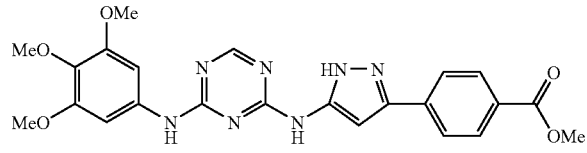
576
-continued
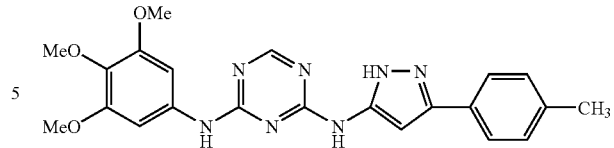
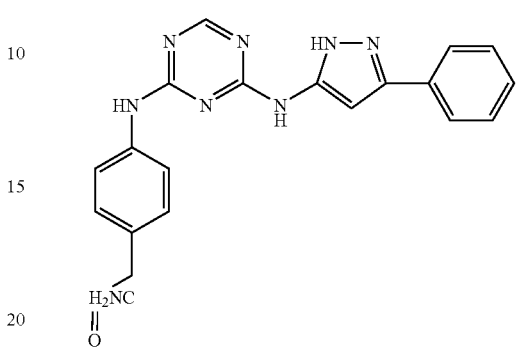
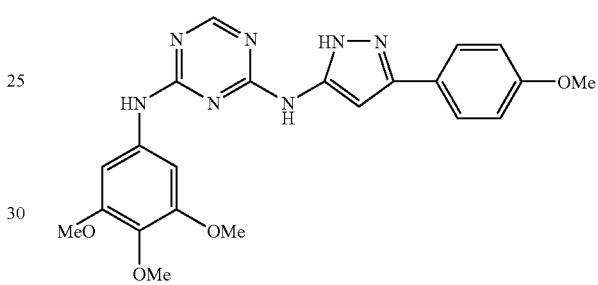
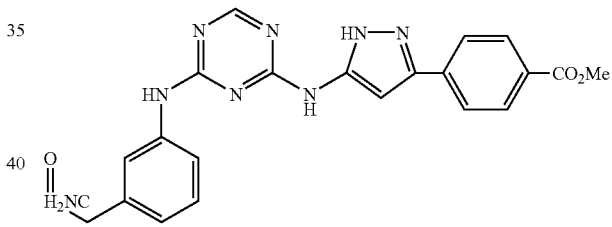
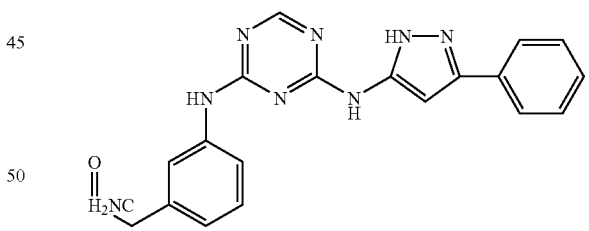
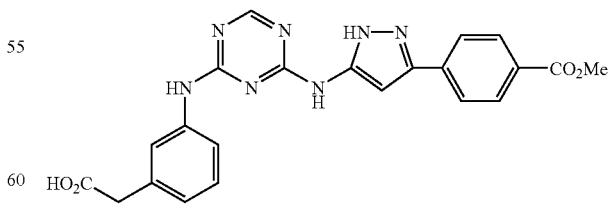
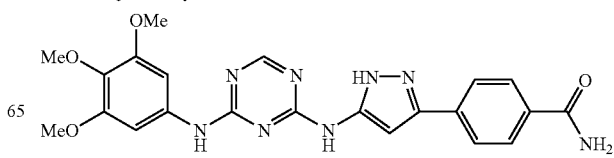

577
-continued
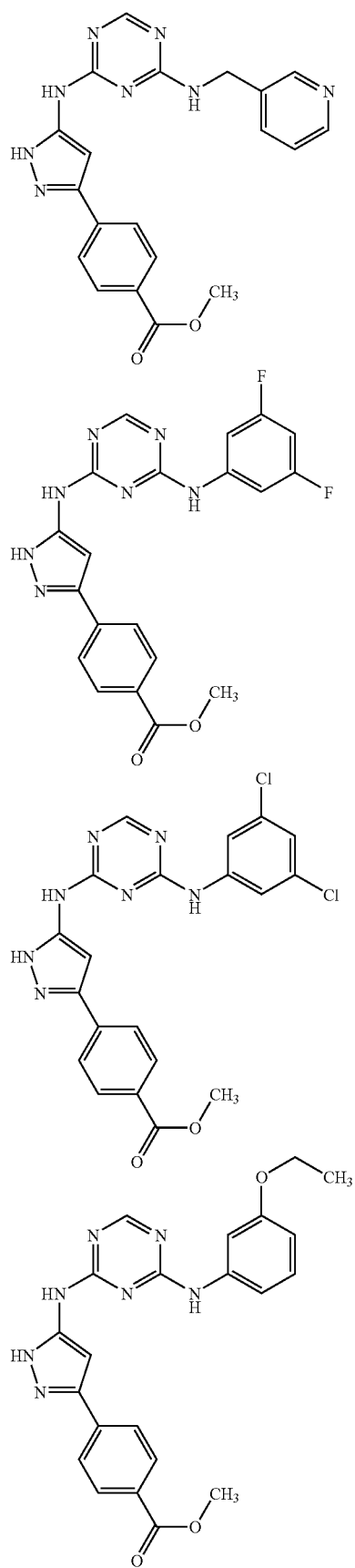
578
-continued
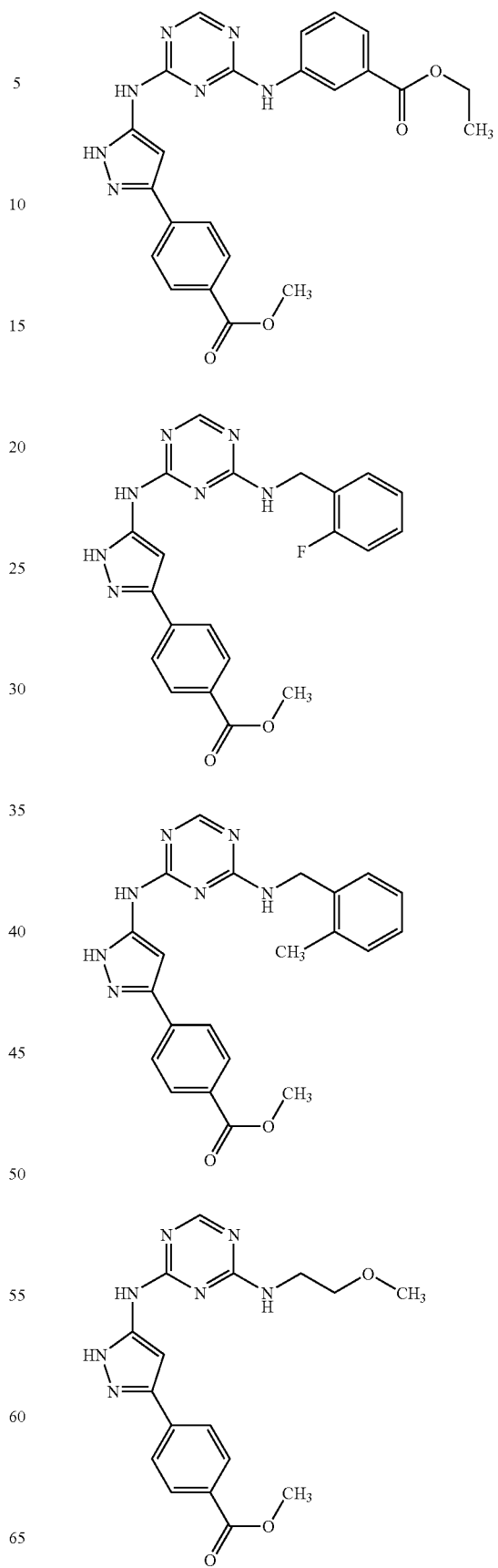

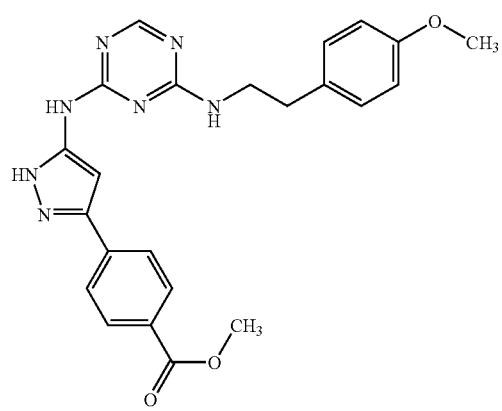
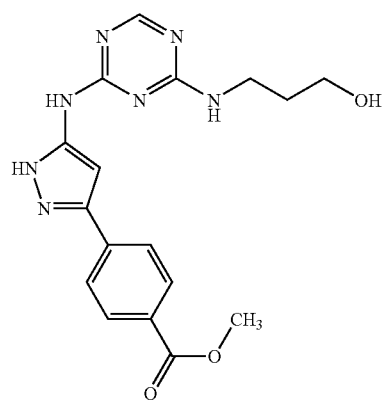
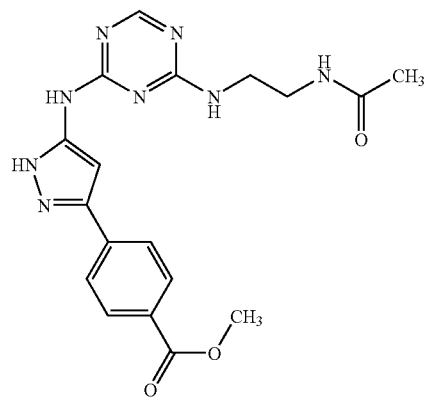
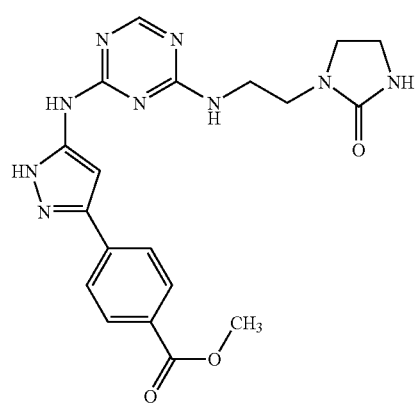
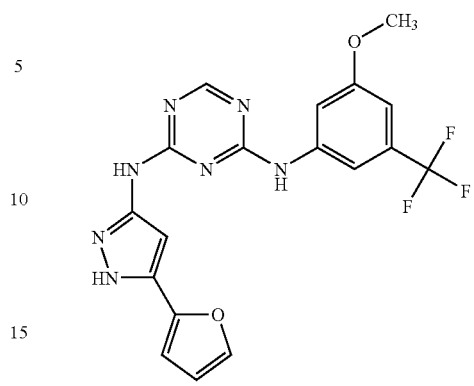
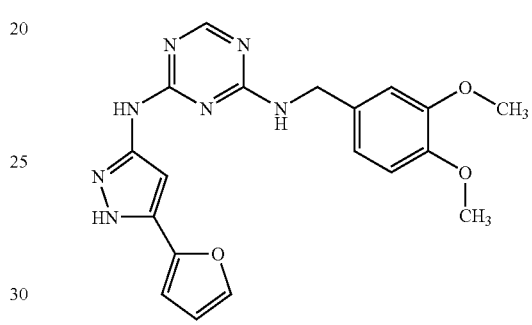
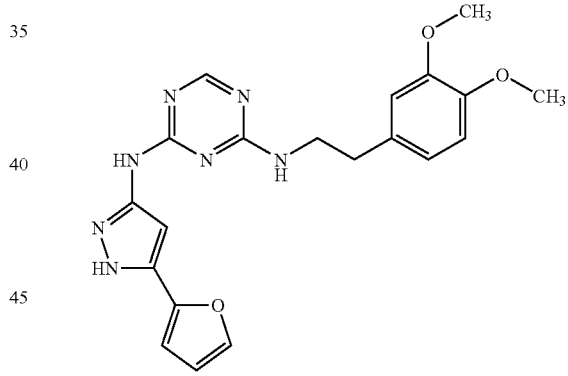
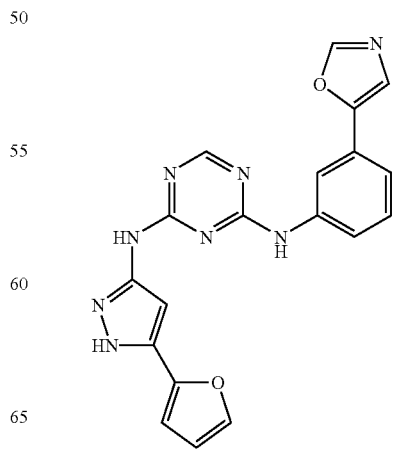

581
-continued
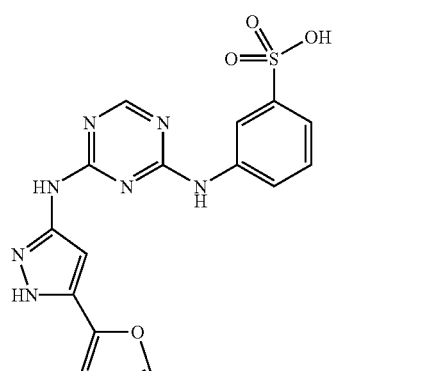
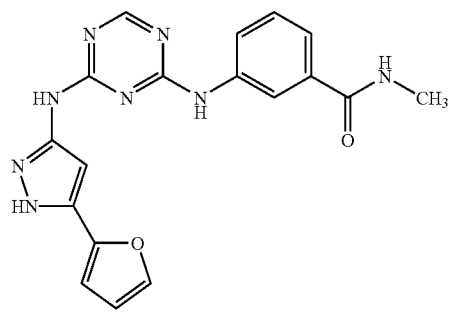
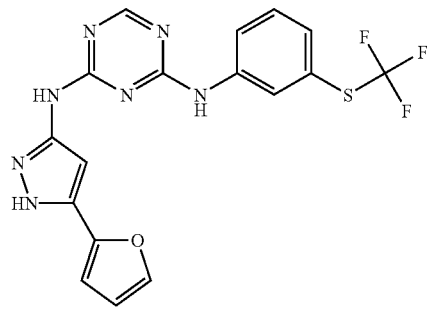
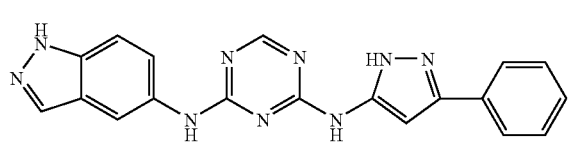
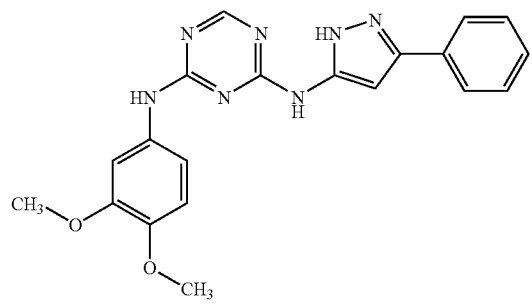
582
-continued
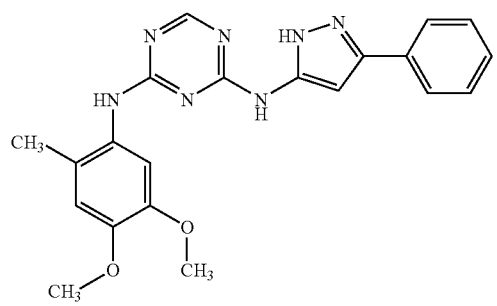
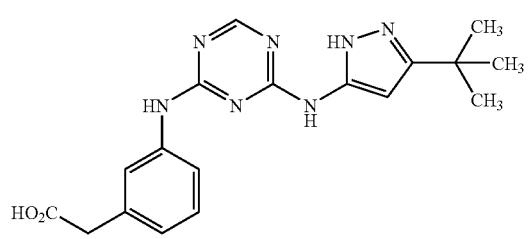
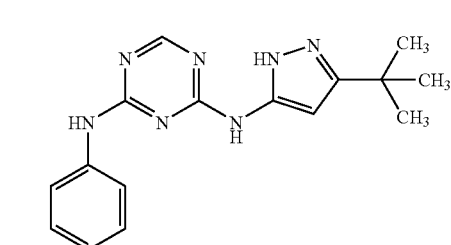
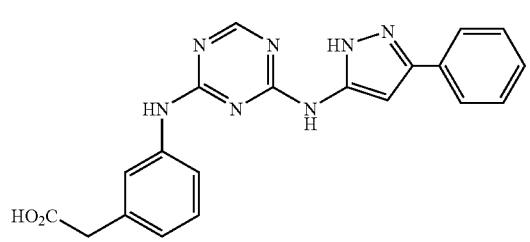
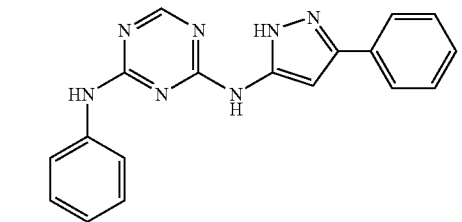
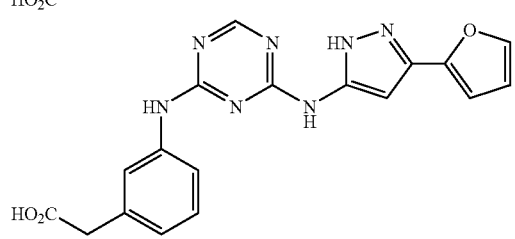

583
-continued
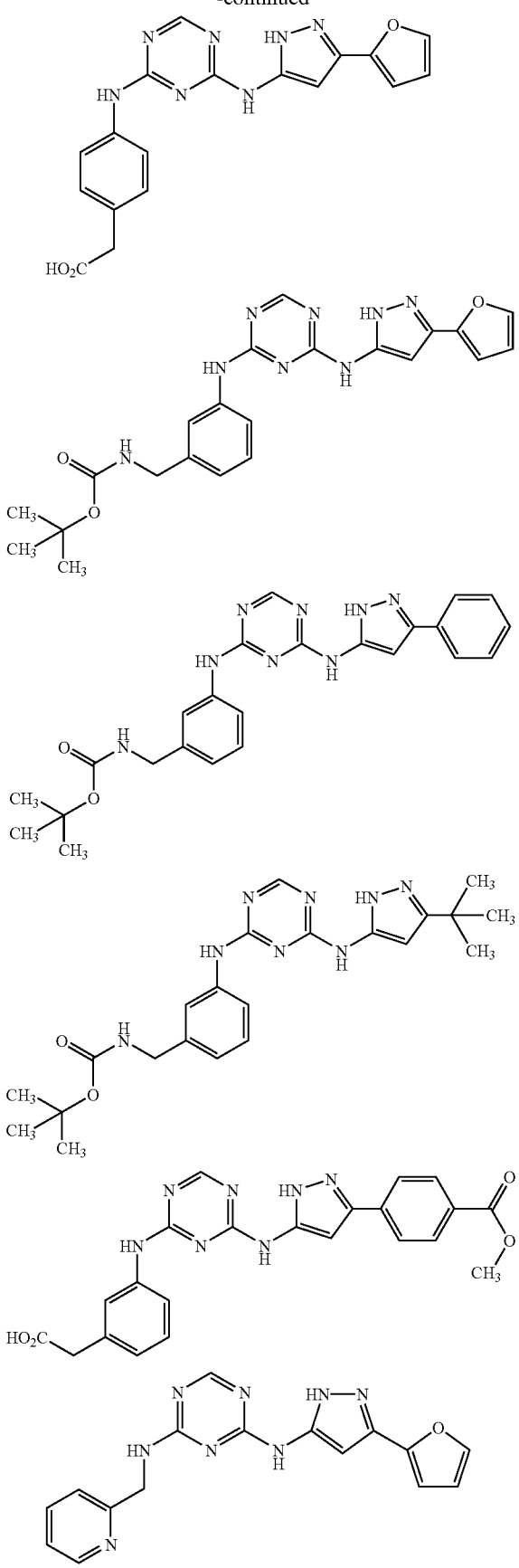
584
-continued
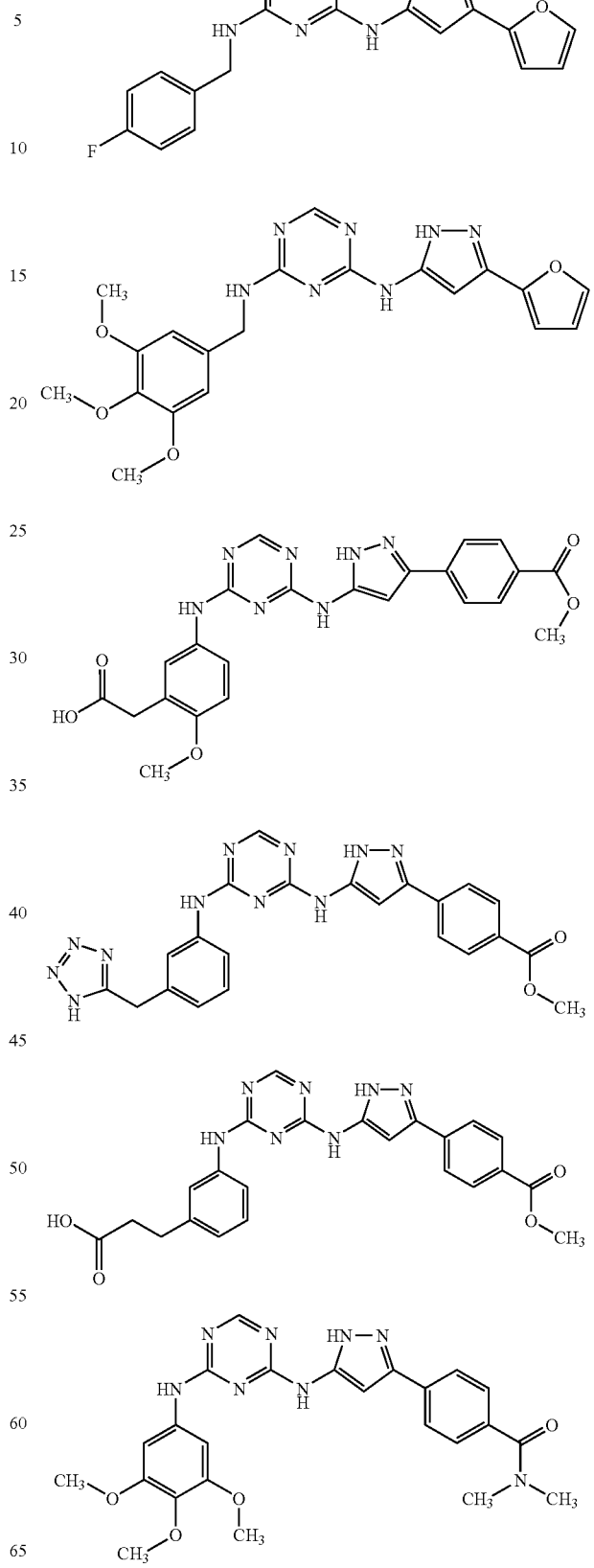

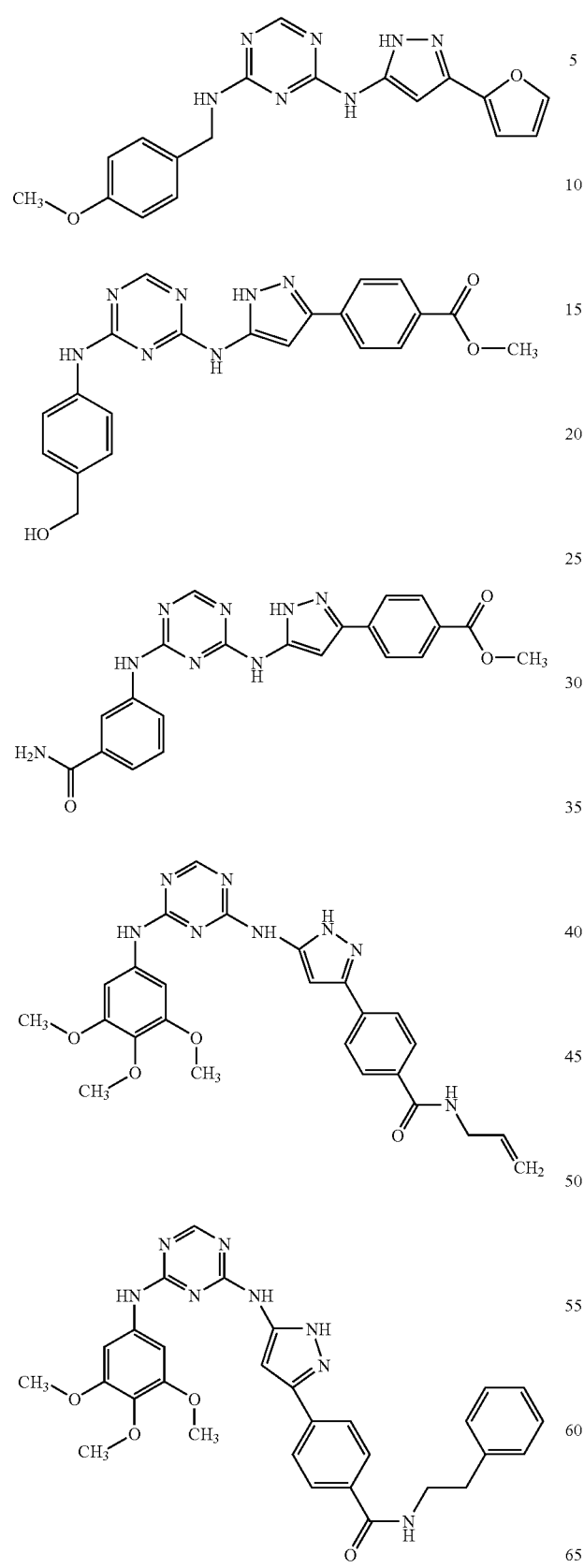
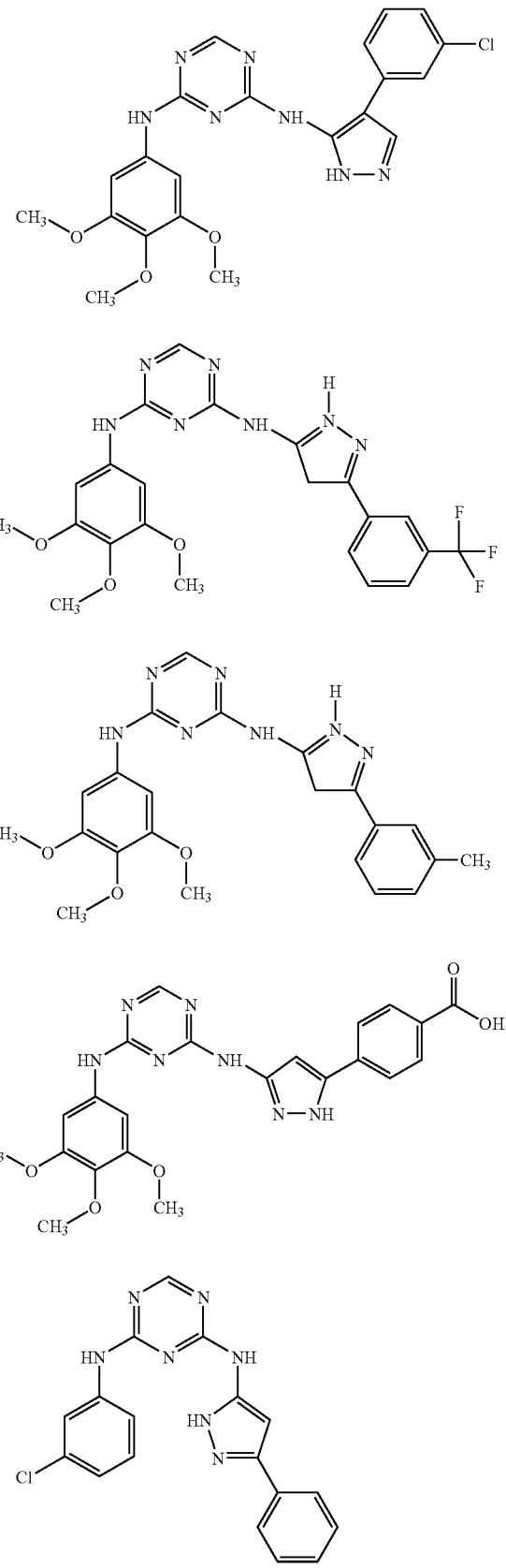

587
-continued
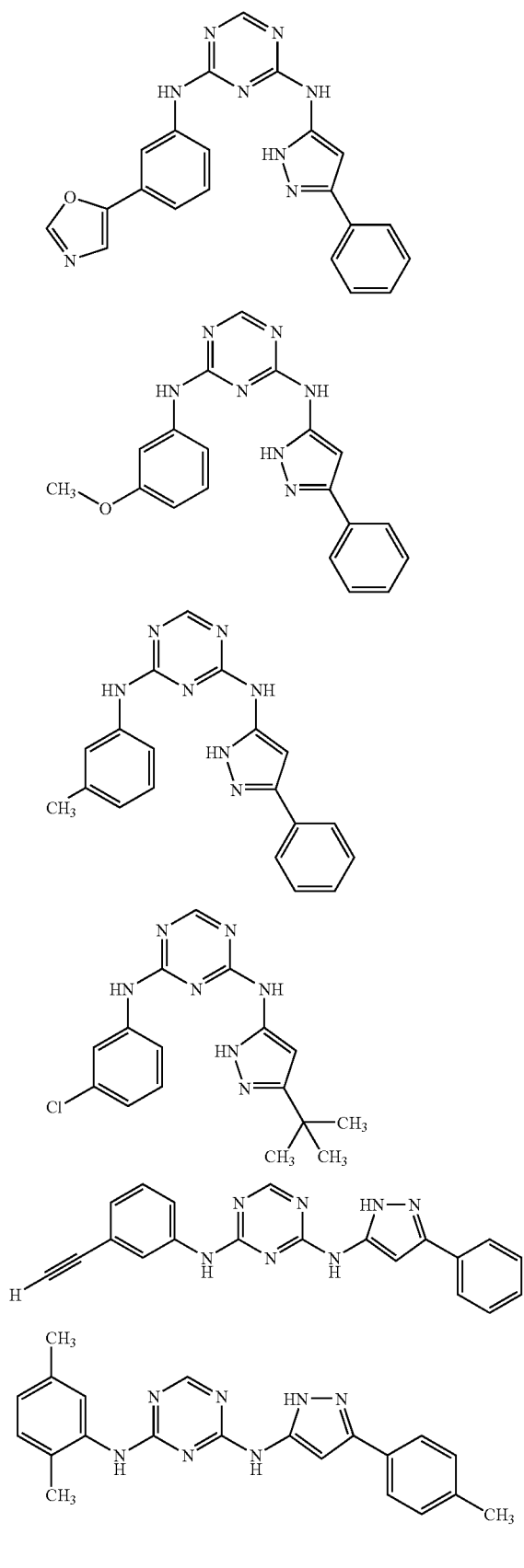
588
-continued
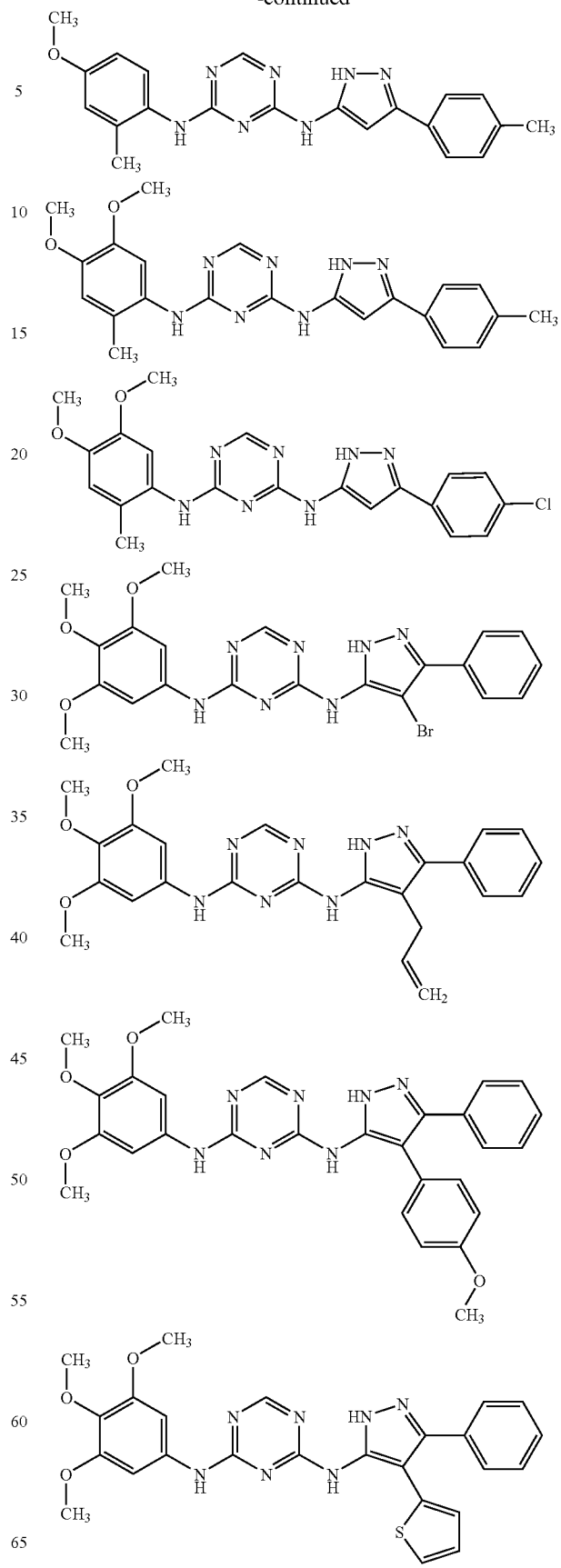

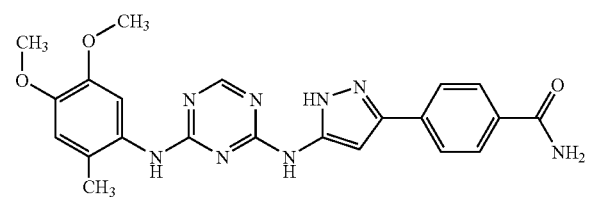
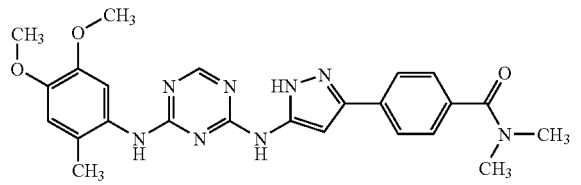
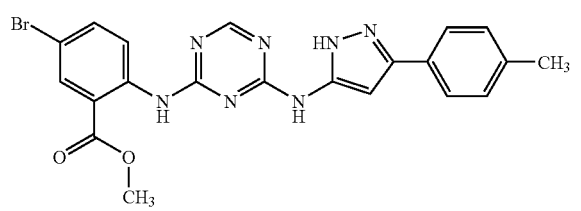
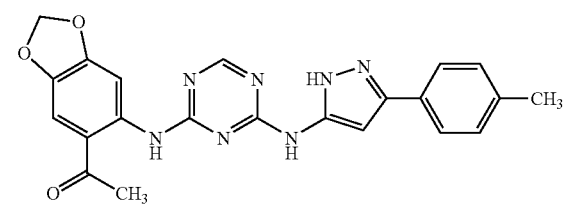
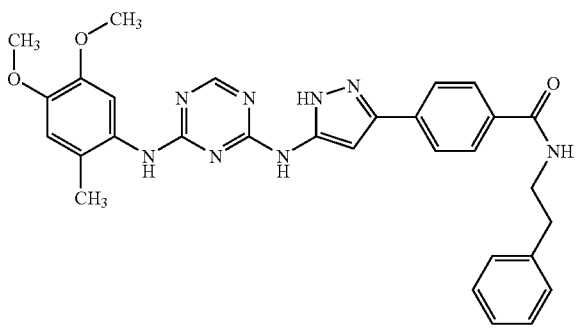
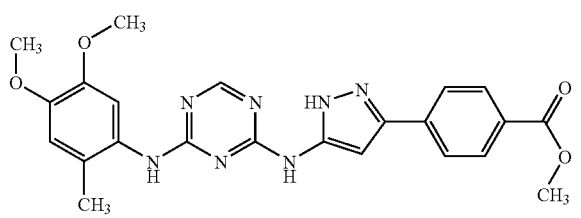
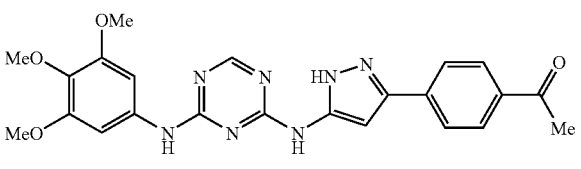
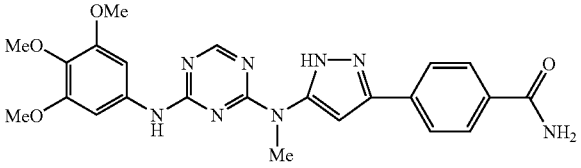
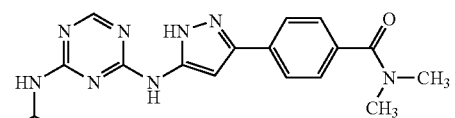
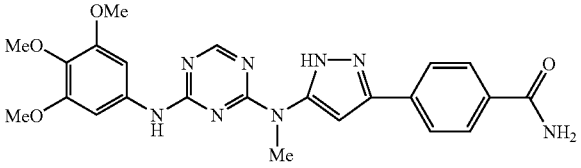

591

-continued

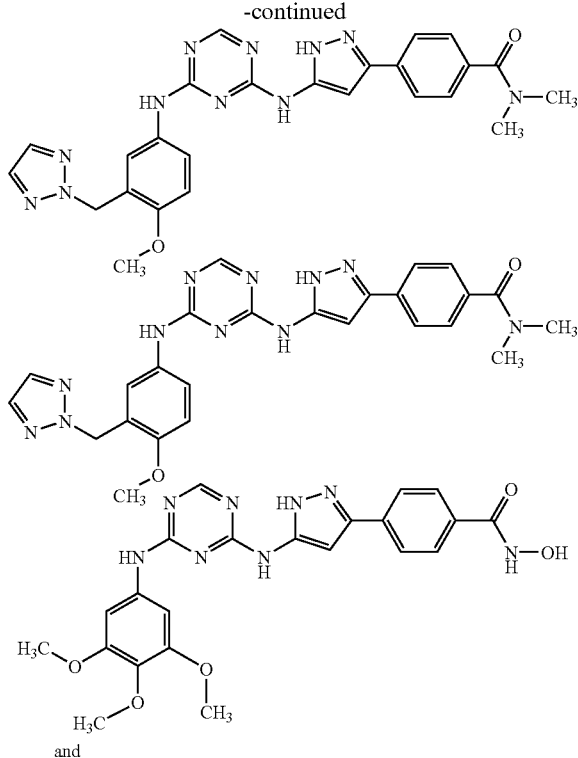

and

592

-continued

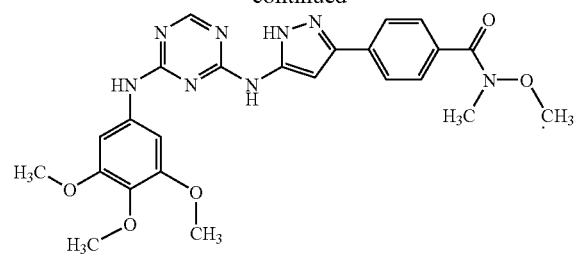

3. A composition comprising a compound of any of claims 1 and 2 and a pharmaceutically acceptable carrier.

4. The composition of claim 3, further comprising at least one additional therapeutic agent.

5. A method of inhibiting angiogenesis or vasculogenesis activity in a mammal comprising administration of a composition comprising an effective amount of a compound of any of claims 1 and 2.

6. A method of making a pharmaceutically useful composition comprising combining an effective amount of a compound of any of claims 1 and 2 with one or more pharmaceutically acceptable carriers.

7. The method of claim 6, further comprising combining an effective amount of an additional therapeutic agent.

\* \* \* \* \*